US005744580A

United States Patent [19]

Better et al.

[11] Patent Number: 5,744,580
[45] Date of Patent: *Apr. 28, 1998

[54] IMMUNOTOXINS COMPRISING RIBOSOME-INACTIVATING PROTEINS

[75] Inventors: Marc D. Better, Los Angeles; Stephen F. Carroll, Walnut Creek; Gary M. Studnicka, Santa Monica, all of Calif.

[73] Assignee: Xoma Corporation, Berkeley, Calif.

[*] Notice: The term of this patent shall not extend beyond the expiration date of Pat. No. 5,621,083.

[21] Appl. No.: 488,113

[22] Filed: Jun. 7, 1995

Related U.S. Application Data

[63] Continuation of Ser. No. 425,336, Apr. 18, 1995, Pat. No. 5,621,083, which is a continuation of Ser. No. 64,691, May 12, 1993, abandoned, which is a continuation-in-part of Ser. No. 988,430, Dec. 9, 1992, Pat. No. 5,416,202, which is a continuation-in-part of Ser. No. 901,707, Jun. 19, 1992, Pat. No. 5,376,546, which is a continuation-in-part of Ser. No. 787,567, Nov. 4, 1991, abandoned.

[51] Int. Cl.⁶ .............................. A23J 1/14; A61K 35/78; C07K 16/00; C12P 21/08
[52] U.S. Cl. ........................ 530/377; 530/351; 530/370; 530/391.1; 530/391.5; 530/391.7; 530/391.9; 530/399; 530/387.3
[58] Field of Search .......................... 530/387.3, 351, 530/370, 377, 391.1, 391.5, 391.7, 391.9, 399

[56] References Cited

U.S. PATENT DOCUMENTS

| | | |
|---|---|---|
| 4,675,382 | 6/1987 | Murphy . |
| 4,769,326 | 9/1988 | Rutter . |
| 4,853,871 | 8/1989 | Pantoliano et al. . |
| 4,888,415 | 12/1989 | Lambert et al. . |
| 4,894,443 | 1/1990 | Greenfield et al. . |
| 4,925,673 | 5/1990 | Steiner et al. . |
| 4,946,778 | 8/1990 | Ladner et al. . |
| 5,013,653 | 5/1991 | Huston et al. . |
| 5,028,530 | 7/1991 | Lai et al. . |
| 5,091,513 | 2/1992 | Huston et al. . |
| 5,093,475 | 3/1992 | Carroll et al. . |
| 5,101,025 | 3/1992 | Piatak, Jr. et al. . |
| 5,169,939 | 12/1992 | Gefter et al. . |
| 5,376,546 | 12/1994 | Bernhard et al. . |
| 5,416,202 | 5/1995 | Bernhard et al. . |

FOREIGN PATENT DOCUMENTS

| | | |
|---|---|---|
| A-27617/88 | 7/1989 | Australia . |
| 192 002 A1 | 8/1986 | European Pat. Off. . |
| 0 239 400 | 9/1987 | European Pat. Off. . |
| 438 310 A1 | 7/1991 | European Pat. Off. . |
| 170 697 B1 | 10/1991 | European Pat. Off. . |
| 506 124 A1 | 9/1992 | European Pat. Off. . |
| 519 596 A1 | 12/1992 | European Pat. Off. . |
| 2 216 891 | 10/1989 | United Kingdom . |
| WO 83/03971 | 11/1983 | WIPO . |
| WO 85/03508 | 8/1985 | WIPO . |
| WO 86/00090 | 1/1986 | WIPO . |
| WO 86/05098 | 9/1986 | WIPO . |
| WO 87/02987 | 5/1987 | WIPO . |
| WO 88/01649 | 3/1988 | WIPO . |
| WO 88/07085 | 9/1988 | WIPO . |
| WO 88/09344 | 12/1988 | WIPO . |
| WO 89/00999 | 2/1989 | WIPO . |
| WO 89/06967 | 8/1989 | WIPO . |
| WO 89/06968 | 8/1989 | WIPO . |
| WO 89/09622 | 10/1989 | WIPO . |
| WO 90/02569 | 3/1990 | WIPO . |
| WO 90/10015 | 9/1990 | WIPO . |
| WO 90/12592 | 11/1990 | WIPO . |
| WO 91/02000 | 2/1991 | WIPO . |
| WO 91/19745 | 12/1991 | WIPO . |
| WO 92/03144 | 3/1992 | WIPO . |
| WO 92/06117 | 4/1992 | WIPO . |
| WO 92/08495 | 5/1992 | WIPO . |
| WO 92/09613 | 6/1992 | WIPO . |
| WO 92/11018 | 7/1992 | WIPO . |
| WO 92/14491 | 9/1992 | WIPO . |
| WO 92/15327 | 9/1992 | WIPO . |
| WO 92/22324 | 12/1992 | WIPO . |
| WO 93/05168 | 3/1993 | WIPO . |
| WO 93/09130 | 5/1993 | WIPO . |

OTHER PUBLICATIONS

Bacha, P. et al., *J. Exp. Med.*, 167: 612–622 (Feb. 1988) "Interleukin 2 Receptor–Targeted Cytotoxicity".

Batra, J.K. et al., *J. Biol. Chem.*, 265 (25): 15198–15202 (Sep. 1990) "Anti–Tac(Fv)–PE40, a Single Chain Antibody *Pseudomonas* Fusion Protein Directed at Interleukin 2 Receptor Bearing Cells".

Chaudhary, V.K. et al., *Nature*, 339: 394–397 (Jun. 1989) "A Recombinant Immunotoxin Consisting of Two Antibody Variable Domains Fused to Pseudomonas Exotoxin".

Colombatti, M. et al., *J. Immunol.*, 131 (61): 3091–3095 (Dec. 1983) "Selective Killing of Target Cells By Antibody–Ricin A Chain or Antibody–Gelonin Hybrid Molecules: Comparison of Cytotoxic Potency and Use in Immunoselection Procedures".

Descotes, G. et al., *J. Immunopharmac.*, 7 (4): 455–463 (1985) "The Immunological Activity of Plant Toxins Used in the Preparation of Immunotoxins –II. The Immunodepressive Activity of Gelonin".

(List continued on next page.)

*Primary Examiner*—Christina Y. Chan
*Assistant Examiner*—Patrick Nolan
*Attorney, Agent, or Firm*—McAndrews, Held & Malloy, Ltd.

[57] ABSTRACT

The present invention provides purified and isolated polynucleotides encoding Type I ribosome-inactivating proteins (RIPS) and analogs of the RIPs having a cysteine available for disulfide bonding to targeting molecules. Vectors comprising the polynucleotides and host cells transformed with the vectors are also provided. The RIPs and RIP analogs are particularly suited for use as components of cytotoxic therapeutic agents of the invention which include gene fusion products and immunoconjugates. Cytotoxic therapeutic agents or immunotoxins according to the present invention may be used to selectively eliminate any cell type to which the RIP component is targeted by the specific binding capacity of the second component of the agent, and are suited for treatment of diseases where the elimination of a particular cell type is a goal, such as autoimmune disease, cancer and graft-versus-host disease.

36 Claims, 15 Drawing Sheets

OTHER PUBLICATIONS

Kohr, W.J. et al., Abstr. T15, *The Protein Society, 4th Symposium,* Aug. 11–15, 1990, San Diego, California "The Amino Acid Sequence of Gelonin".

Montecucchi, P.C. et al., *Int. J. Peptide Protein Res.,* 33: 263–267 (1989) "N-terminal Sequence of Some Ribosome–Inactivating Proteins".

O'Hare, M. et al., *FEBS,* 273 (1,2): 200–204 (Oct. 1990) "Cytotoxicity of a Recombinant Ricin–A–Chain Fusion Protein Containing a Proteolytically–Cleavable Spacer Sequence".

Sivam, G. et al., *Cancer Research,* 47: 3169–3173 (Jun. 1987) "Immunotoxins to a Human Lemanoma–Associated Antigen: Comparison of Gelonin With Ricin and Other A Chain Conjugate".

Stirpe, F. et al., *J. Biol. Chem.,* 255 (14): 6947–6953 (Jul. 1980) "Gelonin, A New Inhibitor of Protein Synthesis, Nontoxic to Intact Cells".

Westby, M. et al. *Bioconjugate Chem.,* 3 (5): 375–381 (Sep. 1992) "Preparation and Characterization of Recombinant Proricin Containing an Alternative Protease–Sensitive Linker Sequence".

Williams, D.P. et al., *Protein Engineering,* 1 (6): 493–498 (1987) "Diptheria Toxin Receptor Binding Domain Substitution with Interleukin–2: Genetic Construction and Properties of a Diphtheria Toxin–Related Interleukin–2 Fusion Protein".

Batra, J.K. et al., *Mol. and Cell. Biology,* 11: 2200–2205 (Apr. 1991) "Single–Chain Immunotoxins Directed at the Human Transferrin Receptor Containing Pseudomonas Exotoxin A or Diphtheria Toxin: Anti–TFR(Fv)–PE40 and DT388–Anti–TFR(Fv)".

Queen, C. et al., *Proc. Nat'l Acad., Sci. (USA),* 86: 10029–10033 (Dec. 1989) "A Humanized Antibody that Binds to the Interleukin 2 Receptor".

Nolan, P.A. et al., *Gene,* 134: 223–227 Dec. (1993) "Cloning and Expression of a Gene Encoding Gelonin, A Ribosome–Inactivating Protein from *Gelonium Multiflorum*".

Ebert, R.F. et al., *Bioconjugate Chem.,* 1: 331–336 (Feb. 1990) "Immunotoxin Construction with a Ribosome–Inactivating Protein from Barley".

Kernan, N.A. et al., *J. Immunol.,* 133 (1): 137–146 (Jul. 1984) "Specific Inhibition of In Vitro Lymphocyte Transformation By An Anti–Pan T Cell (gp67) Ricin A Chain Immunotoxin".

Kong, K. et al., *American College of Toxicology,* Oct. (1992) San Francisco, CA "*Subacute Intravenous Toxicity of a Ribosomal Inhibitory Protein rGelonin in Rats*" (Poster).

Kohn, F.R. et al., *Int. J. Immunopharmac.,* 15 (8): 871–878 (Nov. 1993) "Efficacy of Anti–CD5 F(AB')$_2$ and Fab' Immunoconjugates In Human Peripheral Blood Lymphocyte–Reconstituted Severe Combined Immunodeficient Mice".

Better, M. et al., *Proc. Natl. Acad. Sci. USA,* 90: 457–461 (Jan. 1993) "Potent Anti–CD5 Ricin A Immunoconjugates from Bacterially Produced Fab' and F(ab')$_2$".

Better, M. et al., *J. Biol. Chem.,* 267 (23) 16712–16718 (Aug. 1992) "Activity of Recombinant Mitogillin and Mitogillin Immunoconjugates".

Better, M. et al., *J. Biol. Chem.,*269 (13): 9644–9650 (Apr. 1994) "Gelonin Analogs with Engineered Cysteine Residues Form Antibody Immunoconjugates with Unique Properties".

Lambert, J.M. et al., *J. Biol. Chem.,* 260 (22): 12035–12041 (Oct. 1985) "Purified Immunotoxins That Are Reactive with Human Lymphoid Cells".

Better, M. et al., 3rd Int'l Symposium Immunotoxins, Jun. 19–21 (1992) Orlando, FL "*Generation of Potent Immunoconjugates from Microbially Produced Fab', F(ab')$_2$, and Recombinant Ribosome Inactivating Proteins*" (Poster).

Brown, D. et al. The Washington Post, A1 and A4, Aug. 21, 1992 "Customizing Lab Mice".

Strockbine, N.A. et al., *J. Bact.,* 170: 1116–1122 (1988) "Cloning and Sequencing of the Genes for Shiga Toxin from *Shigella dysenteriae* Type 1".

Tolan, D.R. et al., *J. Biol. Chem.* 259 (2): 1127–1131 (1984) "The Complete Nucleotide Sequence for Rabbit Muscle Aldolase A Messenger RNA".

Riechmann, L. et al., *Nature,* 332: 323–327 (Mar. 1988) "Reshaping Human Antibodies for Therapy".

Royston, I. et al., *J. Immunol.,* 125 (2):725–731 (Aug. 1980) "Human T Cell Antigens Defined By Monoclonal Antibodies: The 65,000–Dalton Antigen of T Cells (T65) Is Also Found On Chronic Lymphocytic Leukemia Cells Bearing Surface Immunoglobulin".

Stirpe, F. et al., *FEBS,* 195 (1, 2): 1–8 (Jan. 1986) "Ribosome–inactivating proteins up to date".

Ready, M. et al., *J. Biol. Chem.,* 259 (24): 15252–15256 (Dec. 1984) "Ricin–like Plant Toxins Are Evoluntionarily Related to Single–chain Ribosome–inhibiting Proteins from Phytolacca*".

Katzin, B.J. et al., *Proteins,* 10: 251–259 (Jun. 1991) "Structure of Ricin A–Chain at 2.5 Å".

Myers, E.W. et al., *Cabios Communications,* 4 (1): 11–17 (1988) "Optimal alignments in linear space".

Islam, M.R. et al., *Agricultural Biological Chem.,* 54 (5): 1343–1345 (May 1990) "Complete Amino Acid Sequence of Luffin–a, a Ribosome–inactivating Protein from the Seeds of *Luffa cylindrica**".

Chow, T. et al., *J. Biol. Chem.,* 265: 8670–8674 (May 1990) "Isolation and DNA Sequence of a Gene Encoding α–Trichosanthin, a Type I Ribosome–inactivating Protein*".

Ho, W.K. et al., *Biochem. Biophys. Acta,* 1088: 311–314 (Feb. 1991) "Cloning of the cDNA of α–momorcharin: a ribosome inactivating protein".

Habuka, N. et al., *J. Biol. Chem.,* 264 (12): 6629–6637 (Apr. 1989) "Amino Acid Sequence of Mirabilis Antiviral Protein, Total Synthesis of Its Gene and Expression in *Escherichia coli**".

Kung, S.–S. et al., *Agricultural Biological Chem.,* 54 (12): 3301–3318 (Dec. 1990) "The Complete Amino Acid Sequence of Antiviral Protein from the Seeds of Pokeweed (*Phytolacca americana*)*".

Benatti, L. et al., *Eur. J. Biochem.,* 183: 465–470 (1989) "Nucleotide sequence of cDNA coding for saporin–6, a type–1 ribosome–inactivating protein from *Saponaria officinalis*".

Halling, K.C. et al., *Nucleic Acids Res.,* 13 (22): 8019–8033 (1985) "Genomic cloning and characterization of a ricin gene from *Ricinus communis*".

Barry B.W. ed, Dermatological Formulations –Percutaneous Absorption, Marcel Dekka, Inc. New York p. 180–181 (1983).

Dower, W.J. et al., *Nucleic Acids Res.,* 16 (13): 6127–6145 (1988) "High efficiency transformation of *E. coli* by high voltage electroporation".

Better, M. et al., *Science*, 240: 1041–1043 (May 1988) "*Escherichia coli* Secretion of an Active Chimeric Antibody Fragment".

Asano, K. et al., Carlsberg Res. Comm., 49: 619–626 (1984) "Isolation and Characterization of Inhibitors of Animal Cell–Free Protein Synthesis from Barley Seeds".

Press, O.W. et al., *Immunol. Letters*, 14: 37–41 (1986) "A simplified microassay for inhibition of protein synthesis in reticulocyte lysates by immunotoxins*".

Morishima, Y. et al., *J. Immunol.*, 129: 1091 (Sep. 1982) "Functionally Different T Lymphocyte Subpopulations Determined By Their Sensitivity to Complement–Dependent Cell Lysis With the Monoclonal Antibody 4A[1]".

Goff, D.A. et al., *Bioconjugate Chem.*, 1: 381–386 (Jan. 1991) "Substituted 2–Iminothiolanes: Reagents for the Preparation of Disulfide Cross–Linked Conjugates with Increased Stability".

Ellman G.L., *Arch. Biochem. Bipophys.*, 82: 70–77 (1959) "Tissue Sulfydryl Groups".

Knowles, P.P. et al., *Analyt. Biochem.*, 160: 440–443 (1987) "Purification of Immunotoxins Containing Ricin A–Chain and Abrin A–Chain Using Blue Sepharose CL–68".

Thorpe, P.E. et al., *Cancer Res.*, 47: 5924–5931 (1987) "New Coupling Agents for the Synthesis of Immunotoxins Containing a Hindered Disulfide Bond with Improved Stability in Vivo".

Thorpe, P.E. et al., *Cancer Res.*, 48: 6396–6403 (1988) "Improved Antitumor Effects of Immunotoxins Prepared with Deglycosylated Ricin A–Chain and Hindered Disulfide Linkages".

Wawrzynczak, E.J. et al., *Cancer Res.*, 50: 7519–7526 (Dec. 1990) "Pharmacokinetics in the Rat of a Panel of Immunotoxins Made with Abrin A Chain, Ricin A Chain, Gelonin, and Momordin[1]".

Li, S.S. et al., *Experientia*, 36: 524–527 (1980) "Purification and partial characterization of two lectins from *Momordica charantia*[1]".

Robinson, R.R. et al., *Human Antibodies and Hybridomas*, 2: 84–93 (Apr. 1991) "Chimeric mouse–human anti–carcinoma antibodies that mediate different anti–tumor cell biological activities".

Fishwild, D.M. et al., *Clin. Exp. Immunol.*, 97: 10–18 (Jul. 1994) "Characterization of the Increased Cytotoxicity of Gelonin Anti–T Cell Immunoconjugates Compared with Ricin A Chain Immunoconjugates".

Pastan, I. et al., *Science*, 254: 1173–1177 (Nov. 1991) "Recombinant Toxins for Cancer Treatment".

Huston, J.S. et al., *Proc. Natl. Acad. Sci. USA*, 85: 5879–5883 (Aug. 1988) "Protein engineering of antibody binding sites: Recovery of specific activity in an anti–digoxin single–chain Fv analogue produced in *Escherichia coli*".

Glockshuber, R. et al., *Biochemistry*, 29: 1362–1367 (Feb. 1990) "A Comparison of Strategies To Stablize Immunoglobulin $F_v$–Fragments†".

Cheadle, C. et al., *Mol. Immunol.*, 29: (1): 21–30 (Jan. 1992) "Cloning and Expression of the Variable Regions of Mouse Myeloma Protein MOPC315 in *E. coli*: Recovery of Active $F_v$ Fragments".

Junghans, R.P. et al., *Cancer Res.*, 50: 1495–1502 (Mar. 1990) "Anti–Tac–H, a Humanized Antibody to the Interleukin 2 Receptor with New Features for Immunotherapy in Malignant and Immune Disorders".

Jones, P.J. et al., *Nature*, 321: 522–525 (May 1986) "Replacing the complementarity–determining regions in a human antibody with those from a mouse".

Co, M.S. et al., *Proc. Nat. Acad. Sci. USA*, 88: 2869–2873 (Apr. 1991) "Humanized antibodies for antiviral therapy".

Potter, H. et al., *Proc. Natl. Acad. Sci. USA*, 81: 7161–7165 (Nov. 1984) "Enhancer–dependent expression of human κ immunoglobulin genes introduced into mouse pre–B lymphocytes by electroporation".

Munson, P.J. et al., *Analyt. Biochem.*, 107: 220–239 (1980) "Ligand: A Versatile Computerized Approach for Characterization of Ligand–Binding Systems".

Izzo, P. et al., *Eur. J. Biochem.*, 174: 569:579 (1988) "Human aldolase A gene".

Knebel, K.D. et al., Abstr. 415, *Cytometry Suppl.*, I: 68 (1987) "Quantitative Equilibrium Binding of Monoclonal Antibodies, Immunotoxins, and Radioimmunoimaging Agents by Flow Cytometry".

Ogata, M. et al., *J. Biol. Chem.*, 265 (33): 20678–20685 (Nov. 1990) "Processing of Pseudomonas Exotoxin by a Cellular Protease Results in the Generation of a 37,000–Da Toxin Fragment That is Translocated to the Cytosol*".

Fishwild, D.M. et al., *Clin and Exp. Immunol.*, 86: 506–513 (Dec. 1991) "Cytotoxicity Against Human Peripheral Blood Mononuclear Cells and T Cell Lines Mediated By Anti–T Cell Immunotoxins in the Absence of Added Potentiator".

Blakey, D.C. et al., *Monoclonal Antibody Therapy.*, 45: 50–90 (1988) "Antibody Toxin Conjugates: A Perspective".

Byers, V.S. et al., *Blood*, 75:1426–1432 (Apr. 1990) "Use of an Anti–Pan T–Lymphocyte Ricin A Chain Immunotoxin in Steroid–Resistant Acute Graft–Versus–Host Disease".

Antin, J.H. et al., *Blood*, 78 (8): 2139–2149 (Oct. 1991) "Selective Depletion of Bone Marrow T Lymphocytes With Anti–CD5 Monoclonal Antibodies: Effective etc . . . Hematologic Malignancies".

Laurent, G. et al., *Bone Marrow Transplantation*, 4: 367–371 (1989) "Donor Bone Marrow Treatment With T101 Fab Fragment–Ricin A–Chain Immunotoxin Prevents Graft–Versus–Host Disease".

Rostaing–Capaillon, O. et al., Cancer Immunol. Immunother, 34: 24–30 (Jan. 1991) "In Vivo Cytotoxic Efficacy of Immunotoxins Prepared From Anti–CD5 Antibody Linked to Ricin A–Chain".

Vallera, D.A., Blood 83 (2):309–317 (Jan. 1994) "Immunotoxins: Will Their Clinical Promise Be Fulfilled?".

Caron, P.C. et al., J. Exp. Med. 186:1191–1195 (Oct. 1992) "Engineered Humanized Dimeric Forms of IgG Are More Effective Antibodies".

Casellas, P. et al., Blood 65 (2):289–297 (Feb. 1985) "Optimal Elimination of Leukemic T Cells From Human Bone Marrow With T101–Ricin–A–Chain Immunotoxin".

Bernhard, S.L. et al., Bioconjugate Chem., 5 (2):126–132 (Mar. 1994) "Cysteine Analogs of Recombinant Barley Ribosome Inactivating Protein Form Antibody Conjugates with Enhanced Stability and Potency in Vitro".

Preijers, F.W.M.B. et al., Blood, 74 (3):1152–1158 (Aug. 1989) "Autologous Transplantation of Bone Marrow Purged In Vitro With Anti–CD7–(WT1–) Ricin A Immunotoxin in T–Cell Lymphoblastic Leukemia and Lymphoma".

Rowley, S.C., et al., Blood, 74 (1):501–506 (Jul. 1989) "Efficacy of Ex Vivo Purging for Autologous Bone Marrow Transplantation in the Treatment of Acute Nonlymphoblastic Leukemia".

Mountain, A. et al., Biotechnol. Genet. Eng. Rev., 10:1–142 Dec.(1992) "Engineering Antibodies for Therapy –Monoclonal Antibody Engineering and Humanized Antibody Production; A Review".

Rosenblum, M.G. et al. Mol. Biother., 3:6–13, (Mar. 1991) "A Specific and Potent Immunotoxin Composed of Antibody ZME–018 and the Plant Toxin Gelonin".

Singh, V. et al., Biochemistry International, 24 (3):531–536 (Oct. 1991) "Hormonotoxins: Abrogation of Ribosome Inactivating Property of Gelonin in the Disulfide Linked Ovine Luteinizing Hormone–Gelonin Conjugates".

Lee–Huang, S. et al., FEBS 291 (1):139–144 (Oct. 1991) "A New Class of Anti–HIV Agents: GAP31, DAPs 30 and 32".

Reimann, K.A. et al., J. Clin. Invest. 82:129–138 (Jul. 1988) "In Vivo Administration of Lymphocyte–Specific Monoclonal Antibodies in Nonhuman Primates".

Lambert, J.M. et al., The Journal of Biological Chemistry, 260 (22):12035–12041 (Oct. 5, 1985) "Purified Immunotoxins That Are Reactive With Human Lymphoid Cells".

Delprino, L. et al., Journal of Pharmaceutical Sciences, 82 (7):669–704 (Jul. 1993) "Toxin–Targeted Design for Anticancer Therapy. II: Preparation and Biological Comparison of Different Chemically Linked Gelonin–Antibody Conjugates".

Scott, C.F. et al., Cancer Immunology Immunotherapy 25:31–40 (Jul. 1987) "The Antileukemic Efficacy of an Immunotoxin Composed of a Monoclonal Anti–Thy–1 Antibody Disulfide Linked to the Ribosome–Inactivating Protein Gelonin".

Harris, P. et al., Cellular Immunology, 134:85–95 (Apr. 1991) "In Vitro Studies of the Effect of MAb NDA 4 Linked to Toxin on the Proliferation of a Human EBV–Transformed Lymphoblastoid B Cell Line and of Gibbon MLA Leukemia Cell Line".

Sperti, S. et al., Biochem. J., 277:281–284 (Jul. 1991) "Requirements for the Inactivation of Ribosomes by Gelonin".

Stirpe, F. et al., Nucleic Acids Research, 16 (4):1348–1357 (Feb. 1988) "Modification of Ribosomal RNA by Ribosomal RNA by Ribsome–Inactivating Proteins From Plants".

Madan, S. et al., Experimental Cell Research, 198:52–58 (Jan. 1992) Interaction of Gelonin With Macrophages: Effect of Lysosomotropic Amines.

Bolognesi, A. et al., Clin. Exp. Immunol., 89:341–346 (Sep. 1992) "A Comparison of Anti–Lymphocyte Immunotoxins Containing Different Ribosome–Inactivating Proteins and Anti–bodies".

```
RTA       IFPKQYPIINFTTAGATVQSYTNFIRAVRGRLTTGADVRHEIPVLPNRVG  50
                              *       *
GELONIN   GLD----TVSFSTKGATYITYVNFLNELRVKLKPEGN-SHGIPLLRKKCD  45

RTA       LPINQRFILVELSNHAELSVTLALDVTNAYVVGYRAGNSAYFFHPDNQED  100
                                       *
GELONIN   DP-GKCFVLVALSNDNGQLAEIAIDVTSVYVVGYQVRNRSYFF----KDA  90

RTA       AEAITHLFTDVQNRYTFAFGGNYDRLEQLAGNLRENIELGNGPLEEAISA  150
                                *                    *
GELONIN   PDAAYEGLFKNTIKTRLHFGGSYPSLEG-EKAYRETTDLGIEPLRIGIKK  139

RTA       LYYYSTGGTQLPTLARSFIICIQMISEAARFQYIEGEMRTRIRYNRRSAP  200
                                    ** *
GELONIN   LDENAIDNYKPTEIASSLLVVIQMVSEAARFTFIENQIRNN--FQQRIRP  187

RTA       DPSVITLENSWGRLSTAIQESN-QGAFASPIQLQRRNGSKFSVYDVSILI  249
                    *
GELONIN   ANNTISLENKWGKLSFQIRTSGANGMFSEAVELERANGKKYYVTAVDQVK  237

RTA       PIIALMVYRCAPPPSSQF                                  267
GELONIN   PKIALLKFVDKDPK                                      251
```

FIG. 1

```
RTA   I------FPKQYPIINFTTAGATVQSYTNFIRAVRGRLTTGADVRHEIPV  44
                                *       *
BRIP  AAKMAKNVDKPLFTATFNVQASSAD-YATFIAGIRNKLRNPAHFSHNRPV  49

RTA   LPN-RVGLPINQRFILVELSNHAELSVTLALDVTNAYVVGYRAGNSAYFF  93
                                          *
BRIP  LPPVEPNVPPSRWFHVVLKASPTSAGLTLAIRADNIYLEGFKSSDGTWWE  99

RTA   HPDNQEDAEAITHLFTDVQNRYTFAFGGNYDRLEQLAGNLRENIELGNGP  143
                                   *
BRIP  LTPGLIPGATYV------------GFGGTYRDLLGDTDKL-TNVALGRQQ  136

RTA   LEEAISALY----YYSTGGTQLPTLARSFIICIQMISEAARFQ----YIE  185
      *                                    ** *
BRIP  LADAVTALHGRTKADKASGPKQQQAREAVTTLVLMVNEATRFQTVSGFVA  186

RTA   GEMRTRIRYNRRSAPDPSVITLENSWGRLSTAIQESNQGAFASPIQLQRR  235
                               *
BRIP  GLLHPKAVEKKSGKIGNEMKAQVNGWQDLSAALLKTDVKPPPGKSPAKFA  236

RTA   NGSKFSVYDVSILIPIIALMVYRCAP------------PPSSQF        267
BRIP  PIEKMGVRTAEQAANTLGILLFVEVPGGLTVAKALELFHASGGK        280
```

FIG. 2

```
RTA     IFPKQYPIINFTTAGATVQSYTNFIRAVRGRLTTGADVRHEIPVLPNRVG   50
                            *       *
MOMOII  D-------VNFDLSTATAKTYTKFIEDFRATLPFSHKV-YDIPLLYSTIS   42

RTA     LPINQRFILVELSNHAELSVTLALDVTNAYVVGYRAGNSAYFFHPDNQED  100
                                     *
MOMOII  --DSRRFILLDLTSYAYETISVAIDVTNVYVVAYRTRDVSYFF---KESP   87

RTA     AEAITHLFTDVQNRYTFAFGGNYDRLEQLAGNLRENIELGNGPLEEAISA  150
                              *                    *
MOMOII  PEAYNILFKGTR-KITLPYTGNYENLQTAAHKIRENIDLGLPALSSAITT  136

RTA     LYYYSTGGTQLPTLARSFIICIQMISEAARFQYIEGEMRTRIRYNRRSAP  200
                                  ** *
MOMOII  LFYYNAQSA-----PSALLVLIQTTAEAARFKYIERHVAKYVATNFK--P  179

RTA     DPSVITLENSWGRLSTAI--QESNQGAFASPIQLQRRNGSKFSVYDVS--  246
                  *
MOMOII  NLAIISLENQWSALSKQIFLAQNQGGKFRNPVDLIKPTGERFQVTNVDSD  229

RTA     ILIPIIALMVYRCAPPPSSQF                               267
MOMOII  VVKGNIKLLLNSRASTADENFITTMTLLGESVVN                  263
```

FIG. 3

```
RTA     IFPKQYPIINFTTAGATVQSYTNFIRAVRGRLTTGADVRHEIPVLPNRVG           50
LUFFIN  D-------VRFSLSGSSSTSYSKFIGDLRKALPSNGTVVNLTILLSSASG           43
                            *

RTA     LPINQRFILVELSNHAELSVTLALDVTNAYVVGYRAGNSAYFFHPDNQED          100
LUFFIN  ---ASRYTLMTLSNYDGKAITVAVDVSQLYIMGYLVNSTSYFF---NESD           87
                   *

RTA     AEAITHLFTDVQNRYTFAFGGNYDRLEQLAGNLRENIELGNGPLEEAISA          150
LUFFIN  AKLASQYVFKGSTIVTLPYSGNYEKLQTAAGKIREKIPLGFPALDSALTT          137
                                       *

RTA     LYYYSTGGTQLPTLARSFIICIQMISEAARFQYIEGEMRTRIRYNRRSAP          200
LUFFIN  IFHYDSTAA------AAAFLVILQTTAEASRFKYIEGQIIERI--SKNQVP         180
                                     * *

RTA     DPSVITLENS-WGRLSTAIQ--ESNQGAFASPIQLQRRNGSKFSVYDVSI          247
LUFFIN  SLATISLSENSLWSALSKQIQLAQTNNGTFKTPVVITDDKQQRVEITNVTS         230
                *

RTA     LIPIIALMVYRCAPPPSSQF                                        267
LUFFIN  KVVTKNIQLLLNYKQNVA                                          248
```

```
RTA     IFPKQYP

FIG. 6

```
RTA    IFPKQYPIINFTTAGATVQSYTNFIRAVRGRLTTGADVRHEIPVLPNRVG           50
MOMOI  D-------VSFRLSGADPRSYGMFIKDLRNALPFREKVYNIPLLLPSVSG           43
                        *

RTA    LPINQRFILVELSNHAELSVTLALDVTNAYVVGYRAGNSAYFFHPDNQED          100
MOMOI  ---AGRYLLMHLFNYDGKTITVAVDVTNVYIMGYLADTTSYFFNEPAAEL           90
                       *

RTA    AEAITHLFTDVQNRYTFAFGGNYDRLEQLAGNLRENIELGNGPLEEAISA          150
MOMOI  ASQ--YVFRDARRKITLPYSGNYERLQIAAGKPREKIPIGLPALDSAIST          138
                                                  *

RTA    LYYYSTGGTQLPTLARSFIICIQMISEAARFQYIEGEMRTRIRYNRRSAP          200
MOMOI  LLHYDSTAA-----AGALLVLIQTTAEAARFKYIEQQIQERA--YRDEVP          181
                             * **

RTA    DPSVITLENSWGRLSTAIQ--ESMQGAFASPIQLQRRNGSKFSVYDVSIL          248
MOMOI  SLATISLENSWSGLSKQIQLAQGNNGIFRTPIVLVDNKGNRVQITNVTSK          231
                   *

RTA    IPIIALMVY--------RCAPPPSSQF                                 267
MOMOI  VVTSNIQLLLNTRNIAEGDNGDVSTTHGFSST                            263
```

```
RTA     IFPKQYPIINFTTAGATVQSYTNFIRAVRGRLTTGADVRHEIPVLPNRVG   50
                            *       *
MAP     A-PTLETIASLDLNNPT--TYLSFITNIRTKVADKTE-----QCTIQKIS   42

RTA     LPINQRFILVELSNHAELSVTLALDVTNAYVVGYRA---GNSAYFFHPDN   97
                                     *
MAP     KTFTQRYSYIDLIVSSTQKITLAIDMADLYVLGYSDIANNKGRAFFFKDV   92

RTA     QEDAEAITHLFTDVQNRYTFAFGGNYDRLEQLAGNLRENIELGNGPLEEA   147
                                 *                    *
MAP     TEAVANNFFPGATGTNRIKLTFTGSYGDLEK-NGGLRKDNPLGIFRLENS   141

RTA     ISALYYYSTGGTQLPTLARSFIICIQMISEAARFQYIEGEMRTRIRYNRR   197
                                     ** *
MAP     IVNIY---GKAGDVKKQAKFFLLAIQMVSEAARFKYI-SDKIPSEKYEE-   186

RTA     SAPDPSVITLENSWGRLSTAIQESNQGAFASPIQLQRRNGSKFSVYDVSI   247
                     *                               *
MAP     VTVDEYNTALENNWAKLSTAVYNSKPSTTTATKCQLATSPVTISPWIFKT   236

RTA     LIPIIALMVYRCAPPPSSQF                                 267
MAP     VEEIKLVMGLLKSS                                       250
```

FIG. 7

| | | |
|---|---|---|
| RTA | IFPKQYPIINFTTAGATVQSYTNFIRAVRGRLTTGADVRHEIPVLPNRVG | 50 |
| PAPS | I------NTITFDAGNATINKYATFMESLRNEAKDPSLKCYGIPMLPNTNS | 45 |
| RTA | LPINQRFILVELSNHAELSVTLALDVTNAYVVGYRAGNSA-----YFFHP | 95 |
| PAPS | ---TIKYLLVKLQGASLKTITLMLRRNNLYVMGYSDPYDNKCRYHIFNDI | 92 |
| RTA | DNQEDAEAITHLFTDVQNRYT--FAFGGNYDRLEQLAG-NLRENIELGNG | 142 |
| PAPS | KGTEYSDVENTLCPSSNPRVAKPINYNGLYPTLEKKAGVTSRNEVQLGIQ | 142 |
| RTA | PLEEAISALYYYSTGGTQLPTLARSFIICIQMISEAARFQYIEGEMRTRI | 192 |
| PAPS | ILSSDIGKI---SGQGSFTEKIEAKFLLVAIQMVSEAARFKYIENQVKTN- | 189 |
| RTA | RYNRRSAPDPSVITLENSWGRLSTAIQESNQGAFASPIQLQRRNGSKFSV | 242 |
| PAPS | -FNRDFSPNDKVLDLEENWGKISTAIHNSKNGALPKPLELKNADGTKWIV | 238 |
| RTA | YDVSILIPIIALMVYRCAPPPSSQF | 267 |
| PAPS | LRVDEIKPDVGLLNY--VNGTCQAT | 261 |

FIG. 8

```
RTA   IFPKQYPIINFTTAGATVQSYTNFIRAVRGRLTTGADVRHEIPVLPNRVG  50
                          *       *
SAP6  V-----TSITLDLVNPTAQQYSSFVDKIRNNVKDPNLKYGGTDI--AVIG  43

RTA   LPINQRFILVELSNHAELSVTLALDVTNAYVVGYRAGNS-----AYFFHP  95
                                   *
SAP6  PPSKEKFLRINFQSSRG-TVSLGLKRDNLYVVAYLAMDNTNVNRAYYFRS  92

RTA   DNQEDAEAITHLFTDVQNRYTFAFGGNYDRLEQ-----LAGNLRENIELG  140
                                 *
SAP6  EITSAESTALFPEATTANQKALEYTEDYQSIEKNAQITQGDQSRKELGLG  142

RTA   NGPLEEAISALYYYSTGGTQLPTLARSFIICIQMISEAARFQYIEGEMRT  190
         *                                **  *
SAP6  IDLLSTSMEAV---NKKARVVKDEARFLLIAIQMTAEAARFRYIQNLVIK  189

RTA   RIRYNRRSAPDPSVITLENSWGRLSTAI-QESNQGAFASPIQLQRRNGSK  239
                          *
SAP6  N--FPNKFNSENKVIQFEVNWKKISTAIYGDAKNGVFNKDYDFGFGKVRQ  237

RTA   FSVYDVSILIPIIALMVYRCAPPPSSQF  267
SAP6  VKDLQMGLL------MYLGKPKSSNEAN  259
```

FIG. 9

```
pos             10         20         30         40         50
bind   +-+++++ O+++++++++O++++-+-+---     ---+---+-+---      ----
bury   +-+-+-+ O++O+--++++++-+-+-+++    -+  ---OOO+++O+++--+---  +++
mod            • • • • • • • • • • • • • • • • • • • • • • • •
hK1    DIQMTQS PSSLSASVGDRVTITCrASQx  Is    xyLxWYQQKPGkAPkLLIY   aAS
hK3    EIVLTQS PgTLSlSPGERATLSCRASQS  vs    ssyLAWYQQKPGQAPRLLIY  gaS
hK2    DIVMTQS PLSLPVTPGEPASISCRSSQS  Ll    nnYLnWYLQKPGQSPqLLIY  lgS
hL1    xSVLTQP PS aSgtPGQrVtISCsGsSS  iG    xnxVxWYQqlPGtAPKLLIY  n n
hL2    xSALTQP aS VSGSPGQSiTISCtGtss  Vg    ynxVSWyQQhPGkAPK LIy  dv
hL3    SYeLTQP PS vSVsPGQTA ITCsGdx   lx    xxyvxWYQQkPGQaPvlVIY  d
hL6    nfmltqp hs vsespgktvtisctxsxg  ia    sxyvqwyqqrpgsapttviy  edn
hK4    divmtqs pdslavslgeratinckssqs  vl    knylawyqqkpgqppklliy  was
hL4    seltqp ps vsvapgqt ritcsgdx    lg    xydaxwyqqkpgqapliviy  grn
hL5    saltqp ps asgspgqsvtisctgtss   vg    xxyvswyqqh g apk  i   ev pos             60         70         80         90         100
bind   -+OO++O++-+-++--+          -+++++-+++++  +++++--O-------    -O O+++++++++++
bury   ++O++-O+O-+-+O+O++   ---+-+-+++++-+-+++  -+-+=-+===++++===   -+=-+-+-+++++
mod            • • • • • • • • • • • • • • • • • • • • • • • •
hK1    xLxsGVPSRFsGSGSGTx    FTLTIsSLQpeDfATYYCqqyxxxP    xt FGGqGTkv eik
hK3    sRATGIPdRFSGSGSGTD    FTLTIsrLEPGDFAVYYCQQYgssP    xT FGQGTkv EIK
hK2    nRaSGVPDRFSGSGSGTD    FTLkISRVeAEDVGVYYCMQalqxP    xT FGQGTkx EIK
hL1    RPSGvPDRFSGSKSGTS     AsLaIsGLqseDeaDYYCatWDdSLd   pV FGGGTk TVLg
hL2    RPSGv RFSGSKSGnT      ASLTISGLQaeDEAdYYCsSYxgxxx   xV FGgGtkltVLg
hL3    RPSgIPQRFSGS St T     ATLTISGvqa DEADYYCqxwDxxx    vv FGGGTkLTVLg
hL6    rpsgvpdrfsgsss ns     asltisglktedeadycqsydsxx     wv fgggtkltvlg
hK4    resgvpdrfsgsgsgtd     ftltisslqaqdvavyycqqyystp    xt fgqgtkx gik
hL4    rpsgipdrfsgsgsght     asltitslqaqdvavyycqqyystp    vl fgqgtkltvlg
hL5    rpsgvpdrfsgsks nt     aslitvsgl aedeadyycssyxxxxx  fv fg gtk tvl
```

FIG. 10A

```
pos           10          20        30         40        50
bind   o-+o++++o+  +++o+++++++-+oo----- ----ooo+++o+++-o-oo---------
bury   +-+-+-++o+  +o+o+++-+-+-+-+-o+-+ +o+-=-=o=++++o=o=-o=-oo++o++
mod      • • •• •  • • ••• • • •                 • ••
hH3    EVQLvESGGG  LVqPGGSLRLSCAASGFtFs xxxmxWVRQApGKgLEWVxxixxxxxgx
hH1    QVqLvqSGaE  VkKPGxSvxvSCKxSGyyFx xyxixWvRQaPGxGLEWvGxixpxxgxt
hH2    xvtlxesgpx  lvlptqtltltctvsgxsls xxxvxwirqppgkxlewlaxix  xddd pos     60        70        80           90         100       110
bind   -oooo+o+o++o+-+o++o+o++++++++++++++++-o-----------o++++++++++
bury   =o=+o-++o-+-+o+o++o+-+-+-++-+++-+=o-=-=-==ooooo==-=-+=o+-+-++
mod           •  • • • •• • • • •• ••• •                   •  • • ••
hH3    xyadSVkGRFTISRddSKNtlyLqMnsLraeDTAvYYCarxxxxxxxxxxWGqGTlVTvSS
hH1    xyapxfqgRVTxtrdxSxntayMeLxsLrseDtAvYYCArxxxxxxxxxxwgqGtlvtVSS
hH2    xyxtslrsrltiskdtsknqvvlxxxxxdpxdtatyycarxxxxxxxxdvwgqgttvtvss
```

FIG. 10B

```
SH65K-1
AGT CGT CGA CAC GAT GGA CAT GAG GAC CCC TGC TCA GTT TCT TGG CAT CCT CCT ACT CTG GTT
TCC AGG TAT CAA TGA CAT CCA GAT GAC TCA GT

HUH-K1
TGA CTC GCC CGG CAA GTG ATA GTG ACT CTG TCT CCC AGA CAT GCA GAC ATG GAA GAT GAG GAC
TGA GTC ATC TGG ATG TC

HUH-K2
TCA CTT GCC GGG CGA GTC AGG ACA TTA ATA GCT ATT TAA GCT GGT TCC AGC AGA AAC CAG GGA
AAT CTC CTA AGA CCC T

HUH-K3
GAT CCA CTG CCA AAC CTT GAT GGG ACC CCA TCT ACC AAT CTG TTT GCA CGA TAG ATC AGG
GTC TTA GGA GAT TTC C

HUH-K4
GGT TCA GTG GCA GTG GAT CTG GGA CAG ATT ATA CTC TCA CCA GCA GCC TGC AAT ATG AAG
ATT TTG GAA TTT ATT G

HUH-K5
GTT TGA TTT CAA GCT TGG TGC CTC CAC CGA ACG TCC ACG GAG ACT CAT CAT ACT GTT GAC AAT
AAT AAA TTC CAA AAT CTT C

HUH-G1
TGT CGA CAT CAT GGC TTG GGT GTG GAC CTT GCT ATT CCT GAT GGC AGC TGC CCA AAG TGC CCA
AGC ACA GAT CCA GTT GGT GCA G

HUH-G2
AAG GTA TAC CCA GAA GCT GCG CAG GAG ATT CTG ACG GAC CCT CCA GGC TTC TTC AGG CCA GGT
CCA GAC TGC ACC AAC TGG ATC T
```

FIG. 11A

HUH-G3
GCA GCT TCT GGG TAT ACC TTC ACA AAC TAT GGA ATG AAC TGG GTG AAG CAG GCT CCA GGA AAG
GGT TTA AGG TGG ATG GGC TGG

HUH-G4
AAA GAG AAG GTA AAC CGT CCC TTG AAG TC A TCA GCA TAT GTT GGC TCT CCA GTG TGG GTG TTT
ATC CAG CCC ATC CAC CTT AAA C

HUH-G5
GAC GGT TTA CCT TCT CTT TGG ACA CGT CTA AGT GCA CTG CCT ATT TAC AGA TCA ACA GCCTCA GAG
CCG AGG ACA CGG CTA CAT

HUH-G6
AGG AGA CGG TGA CCG TGG TCC CTT GGC CCC AGA CAT CGA AGT ACC AGT CGT AAC CCC GTC TTG
TAC AGA AAT ATG CCG TGT CCT CGG C

H65G-2S
ACT AGT GTC GAC ATC ATG GCT TGG GT

H65-G2
GAG GAG ACG GTG ACC GTG GT

H65K-2S
AGT CGT CGA CAC GAT GGA CAT GAG GAC

JK1-HindIII
GTT TGA TTT CAA GCT TGG TGC

```
pos            10         20         30         40         50
EU    DIQMTQS PSTLSASVGDRVTITCRASQS IN TWLAWYQQKPGKAPKLLMY KAS
hK1   DIQMTQS PSSLSASVGDRVTITCrASQx Is xyLxWYQQKPGkAPkLLIY aAS
TAC   QIVLTQS PAIMSASPGEKVTITCSASSS IS YMHWFQQKPGTSPKLWIY TTS
bind   -+-++++  O++++++++ -- --------  ---
bury  +-+-+-+  O++O+-++-+-++++  -+  --OOO+++O++-+- -- ---
mod   ●        ●          ●       ●                  +++
M/H   ● H HM   ● HHM HHH M HH     ● h M              ●
prop  H HM     HHM                M MM M     hM M    MM
Que   DIQLTQS PSSMSASPGDRVTITCRASSS IS YMHWFQQKPGKSPKLWIY TTS
       DIQMTQS PSTLSASVGDRVTITCSASSS IS YMHWYQQKPGKAPKLLIY TTS pos            60         70         80         90        100
EU    SLESGVPSRFIGSSGSGTE FTLTISSLQPDDFATYYCQQYNSDS KM FGQGTKV EVK
hK1   xLxsGVPSRFsGSGSGTx  FTlTIsSLQpeDfATYYCqqyxxxP xt FGqGTKv eik
TAC   NLASGVPARFSGSGSGTS  YSLTISRMEAEDAATYYCHQRSTYP LT FGSGTKL ELK
bind  -+00++0++- --+ ●    -+++-+-++-+++++++  ●       -0 O+++++++ +++
bury  ++0+-+-0+0-+-+0+0++ -+-+-+-+++++-+-=++=  ●    == =-+==-+- +++
mod       ●     ●          ●          ●              ●  ●      ●●●
M/H   M M  ● H   ● m        MH   hMHm h    M MMMM    M   h  M    m
prop
Que   NLASGVPSRFSGSGSGTS  YTLTISSMQAEDFATYYCHQRSTYP LT FGQGTKL ELK
       NLASGVPARFSGSGSGTE  FTLTISSLQPDDFATYYCHQRSTYP LT FGQGTKV EVK
```

```
pos              10        20         30         40         50
EU      QVQLVQSGAE VKKPGSSVKVSCKASGGTFS RSAIIWVRQAPGQGLEWMGGIVPMFGPP
hH1     QVqLvqSGaE VkKPGxSvxvSCKxSGyyFx xyxixWvRQaPGxGLEWvGxixpxxgxt
TAC     QVQLQQSGAE LAKPGASVKMSCKASGYTFT SYRMHWVKQRPGQGLEWIGYINPSTGYT
bind            0- ++0++++++0+

IMMUNOTOXINS COMPRISING RIBOSOME-INACTIVATING PROTEINS

This is a continuation of application Ser. No. 08/425,336, filed Apr. 18, 1995, now U.S. Pat. No. 5,621,083; which is a continuation of application Ser. No. 08/064,691, filed May 12, 1993, abandoned; which is a continuation-in-part of application Ser. No. 07/988,430, filed Dec. 9, 1992, now U.S. Pat. No. 5,416,202; which is a continuation-in-part of application Ser. No. 07/901,707, filed Jun. 19, 1992, now U.S. Pat. No. 5,346,546; which is a continuation-in-part of application Ser. No. 07/787,567, filed Nov. 4, 1991, abandoned.

FIELD OF THE INVENTION

The present invention generally relates to materials useful as components of cytotoxic therapeutic agents. More particularly, the invention relates to ribosome-inactivating proteins, to analogs of ribosome-inactivating proteins, to polynucleotides encoding such proteins and analogs, some of which are specifically modified for conjugation to targeting molecules, and to gene fusions of polynucleotides encoding ribosome-inactivating proteins to polynucleotides; encoding targeting molecules.

BACKGROUND

Ribosome-inactivating proteins (RIPs) comprise a class of proteins which is ubiquitous in higher plants. However, such proteins have also been isolated from bacteria. RIPs are potent inhibitors of eukaryotic protein synthesis. The N-glycosidic bond of a specific adenine base is hydrolytically cleaved by RIPs in a highly conserved loop region of the 28S rRNA of eukaryotic ribosomes thereby inactivating translation.

Plant RIPs have been divided into two types. Stirpe et al., *FEBS Lett.*, 195(1,2): 1–8 (1986). Type I proteins each consist of a single peptide chain having ribosome-inactivating activity, while Type II proteins each consist of an A-chain, essentially equivalent to a Type I protein, disulfide-linked to a B-chain having cell-binding properties. Gelonin, dodecandrin, tricosanthin, tricokirin, bryodin, Mirabilis antiviral protein (MAP), barley ribosome-inactivating protein (BRIP), pokeweed antiviral proteins (PAPS), saporins, luffins, and momordins are examples of Type I RIPs; whereas Ricin and abrin are examples of Type II RIPS.

Amino acid sequence information is reported for various ribosome-inactivating proteins. It appears that at least the tertiary structure of RIP active sites is conserved among Type I RIPs, bacterial RIPS, and A-chains of Type II RIPs. In many cases, primary structure homology is also found. Ready et al., *J. Biol. Chem.*, 259(24):15252–15256 (1984) and other reports suggest that the two types of RIPs are evolutionarily related.

Type I plant ribosome-inactivating proteins may be particularly suited for use as components of cytotoxic therapeutic agents. A RIP may be conjugated to a targeting agent which will deliver the RIP to a particular cell type in vivo in order to selectively kill those cells. Typically, the targeting agent (e.g., an antibody) is linked to the toxin by a disulfide bond which is reduced in vivo allowing the protein toxin to separate from the delivery antibody and become active intracellularly. Another strategy for producing targeted cytotoxic proteins is to express a gene encoding a cytotoxic protein fused to a gene encoding a targeting moiety. The resulting protein product is composed of one or more polypeptides containing the cytotoxic protein linked to, for example, at least one chain of an antibody.

A variety of such gene fusions are discussed in Pastan et al., *Science*, 254:1173–1177 (1991). However, these fusion proteins have been constructed with sequences from diphtheria toxin or *Pseudomonas aeruginosa* exotoxin A, both of which are ADP-ribosyltransferases of bacterial origin. These protein toxins are reported to intoxicate cells and inhibit protein synthesis by mechanisms which differ from those of the RIPs. Moreover, diphtheria toxin and exotoxin A are structurally different from, and show little amino acid sequence similarity with, RIPs. In general, fusion proteins made with diphtheria toxin or exotoxin A have been immunogenic and toxic in animals, and are produced intracellularly in relatively low yield. Another strategy for producing a cytotoxic agent is to express a gene encoding a RIP fused to a gene encoding a targeting moiety. The resulting protein product is a single polypeptide containing a RIP linked to, for example, at least one chain of an antibody.

Because some RIPs, such as the Type I RIP gelonin, are primarily available from scarce plant materials, it is desirable to clone the genes encoding the RIPs to enable recombinant production of the proteins. It is also desirable to develop analogs of the natural proteins which may be easily conjugated to targeting molecules while retaining their natural biological activity because most Type I RIPs have no natural sites (i.e. available cysteine residues) for conjugation to targeting agents. Alternatively, it is desirable to develop gene fusion products including Type I RIPs as a toxic moiety and antibody substances as a targeting moiety.

The present invention also provides novel humanized or human-engineered antibodies and methods for producing such antibodies which may be conjugated or fused to various toxins. Such conjugations or fusions are useful in the treatment of various disease states, including autoimmune diseases and cancer.

There are several reports relating to replacement of amino acids in a mouse antibody with amino acids normally occurring at the analogous position in the human form of the antibody. See, e.g., Junghaus, et al., *Cancer Res.*, 50:1495–1502 (1990) and other publications which describe genetically-engineered mouse/human chimeric antibodies. Also by genetic engineering techniques, the genetic information from murine hypervariable complementarity determining regions (hereinafter referred to as "CDRs") may be inserted in place of the DNA encoding the CDRs of a human monoclonal antibody to generate a construct encoding a human antibody with murine CDRs. See, e.g., Jones, et al., *Nature*, 321: 522–525 (1986).

Protein structure analysis on such "CDR-grafted" antibodies may be used to "add back" murine residues in order to restore lost antigen-binding capability, as described in Queen, et al, *Proc. Natl. Acad. Sci. (USA)*, 86:10029–10033 (1989); Co, et al., *Proc. Nat. Acad. Sci. (USA)*, 88: 2869–2873 (1991). However, a frequent result of CDR-grafting is that the specific binding activity of the resulting humanized antibodies may be diminished or completely abolished.

As demonstrated by the foregoing, there exists a need in the art for cloned genes encoding Type I RIPs, for analogs of Type I RIPs which may be easily conjugated to targeting molecules, and for gene fusion products comprising Type I RIPs, and especially wherein such gene fusions also comprise an humanized antibody portion.

SUMMARY OF THE INVENTION

The present invention provides purified and isolated polynucleotides encoding Type I RIPs, Type I RIPs having a cysteine available for disulfide bonding to targeting molecules and fusion products comprising Type I RIPs. Vectors comprising the polynucleotides and host cells transformed with the vectors are also provided.

A purified and isolated polynucleotide encoding natural sequence gelonin (SEQ ID NO: 11), and a host cell including a vector encoding gelonin of the type deposited as ATCC Accession No. 68721 are provided. Further provided are a purified and isolated polynucleotide encoding natural sequence barley ribosome-inactivating protein and a purified and isolated polynucleotide encoding momordin II.

Some of the polynucleotides mentioned above encode fusion proteins of the present invention comprising gelonin (SEQ ID NO: 2) or another RIP and an antibody or a fragment comprising an antigen-binding portion thereof. Several alternate forms of fusion proteins comprising gelonin are contemplated herein. For example, the fusion protein may contain a single RIP fused to a monovalent antibody binding moiety, such as a Fab or single chain antibody. Alternatively, multivalent forms of the fusion proteins may be made and may have greater activity than the monovalent forms. In preferred embodiments of the invention, gelonin may be fused to either the carboxy or the amino terminus of the antibody or antigen-binding portion of thereof. Also in a preferred embodiment of the invention, the antibody or fragment thereof comprising an antigen-binding portion may be an he3 antibody, an he3-Fab, an he3 Fd, single-chain antibody, or an he3 kappa fragment. The antibody or antigen-binding portion thereof may be fused to gelonin by means of a linker peptide, preferably a peptide segment of shiga-like toxin as shown in SEQ ID NO: 56 or a peptide segment of Rabbit muscle aldolase as shown in SEQ ID NO: 57 or a human muscle aldolase, an example of which is reported in Izzo), et al., Eur. J. Biochem, 174: 569–578 (1988), incorporated by reference herein.

Analogs of a Type I plant RIP, are defined herein as non-naturally occurring polypeptides that share the ribosome-inactivating activity of the natural protein but that differ in amino acid sequence from the natural type I RIP protein in some degree but less than they differ from the amino acid sequences of other Type I plant RIP. Preferred analogs according to the present invention are analogs of Type I plant RIPs each having a cysteine available for disulfide bonding located at a position in its amino acid sequence from the position corresponding to position 251 in SEQ ID NO: 1 to the carboxyl terminal position of the analog. SEQ ID NO: 1 represents the amino acid sequence of ricin A-chain. Other preferred analogs according to the invention are Type I RIPs each having a cysteine available for disulfide bonding at a position in the analog that is on the surface of the protein in its natural conformation and that does not impair native folding or biological activity of the ribosome-inactivating protein. Analogs of bacterial RIPs are also contemplated by the present invention.

The present invention provides an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein and which cysteine is located at a position in the amino acid sequence of the analog corresponding to position 259 in SEQ ID NO: 1 or at a position in the amino acid sequence in the analog corresponding to a position from position 251 in SEQ ID NO: 1 to the carboxyl terminal position of the analog.

An analog according to the present invention may be an analog of gelonin. In an analog of gelonin according to the present invention, the cysteine may be at a position in the analog from position 244 to the carboxyl terminal position of the analog, more preferably at a position in the analog from position 247 to the carboxyl terminal position of the analog, and most preferably at position 244, at position 247, or at position 248 of the amino acid sequence of the analog. In these analogs, it is preferred that the gelonin cysteine residues at positions 44 and 50 be replaced with non-cysteine residues such as alanine.

An analog according to the present invention may be an analog of barley ribosome-inactivating protein. Preferably, a cysteine in such an analog is at a position in the analog from position 256 to the carboxyl terminal position, and more preferably the cysteine is at a position in the amino acid sequence of the analog from position 260 to the carboxyl terminal position of the analog. Most preferably, in these regions, the cysteine is at position 256, at position 270, or at position 277 of the amino acid sequence of the analog.

An analog according to the present invention may be an analog of momordin II.

Analogs according to the present invention may have a cysteine in the amino acid sequence of the analog at a position which corresponds to a position within one amino acid of position 259 of SEQ ID NO: 1. Such an analog may be an analog of gelonin, of barley ribosome-inactivating protein, or of momordin II.

The present invention also provides a polynucleotide encoding an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein, and which cysteine is located at a position in the amino acid sequence of the analog from the position corresponding to position 251 in SEQ ID NO: 1 to the carboxyl terminal position of the analog. The polynucleotide may encode an analog of gelonin, preferably an analog wherein the cysteine is at a position in the amino acid sequence of the analog from position 244 to the carboxyl terminal position of the analog, more preferably wherein the cysteine is at a position in the analog from position 247 to the carboxyl terminal position of the analog, and most preferably the cysteine is at position 244, at position 247 or at position 248 of the amino acid sequence of the analog. It is preferred that a polynucleotide according to the present invention encode a gelonin analog wherein the native gelonin cysteine residues at positions 44 and 50 are replaced with non-cysteine residues, such as alanine.

A polynucleotide according to the present invention may encode an analog of barley ribosome-inactivating protein, preferably an analog wherein the cysteine is at a position in the analog from position 256 to the carboxyl terminal position of the analog, more preferably wherein the cysteine is at a position in the analog from position 260 to the carboxyl terminal position of the analog, and most preferably wherein the cysteine is at position 256, at position 270 or at position 277 of the amino acid sequence of the analog.

A polynucleotide according to the present invention may encode an analog of mormordin II.

The present invention provides a vector including a polynucleotide encoding an analog of a Type I ribosome-inactivating protein, which analog has a cysteine available for intermolecular disulfide bonding at a amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog.

The present invention further provides a host cell including a DNA vector encoding an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog. In such a host cell the vector may encode an analog of gelonin, especially an analog wherein the cysteine is at position 247 of the amino acid sequence of the analog, such as in the host cell deposited as ATCC Accession No. 69009.

A host cell according to the present invention may include a vector encoding barley ribosome-inactivating protein, especially preferred is a host cell containing a BRIP analog wherein the cysteine is at position 277, such as in the host cell deposited on Oct. 2, 1991 with the American Type Culture Collection, 12301 Parklawn Drive, Rockville, Md. 20852 as ATCC Accession No. 68722. Particularly preferred are prokaryotic, host cells because such cells may be less sensitive to the action or RIPs as compared to eukaryotic cells.

The present invention also provides an agent toxic to a cell including an analog of a Type I ribosome-inactivating protein linked by a disulfide bond through a cysteine to a molecule which specifically binds to the cell, which cysteine is at an amino acid position in the analog corresponding to a position not naturally available for intermolecular disulfide bonding in the Type I ribosome-inactivating protein and which cysteine is located in the amino acid sequence of the analog from the position corresponding to position 251 in SEQ ID NO: 1 to the carboxyl terminal position of the analog. The agent may include an analog of gelonin, preferably an analog wherein the cysteine is at a position in the analog from position 247 to the carboxyl terminal position of the analog, and more preferably wherein the cysteine is at position 247 or 248 of the amino acid sequence of analog. An agent including an analog wherein the native gelonin cysteine residues at positions 44 and 50 are replaced with non-cysteine residues, such as alanine is preferred.

An agent according to the present invention may include an analog of barley ribosome-inactivating protein, preferably an analog wherein the cysteine is at a position in the analog from position 260 to the carboxyl terminal position of the analog, more preferably wherein the cysteine is at a position in the analog from position 270 to the carboxyl terminal position of the analog, and most preferably wherein the cysteine is at, position 256, at position 270 or at position 277 of the amino acid sequence of the analog.

An agent according to the present invention may include an analog of momordin II.

The present invention provides an agent wherein the Type I ribosome-inactivating protein is linked to an antibody, particularly to an H65 antibody or to an antibody fragment, more particularly to an antibody fragment selected from the group consisting of chimeric and human engineered antibody fragments, and most particularly to a Fab antibody fragment, a Fab' antibody fragment or a F(ab')$_2$ antibody fragment. It is highly preferred that an agent according to the present invention include a chimeric or human engineered antibody fragment selected from the group consisting of a Fab antibody fragment, a Fab' antibody fragment and a F(ab')$_2$ antibody fragment.

A method according to the present invention for preparing an analog of a Type I ribosome-inactivating protein includes the step of expressing in a suitable host cell a polynucleotide encoding a Type I ribosome-inactivating fusion protein or type I RIP (especially gelonin) having a cysteine available for intermolecular disulfide bonding substituted (e.g., by site-directed mutagenesis of the natural DNA sequence encoding the RIP or by chemical synthesis of a DNA sequence encoding the RIP analog) at an amino acid position (corresponding to a position not naturally available for intermolecular disulfide bonding in the Type I ribosome-inactivating protein, which cysteine is located at a position in the amino acid sequence of the analog from the position corresponding to position 251 in SEQ ID NO: 1 to the carboxyl terminal position of the analog.

A product according to the present invention may be a product of a method including the step of expressing in a suitable host cell a polynucleotide encoding a Type I ribosome-inactivating protein having a cysteine available for intermolecular disulfide bonding substituted at an amino acid position corresponding to a position not naturally available for intermolecular disulfide bonding in the Type I ribosome-inactivating protein, which cysteine is located at a position in the amino acid sequence of the analog from the position corresponding to position 251 in SEQ ID NO: 1 to the carboxyl terminal position of the analog.

The present invention provides a method for preparing an agent toxic to a cell including the step of linking an analog of a Type I ribosome-inactivating protein through a cysteine to a molecule which specifically binds to the cell, which analog has the cysteine at an amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog.

According to the present invention, a method for treating a disease in which elimination of particular cells is a goal may include the step of administering to a patient having the disease a therapeutically effective amount of an agent toxic to the cells including a type I RIP (especially gelonin fused to or an analog of a Type I ribosome-inactivating protein linked through a cysteine to a molecule which specifically binds to the cell, the analog having the cysteine at an amino acid position corresponding to a position not naturally available for intermolecular disulfide bonding in the Type I ribosome-inactivating protein and the cysteine being located at a position in the amino acid sequence of the analog from the position corresponding to position 251 in SEQ ID NO: 1 to the carboxyl terminal position of the analog.

Useful target cells for immunotoxins of the present invention include, but are not limited to, cells which are pathogenic, such as cancer cells, autoimmune cells, and virally-infected cells. Such pathogenic cells may be targeted by antibodies or other targeting agents of the invention which are joined, either by genetic engineering techniques or by chemical cross-linking, to an RIP. Specifically useful targets include tumor-associated antigens (e.g., on cancer cells), cell differentiation markers (e.g., on autoimmune cells), parasite-specific antigens, bacteria-specific antigens, and virus-specific antigens.

The present invention also provides an analog of a Type I ribosome-inactivating protein, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains the ribosome-inactivating activity of the Type I ribosome-inactivating protein.

Such a fusion protein or an analog may be a fusion protein or an analog wherein the Type I ribosome inactivating protein is gelonin, and the analog is preferably an analog of gelonin wherein the cysteine is at position 10 of the amino acid sequence of the analog as encoded in a vector in a host cell deposited with the American Type Culture Collection, 12301 Parklawn Drive, Rockville, Md. 20852 as ATCC Accession No. 69008 on Jun. 9, 1992. Other such gelonin analogs include those wherein the cysteine is at a position 60, 103, 1467 184 or 215 in the amino acid sequence of the gelonin analog. It is preferred that the gelonin cysteine residues at positions 44 and 50 be replaced with non-cysteine residues such as alanine in these analogs.

The present invention further provides an analog of a Type I ribosome-inactivating protein wherein the analog includes only a single cysteine. Such an analog may be an analog of gelonin and is preferably an analog wherein the single cysteine is at position 10, position 44, position 50 or position 247 in the amino acid sequence of the analog, but the cysteine may be located at other positions defined by the invention as well.

The present invention provides a polynucleotide encoding an analog of a Type I ribosome-inactivating protein, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

According to the present invention, a method for preparing an analog of a Type I ribosome-inactivating protein may include the step of expressing in suitable host cell a polynucleotide encoding a Type I ribosome-inactivating protein having a cysteine available for intermolecular disulfide bonding substituted at an amino acid position corresponding to a position not naturally available for disulfide bonding in the Type I ribosome-inactivating protein, the cysteine is located at a position corresponding to an amino acid position on the surface of ricin A-chain in its natural conformation and which analog retains ribosome-inactivating activity of the Type I ribosome-inactivating protein.

The present invention provides an agent toxic to a cell including an analog of a Type I ribosome-inactivating protein linked by a disulfide bond through a cysteine to a molecule which specifically binds to the cell, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

A method according to the present invention for preparing an agent toxic to a cell may include the step of linking an analog of a Type I ribosome-inactivating protein through a cysteine to a molecule which specifically binds to the cell, which analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and which analog retains ribosome-inactivating activity of the Type I ribosome-inactivating protein.

A method according to the present invention for treating a disease in which elimination of particular cells is a goal includes the step of administering to a patient having the disease a therapeutically effective amount of an agent toxic to the cells wherein the agent includes a type I RIP fused to or an analog of a Type I ribosome-inactivating protein linked by a disulfide bond through a cysteine to a molecule which specifically binds to the cell, which analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and which analog retains ribosome-inactivating activity of the Type I ribosome-inactivating protein.

The RIP analogs of the invention are particularly suited for use as components of cytotoxic therapeutic agents. Cytotoxic agents according to the present invention may be used in vivo to selectively eliminate any cell type to which the RIP component is targeted by the specific binding capacity of the second component. To form cytotoxic agents, RIP analogs may be conjugated to monoclonal antibodies, including chimeric and CDR-grafted antibodies, and antibody domains/fragments (e.g., Fab, Fab', F(ab')$_2$, Single chain antibodies, and Fv or single variable domains). Analogs of RIPs conjugated to monoclonal antibodies genetically engineered to include free cysteine residues are also within the scope of the present invention. Examples of Fab' and F(ab')$_2$ fragments useful in the present invention are described in copending, co-owned U.S. patent application Ser. No. 07/714,175, filed Jun. 14, 1991 and in International Publication No. WO 89/00999 published on Feb. 9, 1989, which are incorporated by reference herein.

The RIP analogs of the invention may preferably be conjugated or fused to humanized (Dr human engineered antibodies, such as the he3 antibody described herein. Such humanized antibodies may be constructed from mouse antibody variable domains, such as the mouse antibody H65 (SEQ ID NOS: 123 and 124). Specifically RIP analogs according to the present invention may be conjugated or fused to he3 human-engineered antibody light and heavy chain variable regions (SEQ ID NO: 125 and 126, respectively) or fragments thereof. A cell line producing an intact he3 immunoglobulin was deposited as ATCC Accession No. HB11206 with the American Type Culture Collection, 12301 Parklawn Drive, Rockville, Md. 20852.

RIPs according to the present invention may also be conjugated to targeting agents other than antibodies, for example, lectins which bind to cells having particular surface carbohydrates, hormones, lymphokines, growth factors or other polypeptides which bind specifically to cells having particular receptors. Immunoconjugates including RIPs may be described as immunotoxins. An immunotoxin may also consist of a fusion protein rather than an immunoconjugate.

The present invention provides gene fusions of an antigen-binding portion of an antibody (e.g., an antibody light chain or truncated heavy chain, or a single chain antibody) or any targeting agent listed in the foregoing paragraph, linked to a Type I RIP. Preferably, the antigen-binding portion of an antibody or fragment thereof comprises a single chain antibody, a Fab fragment, or a F(ab')$_2$ fragment. Active antibodies generally have a conserved three-dimensional folding pattern and it is expected that any antibody which maintains that folding pattern will retain binding specificity. Such antibodies are expected to retain target enzymatic activity when incorporated into a fusion protein according to the present invention.

It is sometimes necessary that immunotoxins comprising cytotoxic components, such as RIPs, be attached to targeting agents via cleavable linkers (i.e., disulfides, acid-sensitive linkers, and the like) in order to allow intracellular release of the cytotoxic component. Such intracellular release allows the cytotoxic component to function unhindered by possible negative kinetic or steric effects of the attached antibody. Accordingly, gene fusions of the present invention may comprise a RIP gene fused, via a DNA segment encoding a linker protein as described above, to either the 5' or the 3' end of a gene encoding an antibody. If a linker is used, it preferably encodes a polypeptide which contains two cysteine residues participating in a disulfide bond and forming a loop which includes a protease-sensitive amino acid sequence (e.g., a segment of E. coli shiga-like toxin as in SEQ ID NO: 56) or a segment which contains several cathepsin cleavage sites (e.g., a segment of rabbit muscle aldolase as in SEQ ID NO: 57, a segment of human muscle aldolase, or a synthetic peptide including a cathepsin cleavage amino acid sequence). A linker comprising cathepsin cleavage sites as exemplified herein comprises the C-terminal 20 amino acids of RMA. However, that sequence differs; by only one amino acid from human muscle aldolase and it is contemplated that muscle aldolase from human or other sources may be used as a linker in the manner described below. The Type I RIP portion of the fused genes preferably encodes gelonin, BRIP or momordin II. Also preferably, the antibody portion of the fused genes comprises sequences encoding one of the chains of an antibody Fab fragment (i.e., kappa or Fd) and the fused gene is co-expressed in a host cell with the other Fab gene, or the antibody portion comprises sequences encoding a single chain antibody.

Alternatively, since fusion proteins of the present invention may be of low (approximately 55 kDa) molecular weight while maintaining full enzymatic activity, such fusions may be constructed without a linker and still possess cytotoxic activity. Such low-molecular weight fusions are not as susceptible to kinetic and steric hinderance as are the larger fusions, such as fusions involving IgG molecules. Therefore, cleavage of the RIP away from the fusion may not be necessary to facilitate activity of the RIP.

The present invention also provides a method for purifying a protein or immunotoxin comprising a ribosome-inactivating protein and a portion of an antibody including the steps of passing a solution containing the protein through an anion exchange column; applying the flow-through to a protein C column; and eluting the protein from the protein C column. The method may further comprise steps of introducing the flow-through of the anion exchange column into a cation exchange column; exposing the cation exchange column to an eluent effective to elute said protein; and then applying the eluted protein to a protein G column, rather than applying the anion exchange column flow-through directly to a protein G column.

Immunotoxins according to the present invention, including immunoconjugates and fusion protein (immunofusions), are suited for treatment of diseases where the elimination of a particular cell type is a goal, such as autoimmune disease, cancer, and graft-versus-host disease. The immunotoxins are also suited for use in causing immunosuppression and in treatment of infections by viruses such as the Human Immunodeficiency Virus.

Specifically illustrating polynucleotide sequences according to the present invention are the inserts in the plasmid pING3731 in *E. coli* MC1061 (designated strain G274) and in the plasmid pING3803 in *E. coli E*104 (designated strain G275), both deposited with the American Type Culture Collection (ATCC), 12301 Parklawn Drive, Rockville, Md., on Oct. 2, 1991, and assigned ATCC Accession Nos. 68721 and 68722, respectively. Additional polynucleotide sequences illustrating the invention are the inserts in the plasmid pING3746 in *E. coli* E104 designated strain G277) and in the plasmid pING3737 in *E. coli* E104 (designated strain G276), which were both deposited with the ATCC on Jun. 9, 1992, and were respectively assigned Accession Nos. 69008 and 69009. Still other polynucleotide sequences; illustrating the invention are the inserts in the plasmid pING3747 in *E. coli* E104 (designated strain G278), in the plasmid pING3754 in *E. coli* E104 (designated strain G279), in the plasmid pING3758 in *E. coli* E104 (designated strain G280) and in the plasmid pING3759 in *E. coli* E104 (designated strain G281), which plasmids were all deposited with the ATCC on Oct. 27, 1992 and were assigned ATCC Accession Nos. 69101, 69102, 69103 and 69104, respectively.

As noted above, RIPs may preferably be conjugated or fused to humanized or human-engineered antibodies, such as he3. Thus, the present invention also provides novel proteins comprising a humanized antibody variable domain which is specifically reactive with an human CD5 cell differentiation marker. Specifically, the present invention provides proteins comprising the he3 light and heavy chain variable regions as shown in SEQ ID NOS: 125 or 126, respectively. DNA encoding certain he3 proteins is shown in SEQ ID NOS: 72 and 71.

In a preferred embodiment of the present invention, the protein comprising an humanized antibody variable region is an intact he3 immunoglobulin deposited as ATCC HB 11206.

Also in a preferred embodiment of the invention, the protein comprising a humanized antibody variable region is a Fab or $F(ab'')_2$ or Fab fragment.

Proteins according to the present invention may be made by methods taught herein and in co-pending, co-owned U.S. patent application Ser. No. 07/808,464 by Studnicka et al. incorporated by reference herein; and modified antibody variable domains made by such methods may be used in therapeutic administration to humans either alone or as part of an immunoconjugate as taught in co-owned, co-pending U.S. patent application Ser. No. 07/787,567 by Better et al.

The present invention also provides methods for preparing a modified antibody variable domain useful in preparing immunotoxins and immunofusions by determining the amino acids of a subject antibody variable domain which may be modified without diminishing the native affinity of the domain for antigen while reducing its immunogenicity with respect to a heterologous species. As used herein, the term "subject antibody variable domain" refers to the antibody upon which determinations are made. The method includes the following steps: determining the amino acid sequence of a subject light chain and a subject heavy chain of a subject antibody variable domain to be modified;

aligning by homology the subject light and heavy chains with a plurality of human light and heavy chain amino acid sequences; identifying the amino acids in the subject light and heavy chain sequences which are least likely to diminish the native affinity of the subject variable domain for antigen while, at the same time, reducing its immunogenicity by selecting each amino acid which is not in an interface region of the subject antibody variable domain and which is not in a complementarity-determining region or in an antigen-binding region of the subject antibody variable domain, but which amino acid is in a position exposed to a solvent containing the antibody; changing each residue identified above which aligns with a highly or a moderately conserved residue in the plurality of human light and heavy chain amino acid sequences if said identified amino acid is different from the amino acid in the plurality.

Another group of sequences, such as those in FIGS. 1A and 1B may be used to determine an alignment from which the skilled artisan may determine appropriate changes to make.

The present invention provides a further method wherein the plurality of human light and heavy chain amino acid sequences is selected from the human consensus sequences in FIGS. 10A and 10B.

In general, human engineering according to the above methods may be used to treat various diseases against which monoclonal antibodies generally may be effective. However, humanized antibodies possess the additional advantage of reducing the immunogenic response in the treated patient.

Additional aspects and applications of the present invention will become apparent to the skilled artisan upon consideration of the detailed description of the invention which follows.

BRIEF DESCRIPTION OF THE DRAWINGS

FIG. 1 is a computer-generated alignment of the amino acid sequence of the ricin A-chain (RTA) (SEQ ID NO: 1) with the amino acid sequence of the Type I ribosome-inactivating protein gelonin (SEQ ID NO: 2), wherein starred positions indicate amino acids invariant among the ricin A-chain and the Type I RIPs;

FIG. 2 is a computer-generated alignment of the amino acid sequence of the ricin A-chain (SEQ ID NO: 1) with the amino acid sequence of the Type I ribosome-inactivating protein BRIP (SEQ ID NO: 3), wherein starred positions indicate amino acids invariant among the ricin A-chain and the Type I RIPs;

FIG. 3 is a computer-generated alignment of the amino acid sequence of the ricin A-chain (SEQ ID NO: 1) with the amino acid sequence of the Type I ribosome-inactivating protein momordin II (MOMOII) (SEQ ID NO: 4), wherein starred positions indicate amino acids invariant among the ricin A-chain and the Type I RIPs;

FIG. 4 is a computer-generated alignment of the amino acid sequence of the ricin A-chain (SEQ ID NO: 1) with the amino acid sequence of the Type I ribosome-inactivating protein luffin (SEQ ID NO: 5), wherein starred positions indicate amino acids invariant among the ricin A-chain and the Type I RIPs;

FIG. 5 is a computer-generated alignment of the amino acid sequence of the ricin A-chain (SEQ ID NO: 1) with the amino acid sequence of the Type I ribosome-inactivating protein αtrichosanthin (TRICHO) (SEQ ID NO: 6), wherein starred positions indicate amino acids invariant among the ricin A-chain and the Type I RIPs;

FIG. 6 is a computer-generated alignment of the amino acid sequence of the ricin A-chain (SEQ ID NO: 1) with the amino acid sequence of the Type I ribosome-inactivating protein momordin I (MOMOI) (SEQ ID NO: 7), wherein starred positions indicate amino acids invariant among the ricin A-chain and the Type I RIPs;

FIG. 7 is a computer-generated alignment of the amino acid sequence of the ricin A-chain (SEQ ID NO: 1) with the amino acid sequence of the Type I ribosome-inactivating protein Mirabilis anti-viral protein (MAP) (SEQ ID NO: 8), wherein starred positions indicate amino acids invariant among the ricin A-chain and the Type I RIPs;

FIG. 8 is a computer-generated alignment of the amino acid sequence of the ricin A-chain (SEQ ID NO: 1) with the amino acid sequence of the Type I ribosome-inactivating protein pokeweed antiviral protein from seeds (PAPS) (SEQ ID NO: 9), wherein starred positions indicate amino acids invariant among the ricin A-chain and the Type I RIPs;

FIG. 9 is a computer-generated alignment of the amino acid sequence of the ricin A-chain (SEQ ID NO: 1) with the amino acid sequence of the Type I ribosome-inactivating protein saporin 6 (SAP6) (SEQ ID NO: 10), wherein starred positions indicate amino acids invariant among the ricin A-chain and the Type I RIPs;

FIGS. 10A and 10B are alignments of the consensus amino acid sequences for the subgroups of light [hK1 (SEQ ID NO: 149) (human kappa light chain subgroup 1), hK5 (SEQ ID NO: 150) (human kappa light chain subgroup 3), hK2 (SEQ ID NO: 151) (human kappa light chain subgroup 2), hL1 (SEQ ID NO: 152) (human lambda light chain subgroup 1), hL2 (SEQ ID NO: 153) (human lambda light chain subgroup 2), hL3 (SEQ ID NO: 154) (human lambda light chain subgroup 3), hL6 (SEQ ID NO: 155) (human lambda light chain subgroup 6), hK4 (SEQ ID NO: 156) (human kappa light chain subgroup 4), hL4 (SEQ ID NO: 157) (human lambda light chain subgroup 4) and hL5 (SEQ ID NO: 158) (human lambda light chain subgroup 5] and heavy chains [hH3 (SEQ ID NO: 159) (human heavy chain subgroup 3), hH1 (SEQ ID NO: 160) (human heavy chain subgroup 1) and hH2 (SEQ ID NO: 161) (human heavy chain subgroup 2)], respectively, of human antibody variable domains;

FIG. 11 sets out the nucleotide sequences of the oligonucleotides utilized in the construction of the genes encoding modified V/J-regions of the light and heavy chains of the H65 mouse monoclonal antibody variable domain sequence $H65K-1: SEQ ID NO. 117; HUH-K1: SEQ ID NO. 141; HUH-K2: SEQ ID NO. 142; HUH-K3: SEQ ID NO. 143; HUH-K4: SEQ ID NO. 121, HUH-K5: SEQ ID NO. 122, HUH-G1: SEQ ID NO. 144; HUH-G2: SEQ ID NO. 145; HUH-G3: SEQ ID NO. 137; HUH-G4: SEQ ID NO. 138; HUH-G5: SEQ ID NO. 139; HUH-G6: SEQ ID NO. 140; H65G-2S: SEQ ID NO. 146; H65-G2: SEQ ID NO. 85; H65K-2S: SEQ ID NO. 116; JK1-HindIII: SEQ ID NO. 87; and FIGS. 12A and 12B are alignments of human light chain consensus hK1 (SEQ ID NO: 149) and heavy chain consensus hH1 (SEQ ID NO: 160) with the light and heavy chain sequences, respectively, of the variable domain of human antibody EU (SEQ ID NO: 162and 166), human antibody TAC, human antibody TAC (SEQ ID NO: 163 and 167) modified according to the present invention (prop) (SEQ ID NO: 164 and 168) and human antibody TAC modified according to a different method (Que) (SEQ ID NO: 165 and 169).

DETAILED DESCRIPTION

Nucleotide sequences of genes encoding three plant Type I RIPs and expression vectors containing the genes are provided by the present invention. A first plant RIP, gelonin, is produced by seeds of *Gelonium multiflorum*, a plant of the Euphorbiaceae family native to the tropical forests of eastern Asia, while a second plant RIP, BRIP, is synthesized by the common cereal grain barley. Momordin II, a third plant RIP, is produced in *Momordica balsamina* seeds. Analogs of BRIP are also provided by the present invention. The analogs were genetically engineered to include a cysteine free to participate in a intermolecular disulfide bond and were conjugated to antibody molecules without non-specific chemical derivatization of the RIP with crosslinking agents.

Type I RIP analogs of the present invention offer distinct advantages over the natural proteins for use as components of immunotoxins. Chemical treatment to introduce free sulfhydryl groups in the natural proteins lacking free cysteines typically involves the non-selective modification of amino acid side chains. This non-selectivity often results in antibodies conjugated to different sites on different RIP molecules (i.e., a heterogeneous population of conjugates) and also in a decrease in RIP activity if antibodies are conjugated in or near important regions of the RIP (e.g., the active site or regions involved in translocation across cell membranes). In contrast, RIP analogs according to the present invention may be conjugated to a single antibody through a disulfide bond to a specific residue of the analog resulting in reduced batch to batch variation of the immunoconjugates and, in some cases, immunoconjugates with enhanced properties (e.g., greater cytotoxicity or solubility).

Type I plant RIPs, as well as bacterial RIPs such as shiga and shiga-like toxin A-chains, are homologous to the ricin A-chain and are useful in the present invention.

Type I RIPs may be defined and sites for substitution of a cysteine in a RIP may be identified by comparing the primary amino acid sequence of the RIP to the natural ricin A-chain amino acid sequence, the tertiary structure of which has been described in Katzin et al., *Proteins*, 10:251–259 (1991), which is incorporated by reference herein.

Amino acid sequence alignment: defines Type I RIPs in that the ricin A-chain and the Type I plant RIPs have nine invariant amino acids in common. Based on the ricin sequence the invariant amino acids are tyrosine$_{21}$, arginine$_{29}$, tyrosine$_{80}$, tyrosine$_{123}$, leucine$_{144}$, glutamic acid$_{177}$, alanine$_{178}$, arginine$_{180}$, and tryptophan$_{211}$. The ricin A-chain may be used as a model for the three-dimensional structure of Type I RIPs. A protein lacking a cysteine available for conjugation while having ribosome-inactivating activity and having the nine invariant amino acids when its primary sequence is compared to the primary sequence of the ricin A-chain [according to the alignment algorithm of Myers et al., *CABIOS COMMUNICATIONS*, 4(1):11–17 (1988), implemented by the PC/GENE program PALIGN (Intelligenetics, Inc., Mountain View, Calif.) and utilizing the Dayhoff Mutation Data Matrix (MDM-78) as described in Schwartz et al., pp. 353–358 in *Atlas of Protein Sequence and Structure*, 5 Supp. 3, National Biomedical Research Foundation, Washington, D.C. (1978)] is defined as a Type I RIP herein and is expected to be useful in the present invention. "Corresponding" refers herein to amino acid positions which align when two amino acid sequences are compared by the strategy of Myers et al., supra.

Figure 5:
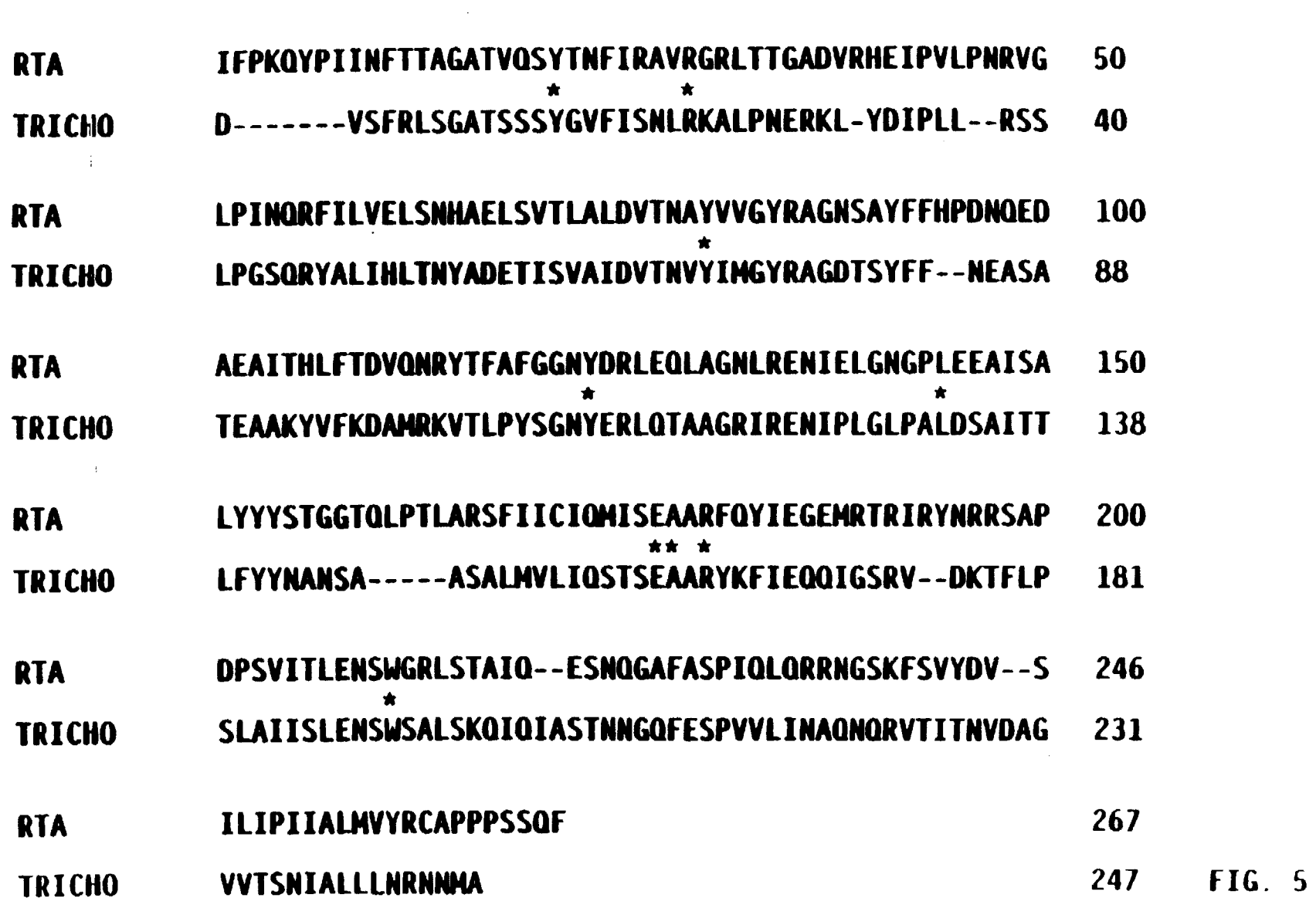

The primary amino acid sequences of the Type I RIPs:gelonin, BRIP, momordin II, luffin [see Islam et al., *Agricultural Biological Chem.*, 54(5):1343–1345 (199)], αtrichosanthin [see Chow et al., *J. Biol. Chem.*, 265:8670–8674 (1990)], momordin I [see Ho et al., *BBA*, 1088:311–314 (1991)], Mirabilis anti-viral protein see Habuka et al., *J. Biol. Chem.*, 264(12):6629–6637 (1989), pokeweed antiviral protein isolated from seeds; [see Kung et al., *Agric. Biol. Chem.*, 54(12):3301–3318 (1990)] and saporin [see Benatti et al., *Eur. T. Biochem.*, 183:465–470 (1989)] are individually aligned with the primary sequence of the ricin A-chain [see Halling et al., *Nucleic Acids Res.*, 13:8019–8033 (1985)] in FIGS. 1–9, respectively, according to the algorithm of Myers et al., supra, as specified above.

FIGS. 1–9 may be utilized to predict the amino acid positions of the Type I RIPs where cysteine residues may be substituted. Preferred amino acids for cysteine substitution are on the surface of the molecule and include any solvent accessible amino acids which will not interfere with proper folding of the protein if replaced with a cysteine. A region of the ricin A-chain comprising such amino acids is the carboxyl terminal region. Amino acids that should be avoided for replacement are those critical for proper protein folding, such as proline, and those that are solvent inaccessible. Also to be avoided are the nine amino acids invariant among RIPs, and the amino acids in or near regions comprising the active site of ricin A-chain as depicted in FIG. 6 of Katzin et al., supra.

Therefore, a preferred region of substitution for Type I RIPs is their carboxyl terminal region which is solvent accessible and corresponds to the carboxyl terminal region where Type II RIP A-chains and B-chains are naturally linked by a disulfide bond. As shown in the examples, a cysteine may be substituted in positions in the amino acid sequence of a Type I RIP from the position corresponding to position 251 in SEQ ID NO: 1 to the carboxyl terminal position of said Type I RIP, resulting in RIP analogs which retain enzymatic activity and gain disulfide cross-linking capability. One preferred cysteine substitution position is near the position which corresponds to the cysteine at position 259 in the ricin A-chain.

For purposes of the present invention, immunotoxins comprise a class of compounds of which toxin-antibody fusions and immunoconjugates are examples. Immunotoxins are particularly suited for use in treatment of human autoimmune diseases and in the treatment of diseases in which depletion of a particular cell type is a goal, such as cancer. For example, treatment of autoimmune diseases with immunotoxins is described in International Publication No. WO89/06968 published Aug. 10, 1989, which is incorporated by reference herein.

In any treatment regimen, the immunotoxins may be administered to a patient either singly or in a cocktail containing two or more immunotoxins, other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally-accepted efficacious dose ranges such as those disclosed in the *Physician's Desk Reference*, 41st Ed., Publisher Edward R. Barnhart, New Jersey (1987). Patent Cooperation Treaty (PCT) patent application WO 89/069767 published on Aug. 10, 1989, discloses; administration of an immunotoxin as an immunosuppressive agent and is incorporated by reference herein.

Immunotoxins of the present invention may be formulated into either an injectable or topical preparation. Parenteral formulations are known and are suitable for use in the invention, preferably for intramuscular or intravenous administration. The formulations containing therapeutically-effective amounts of immunotoxins are either sterile liquid solutions, liquid suspensions, or lyophilized versions, and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where the biological activity is less than or equal to 20 ng/ml when measured in a reticulocyte lysate assay. Typically, the pharmaceutical compositions containing immunotoxins of the present invention are administered in a therapeutically effective dose in a range of from about 0.01 mg/kg to about 5 mg/kg of the patient. A preferred, therapeutically effective dose of the pharmaceutical composition containing immunotoxins of the invention is in a range of from about 0.01 mg/kg to about 0.5 mg/kg body weight of the patient administered over several days to two weeks by daily intravenous infusion, each given over a one hour period, in a sequential patient dose-escalation regimen.

Immunotoxin compositions according to the invention may be formulated into topical preparations for local therapy by including a therapeutically effective concentration of immunotoxin in a dermatological vehicle. The amount of immunotoxin to be administered, and the immunotoxin concentration in the topical formulations, depend upon the vehicle selected, the clinical condition of the patient, the systemic toxicity and the stability of the immunotoxin in the formulation. Thus, a physician knows to employ the appropriate preparation containing the appropriate concentration of immunotoxin in the formulation, as well as the appropriate amount of formulation to administer depending upon clinical experience with the patient in question or with similar patients. The concentration of immunotoxin for topical formulations is in the range of greater than from about 0.1 mg/ml to about 25 mg/ml. Typically, the concentration of immunotoxcin for topical formulations is in the range of greater than from about 1 mg/ml to about 20 mg/ml. Solid dispersions of immunotoxins according to the invention, as well as solubilized preparations, may be used. Thus, the precise concentration to be used in the vehicle is subject to modest experimental manipulation in order to optimize the therapeutic response. For example, greater than about 10 mg immunotoxin/100 grams of vehicle may be useful with 1% w/w hydrogel vehicles in the treatment of skin inflammation. Suitable vehicles, in addition to gels, are oil-in-water or water-in-oil emulsions using mineral oils, petroleum and the like.

Immunotoxins according to the invention may be optionally administered topically by the use of a transdermal therapeutic system [Barry, *Dermatological Formulations*, p. 181 (1983) and literature cited therein]. While such topical delivery systems may be been designed for transdermal administration of low molecular weight drugs, they are capable of percutaneous delivery. Further, such systems may be readily adapted to administration of immunotoxin or derivatives thereof and associated therapeutic proteins by appropriate selection of the rate-controlling microporous membrane.

Topical preparations of immunotoxin either for systemic or local delivery may be employed and may contain excipients as described above for parenteral administration and other excipients used in a topical preparation such as cosolvents, surfactants, oils, humectants, emollients, preservatives, stabilizers and antioxidants. Pharmacologically-acceptable buffers may be used, e.g., Tris or phosphate buffers. The topical formulations may also optionally include one or more agents variously termed enhancers, surfactants, accelerants, adsorption promoters or penetration enhancers, such as an agent for enhancing percutaneous penetration of the immunotoxin or other agents. Such agents should desirably possess some or all of the following features as would be known to the ordinarily skilled artisan: pharmacological inertness, non-promotive of body fluid or electrolyte loss, compatible with immunotoxin (non-inactivating), and capable of formulation into creams, gels or other topical delivery systems as desired.

Immunotoxins according to the present invention may also be administered by aerosol to achieve localized delivery to the lungs. This is accomplished by preparing an aqueous aerosol, liposomal preparation or solid particles containing immunotoxin. Ordinarily, an aqueous aerosol is made by formulating an aqueous solution or suspension of immunotoxin together with conventional pharmaceutically acceptable carriers and stabilizers. The carriers and stabilizers vary depending upon the requirements for the particular immunotoxin, but typically include: nonionic surfactants (Tweens, Pluronics, or polyethylene glycol); innocuous proteins like serum albumin, sorbitan esters, oleic acid, lecithin; amino acids such as glycine; and buffers, salts, sugars or sugar alcohols. The formulations may also include mucolytic agents as well as bronchodilating agents. The formulations are sterile. Aerosols generally are prepared from isotonic solutions. The particles optionally include normal lung surfactants.

Alternatively, immunotoxins of the invention may be administered orally by delivery systems such as proteinoid encapsulation as described by Steiner, et al., U.S. Pat. No. 4,925,673, incorporated by reference herein. Typically, a therapeutically-(effective oral dose of an immunotoxin according to the invention is in the range from about 0.05 mg/kg body weight to about 50 mg/kg body weight per day. A preferred effective dose is in the range from about 0.05 mg/kg body weight to about 5 mg/kg body weight per day.

Imunotoxins according to the present invention may be administered systemically, rather than topically, by injection intramuscularly, subcutaneously, intrathecally or intraperitoneally or into vascular spaces, particularly into the joints, e.g., intraarticular injection at a dosage of greater than about 1 µg/cc joint fluid/day. The dose will be dependent upon the properties of the specific immunotoxin employed, e.g., its activity and biological half-life, the concentration of immunotoxin in the formulation, the site and rate of dosage, the clinical tolerance of the patient involved, the disease afflicting the patient and the like, as is well within the skill of the physician.

The immunotoxins of the present invention may be administered in solution. The pH of the solution should be in the range of pH 5 to 9.5, preferably pH 6.5 to 7.5. The immunotoxin or derivatives thereof should be in a solution having a suitable pharmaceutically-acceptable buffer such as phosphate, Tris (hydroxymethyl) aminomethane-HCl or citrate and the like. Buffer concentrations should be in the range of 1 to 100 mM. The immunotoxin solution may also contain a salt, such as sodium chloride or potassium chloride in a concentration of 50 to 150 mM. An effective amount of a stabilizing agent such as an albumin, a globulin, a gelatin, a protamine or a salt of protamine may also be included, and may be added to a solution containing immunotoxin or to the composition from which the solution is prepared.

Systemic administration of immunotoxin may be made daily and is generally by intramuscular injection, although intravascular infusion is acceptable. Administration may also be intranasal or by other nonparenteral routes. Immunotoxins of the present invention may also be administered via microspheres, liposomes or other microparticulate delivery systems placed in certain tissues including blood. Topical preparations are applied daily directly to the skin or mucosa and are then preferably occluded, i.e., protected by overlaying a bandage, polyolefin film or other barrier impermeable to the topical preparation.

The following Examples are illustrative of practice of the invention but are not to be construed as limiting the invention. The present application is broadly organized as follows. The first portion of the application broadly teaches the preparation, expression and properties of an exemplary RIP, gelonin. A second portion of the application teaches the preparation of human-engineered antibodies. A third portion of the application teaches the construction and properties of immunoconjugates, comprising an RIP and an antibody or fragment thereof comprising an antigen-binding portion. A forth portion of the application relates to the preparation and properties of immunofusion proteins comprising an RIP and an antibody or fragment thereof comprising an antigen-binding portion. A fifth portion of the application teaches the preparation and properties of the RIP Barley ribosome-inactivating protein and a final aspect of the invention provides the preparation and properties of the RIP momordin.

Specifically, Example 1 relates to the preparation of the RIP gelonin. Construction of expression vector, comprising the gelonin gene, including expression and purification of gelonin, is taught in Example 2. The assembly of gelonin genes with cysteine residues available for conjugation is taught in Example 3 and Example 4 provides results of a reticulocyte lysate assay performed on gelonin.

Example 5 teaches the construction of human-engineered antibodies for use in immunotoxins of the invention and Example 6 demonstrates transfection of he3 genes, expression of those genes, and purification of the products thereof.

Example 7 next teaches the preparation of gelonin immunoconjugates. The procedures and results of whole cell kill assays are next presented in Example 8. Various properties of gelonin immunoconjugates are taught in Example 9 and Examples 10 and 11 teach the pharmacokinetics of two types of immunoconjugates. Examples 12 and 13 teach the immunogenicity of immunoconjugates of the invention and the in vivo efficacy o f those immunoconjugates, respectively.

The construction of genes; encoding gelonin immunofusions is taught in Examples 14, 15 and 16. Example 17 teaches the expression and purification of various genes encoding immunoconjugates and their activity properties are presented in Example 18.

The construction of genes encoding the RIP, BRIP, thin expression, and properties are taught in Examples 19, 20, and 21.

Finally, construction of genes encoding momordin and properties of momordin on expression are taught in Example 22.

EXAMPLE 1

Preparation Of Gelonin

The cloning of the gelonin gene according to the present invention obviates the requirement of purifying the RIP gene product from its relatively scarce natural source, *G. multiflorum* seeds. Cloning also allows development of gelonin analogs which may be conjugated to antibodies without prior chemical derivatization and also allows development of gelonin gene fusion products.

A. Preparation Of RNA From *G. Multiflorum* Seeds

Total RNA was prepared from Gelonium seeds (Dr. Michael Rosenblum, M. D. Anderson Cancer Center, Houston, Tex.) by a modification of the procedure for preparation of plant RNA described in Ausubel et al., eds., *Current Protocols in Molecular Biology*, Wiley & Sons, 1989. Briefly, 4.0 grams of seeds were ground to a fine powder in a pre-cooled (−70° C.) mortar and pestle with liquid $N_2$. The powder was added to 25 ml Grinding buffer (0.18M Tris, 0.09M LiCl, 4.5 mM EDTA, 1% SDS, pH 8.2) along with 8.5 ml of phenol equilibrated with TLE (0.2M Tris, 0.1M LiCl, 5 mM EDTA pH8.2). The mixture was homogenized using a Polytron PT-1035 (#5 setting). 8.5 ml of chloroform was added, mixed and incubated at 50° C. for 20 minutes. The mixture was centrifuged at 3000 g for 20 minutes in a rotor precooled to 4° C. and the aqueous phase was transferred to a new tube. 8.5 ml of phenol was added followed by 8.5 ml of chloroform and the mixture was recentrifuged. This extraction was repeated 3 times. The RNA in the aqueous phase was then precipitated by adding ⅓ volume 8M LiCl, and incubated at 4° C. for 16 hours. Next, the RNA was pelleted by centrifugation for 20 minutes at 4° C. The pellet was washed with 5 ml of 2M LiCl, recentrifuged and resuspended in 2 ml of water. The RNA was precipitated by addition of NaOAc to 0.3M and 2 volumes of ethanol. The RNA was stored in 70% ethanol at −70° C.

B. cDNA Preparation cDNA was prepared from total Gelonium RNA by two methods. The first method involved making a cDNA library in the bacterial expression plasmid pcDNAII using the Librarian II cDNA Library Construction System kit (Invitrogen). Approximately 5 µg of total RNA was converted to first strand cDNA with a 1:1 mixture of random primers and oligo-dT. Second strand synthesis with DNA polymerase I was performed as described by the system manufacturer. Double stranded cDNA was ligated to BstXI linkers and size fractionated. Pieces larger than about 500 bp were ligated into the expression vector provided in the kit. Individual vectors were introduced into *E. coli* either by transformation into high-efficiency competent cells or by electroporation into electrocompetent cells. Electroporation was performed with a BTX100 unit (BTX, San Diego, Calif.) in 0.56µ Flatpack cells as recommended by BTX based on the method of Dower et al., *Nucleic Acids Res.*, 16:6127–6145 (1988), at a voltage amplitude of 850 V and a pulse length of 5 mS. The resulting library consisted of approximately 150,000 colonies.

The second method involved generating cDNA using the RNA-PCR kit sold by Perkin-Elmer-Cetus. About 100 ng of total Gelonium RNA was used as template for cDNA synthesis.

C. Determination Of The Gelonin Protein Sequence

The partial sequence of -the native gelonin protein was determined by direct amino acid sequence analysis using automated Edman degradation as recommended by the manufacturer using an Applied Biosystems model 470A protein sequencer. Proteolytic peptide fragments of gelonin (isolated from the same batch of seeds as the total RNA) were sequenced.

D. Cloning Of The Gelonin Gene

Three overlapping gelonin cDNA fragments were cloned and a composite gelonin gene was assembled from the three fragments.

1. Cloning Of The Fragment Encoding The Middle Amino Acids Of Gelonin In Vector pING3823

Degenerate DNA primers based on the gelonin partial amino acid sequences were used to PCR-amplify segments of the cDNA generated with Perkin-Elmer-Cetus kit. Six primers were designed based on regions of the gelonin amino acid sequence where degeneracy of the primers could be minimized. Appropriate pairs of primers were tested for amplification of a gelonin gene fragment. Products of the expected DNA size were identified as ethidium bromide-stained DNA bands on agarose gels that DNA was treated with T4 DNA polymerase and then purified from an agarose gel. Only the primer pair consisting of primers designated gelo-7 and gelo-5 yielded a relatively pure product of the expected size. The sequences of degenerate primers gelo-7 and gelo-5 are set out below using IUPAC nucleotide symbols.

Gelo-7 (SEQ ID NO: 14)
5' TTYAARGAYGCNCCNGAYGCNGCNTAYGARGG 3'

Gelo-5 (SEQ ID NO: 15)
3' TTYTTYATRATRCANTGNCGNCANCTRGTYCA 5'

Primer gelo-7 corresponds to amino acids 87–97 of gelonin while primer gelo-5 corresponds to amino acids 226–236. The blunt-ended DNA fragment (corresponding to amino acids 87 to 236 of gelonin) generated with primers gelo-7 and gelo-5 was cloned into pUC18 (BRL, Gaithersburg, Md.). The DNA sequence of the insert was determined, and the deduced amino acid sequence based on the resulting DNA sequence matched the experimentally determined gelonin amino acid sequence. The clone containing this gelonin segment was denoted pING3726.

The insert of clone pING3726 was labeled with $^{32}$P and used as a probe to screen the 150,000-member Gelonium cDNA library. Only one clone hybridized to the library plated in duplicate. This clone was purified from the library and its DNA sequence was determined. The clone contains a fragment encoding 185 of the 270 amino acids of gelonin (residues 25–209) and is denoted pING3823.

2. Cloning Of The Fragment Encoding The N-Terminal Amino Acids Of Gelonin

Based on the sequence determined for the gelonin gene segment in pING3726, exact oligonucleotide primers were designed as PCR amplification primers to be used in conjunction with a degenerate primer to amplify a 5' gelonin gene fragment and with a nonspecific primer to amplify a 3' gelonin gene fragment. cDNA generated using the Perkin-Elmer-Cetus RNA-PCR kit was amplified.

To amplify the 5'-end of the gelonin gene, PCR amplification with a degenerate primer gelo-1 and an exact primer gelo-10 was performed. The sequences of the primers are set out below.

Gelo-1 (SEQ ID NO: 16)
5' GGNYTNGAYACNGTNWSNTTYWSNACNAARGG 3'

Gelo-10 (SEQ ID NO: 17)
3' TGTCTGAACCCGTAACTTGGTAA 5'

Primer gelo-1 corresponds to amino acids 1–11 of the gelonin gene while primer gelo-10 corresponds to amino acids 126–133. The product from the reaction was reamplified with gelo-1 (SEQ ID NO: 16) and gelo-11 (an exact primer comprising sequences encoding amino acids 119–125 of gelonin) to confer specificity to the reaction product. The sequence of primer gelo-11 is listed below.

Gelo-11 (SEQ ID NO: 18)
3' CACTCTTCCGTATATCTCTCTGT 5'

Hybridization with an internal probe confirmed that the desired specific gelonin DNA fragment was amplified. That fragment was cloned into pUC18 and the vector generated was designated pING3727. The fragment was sequenced, revealing that the region of the fragment (the first 27 nucleotides) corresponding to part of the degenerate primer gelo-1 could not be translated to yield the amino acid sequence upon which primer gelo-1 was originally based. This was not unexpected considering the degeneracy of the primer. The fragment was reamplified from the Gelonium cDNA with exact primers gelo-111 (SEQ ID NO: 18) and gelo-5' (which extends upstream of the 5' end of the gelonin gene in addition to encoding the first 16 amino acids of gelonin). The sequence of primer gelo-5' is set out below.

Gelo-5' (SEQ ID NO: 19)
5' TCAACCCGGGCTAGATACCGTGTCAT
TCTCAACCAAAGGTGCCACTTATATTA 3'

The resulting DNA fragment encodes the first 125 amino acids of gelonin. While the majority of the sequence is identical to the natural gelonin gene, the first 32 nucleotides of the DNA fragment may be different. For the purposes of this application this N-terminal fragment is referred to as fragment GEL1-125.

3. Cloning Of The Fragment Encoding The C-Terminal Amino Acids Of Gelonin

To amplify the 3'-end of the gelonin gene as well as 3' untranslated sequences, PCR amplification with exact primers gelo-9 and XE-dT was performed. The sequence of each of the primers is set out below.

Gelo-9 (SEQ ID NO: 20)
5' CTTCATTTTGGCGGCACGTATCC 3'

XE-dT (SEQ ID NO: 21)
3' TTTTTTTTTTTTTTTTTTTTTAG
GGTGCATTCGAACGTCGGAGCTC 5'

Primer gelo-9 corresponds to amino acids 107–113 of gelonin. Primer XE-dT consists of a 3' oligo-dT portion and a 5' portion containing the restriction sites HindIII and XhoI, and will prime any poly A-containing cDNA. The reaction product was reamplified with exact primers gelo-8 and XE. The sequences of primers gelo-3 and XE are set out below.

Gelo-8 (SEQ ID NO: 22)
5' CTCGCTGGAAGGTGAGAA 3'

XE (SEQ ID NO: 23)
3' AGGGTGCATTCGAACGTCGGAGCTC 5'

Primer gelo-8 consists of sequences encoding amino acids 115–120 of gelonin while the primer XE corresponds to the 5' portion of the XE-dT primer which contains HindIII and XhoI restriction sites. Hybridization with internal probes confirmed that the desired gelonin gene fragment was amplified. That fragment was then cloned into pUC18 by two different methods. First, it was cloned as a blunt-ended fragment into the SmaI site of pUC18 (the resulting vector was designated pING3728) and, second, it was cloned as an EcoRI to HindIII fragment into pUC18 (this vector was designated pING3729). Both vector inserts were sequenced. The insert of pING3728 encodes amino acids 114–270 of gelonin, while the insert of pING3729 encodes amino acids 184–270 of gelonin plus other 3' sequences.

4. Assembly Of The Overlapping Gelonin DNA Fragments Into A Composite Gelonin Gene To reassemble the C-terminal two-thirds of the gelonin gene, vector pING3729 was cut with SspI (one SspI site is located within the vector and the second is located about 80 bp downstream of the termination codon of the insert in the vector) and an XhoI linker (8 bp, New England Biolabs) was ligated to the resulting free ends. The DNA was then cut with XhoI and EcoRI, and the 350 bp fragment generated, encoding amino acids 185–270 of gelonin, was isolated. This 350 bp fragment was ligated adjacent to a NcoI to EcoRI fragment from pING3823 encoding amino acids 37–185 of gelonin in a intermediate vector denoted pING3730, thus reassembling the terminal 87% of the gelonin gene (amino acids 37–270).

Next, fragment GEL1-125 was cut with SmaI and NcoI, resulting in a fragment encoding amino acids 1–36 of gelonin which was ligated along with the NcoI to XhoI fragment of pING3730 into the vector pIC100. [pIC100 is identical to pING1500 described in Better, et al., *Science*, 240:1041–1043 (1988), incorporated by reference herein], except that it lacks 37 bp upstream of the pelB leader sequence. The 37 bp were eliminated by digestion of pING1500 with SphI and EcoRI, treatment with T4 polymerase, and religation of the vector. This manipulation regenerated an EcoRI site in the vector while eliminating other undesirable restriction sites.] Before ligation, the vector pIC100 had previously been digested with SstI, treated with T4 polymerase, and cut with XhoI. The ligation generated a new vector containing a complete gelonin gene which was designated plasmid pING3731 and deposited with The American Type Culture Collection, 12301 Parklawn Drive, Rockville, Md. 20852 on Oct. 2, 1991 qs Accession No. 68721. The complete DNA sequence of the gelonin gene is set out in SEQ ID NO: 11.

EXAMPLE 2
A. Construction Of Expression Vectors Containing The Gelonin Gene

A first *E. coli* expression vector was constructed containing the gelonin gene linked to the *Erwinia carotovora* pelb leader sequence, and to the *Salmonella typhimurium* araB promoter. A basic vector containing the araB promoter is described in co-owned U.S. Pat. No. 5,028,530 issued Jul. 2, 1991 which is incorporated by reference herein. The vector containing the araB promoter was cut with EcoRI and XhoI. Two DNA fragments were then ligated in tandem immediately downstream of the promoter. The fragment ligated adjacent to the promoter was a 131 bp fragment derived from SstI digestion, T4 polymerase treatment and digestion with EcoRI of the pIC100 vector which includes the leader sequence of the *E. carotovora* pelB gene. The translated leader sequence is a signal for secretion of the respective protein through the cytoplasmic membrane. The fragment ligated downstream of the leader sequence was a SmaI to XhoI fragment from pING3731 which contains the complete gelonin gene. Thus, the expression vector contains the gelonin gene linked to the pelB leader sequence and the araB promoter. This plasmid is designated pING3733.

A second expression vector may be constructed that is identical to the first except that the gelonin gene sequences encoding the nineteen C-terminal amino acids of gelonin are not included. The cDNA sequence of the gelonin gene predicted a 19 residue C-terminal segment that was not detected in any peptide fragments generated for determination of the gelonin amino acid sequence. These 19 amino acids may represent a peptide segment that is cleaved from the mature toxin post-translationally, i.e. that is not present in the native protein. A similar C-terminal amino acid segment was identified in the plant toxin α-trichosanthin [Chow et al., *J. Biol. Chem.*, 265:8670–8674 (1990)]. Therefore, the expression product without the C-terminal fragment is of interest.

For construction of a gelonin expression vector without the 19 C-terminal amino acids of gelonin, PCR was used to amplify and alter the 3'-end of the gene. pING3728 was amplified with primers gelo-14 and gelo-9 (SEQ ID NO: 20). The sequence of primer gelo-14 is set out below.

Gelo-14 (SEQ ID NO: 24)
5' TGATCTCGAGTACTATTTAGGATCTTTATCGACGA 3'

Primer gelo-14, which corresponds to gelonin amino acids 245–256, introduces a termination codon (underlined in the primer sequence) in the gelonin gene sequence which stops transcription of the gene before the sequences encoding the terminal 19 amino acids of the gelonin and also introduces a XhoI site immediately downstream of the termination codon. The PCR product was cut with XhoI and EcoRI, and the resulting 208 bp fragment encoding amino acids 185–251 of gelonin was purified from an agarose gel. This fragment was ligated adjacent to the NcoI to EcoRI fragment from pING3823 encoding amino acids 37–185 of gelonin to generate plasmid pING3732. A final expression vector, pING3734, containing a gelonin gene with an altered 3'-end was generated by substituting an NcoI to XhoI fragment encoding amino acids 37–251 of gelonin from pING3732 into pING3733.

B. Identification Of The Native Gelonin 5'-End

Inverse PCR was used to identify a cDNA clone encoding the 5'-end of the mature gelonin gene. 5 µg of total *G. multiflorum* RNA was converted to cDNA using the Superscript Plasmid System (BRL, Gaithersburg, Md.) with Gelo-11 (SEQ ID NO: 18) as a primer. Gelonin cDNA was self-ligated to generate covalent circular DNA and the ligated DNA was amplified by PCR with oligonucleotides Gelo-9 (SEQ ID NO: 20) and Gelo-16. The sequence of primer Gelo-16 is set out below.

Gelo-16 (SEQ ID NO: 25)
5' GTAAGCAGCATCTGGAGCATCT 3'

The PCR product was size-fractionated on an agarose gel and DNAs larger than 300 bp were cloned into SmaI cut pUC18. Several clones were sequenced with the primer Gelo-18, the sequence of which is set out below.

Gelo-18 (SEQ ID NO: 26)
5' CATTCAAGAAATTCACGTAGG 3'

A clone identified as having the largest gelonin-specific insert was designated pING3826. The DNA sequence of pING3826 included the first 32 nucleotides of the natural, mature gelonin gene not necessarily present in gelonin expression plasmids pING3733 and pING3734. The complete DNA sequence of the natural gelonin genie is set out in SEQ ID NO: 11.

C. Construction Of Expression Vectors Containing A Gelonin Gene With A Natural 53 End Derivatives of expression vectors pING3733 and pING3734 (described above) containing a gelonin gene with the natural 5' sequence were generated as follows. The 5'-end of gelonin was amplified from pING3826 with the PCR primers Gelo-16 (SEQ ID NO: 24) and Gelo-17, the sequence of which is set out below.

Gelo-17 (SEQ ID NO: 27)
5' GGCCTGGACACCGTGAGCTTTAG 3'

The 285 bp PCR product was treated with T4 polymerase and cut with NcoI. The resulting 100 bp 5'-end DNA fragment was isolated from an agarose gel and ligated adjacent to the 120 bp pelB leader fragment from pIC100

(cut with SstI, treated with T4 polymerase and cut with PstI) into either pING3733 or pING3734 digested with PstI and NcoI. The resulting plasmids pING3824 and pING3825 contain the entire native gelonin gene and the native gelonin gene minus the nineteen amino acid carboxyl extension, respectively, linked to the pelb leader and under the transcriptional control of the araB promoter. The gene construct without the nineteen amino acid carboxyl extension in both pING3734 and pING3825 encodes a protein product referred to in this application as "recombinant gelonin".

D. Purification Of Recombinant Gelonin

Recombinant gelonin was purified by the following procedure: E. coli fermentation broth was concentrated and buffer-exchanged to 10 mM sodium phosphate at pH 7.0 by using an S10Y10 cartridge over a DC10 unit (Amicon) the concentrated and buffer-exchanged material was applied to a CM52 column (100 g, 5×10 cm). The column was washed with 1 L of starting buffer and eluted with a 0 to 300 mM NaCl gradient in starting buffer (750 ml total volume).The pure gelonin containing fractions were pooled (elution was from 100–250 mM NaCl), concentrated over an Amicon YM10 membrane, equilibrated with 10 mM sodium phosphate buffer, pH 7.0, and stored frozen at −20° C. A further purification step was attempted using Blue Toyopearl chromatography. However, this procedure did not result in an increased purity of material and resulted in an approximate 50% loss of the starting material.

EXAMPLE 3
Assembly Of Gelonin Genes With Cysteine Residues Available For Conjugation The wild-type gelonin protein has two cysteine residues at positions 44 and 50 which are linked by an endogenous disulfide bond. The protein contains no free cysteine residue directly available or conjugation to antibodies or other proteins. Analogs of gelonin which contain a free cysteine residue available for conjugation were generated by three different approaches. In one approach, various residues along the primary sequence of the gelonin were replaced with a cysteine residue, creating a series of analogs which contain an odd number of cysteine residues. In another approach, one of the two endogenous cysteines was replaced by alanine, creating a molecule which lacks an intrachain disulfide bond but contains a single, unpaired cysteine. In yet another approach both endogenous cysteines were replaced by alanines and a third non-cysteine residue was replaced by a cysteine, creating an analog with a single, unpaired cysteine.

Fifteen analogs of gelonin were constructed. Ten non-cysteine residues of gelonin were targeted for substitution with a cysteine residue. Comparison of the amino acid sequence of gelonin to the natural amino acid sequence and tertiary structure of the ricin A-chain (see FIG. 1) suggested that these positions would be at the surface of the molecule and available for conjugation. Each of the ten gelonin analogs include a cysteine substituted in place of one of the following residues: lysine$_{10}$, asparagine$_{60}$, isoleucine$_{103}$, aspartic acid$_{146}$, arginine$_{184}$, serine$_{215}$, asparagine$_{239}$, lysine$_{244}$, aspartic acid$_{247}$, and lysine$_{248}$, and the analogs have respectively been designated Gel$_{C10}$, Gel$_{C60}$, Gel$_{C103}$, Gel$_{C146}$, Gel$_{C184}$.

Two analogs of gelonin were constructed in which one of the native gelonin cysteines that participates in an endogenous disulfide bond was replaced with a non-cysteine residue. Specifically, the cysteine at position 50 was replaced with an alanine residue, creating a gelonin analog (designated Gel$_{A50(C44)}$, shown in SEQ ID NO: 99) which has a cysteine available for disulfide bonding at position 44.

The Gel$_{A50(C44)}$ analog has been referred to previously as Gel$_{C44}$ (see, e.g. co-owned, co-pending U.S. patent application Ser. No. 07/988,430, incorporated by reference herein). Conversely, the cysteine at position 44 was replaced with an alanine residue, resulting in an analog (designated Gel$_{A44(C50)}$, shown in SEQ ID NO: 100) which has a cysteine available for disulfide bonding at position 50. The Gel$_{A44(C50)}$ analog has been referred to previously as Gel$_{C50}$ (see, e.g., co-owned, co-pending U.S. patent application Ser. No. 07/988,430, incorporated by reference herein). The combined series of the foregoing twelve analogs thus spans the entire length of the mature gelonin protein.

Another gelonin analog (Gel$_{A44A50}$ SEQ ID NO: 101) was constructed in which both native gelonin cysteines were replaced with alanines. The Gel$_{A44A50}$ analog has been referred to previously as Gel$_{C44AC50A}$ (see, e.g., co-owned, co-pending U.S. patent application Ser. No. 07/988,430, incorporated by reference herein). Two additional analogs were constructed which have alanine residues substituted in place of both native cysteines and have either a cysteine residue substituted in place of the native lysine at position 10 (Gel$_{C10A44A50}$, shown in SEQ ID NO: 110) or a cysteine residue substituted in place of the native aspartate at position 247 (Gel$_{C247A44A50}$, shown in SEQ ID NO: 111).

The variants of recombinant gelonin were constructed by restriction fragment manipulation or by overlap extension PCR with synthetic oligonucleotides. The sequences of the primers used for PCR are set out below. In each mutagenic primer sequence, the nucleotides corresponding to the changed amino acid, either a cysteine or an alanine residue, are underlined.

Gelo-9 (SEQ ID NO: 20)
Gelo-11 (SEQ ID NO: 18)
Gelo-16 (SEQ ID NO: 25)
Gelo-17 (SEQ ID NO: 27)
Gelo-18 (SEQ ID NO: 26)

Gelo-19 (SEQ ID NO: 58)
5' CAGCCATGGAATCCCATTGCTG 3'

GeloC-1 (SEQ ID NO: 28)
5' TCGATTGCGATCCTAAATAGTACTC 3'

GeloC-2 (SEQ ID NO: 29)
5' TTTAGGATCGCAATCGACGAACTTCAAG 3'

GeloC-3-2 (SEQ ID NO: 30)
5' GTTCGTCTGTAAAGATCCTAAATAGTACTCGA 3'

GeloC-4 (SEQ ID NO: 31)
5' GGATCTTTACAGACGAACTTCAAGAGT 3'

GeloC-5 (SEQ ID NO: 32)
5' TCTTGTGCTTCGTCGATAAAGATCC 3'

GeloC-6 (SEQ ID NO: 33)
5' ATCGACGAAGCACAAGAGTGCTATTTT 3'

GeloC-9 (SEQ ID NO: 34)
5' GTAAAACCATGCATAGCACTCTTGAAGTTCGT 3'

GeloC-10 (SEQ ID NO: 35)
5' AGTGCTATGCATGGTTTTACTTGATCAACTGC 3'

GeloC-13 (SEQ ID NO: 36)
5' AGCACATGTGGTGCCACTTATATTACCTA 3'

GeloC-14 (SEQ ID NO: 37)
5' TAAGTGGCACCACATGTGCTAAAGCTCACGGTG 3'

GeloC-15 (SEQ ID NO: 38)
5' TGACTGTGGACAGTTGGCGGAAATA 3'

-continued

GeloC-16 (SEQ ID NO: 39)
5' GCCAACTGTCCACAGTCATTTGAAAGCGCTACC 3'

GeloC-17 (SEQ ID NO: 40)
5' GATGATCCTGGAAAGGCTTTCGTTTTGGTAGCGCTT3'

GeloC-18 (SEQ ID NO: 41)
5' AAGCCTTTCCAGGATCATCAGC
TTTTTTGCGCAGCAATGGG 3'

GeloC-19 (SEQ ID NO: 42)
5' AAGCCTTTCCAGGATCATCACAT 3'

GeloC-20 (SEQ ID NO: 59)
5' CACATGTAAAACAAGACTTCATTTTGGC 3'

GeloC-21 (SEQ ID NO: 60)
5' TGAAGTCTTGTTTTAGATGTGTTTTTGAAGAGGCCT3'

GeloC-22 (SEQ ID NO: 61)
5' ATGCCATATGCAATTATAAACCAACGGAGA 3'

GeloC-23 (SEQ ID NO: 62)
5' GGTTTATAATTGCATATGG
CATTTTCATCAAGTTTCTTG 3'

GeloC-24 (SEQ ID NO: 63)
5' CTTTCAACAATGCATTCGCCCGGCGAATAATAC 3'

GeloC-25 (SEQ ID NO: 64)
5' GCGAATGCATTGTTGAAAGTTATTTCTAATTTG 3'

GeloC-26 (SEQ ID NO: 65)
5' GTTTTGTGAGGCAGTTGAATTGGAAC 3'

GeloC-27 (SEQ ID NO: 66)
5' TTCAACTGCCTCACAAAACATTCCATTTGCACCT 3'

GeloC-28 (SEQ ID NO: 67)
5' AAAAGCTGATGATCCTGGAAAGTG 3'

GeloC-29 (SEQ ID NO: 68)
5' TCCAGGATCATCAGCTTTTTTGCGCAGCAATGGGA 3' araB2 (SEQ ID NO: 43)
5' GCGACTCTCTACTGTTTC 3'

HINDIII-2 (SEQ ID NO: 44)
5' CGTTAGCAATTTAACTGTGAT 3'

(1) Specifically, a cysteine was introduced at amino acid 247 of gelonin (which is normally occupied by an aspartic acid which corresponds to the cysteine at position 259 in the ricin A-chain) by PCR with mutagenic primers GeloC-3-2 and GeloC-4 in conjunction with primers HINDIII-2 (a primer located in the vector portion of pING3734 or pING3825), Gelo-9 and Gelo-8. Template DNA (pING3734) was amplified with GeloC-3-2 and HINDIII-2 and in a concurrent reaction with GeloC-4 and Gelo-9. The products of these reactions were mixed and amplified with the outside primers Gelo-8 and HINDIII-2. The reaction product was cut with EcoRI and XhoI, purified, and was inserted into plasmid pING3825 in a three-piece ligation. The DNA sequence of the $Gel_{C247}$ variant (SEQ ID NO: 102) was then verified. The plasmid containing the sequence encoding $Gel_{C247}$ was designated pING3737 and was deposited with the American Type Culture Collection, 12301 Parklawn Drive, Rockville, Md. 20852 on Jun. 9, 1992 as ATCC Accession No. 69009.

(2–3) In the same manner, a cysteine residue was introduced in place of the amino acid at position 248 (a lysine) of gelonin with the mutagenic oligonucleotides GeloC-1 and GeloC-2 to generate analog $Gel_{C248}$ (SEQ ID NO: 103) in plasmid pING3741, and a cysteine residue was introduced at amino acid position 239 (normally occupied by a lysine) with primers GeloC-9 and GeloC-10 to generate analog $Gel_{239}$ (SEQ ID NO: 104) in plasmid pING3744.

(4) Also in the same manner, a cysteine residue was introduced at amino acid 244 (a lysine) of gelonin with mutagenic primers GeloC-5 and GeloC-6 to generate analog $Gel_{C244}$ (SEQ ID NO: 105) in a plasmid designated pING3736. This variant was prepared by PCR using plasmid pING3734 as template DNA rather than pING3825. It therefore encodes the same N-terminal gelonin amino acid sequence as plasmids pING3737, pING3741, and pING3744, but includes the PCR primer-derived 5'-end 32 nucleotides instead of the native gelonin 5'-end nucleotides.

(5) A cysteine residue was introduced in place of the amino acid (normally occupied by a lysine) at position 10 of gelonin by a similar procedure. A cysteine was introduced with mutagenic primers GeloC-13 and GeloC-14 by amplifying pING3824 with araB2 (a vector primer) and GeloC-14, and in a separate reaction, with GeloC-13 and Gelo-11. These reaction products were mixed and amplified with the outside primers araB2 and Gelo-11. The PCR product was cut with PstI and NcoI, purified, and cloned back into pING3825 to generate analog $Gel_{C10}$ (SEQ ID NO: 106) in the plasmid designated pING3746 and deposited with the American Type Culture Collection, 12301 Parklawn Drive, Rockville, Md. 20852 on Jun. 9, 1992 as ATCC Accession No. 69008.

(6) The asparagine at position 60 of gelonin was replaced with a cysteine residue using two mutagenic oligos, GeloC-15 and GeloC-16, in conjunction with oligos araB2 and Gelo-11 in the same manner as for the $Gel_{C10}$ variant. The plasmid encoding the $Gel_{C60}$ (SEQ ID NO: 107) analog was designated pING3749.

(7) A cysteine was introduced at amino acid 103 (an isoleucine) by PCR with mutagenic primers GeloC-20 and GeloC-21 in conjunction with primers araB2 and HINDIII-2. Template DNA (pING3733) was amplified with GeloC-21 and araB2 and separately with GeloC-20 and HINDIII-2. The products of these reactions were mixed and amplified with the outside primers araB2 and HINDIII-2. The reaction product was cut with NcoI and BclI, purified, and inserted into pING3825 digested with NcoI and BclI. The oligonucleotides used to place a cysteine at residue 103 also introduced an AflIII restriction site which was verified in the cloned gene. The plasmid containing the $Gel_{C103}$ (SEQ ID NO: 108) analog was designated pING3760.

(8) A cysteine was introduced at position 146 (an aspartic acid) by a similar strategy. Template DNA (pING3733) was amplified with mutagenic primer GeloC-22 and Gelo-14 and separately with mutagenic primer GeloC-23 and Gelo-19. The products of these reactions were mixed, and amplified with Gelo-19 and Gelo-14. The reaction product was cut with BglII and EcoRI, and can be inserted into pING3825 in a three-piece ligation. The oligonucleotides used to place a cysteine at residue 146 also introduced a NdeI restriction site which can be verified in the cloned gene.

(9) To introduce a cysteine at position 184 (normally occupied by an arginine) of gelonin, template DNA (pING3733) was amplified with mutagenic primer GeloC-25 and araB-2 and separately with mutagenic primer GeloC-24 and HINDIII-2. The products of these reactions were mixed, and amplified with araB2 and Gelo-14. The reaction product was cut with NcoI and BclI, and inserted into pING3825 previously digested with NcoI and BclI. The oligonucleotides used to place a cysteine at residue 184 also introduced an NsiI restriction site which was verified in the cloned gene. The plasmid containing the sequence encoding the $Gel_{C184}$ (SEQ ID NO: 109) variant was designated pING3761.

(10) A cysteine may be introduced at position 215 (a serine) by a similar strategy. Template DNA (pING3733) was amplified with mutagenic primer GeloC-27 and araB2 and separately with mutagenic primer GeloC-26 and HINDIII-2. The products of these reactions were mixed, and amplified with araB2 and HINDIII-2. The reaction product was cut with EcoRI and BclI, and may be inserted into pING3825 in a three-piece ligation.

(11) Another gelonin variant with a free cysteine residue was generated by replacing one of the two naturally occurring gelonin cysteine residues, the cysteine a position 50, with an alanine. Plasmid pING3824 was amplified with primers GeloC-17 and Gelo-11, and concurrently in a separate reaction with primers GeloC-19 and araB2. The reaction products were mixed and amplified with araB2 and Gelo-11. This product was cut with NcoI and BglII, and cloned back into the vector portion of pING3825 to generate pING3747 (ATCC 69101). This analog was designated $Gel_{A50(C44)}$ and it contains a cysteine available for disulfide bonding at amino acid position 44. Non-cysteine residues, other than alanine, which do not disrupt the activity of gelonin, also may be inserted at position 50 in natural gelonin in order to generate a gelonin analog with a single cysteine at position 44.

(12) A gelonin variant in which the natural cysteine at position 44 was changed to alanine was constructed by amplifying pING3733 using the mutagenic oligonucleotides GeloC-28 and GeloC-29 in conjunction with primers araB2 and HINDIII-2. The amplified DNA was cut with NcoI and BglII and cloned into a gelonin vector, generating pING3756. That variant generated was designated $Gel_{A44(C50)}$. Non-cysteine residues, other than alanine, which do not disrupt gelonin activity, also may be inserted at position 44 in order to generate a gelonin analog with a single cysteine at position 50.

(13) A gelonin variant in which both the cysteine at position 44 and the cysteine at position 50 of gelonin were changed to alanine residues was constructed by overlap PCR of pING3824 using the mutagenic oligonucleotides GeloC-17 and GeloC-18 in conjunction with primers araB2 and Gelo-11. This analog, like the native gelonin protein, has no cysteine residues available for conjugation. The plasmid encoding the analog was designated pING3750. The analog generated was designated $Gel_{A44A50}$ (SEQ ID NO: 101). Non-cysteine residues, other than alanine, which do not disrupt gelonin activity, also may be substituted at both positions 44 and 50 in order to generate a gelonin analog with no cysteine residues.

(14) The triple mutant $Gelonin_{C247A44A50}$ (SEQ ID NO: 111) was constructed from the plasmids pING3824, pING3750 and pING3737. This variant contains an introduced cysteine at position 247 while both of the naturally occurring cysteine residues at positions 44 and 50 have been replaced with alanine. The analog is desirable because, in this analog, disulfide linkage to an antibody is only assured at a single cysteine residue. Plasmid pING3824 was cut with NcoI and XhoI and the vector fragment was purified in an agarose gel. pING3750 was cut with NcoI and EcoRI and pING3737 was cut with EcoRI and XhoI. The NcoI-EcoRI fragment encodes the alanines at positions 44 and 50 while the EcoRI-XhoI fragment encodes the cysteine at position 247. Each of these fragments was purified and ligated to the NcoI to XhoI vector fragment. The resulting plasmid is named pING3752.

(15) The triple mutant $Gelonin_{C10A44A50}$ (SEQ ID NO: 110) was also constructed by assembly from previously assembled plasmids. In this case, pING3746 was cut with PstI and NcoI, while pING3750 was cut with NcoI and XhoI. Each of the insert fragments were purified by electrophoresis in an agarose gel, and the fragments were ligated into a PstI and XhoI digested vector fragment. The resulting vector was designated pING3753. The $Gel_{C10A44A50}$ analog has been referred to previously as $Gel_{C10C44AC50A}$ (see, e.g., co-owned, co-pending U.S. patent application Ser. No. 07/988,430, incorporated by reference herein).

Each of the gelonin variants constructed was transformed into *E. coli* strain E104. Upon induction of bacterial cultures with arabinose, gelonin polypeptide could be detected in the culture supernatants with gelonin-specific antibodies. There were no significant differences detected in the expression levels of gelonin from plasmids pING3734 and pING3825, or in the levels from any of the gelonin variants. Each protein was produced in *E. coli* at levels of approximately 1 g/l.

EXAMPLE 4

Reticulocyte Lysate Assay

The ability of gelonin and recombinant gelonin analogs to inhibit protein synthesis in vitro was tested using a reticulocyte lysate assay (RLA) described in Press et al., *Immunol. Letters*, 14:37–41 (1986). The assay measures the inhibition of protein synthesis in a cell-free system using endogenous globin mRNA front a rabbit red blood cell lysate. Decreased incorporation of tritiated leucine ($^3$H-Leu) was measured as a function of toxin concentration. Serial log dilutions of standard toxin (the 30 kD form of ricin A-chain, abbreviated as RTA 30), native gelonin, recombinant gelonin (rGelonin or rGel) and gelonin analogs were tested over a range of 1 μg/ml to 1 pg/ml. Samples were tested in triplicate, prepared on ice, incubated for 30 minutes at 37° C., and then counted on an Inotec Trace 96 cascade ionization counter. By comparison with an uninhibited sample, the picomolar concentration of toxin (pM) which corresponds to 50% inhibition of protein synthesis ($IC_{50}$) was calculated. As is shown in Table 1 below, recombinant gelonin and most of its analogs exhibit activity in the PLA comparable to that of native gelonin. For some of the analogs (such as $Gel_{C239}$), RLA activity was diminished.

TABLE 1

| Toxin | $IC_{50}$ (pM) |
|---|---|
| RTA 30 | 2.5 |
| Gelonin | 15 |
| rGelonin | 11 |
| $Gel_{C10}$ | 60 |
| $Gel_{A50(C44)}$ | 20 |
| $Gel_{A44(C50)}$ | 47 |
| $Gel_{C60}$ | 26 |
| $Gel_{C239}$ | 955 |
| $Gel_{C244}$ | 32 |
| $Gel_{C247}$ | 12 |
| $Gel_{C248}$ | 47 |
| $Gel_{A44A50}$ | 16 |
| $Gel_{C10A4450A}$ | 7 |
| $Gel_{C247A44A50}$ | 20 |

EXAMPLE 5

Human-Engineered Antibodies For Construction Of Immunotoxins

Antibodies for use in constructing immunotoxins according to the present invention may be humanized antibodies, such as he3 and fragments thereof which display increased content of human amino acids and a high affinity for human CD5 cell differentiation marker. he3 is a humanized form of a mouse H65 antibody (H65 is a preferred monoclonal antibody for use in preparing humanized antibodies according to the present invention and is produced by hybridoma cell line XMMLY-H65 (H65) deposited with the American Type Culture Collection in Rockville, Md. (A.T.C.C.) and given the Accession No. HB9286).

Humanized antibodies for use in the present invention are prepared as disclosed herein using the humanized forms of the murine H65 antibody in which both low and moderate risk changes described below were made in both variable regions. Such humanized antibodies should have less immunogenicity and have therapeutic utility in the treatment of autoimmune diseases in humans. For example, because of their increased affinity over existing therapeutic monoclonal antibodies such as H65, he3 antibodies of the invention may be administered in lower doses than H65 anti-CD5 antibodies in order to obtain the same therapeutic effect.

Humanized antibodies, such as he3, are useful in reducing the immunogenicity of foreign antibodies and also results in increased potency when used as a portion of an immunoconjugate.

Construction of humanized antibody variable domains according to the present invention and for use as components of immunotoxins may be based on a method which includes the steps of: (1) identification of the amino acid residues of an antibody variable domain which may be modified without diminishing the native affinity of the domain for antigen while reducing its immunogenicity with respect to a heterologous species; and (2) the preparation of antibody variable domains having modifications at the identified residues which are useful for administration to heterologous species. The methods of the invention are based on a model of the antibody variable domain described herein and in U.S. co-owned U.S. patent application Ser. No. 07/808,464 by Studnicka et al. which predicts the involvement of each amino acid in the structure of the domain.

Unlike other methods for humanization of antibodies, which advocate replacement of the entire classical antibody framework regions with those from a human antibody, the methods described herein and in U.S. co-owned U.S. patent application Ser. No. 07/808,464 by Studnicka et al. introduce human residues into the variable domain of an antibody only in positions which are not critical for antigen-binding activity and which are likely to be exposed to immunogenicity-stimulating factors. The present methods are designed to retain sufficient natural internal structure of the variable domain so that the antigen-binding capacity of the modified domain is not diminished in comparison to the natural domain.

A. Assembly Of Moderate Risk Heavy Chain Expression Vectors

The humanized H65 heavy chain containing the moderate risk residues was assembled by the following strategy. The moderate-risk expression vector was assembled from intermediate vectors. The six oligonucleotide sequences (oligos), disclosed in FIG. 11 and labelled HUH-G11, HUH-G12, HUH-G3, HUH-G4, HUH-G5, and HUH-G6 (the sequences of HUH-G11 and HUH-C12 are set out in SEQ ID Nos. 131 and 132 and HUH-G3, HUH-G4, HUH-G5, and HUH-G6 are set out in SEQ ID NOS: 137–140) were assembled by PCR. Oligonucleotides containing the synthetic humanized antibody gene were mixed in pairs (HUH-G11+HUH-G12, HUH-G3+HUH-G4, and HUH-G5+HUH-G6) in a 100 µl reaction with 1 µg of each DNA and filled in as described above. A portion of each reaction product was mixed in pairs (HUH-G11, 12+HUH-G3, 4; HUH-G3, 4+HUH-G5, 6), 2.5 U Taq was added and samples were reincubated as described above. The V-J region was assembled by mixing equal amounts of the HUH-G11, 12, 3, 4 reaction product with the HUH-G3, 4, 5, 6 product, followed by PCR with 0.5 ug of primers H65G-2S and H65-G2 as described above. The reaction product was cut with SalI and BstEII and cloned into the expression vector, similar to that described for heavy chain in Robinson et al., Hum. Antibod. Hybridomas 2:84 (1991), generating pING4617. That plasmid was sequenced with Sequenase (USB, Cleveland), revealing that two residues were altered (a G-A at position 288 and a A-T at position 312, numbered from the beginning of the leader sequence). The correct variable region was restored by substitution of this region from pING4612, generating the expected V-region sequence in pING4619.

An intermediate vector containing the other moderate-risk changes was constructed by PCR assembly of the oligos HUH-G13, HUH-G14, HUH-G15, and HUH-G16 (FIG. 11 and SEQ ID Nos: 133–136). Oligos HUH-G13+HUH-G14 and HUH-G15+HUH-G16 were mixed and filled in with Vent polymerase (New England Biotabs) in a reaction containing 10 mM KCl, 20 mM TRIS pH 8.8, 10 mM $(NH_4)_2SO_2$, 2 mM $MgSO_4$, 0.1% Triton X-100, 100 ng/ml BSA, 200 uM of each dNTP, and 2 units of Vent polymerase in a total volume of 100 µl. The reaction mix was incubated at 94° C. for 1 minute, followed by 2 minutes at 50° C. and 20 minutes at 72° C. The reaction products (40µl) were mixed and amplified with the oligonucleotides H65-G13 and H65-G2 with Vent polymerase in the same reaction buffer and amplified for 25 cycles with denaturation at 94° C. for 1 minute, annealing at 50° C. for 2 minutes and polymerization at 72° C. for 3 minutes. The reaction product was treated with T4 polymerase and then digested with AccI. The 274 base pair (bp) fragment was purified on an agarose gel and ligated along with the 141 bp SalI to AccI fragment from pING4619 into pUC18 cut with SalI and SmaI to generate pING4620. pING4620 contains the entire signal sequence, V-region, and J-region of the moderate-risk H65 heavy chain.

The final expression vector for the moderate-risk H65 heavy chain, pING4621, was assembled by cloning the SalI to BstEII fragment from pING4620 into the same expression vector described above.

B. Assembly Of Moderate-Risk Light Chain Expression Vectors

The moderate-risk humanized V- and J-segments of the light chain were assembled from six oligonucleotides, $H65K-1 (SEQ ID NO: 117), HUH-K7 (SEQ ID NO: 119), HUH-K6 (SEQ ID NO: 118), HUH-K8 (SEQ ID NO: 120), HUH-K4 (SEQ ID NO: 121 and HUH-K5 (SEQ ID NO: 122). The oligonucleotides were amplified with PCR primers H65K-2S and JK1-HindIII. Oligonucleotides containing the synthetic humanized antibody gene were mixed in pairs ($H65-K1+HUH-K7, HUH-K6+HUH-K4+HUH-K5) and incubated with Vent polymerase as described for the moderate-risk heavy chain. A portion of each reaction product (40 ul) was mixed in pairs ($H65H-K1/HUH-K7+HUH-K6, 8; HUH-K6, 8+HUH-K4, 5) and filled in as above. The light chain gene was then assembled by amplifying the full length gene with the PCR primers H65K-2S and JK1-HindIII with Vent polymerase for 25 cycles as outlined above. The assembled V/J region was cut with SalI and HindIII, purified by electrophoresis on an agarose gel, and assembled into a light chain antibody expression vector, pING4630.

EXAMPLE 6

Transfection Of he3 Genes And Purification Of Expression Products

A. Stable Transfection Of Mouse Lymphoid Cells For The Production Of he3 Antibody The cell line Sp2/0 (American Type Culture Collection Accession No. CRL1581) was grown in Dulbecco's Modified Eagle Medium plus 4.5 g/l glucose (DMEM, Gibco) plus 10% fetal bovine serum. Media were supplemented with glutamine/penicillin/streptomycin (Irvine Scientific, Irvine, Calif.).

The electroporation method of Potter, H., et al., *Proc. Natl. Acad. Sci., USA*, 81:7161 (1984) was used. After transfection, cells were allowed to recover in complete DMEM for 24–48 hours, and then seeded at 10,000 to 50,000 cells per well in 96-well culture plates in the presence of selective medium. Histidinol (Sigma) selection was at 1.71 µg/ml, and mycophenolic acid (Calbiochem) was at 6 µg/ml plus 0.25 mg/ml xanthine (Sigma). The electroporation technique gave a transfection frequency of $1-10\times10^{-5}$ for the Sp2/0 cells.

The he3 light chain expression plasmid pING4630 was linearized by digestion with PvuI restriction endonuclease and transfected into Sp2/0 cells, giving mycophenolic acid-resistant clones which were screened for light chain synthesis.

Four of the top-producing subclones, secreting 4.9–7.5 µg/ml were combined into two pools (2 clones/pool) and each pool was transfected with plasmid pING42621, containing the moderate-risk heavy chain. After selection with histidinol, the clones producing the most light plus heavy chain, Sp2/0-4630 and 4621 Clones C1705 and C1718, secreted antibody at approximately 15 and 22 µg/ul respectively in the presence of $10^{-7}$M dexamethasone in an overgrown culture in a T25 flask. Clone C1718 was deposited with the American Type Culture Collection, 1230 Parklawn Drive, Rockville, Md., 20852 on Dec. 1, 1992 as ATCC HB 11206. The best producer is a subclone of Clone C1718 which is produced by limiting dilution subcloning of Clone C1718.

B. Purification Of he3 Antibody Secreted In Tissue Culture

Sp2/0-4630+4621 Clone C1705cells were grown in culture medium HB101 (Hana Biologics)+1% Fetal Bovine Serum, supplemented with 10 mM HEPES, 1× Glutamine-Pen-Strep (Irvine Scientific #9316). The spent medium was centrifuged at about 5,000×g for 20 minutes. The antibody level was measured by ELISA. Approximately 200 ml of cell culture supernatant was loaded onto a 2 ml Protein A-column (Sigma Chemicals), equilibrated with PBS (buffer 0.15M NaCl, 5 mM sodium phosphate, 1 mM potassium phosphate, buffer pH 7.2). The he3 antibody was eluted with a step pH gradient (pH 5.5, 4.5 and 2.5). A fraction containing he3 antibody (9% yield) but not bovine antibody, was neutralized with 1M Tris pH 8.5, and then concentrated 10-fold by Centricon 30 (Amicon) diluted 10-fold with PBS, reconcentrated 10-fold by Centricon 30, diluted 10-fold with PBS, and finally reconcentrated 10-fold. The antibody was stored in 0.25 ml aliquots at −20° C.

C. Affinity Measurements Of he3 IgG For CD5

The affinity of he3 IgG for CD5 was determined using Molt-4M cells, which express CD5 on their surface, and $I^{125}$-labeled chimeric H65 IgG in a competitive binding assay. Culture supernatants from Clone C1705 and C1718 and purified IgG from C1705 were used as the sources of he3 IgG.

For this assay, 20 vg of chimeric H65 IgG (cH65 IgG) was iodinated by exposure to 100 µl lactoperoxidase-glucose oxidase immobilized beads (Enzymobeads, BioRad), 100 µl of PBS, 1.0 MCi $I^{125}$ (Amersham, IMS30), 50 µl of 55 mM b-D-glucose for 45 minutes at 23° C. The reaction was quenched by the addition of 20 µl of 105 mM sodium metabisulfite and 120 mM potassium iodine followed by centrifugation for 1 minute to pellet the beads. $^{125}$I-cH65 IgG was purified by gel filtration using 7 mls of sephadex G25, using PBS (137 mM NaCl, 1.47 mM KH$_2$PO$_4$, 8.1 mM Na$_2$HPO$_4$, 2.68 mM KCl at pH 7.2–7.4) plus 0.1% BSA. $^{125}$I-cH65 IgG recovery and specific activity were determined by TCA precipitation.

Competitive binding was performed as follows: 100 µl of Molt-4M cells were washed two times in ice-cold DHB binding buffer (Dubellco's modified Eagle's medium (Gibco, 320-1965PJ), 1.0% BSA and 10 mM Hepes at pH 7.2–7.4). Cells were resuspended in the same buffer, plated into 96 v-bottomed wells (Costar) at $3\times10^5$ cells per well and pelleted at 4° C. by centrifugation for 5 min at 1,000 rpm using a Beckman JS 4.2 rotor; 50 µl of 2×-concentrated 0.1 nM $^{125}$-cH65 IgG in DHB was then added to each well and competed with 50 µl of 2×-concentrated cH65 IgG or humanized antibody in DHB at final antibody concentrations from 100 nM to 0.0017 nM. Humanized antibody was obtained from culture supernatants of Sp2/0 clone C1718 which expresses he3 IgG. The concentration of the antibody in the supernatants was established by ELISA using a chimeric antibody as a standard. The concentration of the antibody in the purified preparation was determined by binding was allowed to proceed at 40° C. for 5 hrs and was terminated by washing cells three times with 200 µl of DHB binding buffer by centrifugation for 5 min at 1,000 rpm. All buffers and operations were at 4° C. Radioactivity was determined by solubilizing cells in 100 µl of 1.0M NaOH and counting in a Cobra II auto gamma counter (Packard). Data from binding experiments were analyzed by the weighted nonlinear least squares curve fitting program, MacLigand, a Macintosh version of the computer program "Ligand" from Munson, *Analyt. Biochem.*, 107:220 (1980). Objective statistical criteria (F, test, extra sum squares principle) were used to evaluate goodness of fit and for discriminating between models. Nonspecific binding was treated as a parameter subject to error and was fitted simultaneously with other parameters.

Data showing relative binding of he3 and CH65 to CD5 on molt-4M cells in a competition binding assay demonstrate that the moderate-risk changes made in he3 IgG result in an antibody with a higher affinity than the chimeric mouse-human form of this antibody (cH65) for its target, CD5.

EXAMPLE 7

Preparation of Gelonin Immunoconjugates

Gelonin analogs of the invention were variously conjugated to murine (ATCC HB9286) and chimeric H65 (cH65) antibody, cH65 antibody domains (including cFab, cFab' and cF(ab')$_2$ fragments), and humanized antibodies and antibody domains, all of which are specifically reactive with the human T cell determinant CD5. H65 antibody was prepared and purified by methods described in U.S. patent application Ser. No. 07/306,433, supra and International Publication No. WO 89/06968, supra. Chimeric H65 antibody was prepared according to methods similar to those described in Robinson et al., *Human Antibodies and Hybridomas*, 2:84–93 (1991), incorporated by reference herein. Chimeric H65 Fab, Fab', and F(ab')$_2$ proteins were prepared as described in Better, et al., *Proc. Nat. Acad. Sci. (USA)*, 90: 457–461 (1993), incorporated by reference herein. Finally, he3 humanized antibodies were prepared according to the procedures described in U.S. patent application Ser. No. 07/808,464, incorporated by reference herein.

A. Conjugation To H65 Antibodies

To expose a reactive sulfhydryl, the unpaired cysteine residues of the gelonin analogs were first reduced by incubation with 0.1 to 2 mM DTT (30–60 minutes at room temperature), and then were desalted by size-exclusion chromatography.

Specifically, the Gel$_{C248}$ analog (3.8 mg/ml) was treated with 2 mM DTT for 60 minutes in 0.1M Naphosphate, 0.25M NaCl, pH 7.5 buffer. The Gel$_{C244}$ variant (7.6 mg/ml) was treated with 2 mM DTT for 30 minutes in 0.1M Naphosphate, 0.25M NaCl, pH 7.5 buffer. The Gel$_{C247}$ analog (4 mg/ml) was treated with 2 mM DTT for 30 minutes in 0.1M Naphosphate, 0.5M NaCl, pH 7.5 buffer with 0.5 mM EDTA. The Gel$_{C239}$ variant (3.2 mg/ml) was treated with 2 mM DTT for 30 minutes in 0.1 m Naphosphate, 0.5M NaCl, pH 7.5 buffer with 0.5 mM EDTA. The Gel$_{A50(C44)}$ analog (4.2 mg/ml) was treated with 0.1 mM DTT for 30 minutes in 0.1M Naphosphate, 0.1M NaCl, pH 7.5 buffer with 0.5 mM EDTA. Lastly, the Gel$_{C10}$ variant (3.1 mg/ml) was treated with 1 mM DTT for 20 minutes in 0.1M Naphosphate, 0.1M NaCl, pH 7.5 buffer with 1 mM EDTA.

The presence of a free sulfhydryl was verified by reaction with DTNB and the average value obtained was 1.4±0.65 SH/molecule. No free thiols were detected in the absence of reduction.

H65 antibody and chimeric H65 antibody were chemically modified with the hindered linker 5-methyl-2-iminothiolane (M2IT) at lysine residues to introduce a reactive sulfhydryl group as described in Goff et al., *Bioconjugate Chem.*, 1:381–386 (1990) and co-owned Carroll et al., U.S. Pat. No. 5,093,475, incorporated by reference herein.

Specifically, for conjugation with Gel$_{C248}$ and Gel$_{C244}$, murine H65 antibody at 4 mg/mL was derivitized with 18× M2IT and 2.5 mM DTNB in 25 mM TEOA, 150 mM NaCl, pH 8 buffer for 1 hour at 23° C. The reaction gave 1.9 linkers per antibody as determined by DTNB assay.

For conjugation with Gel$_{C247}$ and Gel$_{C239}$, H65 antibody at 4.7 mg/mL was derivitized with 20× M2IT and 2.5 mM DTNB in 25 mM TEOA 150 mM NaCl, pH 8 buffer for 50 minutes at 23° C. The reaction gave 1.6 linkers per antibody as determined by DTNB assay.

Before reaction with Gel$_{A50(C44)}$, H65 antibody at 5.8 mg/mL was derivitized with 20× m2IT and 2.5 mM DTNB in 25 mM TEOA, 150 mM NaCl, pH 8 buffer for 30 minutes at 23° C. The reaction gave 1.5 linkers per antibody as determined by DTNB assay.

For conjugation with Gel$_{C10}$, H65 antibody at 2.2 mg/mL was derivitized with 10× m2IT and 2.5 mM DTNB in 25 mM TEOA, 150 mM NaCl, pH 8 buffer for 1 hour at 23° C. The reaction gave 1.4 linkers per antibody as determined by DTNB assay.

Chimeric H65 antibody was prepared for conjugation in a similar manner to murine H65 antibody.

Two methods were initially compared for their effectiveness in preparing immunoconjugates with recombinant gelonin. First, the native disulfide bond in recombinant gelonin was reduced by the addition of 2 mM DTT at room temperature for 30 minutes. The reduced gelonin was recovered by size-exclusion chromatography on a column of Sephadex GF-05LS and assayed for the presence of free sulfhydryls by the DTNB assay. 1.4 free SH groups were detected. This reduced gelonin was then reacted with H65-(M2IT)-S-S-TNB (1.8 TNB groups/H65). Under these experimental conditions, little or no conjugate was prepared between reduced gelonin and thiol-activated H65 antibody.

In contrast, when both the recombinant gelonin and the H65 antibody were first derivitized with the crosslinker M2IT (creating gelonin-(M2IT)-SH and H65-(M2IT)-S-S-TNB) and then mixed together, H65-(M 2IT)-S-S-(M2IT)-gelonin conjugate was prepared in good yield (toxin/antibody ratio of 1.6). The starting materials for this conjugation (gelonin-(M2IT)-SH and H65-(M2IT)-S-S-TNB) contained linker/protein ratios of 1.2 and 1.4, respectively. Native gelonin was derivatized in a similar manner prior to conjugation to murine or chimeric H65 antibody.

The reduced gelonin analogs were mixed with H65-(M2IT)-S-S-TNB to allow conjugation. The following conjugation reactions were set up for each analog: 23 mg (in 7.2 ml) of H65-M2IT-TNB were mixed with a 5-fold molar excess of $Gel_{C248}$ (23 mg in 6 ml) for 2 hours at room temperature, then for 18 hours overnight at 4° C.; 23 mg (in 7.3 ml) of H65-m2IT-TNB were mixed with a 5-fold molar excess of $Gel_{C244}$ (23 mg in 3 ml) for 3 hours at room temperature, then for 18 hours overnight at 4° C.; 9 mg (in 2.8 mL) of H65-m2IT-TNB were mixed with a 5-fold molar excess of $Gel_{C247}$ (9 mg in 2.25 mL) for 2 hours at room temperature, then for 5 nights at 4° C.; 9 mg (in 2.8 mL) of H65-m2IT-TNB were mixed with a 5-fold molar excess of $Gel_{C239}$ (9 mg in 2.6 mL) for 2 hours at room temperature, then at 4° C. for 3 days; 12 mg (in 1.9 mL) of H65-m2IT-TNB were mixed with a 5.6-fold molar excess of $Gel_{A50(C44)}$ (13.44 mg in 3.2 mL) for 4.5 hours at room temperature, then 4° C. overnight; and 11 mg of H65-m2IT-TNB were mixed with a 5-fold molar excess of $Gel_{C10}$ (11 mg in 3.5 mL) for 4 hours at room temperature, then at 4° C. overnight.

Following conjugation, unreacted M2IT linkers on the antibody were quenched with 1:1 mole cysteamine to linker for 15 minutes at room temperature. The quenched reaction solution was then loaded onto a gel filtration column [Sephadex G-150 (Pharmacia) in the case of $Gel_{C248}$, $Gel_{C247}$, $Gel_{C244}$ and $Gel_{C239}$ and an AcA-44 column (IBF Biotecnics, France) in the case of $Gel_{A50(C44)}$ and $Gel_{C10}$]. The reactions were run over the gel filtration columns and eluted with 10 mM Tris, 0. 15M NaCl pH 7. The first peak off each column was loaded onto Blue Toyopearl® resin (TosoHaas, Philadelphia, Pa.) in 10 mM Tris, 30 mM NaCl, pH 7 and the product was eluted with 10 mM Tris, 0.5 M NaCl, pH 7.5.

Samples of the final conjugation products were run on 5% non-reduced SDS PAGE, Coomassie stained and scanned with a Shimadzu laser densitometer to quantitate the number of toxins per antibody (T/A ratio). The yield of final product for each analog conjugate was as follows: $Gel_{C248}$, 17 mg with a T/A ration of 1.6; $Gel_{C247}$, 1.1 mg with a T/A ratio of 1; $Gel_{C244}$, 4.5 mgs with a T/A ratio of 1.46; $Gel_{C239}$, 2.9 mg with a T/A ratio of 2.4; $Gel_{A50(C44)}$, 7.3 mg with a T/A ratio of 1.22; and $Gel_{C10}$, 6.2 mg with a T/A ratio of 1.37. Conjugation efficiency (i.e., conversion of free antibody to immunoconjugate) was significantly greater (~80%) for some analogs ($Gel_{C10}$, $Gel_{A50(C44)}$, $Gel_{C239}$, $Gel_{C247}$, and $Gel_{C248}$) than for others (~10%, $Gel_{C244}$).

B. Gelonin Immunoconjugates With Chimeric And Humanized Antibodies

Analogs $Gel_{C247}$ and $Gel_{A50(C44)}$ were also conjugated to various chimeric [cH65Fab, cH65Fab' and cH65F(ab')$_2$] and "human engineered" [he1 Fab, he2-Fab, he3-Fab, he1 Fab' and he1 F(ab')$_2$] antibody fragments. Chimeric H65 antibody fragments may be prepared according to the methods described in International Publication No. WO 89/00999, supra. The DNA sequences encoding the variable regions of H65 antibody fragments that were human engineered (referring to the replacement of selected murine-encoded amino acids to make the H65 antibody sequences less immunogenic to humans) according to the methods described above in Example 5, are set out in SEQ ID NO: 69 (variable region of the kappa chain of he1 and he2), SEQ ID NO: 70 (variable region of the gamma chain of he1), SEQ ID NO: 71 (variable region of the gamma chain of he2 and he3) and SEQ ID NO: 72 (the kappa chain of he3)

The chimeric H65 antibody fragments were conjugated to the Gel$_{C247}$ analog in the same manner as described below for conjugation of human engineered Fab and Fab' fragments to Gel$_{C247}$ and Gel$_{A50(C44)}$.

(i) he1 Fab-Gel$_{C247}$

The he1 Fab was dialyzed into 25 mM TEOA buffer, 250 mM NaCl, pH 8 and then concentrated to 6.8 mg/mL prior to derivitization with the M2IT crosslinker. For the linker reaction, M2IT was used at 20-fold molar excess, in the presence of 2.5 mM DTNB. The reaction was allowed to proceed for 30 minutes at room temperature, then desalted on GF05 (gel filtration resin) and equilibrated in 0.1M Na phosphate, 0.2M NaCl, pH 7.5. A linker number of 1.8 linkers per Fab was calculated based on the DTNB assay. The he1 Fab-M2IT-TNB was concentrated to 3.7 mg/mL prior to conjugation with Gel$_{C247}$.

Gel$_{C247}$ at 12.8 mg/mL in 10 mM Na phosphate, 0.3M NaCl, was treated with 1 mM DTT, 0.5 mM EDTA for 20 minutes at room temperature to expose a reactive sulfhydryl for conjugation and then was desalted on GF05 and equilibrated in 0.1M Na phosphate, 0.2M NaCl, pH 7.5. Free thiol content was determined to be 0.74 moles of free SH per mole of Gel$_{C247}$ using the DTNB assay. The gelonin was concentrated to 8.3 mg/mL prior to conjugation with activated antibody.

The conjugation reaction between the free thiol on Gel$_{C247}$ and the derivitized he1 Fab-M2IT-TNB, conditions were as follows. A 5-fold excess of the gelonin analog was added to activated he1 Fab-M2IT-TNB (both proteins were in 0.1M Na phosphate, 0.2M NaCl, pH7.5) and the reaction mixture was incubated for 3.5 hours at room temperature and then overnight at 4° C. Following conjugation, untreated M2IT linkers were quenched with 1:1 mole cysteamine to linker for 15 minutes at room temperature. The quenched reaction solution was loaded onto a gel filtration column (G-75) equilibrated with 10 mM Tris, 150 mM NaCl, pH 7. The first peak off this column was diluted to 30 mM NaCl with 10 mM Tris, pH7 and loaded on Blue Toyopearl®. The product was eluted with 10 mM Tris, 0.15M NaCl, pH 7.5.

(ii) he1 Fab'-Gel$_{C247}$

Similarly, the H65 he1 Fab' fragment was dialyzed into 25 mM TEOA buffer, 400 mM NaCl, pH 8 at 2.9 mg/mL prior to derivitization with the M2IT crosslinker. For the linker reaction, M2IT was used at 20-fold molar excess, in the presence of 2.5 mM DTNB. The reaction was allowed to proceed for 1 hour at room temperature then it was desalted on GF05 (gel filtration resin) and equilibrated in 0.1M Na phosphate, 0.2M NaCl, pH 7.5. A linker number of 1.6 linkers per Fab' was calculated based on the DTNB assay. The he1 Fab'-M2IT-TNB was concentrated to 3.7 mg/mL prior to conjugation with Gel$_{C247}$ The Gel$_{C247}$ at 77 mg/mL was diluted with 10 mM Na phosphate, 0.1M NaCl to a concentration of 5 mg/mL, treated with 1 mM DTT, 0.5 mM EDTA for 30 minutes at room temperature to expose a free thiol for conjugation and then was desalted on GF05 and equilibrated in 0.1M Na phosphate, 0.2M NaCl, pH 7.5. Free thiol content was determined to be 1.48 moles of free SH per mole of Gel$_{C247}$ using the DTNB assay. The Gel$_{C247}$ was concentrated to 10 mg/mL prior to conjugation with activated he1 Fab'-M2IT-TNB.

For the reaction between the free thiol on Gel$_{C247}$ and the derivitized he1 Fab'-M2IT-TNB, conditions were as follows. A 5.7-fold molar excess of gelonin was added to activated he1 Fab'-M2IT-TNB and the final salt concentration was adjusted to 0.25M. The reaction mix was incubated for 1.5 hours at room temperature and then over the weekend at 4° C. Following conjugation, unreacted M2IT linkers were quenched with 1:1 mole cysteamine to linker for 15 minutes at room temperature. The quenched reaction solution was loaded onto a gel filtration column (AcA54) equilibrated with 10 mM Tris, 250 mM NaCl, pH 7.5. The first peak off this column was diluted to 20 mM NaCl with 10 mM Tris, pH 7 and loaded on Blue Toyopearl® which was equilibrated in 10 mM Tris, 20 mM NaCl, pH 7. The column was then washed with 10 mM Tris, 30 ml Nacl, pH 7.5. The product was eluted with 10 mM Tris, 1M NaCl, pH 7.5.

(iii) he2-Fab Gel$_{A50(C44)}$

The he2-Fab was dialyzed overnight into 25 mM TEOA, 0.25M NaCl, pH 8 buffer and then concentrated to 13.3 mg/mL prior to derivitization with the M2IT crosslinker. For the linker reaction, M2IT was used in a 20-fold molar excess in the presence of 2.5 mM DTNB. The reaction was allowed to proceed for 20 minutes at room temperature and was then desalted on a GF05-LS (gel filtration) column, equilibrated in 0.1M Na phosphate, 0.2M NaCl with 0.02% Na azide. A linker number of 1.7 linkers per Fab-M2IT-TNB was calculated based on the DTNB assay. After derivitization and gel filtration, the he2-Fab concentration was 5.2 mg/mL.

Gel$_{A50(C44)}$ at 8.33 mg/mL in 10 mM Na phosphate, pH 7.2 was treated with 5 mM DTT and 0.5 mM EDTA for 30 minutes at room temperature to expose a reactive thiol for conjugation and then was desalted on GF05-LS resin equilibrated in 0.1M Na phosphate, 0.1M NaCl with 0.5 mM EDTA plus 0.02% Na azide, pH 7.5. Free thiol content was determined to be 0.83 moles of free SH per mole of Gel$_{A50(C44)}$ using the DTNB assay. The gelonin was concentrated to 11.4 mg/mL prior to conjugation with activated he2-Fab.

The conjugation reaction conditions between the free thiol on Gel$_{A50(C44)}$ and the derivitized he2-Fab-M2IT-TNB were as follows. A 3-fold excess of the gelonin analog was added to activated he2-Fab-M2IT-TNB (both proteins were in 0.1M Na phosphate, 0.1M NaCl, pH 7.5 but the gelonin solution contained 0.5 mM EDTA as well). The reaction mixture was concentrated to half its original volume, then the mixture was incubated for 4 hours at room temperature followed by 72 hours at 4° C. Following the incubation period the efficiency of conjugation was estimated at 70–75% by examination of SDS PAGE.

Following conjugation the excess M2IT linkers were quenched by incubation with 1:1 mole cysteamine to linker for 15 minutes at room temperature. The quenched reaction as loaded onto a gel filtration column (G-75) equilibrated in 10 mM Tris, 0.15M NaCl, pH 7. The first peak off this column was diluted to 30 mM NaCl with 10 mM Tris, pH 7 and loaded onto a Blue Toyopearl® (TosoHaas) column. The product was eluted with 10 mM Tris, 1M NaCl, pH 7.5.

(iv) he3-Fab Gel$_{A50(C44)}$

Similarly, the he3-Fab was dialyzed overnight into 25 mM TEOA, 0.25M NaCl, pH 8 buffer and then concentrated to 5 mg/mL prior to derivitization with the M2IT crosslinker. For the linker reaction, M2IT was used in a 10-fold molar excess in the presence of 2.5 mM DTNB. The reaction was allowed to proceed for, 45 minutes at room temperature and was then desalted on a GF05-LS (gel filtration) column, equilibrated in 0.1M Na phosphate, 0.2M NaCl with 0.02% Na azide. A linker number of 1 M2IT per Fab-M2IT-TNB was calculated based on the DTNB assay. After derivitization and gel filtration, the he3-Fab concentration was 5.3 mg/mL.

Gel$_{A50(C44)}$ at 7.8 mg/mL in 0.1M Na phosphate, 0.1M NaCl, pH 7.5 was treated with 1.5 mM DTT and 1 mM EDTA for 30 minutes at room temperature to expose a reactive thiol for conjugation and then was desalted on GF05-LS resin equilibrated in 0.1M Na phosphate, 0.1M NaCl plus 0.02% Na azide, pH 7.5. Free thiol content was determined to be 0.66 moles of free SH per mole of $Gel_{A50(C44)}$ using the DTNB assay. The gelonin was concentrated to 5.2 mg/mL prior to conjugation with activated he3-Fab.

The conjugation reaction conditions between the free thiol on $Gel_{A50(C44)}$ and the derivitized he3-Fab-M2IT-TNB were as follows. A 5-fold excess of the gelonin analog was added to activated he3-Fab-M2IT-TNB (both proteins were in 0.1M Na phosphate 0.1M NaCl, pH 7.5). The reaction mixture was incubated for 2 hours at room temperature followed by 72 hour at 4° C. Following the incubated period the efficiency of conjugation was estimated at 70–75% by examination of SDS PAGE.

Following conjugation, the excess M2IT linkers were quenched by incubation with 1:1 mole cysteamine to linker for 15 minutes at room temperature. The quenched reaction was loaded onto a GammaBind G (immobilized protein G affinity resin, obtained from Genex, Gaithersburg, Md.) equilibrated in 10 mM Na phosphate, 0.15M NaCl, pH 7. It was eluted with 0.5M NaOAc, pH 3 and neutralized with Tris. It was dialyzed into 10 mM Tris, 0.15M NaCl, pH 7 overnight, then diluted to 30 mM NaCl with 10 mM Tris, pH 7 and loaded onto a blue Toyopearl® (TosoHaas) column. The product was eluted with 10 mM Tris, 1M NaCl, pH 7.5

EXAMPLE 8
Whole Cell Kill Assays

Immunoconjugates prepared with gelonin and gelonin analogs were tested for cytotoxicity against an acute lymphoblastoid leukemia T cell line (HSB2 cells) and against human peripheral blood mononuclear cells (PBMCs). Immunoconjugates of ricin A-chain with H65 antibody (H65-RTA) and antibody fragments were also tested. The ricin A-chain (RTA) as well as the H65-RTA immunoconjugates were prepared and purified according to methods described in U.S. patent application Ser. No. 07/306,433, supra and in International Publication No. WO 89/06968, supra.

Briefly, HSB2 cells were incubated with immunotoxin and the inhibition of protein synthesis in the presence of immunotoxin was measured relative to untreated control cells. The standard immunoconjugates H65-RTA (H65-derivitized with SPDP linked to RTA), H65-Gelonin and H65-rGelonin, H65 fragment immunoconjugate, and gelonin immunoconjugate samples were diluted with RPMI without leucine at half-log concentrations ranging from 2000 to 0.632 ng/ml. All dilutions were added in triplicate to wells of microtiter plates containing $1 \times 10^5$ HSB2 cells per well. HSB2 plates were incubated for 20 hours at 37° C. and then pulsed with $^3$H-Leu for 4 hours before harvesting. Samples were counted on the Inotec Trace 96 cascade ionization counter. By comparison with an untreated sample, the picomolar concentration (pM) of immunotoxin which resulted in a 50% inhibition of protein synthesis ($IC_{50}$) was calculated. In order to normalize for conjugates containing differing amounts of toxin or toxin analog, the cytotoxicity data were converted to picomolar toxin (pM T) by multiplying the conjugate $IC_{50}$ (in pM) by the toxin/antibody ratio which is unique to each conjugate preparation.

The PMBC assays were performed as described by Fishwild et al., *Clin. and Exp. Immunol.*, 86:506–513 (1991) and involved the incubation of immunoconjugates with PBMCs for a total of 90 hours. During the final 16 hours of incubation, $^3$H-thymidine was added; upon completion, immunoconjugate-induced inhibition of DNA synthesis was quantified. The activities of the HE65 and chimeric H65 antibody conjugates against HSB2 cells and PBMC cells are listed in Table 2 below.

TABLE 2

| | $IC_{50}$ (pM T) | |
|---|---|---|
| Conjugate | HSB2 Cells | PBMCs |
| H65-RTA | 143 | 459 |
| H65-(M2IT)-S-S-(M2IT)-Gelonin | 1170 | 81 |
| H65-(M2IT)-S-S-(M2IT)-rGelonin | 276 | 75 |
| H65-(M2IT)-S-S-Gel$_{C10}$ | 140 | 28 |
| H65-(M2IT)-S-S-Gel$_{A50(C44)}$ | 99 | 51 |
| H65-(M2IT)-S-S-Gel$_{C239}$ | 2328 | 180 |
| H65-(M2IT)-S-S-Gel$_{C244}$ | >5000 | >2700 |
| H65-(M2IT)-S-S-Gel$_{C247}$ | 41 | 35 |
| H65-(M2IT)-S-S-Gel$_{C248}$ | 440 | 203 |
| cH65-RTA$_{30}$ | 60 | 400 |
| cH65-(M2IT)-S-S-(M2IT)-(Gelonin | 1770 | 140 |
| cH65-(M2IT)-S-S-(M2IT)-rGelonin | 153 | 120 |
| cH65-(M2IT)-S-S-Gel$_{C239}$ | >7000 | 290 |
| cH65-(M2IT)-S-S-Gel$_{C247}$ | 34 | 60 |
| cH65-(M2IT)-S-S-Gel$_{C248}$ | 238 | 860 |
| H65-(M2IT)-S-S-Gel$_{A44(50)}$ | 338 | ND* |
| H65-(M2IT)-S-S-Gel$_{C247A44A50}$ | 71 | ND* |

*Not determined

Against HSB2 cells, many of the gelonin analog immunoconjugates were significantly more potent than conjugates prepared with native gelonin or recombinant, unmodified gelonin, both in terms of a low $IC_{50}$ value, but also in terms of a greater extent of cell kill. Against human PBMCs, the gelonin analog conjugates were at least as active as native and recombinant gelonin conjugates. Importantly, however, some of the conjugates (for example, Gel$_{C10}$, Gel$_{A50(C44)}$ and Gel$_{C247}$) exhibited an enhanced potency against PBMCs compared to native and recombinant gelonin conjugates, and also exhibited an enhanced level of cell kill.

The activities of the H65 antibody fragment conjugates against HSB2 cells and PBMC cells are listed in Tables 3 and 4 below, wherein extent of kill in Table 3 refers to the percentage of protein synthesis inhibited in HSB2 cells at the highest immunotoxin concentration tested 1 µg/ml).

TABLE 3

| | $IC_{50}$ (pM T) | |
|---|---|---|
| Conjugate | HSB2 Cells | PBMCs |
| cH65Fab'-RTA 30 | 530 | 1800 |
| cH65Fab'-rGelonin | 135 | 160 |
| cH65Fab'-Gel$_{C247}$ | 48 | 64 |
| cH65F(ab')$_2$-RTA 30 | 33 | 57 |
| cH65F(ab')$_2$-rGelonin | 55 | 34 |
| cH65F(ab')$_2$-Gel$_{C247}$ | 23 | 20 |
| cH65F(ab')$_2$-Gel$_{C248}$ | 181 | 95 |

TABLE 4

| | $IC_{50}$ (pM T) | |
|---|---|---|
| Conjugate | HSB2 Cells | Extent of Kill |
| he1 Fab'-Gel$_{247}$ | 57.7 | 93% |
| he1 Fab-Gel$_{C247}$ | 180.0 | 94% |
| he2-Fab-Gel$_{A50(C44)}$ | 363.0 | 91% |
| he3-Fab-Gel$_{A50(C44)}$ | 191.0 | 93% |
| cH65Fab'-Gel$_{C247}$ | 47.5 | 93% |
| cH65F(ab')$_2$-rGelonin | 45.4 | 85% |
| cH65F(ab')$_2$-Gel$_{C247}$ | 77.5 | 83% |
| cH65F(ab')$_2$-Gel$_{C247}$ | 23.2 | 85% |

The data in Table 3 show that monovalent (Fab or Fab') fragments conjugated to various forms of gelonin are more potent than RTA conjugates. Table 4 shows that the human-engineered gelonin-Fab conjugates exhibit a very high degree of extent of kill.

EXAMPLE 9
Properties Of Gelonin Immunoconjugates
A. Solubility

Recombinant gelonin and the gelonin analogs exhibited enhanced solubility in comparison to both native gelonin and RTA30. In addition, recombinant gelonin and gelonin analog immunoconjugates exhibited enhanced solubility relative to immunoconjugates prepared with native gelonin and RTA30. This enhanced solubility was particularly noteworthy for recombinant gelonin and analog conjugates prepared with chimeric Fab fragments.

B. Disulfide Bond Stability Assay

The stability of the disulfide bond linking a RIP to a targeting molecule (such as an antibody) is known to influence the lifespan of immunoconjugates in vivo [See Thorpe et al., Cancer Res., 47:5924–5931 (1987), incorporated by reference herein]. For example, conjugates in which the disulfide bond is easily broken by reduction in vitro are less stable and less efficacious in animal models [See Thorpe et al., Cancer Res., 48:6396–6403 (1988), incorporated by reference herein].

Immunoconjugates prepared with native gelonin, recombinant gelonin and gelonin analogs were therefore examined in an in vitro disulfide bond stability assay similar to that described in Wawrzynczak et al., Cancer Res., 50:7519–7526 (1990), incorporated by reference herein. Conjugates were incubated with increasing concentrations of glutathione for 1 hour at 37° C. and, after terminating the reaction with iodoacetamide, the amount of RIP released was quantitated by size-exclusion HPLC on a TosoHaas TSK-G2000SW column.

By comparison with the amount of RIP released by high concentrations of 2-mercaptoethanol (to determine 100% release), the concentration of glutathione required to release 50% of the RIP (the $RC_{50}$) was calculated. The results of assays for H65 antibody conjugates are set out in Table 5 below.

TABLE 5

| Conjugate | $RC_{50}$ (mM) |
| --- | --- |
| H65-RTA 30 | 3.2 |
| H65-(M2IT)-S-S-(M2IT)-gelonin | 11.1 |
| H65-(M2IT)-S-S-(M2IT)-rGelonin | 3.0 |
| H65-(M2IT)-S-S-Gel$_{C10}$ | 2.5 |
| H65-(M2IT)-S-S-Gel$_{A50(C44)}$ | 0.6 |
| H65-(M2IT)-S-S-Gel$_{C239}$ | 774.0 |
| H65-(M2IT)-S-S-Gel$_{C244}$ | 1.2 |
| H65-(M2IT)-S-S-Gel$_{C247}$ | 0.1 |
| H65-(M2IT)-S-S-Gel$_{C248}$ | 0.4 |
| cH65-RTA 30 | 2.50 |
| cH65-(M2IT)-S-S-(M2IT)-rGelonin | 2.39 |
| cH65-(M2IT)-S-S-Gel$_{C247}$ | 0.11 |
| cH65-(M2IT)-S-S-Gel$_{C248}$ | 0.32 |
| H65-(M2IT)-S-S-Gel$_{A44(C50)}$ | 9.2 |
| H65-(M2IT)-S-S-Gel$_{C247A44A50}$ | 0.3 |

The foregoing results indicate that the stability of the bonds between the different gelonin proteins and H65 antibody varied greatly. With the exception of Gel$_{C10}$ and Gel$_{C239}$, most of the gelonin analogs resulted in conjugates with linkages that were somewhat less, stable in the in vitro assay than the dual-linker chemical conjugate. The stability of the Gel$_{C239}$ analog, however, was particularly enhanced.

The results of the assay for H65 antibody fragment conjugates are set out in Table 6 below.

TABLE 6

| Conjugate | $RC_{50}$ (mM) |
| --- | --- |
| he1 Fab'-Gel$_{C247}$ | 0.07 |
| cFab'-Gelonin | 1.27 |
| cFab'-Gel$_{C247}$ | 0.08 |
| cF(ab')$_2$-RTA 30 | 1.74 |
| cF(ab')$_2$-rGelonin | 2.30 |
| cF(ab')$_2$-Gel$_{C247}$ | 0.09 |
| CF(ab')$_2$-Gel$_{C248}$ | 0.32 |
| he2-Fab-Gel$_{A50(C44)}$ | 0.46 |
| he3-Fab-Gel$_{A50(C44)}$ | 0.58 |

From the $RC_{50}$ results presented in Tables 5 and 6, it appears that the particular RIP analog component of each immunotoxin dictates the stability of the immunotoxin disulfide bond in vitro.

EXAMPLE 10
Pharmacokinetics Of Conjugates To H65 Antibody

The pharmacokinetics of gelonin analogs Gel$_{C247}$, Gel$_{A50}$ (C44), and Gel$_{C10}$ linked to whole H65 antibody was investigated in rats. An IV bolus of 0.1 mg/kg of $^{125}$I-labelled immunoconjugate H65-(M2IT)-S-S-Gel$_{C247}$, H65-(M2IT)-S-S-Gel$_{A50(C44)}$ or H65-(M2IT)-S-S-Gel$^{C10}$ was administered to male Sprague-Dawley rats weighing 134–148 grams. Serum samples were collected from the rats at 3, 15, 30 and 45 minutes, and at 1.5, 2, 4, 6, 8, 18, 24, 48, 72, and 96 hours. Radioactivity (cpm/ml) of each sample was measured, and SDS-PAGE was performed to determine the fraction of radioactivity associated with whole immunoconjugate. Immunoconjugate-associated serum radioactivity was analyzed using the computer program PCNONLIN (SCI Software, Lexington, Ky.). Table 7 below lists the pharmacokinetic parameters of the immunoconjugates. In that table, the standard error for each value is indicated and a one way analysis of variance is presented. IC is the immunoconjugate (specified by the abbreviation for the gelonin variant that is part of the immunoconjugate), n is the number of animals in the study, Vc is the central volume of distribution, Cl is the clearance, MRT is the total body mean residence time, Alpha is the α half-life and Beta is the β half-life of the immunoconjugate.

TABLE 7

| IC | Vc (ml/kg) | Cl (ml/hr/kg) | MRT (hours) | Alpha (hours) | Beta (hours) |
| --- | --- | --- | --- | --- | --- |
| H65 Gel$_{C247}$ n = 32 | 65.3 ± 3.4 | 11.0 ± 0.4 | 16.5 ± 1.9 | 2.3 ± 0.2 | 20.5 ± 3.0 |
| H65 Gel$_{A50(C44)}$ n = 38 | 61.9 ± 2.4 | 4.1 ± 0.1 | 22.7 ± 0.7 | 3.0 ± 0.7 | 17.8 ± 0.8 |
| H65 Gel$_{C10}$ n = 45 | 59.2 ± 1.3 | 2.5 ± 0.04 | 42.7 ± 1.1 | 3.3 ± 0.3 | 32.9 ± 1.1 |
| p-value | 0.176 | <0.0001 | <0.0001 | 0.303 | <0.0001 |

The Gel$_{C247}$ immunoconjugate was found to have a α and β half lives of 2.3 and 20 hours, with a total mean residence time of 17 hours. The 72 and 96 hour time points were excluded from analysis because of the poor resolution of immunoconjugate associated radioactivity on the SDS-PAGE gel for these serum samples.

Because in vitro studies suggested that the Gel$_{C10}$ immunoconjugate had greater disulfide bond stability, it was anticipated that its half lives in vivo would be longer relative to the cys$_{247}$, form of the immunoconjugate. The β half life of the immunoconjugate was about 33 hours compared to 20 hours for the $Gel_{C247}$ conjugate. The total mean residence time was also much greater for the $Gel_{C10}$ immunoconjugate (42 hours versus 42 hours for the $Gel_{247}$ conjugate). In addition, the clearance of the $Gel_{C10}$ immunoconjugate was 2.5 ml/hr/kg, about four times less than that of the $Gel_{C247}$ immunoconjugate (11 ml/hr/kg). As also predicted from the in vitro disulfide stability data, the clearance of the $Gel_{A50(C44)}$ immunoconjugate was intermediate between those of the $Gel_{C10}$ and $Gel_{C247}$ immunoconjugates.

Based on these studies, the $Gel_{C10}$ analog conjugated to H65 antibody has greater in vivo stability than the $Gel_{A50(C44)}$ and $Gel_{24}$ analogs conjugated to H65 antibody (as determined by the longer mean residence time and clearance rates), although the properties of the $Gel_{A50(C44)}$ immunoconjugate more closely resembled those of the $Gel_{C10}$ immunoconjugate than the $Gel_{C247}$ immunoconjugate.

EXAMPLE 11
Pharmacokinetics Of Conjugates To H65 Antibody Fragments

The pharmacokinetics of $Gel_{C247}$ and $Gel_{A50(C44)}$ analogs linked to human engineered H65 Fab fragments were also investigated in rats. An IV bolus of 0.1 mg/kg of $^{125}$I-labelled he1 H65 Fab-$Gel_{C247}$, he2 H65 Fab-$Gel_{A50(C44)}$ or he3 H65 Fab-$Gel_{A50(C44)}$ was administered to male Sprague-Dawley rats weighing 150–180 grams. Serum samples were collected at 3, 5, 15, 20, 30, and 40 minutes, and 1, 1.5, 3, 6, 8, 18, 24, 32, 48, and 72 hours, and were analyzed by ELISA using rabbit anti-Gelonin antibody as the capture antibody and biotin-labelled goat anti-human kappa light chain antibody as the secondary antibody. Results of the analysis are presented in Table 8 below. In the table, the standard error for each value is shown, and IC is the immunoconjugate, n is the number of animals in the study, Vc is the central volume of distribution, Vss is the steady state volume of distribution, Cl is the clearance, MRT is the total body mean residence time, Alpha is the α half-life and Beta is the half-life of the indicated conjugate.

EXAMPLE 12
Immunogenicity Of Immunoconjugates

Outbred Swiss/Webster mice were injected repeatedly (0.2 mg/kg each injection.) with murine H65 antibody conjugates prepared with RTA, RTA30 and recombinant gelonin. The cycle was such that each animal was injected on days 1 and 2, and then the injections were repeated 28 and 29 days later. The animals received 5 such cycles of injections. One week and three weeks following each series of injections, blood was collected and the amount of anti-RIP antibodies present was determined by ELISA; peak titers for each cycle are shown in Table 9. RTA and RTA30 generated strong responses which began immediately following the first cycle of injections and remained high throughout the experiment. In contrast, no immune response was detected for the gelonin conjugate, even after 5 cycles of injections. When the conjugates were mixed with Complete Freund Adjuvant and injected i.p. into mice, anti-PTA and RTA-30 antibodies were readily detected after several weeks. These data indicate that anti-gelonin antibodies, if generated, would have been detected by the ELISA assay, and suggest that recombinant gelonin may be much less immunogenic in animals than is RTA.

TABLE 9

| Cycle | H65-RTA | H65-RTA30 | H65-rGel |
| --- | --- | --- | --- |
| Prebleed | 100 | 100 | 100 |
| Cycle 1 | 168 | 117 | 100 |
| Cycle 2 | 4208 | 1008 | 100 |
| Cycle 3 | 7468 | 3586 | 100 |
| Cycle 4 | 5707 | 3936 | 100 |
| Cycle 5 | 4042 | 2505 | 100 |

EXAMPLE 13
In vivo Efficacy Of Immunoconjugates

A human peripheral blood lymphocyte (PBL)-reconstituted, severe combined immunodeficient mouse model was utilized to evaluate the in vivo efficacy of various

TABLE 8

| IC | Vc (ml/kg) | Vss (ml/hr/kg) | Cl (ml/hr/kg) | MRT (hours) | Alpha (hours) | Beta (hours) |
| --- | --- | --- | --- | --- | --- | --- |
| he1 $Gel_{C247}$ n = 27 | 48 ± 3 | 133 ± 7 | 62 ± 3 | 2.1 ± 0.1 | 0.33 ± 0.03 | 3.0 fixed |
| he2 $Gel_{A50(C44)}$ n = 28 | 54 ± 5 | 141 ± 8 | 53 ± 3 | 2.7 ± 0.2 | 0.37 ± 0.04 | 3.1 fixed |
| he3 $Gel_{A50(C44)}$ n = 33 | 77 ± 6 | 140 ± 20 | 57 ± 3 | 2.5 ± 0.4 | 0.58 ± 0.11 | 3.0 ± 1.0 | comparing the three immunoconjugates, the pharmacokinetics of he1 H65 Fab-$Gel_{C247}$, he2 H65 Fab-$Gel_{A50(C44)}$ and he3-Fab-$Gel_{A50(C44)}$ were very similar, having similar alpha and beta half-lives, mean residence times, and clearance, particularly when comparing parameters obtained from the ELISA assayed curves. This is in contrast to their whole antibody immunoconjugate counterparts, where the clearance of $Gel_{C247}$ immunoconjugate (11 ml/kg/hr) was threefold greater than that of $Gel_{A50(C44)}$ immunoconjugate (4 ml/kg/hr). This suggests that cleavage of the disulfide bond linking the Fab fragment and gelonin is not as important for the serum clearance of Fab immunoconjugates as for whole antibody immunoconjugates.

immunoconjugates comprising the gelonin analogs $Gel_{C247}$ and $Gel_{A50(C44)}$. Immunoconjugates were tested for the capacity to deplete human blood cells expressing the CD5 antigen.

A. Human PBL Donors And Cell Isolation

Human peripheral blood cells were obtained from lymphapheresis samples (HemaCare Corporation, Sherman Oaks, Calif.) or venous blood samples (Stanford University Blood Bank, Palo Alto, Calif.) collected from healthy donors. Blood cells were enriched for PBLs using Ficoll-Hypaque density gradient centrifugation (Ficoll-Paque®; Pharmacia, Piscataway, N.J.) and subsequently washed 4 times with PBS. Residual erythrocytes were lysed with RBC lysing buffer (16 μM ammonium chloride, 1 mM potassium bicarbonate, 12.5 µM EDTA) during the second wash. Cell viability in the final suspension was >95% as assessed by trypan blue dye exclusion.

B. Animals And Human PBL Transfer

CB.17 scid/scid (SCID) mice were purchased from Taconic (Germantown, N.Y.) or were bred under sterile conditions in a specific pathogen-free animal facility (original breeding pairs were obtained from Hana Biologics, Alameda, Calif.). Animals were housed in filter-top cages and were not administered prophylactic antibiotic treatment. Cages, bedding, food and water were autoclaved before use. All manipulations with animals were performed in a laminar flow hood.

Untreated SCID mice were bled for determination of mouse Ig levels. Human PBL-injected mice were bled at various intervals for quantitation of human Ig and sIL-2R. Blood collection was from the retro-orbital sinus into heparinized tubes. Blood samples were centrifuged at 300×g for 10 min, and plasma was collected and stored at −70° C. Mouse and human Ig were quantified using standard sandwich ELISAs. Briefly, flat-bottom microtiter plates (MaxiSorp Immuno-Plates, Nunc, Roskilde, Denmark) were coated overnight at 4° C. with goat anti-mouse IgG+IgA+ IgM (Zymed Laboratories, Inc., South San Francisco, Calif.) or goat anti-human Igs (Tago, Inc., Burlingame, Calif.) in bicarbonate buffer, pH 9.6. Plates were blocked for 2 hours at room temperature with 1% BSA in Tris-buffered saline, pH 7.5 (TBS), and then incubate at 37° C. for 1 hour with standards or samples serially-diluted in TBS/1% BSA/ 0.05% Tween 20. Standards used were a monoclonal mouse IgG2a (IND1 anti-melanoma; XOMA Corporation, Berkeley, Calif.) and polyclonal human Ig (Sigma Chemical Co., St. Louis, Mo.). Subsequently, plates were washed with TBS/Tween 20 and incubated at 37° C. for 1 hour with alkaline phosphatase-conjugated goat anti-mouse IgG+IgA+ IgM or goat anti-human Igs (Caltag Laboratories, South San Francisco, Calif.). Detection was by measurement of absorbance at 405 nm following incubation with 1 mg/ml p-nitrophenylphosphate (Sigma) in 10% diethanolamine buffer, pH 9.8. Plasma from a normal BALB/c mouse was used as a positive control in the mouse Ig ELISA. Plasma samples from naive SCID mice or normal BALB/c mice did not have detectable levels of human Ig. Human sIL-2R was quantified using an ELISA kit (Immunotech S.A., Marseille, France) as per the manufacturer's instructions.

Five-to-seven week old mice with low plasma levels of mouse Ig (<10 µg/ml) were preconditioned with an i.p. injection of cyclophosphamide (Sigma) at 200 mg/kg. Two days later, they were injected i.p. with 25–40×10⁶ freshly-isolated human PBL suspended in 0.8 ml PBS.

C. Immunoconjugate Treatment

SCID mice were bled at approximately 2 weeks after human PBL transplantation. Mice with undetectable (<10 pM) or low plasma levels of human sIL-2R were eliminated from the study. The cut-off for exclusion of mice with detectable, but low, levels of human sIL-2R was empirically determined for each study and was generally 20 pM. The remaining mice were divided into groups and were administered vehicle or immunoconjugate as an i.v. bolus (0.2 mg/kg) daily for 5 consecutive days. Animals were sacrificed 1 day after cessation of treatment for quantitation of human T cells in tissues and human sIL-2R in plasma.

D. Collection Of Tissues And Analysis Of PBL Depletion

Blood was collected from the retro-orbital sinus into heparinized tubes. Mice were then killed by cervical dislocation and spleens were removed aseptically. Single cell suspensions of splenocytes were prepared in HBSS by pressing the spleens between the frosted ends of sterile glass microscope slides. Collected cells were washed twice with PBS. Erythrocytes were eliminated from blood and splenocyte suspensions using RBC lysing buffer. Subsequently, cells were resuspended in PBS for enumeration. Recovered cells were then assayed for Ag expression using flow cytometry.

Two to five hundred thousand cells in 100 µl of PBS/1% BSA/0.1% sodium azide were incubated on ice for 30 min. with saturating amounts of various FITC- or phycoerythrin (PE)-conjugated Abs (Becton-Dickinson, Mountain View, Calif.) Abs used for staining included: HLe-1-FITC (IgG1 anti-CD45), Leu 2-FITC (IgG1 anti-CD8), Leu 3 PE (IgG1 anti-CD4), and Leu M3-PE (IgG2a anti-CD14). Cells were then washed in cold buffer and fixed in 0.37% formaldehyde in PBS. Samples were analyzed on a FACscan (Becton-Dickinson) using log amplifiers. Regions to quantify positive cells were set based on staining of cells obtained from naive SCID mice. The absolute numbers of human Ag-positive cells recovered from SCID tissues were determined by multiplying the percent positive cells by the total number of cells recovered from each tissue sample. The total number of leukocytes in blood was calculated using a theoretical blood volume of 1.4 ml/mouse. The detection limit for accurate quantitation of human cells in SCID mouse tissues was 0.5%. All statistical comparison between treatment groups were made using the Mann-Whitney U test. Treatment groups were determined to be significantly different from buffer control groups when the p value was <0.05. Results are presented in Table 10 below, wherein + indicates a significant difference from controls.—indicates an insignificant difference and NT means the conjugate was not tested. CD5 Plus (XOMA Corporation, Berkeley, Calif.) is mouse H65 antibody chemically linked to RTA and is a positive control. 0X19 Fab-Gel$_{c247}$ is a negative control immunoconjugate. The 0X19 antibody (European Collection of Animal Cell Cultures #84112012) is a mouse anti-rat CD5 antibody that does not cross react with human CD5.

TABLE 10

|  | Human T Cell Depletion | |
| --- | --- | --- |
| Test Article | Spleen | Blood |
| CD5 Plus | + | + |
| cH65 F(ab')$_2$ | − | − |
| cH65 Fab' | − | − |
| H65-rGEL | + | + |
| cH65 F(ab')$_2$-rGel | + | + |
| cH65 Fab'-rGel | + | + |
| cH65 F(ab')$_2$-Gel$_{c247}$ | + | NT |
| cH65 Fab'-Gel$_{c247}$ | + | + |
| he1H65 Fab'-Gel$_{c247}$ | + | NT |
| cH65 Fab'-Gel$_{ASO(C44)}$ | + | + |
| OX19 FAB-Gel$_{c247}$ | − | − |

All the gelonin immunoconjugates were capable of depleting human cells in the SCID mouse model.

EXAMPLE 14

Construction Of Gelonin Immunofusions With Chimeric Antibodies

Several genetic constructs were assembled which included a natural sequence gelonin gene fused to an H65 truncated heavy chain gene (Fd or Fd'), or an H65 light chain gene (kappa). In this Example, H165 Fd, Fd', and H65 light chain refer to chimeric constructs. The H65 Fd sequence consists of the nucleotides encoding the murine H65 heavy chain variable (V), joining (J) and human IgG$_1$, constant (C)

domain 1 regions, including the cysteine bound to light chain IgG$_1$ and has the carboxyl terminal sequence SCDKTHT (SEQ ID NO: 130). The H65 Fd' sequence has the H65 Fd sequence with the addition of the residues CPP from the hinge region of human IgG$_1$ heavy chain, including a cysteine residue which is bound to the other human IgG$_1$ heavy chain and its F(ab')$_2$ fragment. See Better, et al., *Proc. Nat. Acad. Sci. (USA)*, 90: 457–461 (1993), incorporated by reference herein.

The H65 light chain sequence consists of the nucleotides encoding the murine H65 light chain variable (V), joining (J), and human kappa (C$_k$) regions. The DNA sequences of the V and J regions of the H65 Fd and kappa fragment genes linked to the pelB leader can be obtained from GenBank (Los Alamos National Laboratories, Los Alamos, N. Mex.) under Accession Nos. 1M90468 and M90467, respectively. Several of the gene fusions included a gelonin gene linked at the 5' end of an H65 Fab fragment gene while the others included a gelonin gene linked at the 3' end of an H65 Fab fragment gene. A DNA linker encoding a peptide segment of the *E. coli* shiga-like toxin (SLT) (SEQ ID NO: 56), which contains two cysteine residues participating in a disulfide bond and forming a loop that includes a protease sensitive amino acid sequence) or of rabbit muscle aldolase [(RMA) as in SEQ ID NO: 57, which contains several potential cathepsin cleavage sites] was inserted between the gelonin gene and the antibody gene in the constructs. Alternatively, a direct fusion was made between a gelonin gene and an H65 Fab fragment gene without a peptide linker segment. Table 11 below sets out a descriptive name of each gene fusion and indicates the expression plasmid containing the gene fusion and the section of the application in which each is designated. Each plasmid also includes the Fab fragment gene (shown in parentheses in Table 11) with which each particular gene fusion was co-expressed. The inclusion of a cysteine from a hinge region (Fd') allows potential formation of either monovalent Fab' or bivalent F(ab')$_2$ forms of the expression product of the gene fusion.

TABLE 11

| Section | Plasmid | Description |
| --- | --- | --- |
| B(i) | pING3754 | Gelonin::SLT::Fd' (kappa) |
| B(ii) | pING3757 | Gelonin::SLT::kappa (Fd') |
| B(iii) | pING3759 | Gelonin::RMA::Fd' (kappa) |
| B(iv) | pING3758 | Gelonin::RMA::kappa (Fd') |
| A(i) | pING4406 | Fd::SLT::Gelonin (kappa) |
| A(ii) | pING4407 | kappa::SLT::Gelonin (Fd) |
| A(iii) | pING4408 | Fd::RMA::Gelonin (kappa) |
| A(iv) | pING4410 | kappa::RMA::Gelonin (Fd) |
| C(i) | pING3334 | Gelonin::Fd (kappa) |

A. Fusions Of Gelonin At The Carboxyl-Terminus Of Antibody Genes (i) Fd::SLT::Gelonin (kappa)

A gelonin gene fusion to the 3'-end of the H65 Fd chain with the 23 amino acid SLT linker sequence was assembled in a three piece ligation from plasmids pVK1, pING3731 (ATCC 68721) and pING4000. Plasmid pVK1 contains the Fd gene linked in-frame to the SLT linker sequence and some H65 Fd' and kappa gene modules as in pING3217, shown in Better, et al., *Proc. Nat. Acad. Sci. (USA)*: 457–461 (1993), except that the kappa and Fd' regions are reversed. Plasmid pING3731 contains the gelonin gene, and pING4000 contains the H65 kappa and Fd' genes each linked to the pelB leader sequence under the control of the araB promoter as a dicistronic message.

Plasmid pVK1 was designed to link the 3'-end of a human IgG Fd constant region in-frame to a protease-sensitive segment of the SLT gene bounded by two cysteine residues which form an intra-chain disulfide bond. The SLT gene segment (20 amino acids from SLT bounded by cysteine residues, plus three amino acids introduced to facilitate cloning) was assembled from two oligonucleotides, SLT Linker 1 and SLT Linker 2.

SLT Linker 1 (SEQ ID NO: 73)
5'  TGTCATCATCATGCATCGCGAGTTGCCAGAATGGCATCT
GATGAGTTTCCTTCTATGTGCGCAAGTACTC 3'

SLT Linker 2 (SEQ ID NO: 74)
5'  TCGAGAGTACTTGCGCACATAGAAGGAAACTCATCAGAT
GCCATTCTGGCAACTCGCGATGCATGATGATGACATGCA 3'

The two oligonucleotides were annealed and ligated into a vector (pING3185) containing PstI and XhoI cohesive ends, destroying the PstI site and maintaining the XhoI site. Plasmid pING3185 contained an engineered PstI site at the 3'-end of the Fd gene, and contained an XhoI site downstream of the Fd gene. The product of this ligation, pVK1, contained the H65 Fd gene (fused to the pelB leader) in frame with the SLT linker segment, and contained two restriction sites, FspI and ScaI, at the 3'-end of the SLT linker.

Plasmid PVK1 was digested with SauI and ScaI, and the 217 bp fragment containing a portion of the Fd constant domain and the entire SLT gene segment was purified by electrophoresis on an agarose gel. pING3731 was digested with SmaI and XhoI and the 760 bp gelonin gene was similarly purified. Plasmid pING4000 was digested with SauI and XhoI and the vector segment containing the entire kappa gene and a portion of the Fd gene was also purified. Ligation of these three DNA fragments resulted in pING4406 containing the Fd::SLT::Gelonin (kappa) gene fusion vector.

(ii) kappa::SLT::Gelonin (Fd)

A gelonin gene fusion to the 3'-end of the H65 kappa chain with the 25 amino acid SLT linker sequence (20 amino acids from SLT bounded by cysteine residues, plus 5 amino acids introduced to facilitate cloning) was assembled from the DNA segments in pING3731 (ATCC 68721) and pING3713.

Plasmid pING3713 is an Fab expression vector where the H65 Fd and kappa genes are linked in a dicistronic transcription unit containing the SLT linker segment cloned in-frame at the 3'-end of the kappa gene. The plasmid was constructed as follows. In a source plasmid containing the H65 Fd and kappa genes, an EagI site was positioned at the 3-end of the kappa gene by site directed mutagenesis without altering the encoded amino acid sequence. The SLT gene segment from pVK1 was amplified with primers SLT-EagI-5' and SalI for in frame linkage to the EagI site at the 3'-end of the kappa gene.

SLT-Eag-5' (SEQ ID NO: 75)
5' TGTTCGGCCGCATGTCATCATCATGCATCG 3'

SalI (SEQ ID NO: 76)
5' AGTCATGCCCCGCGC 3'

The 140 bp PCR product was digested with EagI and XhoI, and the 75 bp fragment containing the SLT gene segment was cloned adjacent to the Fd and kappa genes in the source plasmid to generate pING3713.

For construction of gene fusion to gelonin, pING3713 was cut with ScaI and XhoI, and the vector fragment containing the Fd gene and kappa::SLT fusion was purified. pING3731 was digested with SmaI and XhoI and the DNA fragment containing the gelonin gene was also purified. The product of the ligation of these two fragments, pING4407, contains the Fd and kappa::SLT::gelonin genes.

(iii) Fd::RMA::Gelonin (kappa)

A gelonin gene fusion to the 3'-end of the H65 Fd chain with the 21 amino acid RMA linker sequence (20 amino acids from RMA, plus 1 amino acid introduced to facilitate cloning) was assembled in a three piece ligation from plasmids pSH4, pING3731 (ATCC 68721) and pING4000.

Plasmid pSH4 contains an Fd (gene linked in frame to the RMA linker sequence. The RMA gene segment was linked to the 3'-end of Fd by overleap extension PCR as follows. The 3'-end (constant region) of the Fd gene was amplified by PCR from a source plasmid with the primers KBA-γ2 and RMAG-1. Any Fd constant region may be used because constant regions of all human $IgG_1$ antibodies are identical in this region.

KBA-γ2 (SEQ ID NO: 77)
5' TCCCGGCTGTCCTACAGT 3'

RMAG-1 (SEQ ID NO: 78)
5' TCCAGCCTGTCCAGATGGTGTGTGAGTTTTGTCACAA 3'

The product of this reaction was mixed with primer RMA-76, which annealed to the amplified product of the first reaction, and the mixture was amplified with primers KBA-γ2 and RMAK-2.

RMA-76 (SEQ ID NO: 79)
5' CTAACTCGAGAGTACTGTATGCATGGTTCGAGATGAACA

AAGATTCTGAGGCTGCAGCTCCAGCCTGTCCAGATGG 3'

RMAK-2 (SEQ ID NO: 80)
5' CTAACTCGAGAGTACTGTAT 3'

The PCR product contained a portion of the Fd constant region linked in-frame to the RMA gene segment. The product also contained a ScaI restriction site useful for in-frame fusion to a protein such as gelonin, and an XhoI site for subsequent cloning.

This PCR product was cut with SauI and XhoI and ligated adjacent to the remainder of the Fd gene to generate pSH4.

For assembly of the gene fusion vector containing the Fd::RMA::Gelonin, kappa genes, pSH4 was cut with SauI and ScaI and the Fd::RMA segment was purified. Plasmid pING3731 was cut with SmaI and XhoI and the 760 bp DNA fragment containing the gelonin gene was purified, and pING4000 was cut with SauI and XhoI and the vector was purified. The product of the ligation of these fragments, pING4408, contained the Fd::RMA::Gelonin and kappa genes.

(iv) kappa::RMA::Gelonin (Fd)

A gelonin gene fusion to the 3'-end of the H65 kappa chain with the 21 amino acid RMA linker sequence was assembled in a three piece ligation from plasmids pSH6, pING4408 (see the foregoing paragraph) and pING3713.

Plasmid pSH6 contains a kappa gene linked in-frame to the RMA linker sequence. The RMA gene segment was linked to the 3'-end of kappa by overlap extension PCR as follows. The 3'-end (constant region)i of the kappa gene was amplified by PCR from a source plasmid with the primers KBA-K2 and RMAK-1.

RMAK-1 (SEQ ID NO: 81)
5' TCCAGCCTGTCCAGATGGACACTCTCCCCTGTTGAA 3'

KBA-K2 (SEQ ID NO: 82)
5' GTACAGTGGAAGGTGGAT 3'

The product of this reaction was mixed with primer RMA-76 (SEQ ID NO: 81), which annealed to the amplified product of the first reaction, and the mixture was amplified with primers KBA-K2 and RMAK-2. The PCR product contained a portion of the kappa constant region linked in-frame to the RMA gene segment. The product also) contained a ScaI restriction site useful for in-frame fusion to a protein such as gelonin, and an XhoI site for subsequent cloning. This POP product was cut with SstI and XhoI and ligated adjacent to the remainder of the kappa gene to generate pSH6.

For assembly of the gene fusion vector containing the kappa::RMA::Gelonin and Fd genes, pSH6 was cut with HindIII and PstI and the DNA fragment containing the kappa constant region and a portion of the RMA linker (the PstI RMA linker segment contains a PstI site) segment was purified. Plasmid pING4408 was cut with PstI and SalI and the DNA fragment containing a segment of the RMA linker, the gelonin gene and a portion of the tetracycline resistance gene in the vector segment was purified. pING3713 was cut with SalI and HindIII and the vector was purified. The product of the ligation of these three fragments, pING4410, contained the kappa::RMA::Gelonin and Fd genes.

B. Fusions Of Gelonin At The Amino-Terminus Of Antibody Genes (I) Gelonin::SLT::Fd' (kappa)

A gelonin gene fusion to the 5'-end of the H65 Fd' chain with a 25 amino acid SLT linker sequence (20 amino acids from SLT bounded by cysteine residues, plus five amino acids introduced to facilitate cloning) was assembled in a three piece ligation from plasmids pING3748, pING3217, and a PCR fragment encoding the H65 heavy chain variable region ($V_H$) gene segment which is the variable region of the Fd' gene in pING3217. Plasmid pING3748 contains the gelonin gene linked in-frame to the SLT linker sequence, and pING3217 contains the H65 Fd' and kappa genes in a dicistronic transcription unit.

Plasmid pING3825 (see Example 2) was amplified with PCR primers gelo3'-Eag and gelo-9 to introduce an EagI restriction site at the 3'-end of the gelonin gene by PCR mutagenesis.

gelo3'-Eag (SEQ ID NO: 83)
5' CATGCGGCCGATTTAGGATCTTTATCGACGA 3'

The PCR product was cut with BclI and EagI and the 56 bp DNA fragment was purified. Plasmid pING3713 was cut with EagI and XhoI, and the 77 bp DNA fragment containing the SLT linker was purified. The 56 bp BclI to EagI fragment and the 77 bp EagI to XhoI fragment were ligated into pING3825 which had been digested with BclI and XhoI to generate pING3748 which contains the gelonin gene linked in-frame to the SLT linker sequence.

For assembly of the gene fusion vector containing the Gelonin::SLT::Fd' and kappa genes, the H65 $V_H$ was amplified by PCR from pING3217 with primers H65-G1 and H65-G2, and the product was treated with T4 polymerase followed by digestion with NdeI.

H65-G1 (SEQ ID NO: 84)
5' AACATCCAGTTGGTGCAGTCTG 3'
H65-G2 (SEQ ID NO: 85)
5' GAGGAGACGGTGACCGTGGT 3'

The 176 bp fragment containing the 5'-End of the H65 heavy chain V-region was purified. Concurrently, pING3217 was digested with NdeI and XhoI, and the 1307 bp DNA fragment containing a portion of the Fd' gene and all of the kappa gene was purified. The two fragments were ligated to pING3748 which had been digested with ScaI and XhoI in a three piece ligation yielding pING3754 (ATCC 69102), which contains the Gelonin::SLT::Fd' and kappa genes.

(ii) Gelonin::SLT::kappa (Fd')

A gelonin gene fusion to the 5'-end of the H65 kappa chain with the 25 amino acid SLT linker sequence was assembled in a three piece ligation from plasmids pING3748 (see the foregoing section), pING4000, and a PCR fragment encoding the H65 light chain variable region ($V_L$) gene segment.

For assembly of the gene fusion vector containing the Gelonin::SLT::kappa and Fd' genes, an H65 $V_L$ fragment was amplified by PCR from pING3217 with primers H65-K1 and JK1-HindIII, and the product was treated with T4 polymerase followed by digestion with HindIII.

H65-K1 (SEQ ID NO: 86)
5' GACATCAAGATGACCCAGT 3'
JK1-HindIII (SEQ ID NO: 87)
5' GTTTGATTTCAAGCTTGGTGC 3'

The 306 bp fragment containing the light chain V-region was purified. Concurrently, pING4000 was digested with HindIII and XhoI, and the 1179 bp DNA fragment containing the kappa constant region and all of the Fd' gene was purified. The two fragments were ligated to pING3748 which had been digested with ScaI and XhoI in a three piece ligation yielding pING3757, which contains the Gelonin::SLT-::kappa and Fd genes.

(iii) Gelonin::RMA::Fd' (kappa)

A gelonin gene fusion to the 5'-end of the H65 Fd' chain with the 24 amino acid RMA linker sequence (20 amino acids from RMA, plus 4 amino acids introduced to facilitate cloning) was assembled in a three piece ligation from plasmids pING3755, pING3217 and a PCR fragment encoding the H65 $V_H$ gene segment. Plasmid pING3755 contains the gelonin gene linked in-frame to the RMA linker sequence, and pING3217 contains the H65 Fd' and kappa genes in a dicistronic transcription unit.

Plasmid pING3755 was assembled to contain the gelonin gene linked to the RMA linker gene segment. The RMA linker gene segment was amplified by PCR from pSH4 with primers RMA-EagI and HINDIII-2.

RMA-EagI (SEQ ID NO: 88)
5' ACTTCGGCCGCACCATCTGGACAGGCTGGAG 3'
HINDIII-2 (SEQ ID NO: 44)
5' CGTTAGCAATTTAACTGTGAT 3'

The 198 bp PCR product was cut with EagI and HindIII, and the resulting 153 bp DNA fragment was purified. This RMA gene segment was cloned adjacent to gelonin using an PstI to EagI fragment from pING3748 and the PstI to HindIII vector fragment from pING3825. The product of this three piece ligation was pING3755.

For assembly of the gene fusion vector containing the Gelonin::RMA::Fd', kappa genes, the H65 $V_H$ was amplified by PCR from pING3217 with primers H65-G1 (SEQ ID NO: 84) and H65-G2 (SEQ ID NO: 85), and the product was treated with T4 polymerase followed by digestion with NdeI. The 186 bp fragment containing the 5'-end of the heavy chain V-region was purified. Concurrently, pING3217 was digested with NdeI and XhoI, and the 1307 bp DNA fragment containing a portion of the Fd' gene and all of the kappa gene was purified. These two fragments were ligated to pING3755 which had been digested with ScaI and XhoI in a three piece ligation yielding pING3759 (ATCC 69104), which contains the Gelonin::RMA::Fd' and kappa genes.

(iv) Gelonin::RMA::kappa (Fd')

A gelonin gene fusion to the 5'-end of the H65 kappa chain with the 24 amino acid RMA linker sequence was assembled in a three piece ligation from plasmids pING3755, pING4000, and a PCR fragment encoding the H65 $V_L$ gene segment.

For assembly of the gene fusion vector containing the Gelonin::RMA::kappa and Fd' genes, an H65 $V_L$ segment was amplified by PCR from pING3217 with primers H65K-1 (SEQ ID NO: 86) and JK1-HindIII, and the product was treated with T4 polymerase followed by digestion with HindIII. The 306 bp fragment containing the 5'-end of the light chain V-region was purified. Concurrently, pING4000 was digested with HindIII and XhoI, and the 1179 bp DNA fragment containing the kappa constant region and all of the Fd' gene was purified. These two fragments were ligated to pING3755 which had been digested with ScaI and XhoI in a three piece ligation yielding pING3758 (ATCC 69103), which contains the Gelonin::RMA::kappa and Fd' genes.

C. Direct Fusions Of Gelonin At The Amino Terminus Of Antibody Genes (i) Gelonin::Fd' (Kappa)

A direct gelonin gene fusion was constructed from pING3754. pING3754 was digested with BglII and XhoI and the vector segment was purified. Concurrently, pING3754 was digested with EagI, treated with T4 polymerase, cut with BglII, and the gelonin gene segment was purified. pING3754 was also cut with FspI and XhoI, and the Fd and kappa gene segment was purified. These fragments were assembled in a three-piece ligation to generate pING3334, which contains a direct gene fusion of gelonin to Fd' in association with a kappa gene.

EXAMPLE 15
Preparation of he3 Fab And Gelonin he3Fab Immunofusions

The sections below detail the construction of human-engineering he3Fab protein and immunofusions of gelonin to he3 Fd and kappa chains.

A. he3-Fab Expression Plasmids

The he3 heavy chain V-region was PCR-amplified from plasmid pING4621 (pING4621 is fully described above in Example 5 above), with primers H65-G3, GAGATCCAGT-TGGTGCAGTCTG (SEQ ID NO: 116) and H65G2 (SEQ ID NO: 85). Amplification was carried at using vent polymerase (New England Biolabs) for 25 cycles, including a 94° C. denaturation for 1 minute, annealing at 50° C. for 2 minutes, and polymerization for 3 minutes at 72° C . The PCR product was treated with polynucleotide kinase and digested with BstEII and the V-region DNA was purified. The purified DNA fragment was then ligated into pIC100, which had been digested with SstI, treated with T4 polymerase, and cut with BstEII. The resulting fragment was then ligated with the BstEII fragment from pING3218 (containing Fab' genes) to make pING4623 which contained the he3 Fd gene linked to the pelb leader sequence.

The he3 kappa V-region was next assembled as described above in Example 5 and in co-owned, co-pending U.S. patent application Ser. No. 07/8083,464, incorporated by reference herein, using six oligonucleotide primers.

SH65k-1, AGT CGT CGA CAC GAT GGA CAT GAG GAC CCC TGC TCA GTT TCT TGG CAT CCT CCT ACT CTG GTT TCC AGG TAT CAA ATG TGA CAT CCA GAT GAC TCA GT (SEQ ID NO: 117);

HUH-K6, TCA CTT GCC GGG CGA ATC AGG ACA TTA ATA GCT ATT TAA GCT GGT TCC AGC AGA AAC CAG GGA AAG CTC CTA AGA CCC T (SEQ ID NO: 118);

HUH-K7, TGA CTC GCC CGG CAA GTG ATA GTG ACT CTG TCT CCT ACA GAT GCA GAC AGG GAA GAT GGA GAC TGA GTC ATC TGG ATG TC (SEQ ID NO: 119);

HUH-K8, GAT CCA CTG CCA CTG AAC CTT GAT GGG ACC CCA GAT TCC AAT CTG TTT GCA CGA TAG ATC AGG GTC TTA GGA GCT TTC C (SEQ ID NO: 120);

HUH-K4, GGT TCA GTG GCA GTG GAT CTG GGA CAG ATT ATA CTC TCA CCA TCA GCA GCC TGC AAT ATG AAG ATT TTG GAA TTT AAT ATT C (SEQ ID NO: 121); and HUH-K5, GTT TGA TTT CAA GCT TGG TGC CTC CAC CGA ACG TCC ACG GAG ACT CAT CAT ACT GTT GAC AAT AAT AAA TTC AAA AAT CTT C (SEQ ID NO: 122)

and amplified with primers HUK-7 (SEQ ID NO: 92) and JK1-HindIII (SEQ ID NO: 87).

The resulting PCR product was treated with T4 polymerase, digested with HindIII, and purified. The purified fragment was then cloned into pIC100, which had first been cut with SstI, treated with T4 polymerase, and digested with XhoI, along with the 353 bp HindIII-XhoI fragment encoding the kappa constant region from pING3217. The resulting plasmid was pING4627 which contains the he3 kappa sequence linked in frame to the pelB leader.

Plasmid pING4628, containing the pelB-linked he3 kappa and Fd genes under transcriptional control of the araB promoter, was assembled from pING4623 and pING4627 as follows.

An expression vector for unrelated kappa and Fd genes, pNRX-2, was first cut with SauI and EcoRI, leaving a vector fragment which contains all the features relevant to plasmid replication, a tetracycline resistance marker, araB transcriptional control, and the 3' end of the Fd constant region. [Plasmid pNRX-2 comprises an EcoRI to XhoI DNA segment from pING 3104 (described in WO 90/02569, incorporated by reference herein). That segment contains the replication, resistance and transcription control features of pING3104 and is joined to an XhoI to SauI DNA segment from pING1444 (described in WO 89/00999, incorporated by reference herein) which contains the 3' end of an Fd constant region.] Next pING4623 was cut with PstI, treated with T4 polymerase, digested with SauI and the pelB::Fd gene segment was then isolated. Plasmid pING4627 was cut with XhoI, treated with T4 polymerase, cut with EcoRI and ligated to the pelB::Fd gene segment and the pNRX-2 vector fragment to generate the he3-Fab expression vector pING4628. That plasmid contains two XhoI sites, one located between the kappa and Fd genes, and another 4 bp downstream of the termination codon for the Fd gene.

A vector, pING4633, which lacks the XhoI site between the kappa and Fd genes was constructed. To assemble pING4633, pING4623 was cut with EcoRI, treated with T4 polymerase, digested with SauI. The pelB::kappa gene segment was then isolated and purified. The pNRX-2 vector fragment and the pelB::Fd gene segment were then ligated to the purified pelB::kappa gene segment to form pING4633.

Both pING4633 and pING4628 are bacterial expression vectors for he3-Fab and each comprises the he3 Fd and Kappa genes which are expressed as a dicistronic message upon induction of the host cell with L-arabinose. Moreover, pING4628 contains two XhoI restriction sites, one located 4 bp past the Fd termination codon and one in the intergenic region between the 3' end of the Kappa gene and the 5' end of the Fd gene. Plasmid pING4633 lacks the XhoI site in the intergenic region.

B. Purification Of he3Fab

Plasmids pING4628 and pING4633 were transformed into E. coli E104. Bacterial cultures were induced with arabinose and cell-free supernatant comprising the he3Fab was concentrated and filtered into 20 mm HEPES, pH 6.8. The sample was then loaded onto a CM Spheradex column (2.5×3 cm), equilibrated in 20 mM HEPEs, 1.5 mM NaCl, pH 6.8. The column was washed with the same buffer and eluted with 20 mm HEPES, 27 mM NaCl, pH 6.8. The eluate was split into 2 aliquots and each was loaded onto and eluted from a protein G (Bioprocessing) column (2.5×2.5 cm) separately. The protein G column was equilibrated in 20 mM HEPES, 75 MM NaCl, pH 6.8 and the sample was eluted with 100 mM glycine, 100 mM NaCl, pH 3.0. The two eluates were combined and diluted two times with 20 mM HEPES, 3 M ammonium sulfate, pH 6.8. The diluted eluates were loaded onto phenyl sepharose high substitution Fast Flow (Pharmacia) column (2.5×3.3 cm), equilibrated n 20 mM HEPES, 1.5M ammonium sulfate, pH 6.8. The column was then eluted with 20 mM HEPES, 0.6M ammonium sulfate, pH 6.8.

C. Gelonin::RMA::he3Kappa, he3Fd Fusions

Other genetic constructs were assembled which included a natural sequence gelonin gene fused to an he3-Fab via a linker.

A fusion comprising Gelonin::RMA::he3Kappa, Fd was assembled from DNA from plasmids pING3755, pING4633, and pING4628. Both pING4633 and pING4628 were assembled in a series of steps whereby the he3 heavy and light V-regions were individually linked in-frame to the pelB leader. The heavy and light V-regions were then placed together in a dicistronic expression vector under under the control of the araB promoter in a bacterial expression vector.

Assembly of the Gelonin::RMA::he3Kappa, he3Fd fusions was accomplished by constructing three DNA fragments from plasmids pING3755, pING4633, and pING4628. The first such fragment was made by digesting pING3755 with ScaI and XhoI which excises the 4 bp between those sites. The resulting vector fragment was purified. The second fragment for use in constructing the above fusions was obtained from plasmid pING4633, which was cut with AseI (which cuts in $V_L$) and XhoI and the resulting 1404 bp fragment, containing the 3' end segment of the Kappa and Fd genes, was purified. The third fragment, comprising the 5' end of the Kappa variable region coding sequence, was prepared from the PCR amplified $V_L$ gene contained in pING4628 using the oligonucleotide primers, Huk-7 and jk1-HindIII. The resulting 322 bp PCR-amplified $V_L$ fragment was treated with T4 polymerase, digested with AseI, and the 86 bp fragments containing the 5' end of $V_L$ was purified. The three fragment produced above were ligated together to form pING3764. The DNA sequence of the PCR amplified V-region was verified by direct DNA sequencing of pING3764.

D. Gelonin::SLT::he3Kappa, he3Fd Fusion

A Gelonin::SLT::he3Kappa, he3Fd fusion was constructed by ligating the pING4633 and pING4628 fragments described in section A immediately above with a fragment produced from pING3748 which contains Gelonin::SLT. The pING3748 fragment was produced using ScaI and XhoI as described immediately above for pING3755. The resulting vector was designated pING3763.

E. Construction of Expression Vector Containing Gelonin::SLT::he3Fd, he3kappa Fusions An expression vector containing the Gelonin::SLT::he3 Fd, he3kappa fusion was constructed in two steps form DNA segments from plasmids pING3825, pING4628, pING4639, pING3217 [described in Better, et al., *Proc. Natl. Acad. Sci. (USA),* 90:457–461 (1993), incorporated by reference herein], and pING4627. pING3825 was digested with NcoI and XhoI, generating a 654 bp fragment containing the 3' end of the gelonin gene and a fragment containing the 5' end of the gelonin gene which were purified. Next, pING4639 was digested with NcoI and NdeI and the 903 bp fragment containing the 3' end of the Gelonin gene, the SLT linker, and the 5' end of $V_H$ which resulted was purified. Finally, pING4628 was cut with NdeI and XhoI, resulting in a 523 bp fragment containing the 3' end of the Fd gene which was purified. The three fragments were then ligated to form plasmid pING3765 which contains a gene encoding a gelonin::SLT::he3Fd fusion.

Three vector fragments were used to assemble the final expression vector (containing the gelonin::SLT::he3Fd and he3 kappa segments). Plasmid pING3765 was digested with XhoI, treated with T4 polymerase, cut with NheI (which releases a 265 bp fragment encoding the tetracycline resistent marker), and the resulting vector fragment was purified. Plasmid pING4627, which contains the he3Kappa gene linked in-frame to the pelB leader was used for the construction of pING4628. Plasmid pING4627 was cut with PstI, treated with T4 polymerase, and further digested with SstI. The resulting 726 bp fragment, containing the Kappa gene (except 40 bp at the 3' end) was purified. Plasmid pING3217 was then cut with SstI and NheI, resulting in a 318 bp fragment containing the 3' end of the Kappa gene and downstream portion, including a portion of the tetracycline resistance gene, which was purified. Ligation of the foregoing three fragments produced the final expression vector, pING3767.

F. Construction Of Expression Vector Containing Gelonin::RMA::he3Kappa Fusions

Gelonin::RMA:he3Kappa, he3Fd fusion expression vectors was constructed in two steps from plasmids pING3825, pING4628, pING3217, and pING4627. The cloning scheme used was identical to that used to generate pING3767 except that pING4638 was substituted for pING4639. Plasmid pING4638 differs from pING4639 as described below in Example 16. The intermediate vector encoding the Gelonin::RMA::Fd fusion was designated pING3766 and the final expression vector was designated pING3768.

EXAMPLE 16

Gelonin-Single Chain Antibody Fusions

The natural sequence gelonin gene was also fused to a single chain form of the human engineered he3 H65 variable region. The gelonin gene was positioned at either the N-terminus or the C-terminus of the fusion gene and the SLT or RMA linker peptide was positioned between the gelonin and antibody domains to allow intracellular processing of the fusion protein with subsequent cytosolic release of gelonin.

A. Construction of Gel:: RMA::SCA ($V_L$-$V_H$), Gel::SLT::SCA ($V_L$-$V_H$), Gel::RMA::SCA ($V_H$-$V_L$), and (Gel::SLT::SCA ($V_H$-$V_L$)

A single chain antibody (SCA) form of the he3 H65 variable domain was assembled from previously constructed genes. This SCA segment consisted of the entire V and J region of the one chain (heavy or light) linked to the entire V and J segment of the other chain (heavy or light) via a 15 amino acid flexible peptide: [(Gly)$_4$Ser]$_3$. This peptide is identical to that described in Huston et al., *Proc. Natl. Acad. Sci. USA,* 85:5879–5883 (1988); Glockshuber et al., *Biochemistry,* 29:1362–1367 (1990); and Cheadle et al., *Molecular Immunol.,* 29:21–30 (1992). The SCA was assembled in two orientations: V-J$_{kappa}$::[(Gly)$_4$Ser]$_3$::V-J$_{Gamma}$ and V-J$_{Gamma}$::[(Gly)$_4$Ser]$_3$::V-J$_{kappa}$. Each SCA segment was assembled and subsequently fused to gelonin.

For assembly of the SCA segment V-J$_{kappa}$::[(Gly)$_4$Ser]$_3$::V-J$_{Gamma}$, primers HUK-7 and SCFV-1 were used to amplify a 352 bp DNA fragment containing the he3 V/J kappa sequences from pING4627 by PCR in a reaction containing 10 mM KCl, 20 mM TRIS pH 8.8, 10 mM (NH$_4$)$_2$SO$_2$, 2 mM MgSO$_4$, 0.1% Triton X-100., 100 ng/ml BSA, 200 uM of each dNTP, and 2 Units of Vent polymerase (New England Biolabs, Beverley, Mass.) in a total volume of 100 μl.

SCFV-1 (SEQ ID NO: 91)
5' CGGACCCACCTCCACCAGATCCACCGC CACCTTTCATCTCAAGCTTGGTGC 3'
HUK-7 (SEQ ID NO: 92)
5' GACATCCAGATGACTCAGT 3'

Concurrently, primers SCFV-2 and SCFV-3 were used to amplify a he3 heavy chain V/J gamma segment from pING4623, generating a 400 bp fragment.

SCFV-2 (SEQ ID NO: 93)
5' GGTGGAGGTGGGTCCGGAGGTGGAGGATCTGA GATCCAGTTGGTGCAGT 3'
SCFV-3 (SEQ ID NO: 94)
5' TGTACTCGAGCCCATCATGAGGAGACGGTGACCGT 3'

The products from these reactions were mixed and amplified with the outside primers HUK-7 and SCFV-3. The product of this reaction was treated with T4 polymerase and then cut with XhoI. The resulting 728 bp fragment was then purified by electrophoresis on an agarose gel. This fragment was ligated into the vectors pING3755 and pING3748 (see Example 10), each digested with ScaI and XhoI. The resulting vectors pING4637 and pING4412 contain the Gelonin::RMA::SCA $V-J_{kappa}$::|(Gly)$_4$Ser|$_3$::$V-J_{Gamma}$ and Gelonin::SLT::SCA $V-J_{kappa}$::|(Gly)$_4$Ser|$_3$::$V-J_{Gamma}$ fusion genes, respectively.

Similarly, the SCA $V-J_{Gamma}$::|(Gly)$_4$Ser|$_3$::$V-J_{kappa}$ was assembled by amplification of pING34627 with primers SCFV-5 and SCFV-6 generating a 367 bp fragment containing he3 V/J kappa sequences.

SCFV-5 (SEQ ID NO: 95)
5' GGTGGAGGTGGGTCCGGAGGTGGAGGATCT
GACATCCAGATGACTCAGT 3'
SCFV-6 (SEQ ID NO: 96)
5' TGTACTCGAGCCCATCATTTCATCTCAAGCTTGGTGC 3' and pING4623 with primers H65-G3 and SCFV-4 generating a 385 bp fragment containing he3 gamma V/J sequences by PCR with Vent polymerase.

H65-G3 (SEQ ID NO: 97)
5' GAGATCCAGTTGGTGCAGTCTG 3'
SCFV-4 (SEQ ID NO: 98)
5' CGGACCCACCTCCACCAGATCC
ACCGCCACCTGAGGAGACGGTGACCGT 3'

The products from these reactions were mixed and amplified with H65-G3 and SCFV-6. The 737 bp product was treated with T4 polymerase and cut with XhoI. Ligation into pING3755 and pING3748 (digested with ScaI and XhoI) resulted in assembly of the Gelonin::RMA::SCA $V-J_{gamma}$::|(Gly)$_4$Ser|$_3$::$V-J_{kappa}$ gene fusion in pING4638 and Gelonin::SLT::SCA $V-J_{Gamma}$::|(Gly)$_4$Ser|$_3$::$V-J_{kappa}$ gene fusion in pING4639, respectively.

The vectors pING4637, pING4412, pING4638 and pING4639 were each transformed into *E. coli* strain E104 and induced with arabinose. Protein products of the predicted molecular weight were identified by Western blot with gelonin-specific antibodies.

B. Construction of SCA($V_L$-$V_H$)::SLT::Gelonin Vectors

The expression vector containing SCA($V_L$-$V_H$)::SLT::Gelonin fusions was assembled using restriction fragments from previously-constructed plasmids pING4640 (containing SCA($V_L$-$V_H$)) pING4407 (containing Kappa::SLT::Gelonin, Fd), and pING3197. Plasmid pING4640 was first cut with BspHI, filled in with T4 polymerase in the presence of only dCTP, treated with mung bean nuclease (MBN) to remove the overhang and to generate a blunt end, and cut with EcoRI. The resulting 849 bp fragment was purified. The SLT-containing fragment from pING4407 was excised by cutting with EagI, blunted with T4 polymerase, cut with XhoI, and the approximately 850 bp fragment which resulted was purified. The two fragments were ligated together into pING3197, which had been treated with EcoRI and XhoI to generate pING4642. The DNA sequence at the BspHI-T4-MBN/EagI junction revealed that two of the expected codons were missing but that the fusion protein was in frame.

C. Construction of SCA($V_H$-$V_L$)::SLT::Gelonin Vectors

The expression vector containing the SCA($V_H$-$V_L$)::SLT::Gelonin fusions was assembled using DNA from plasmids pING4636, (the *E. coli* expression vector for SCA($V_H$-$V_L$)) and pING4407. Plasmid pING4636 was cut with BstEII and XhoI and the resulting vector fragment was purified. Concurrently, pINg4636 was used as a template for PCR with primers SCFV-7, 5'TGATGCGGCCGACATCT-CAAGCTTGGTGC (SEQ ID NO: 112) and H65-G13, TGATGCGGCCGACATCTCAAGCTTGGTGC3' (SEQ ID NO: 113). The amplified product was digested with EagI and BstEII and the resulting approximately 380 bp fragment was purified. Plasmid pING4407 was then cut with EagI and XhoI, resulting in an approximately 850 bp fragment, which was purified. The three above fragments were ligated together to produce pING4643.

D. Construction of SCA($V_L$-$V_H$)::RMA::Gelonin Vectors

Expression vectors containing SCA($V_L$-$V_H$)::RNA::Gelonin fusions were assembled using DNA from pING4640, pING4408, and pING3825. Plasmid pING4640 was cut with SalI and BstEII and the resulting approximately 700 bp vector fragment (containing the tetracycline resistance matter) was purified. Next, pING3825 was digested with NcoI and SalI, resulting in an approximately 1344 bp fragment containing the 3' end of the gelonin gene and adjacent vector sequences. That fragment was purified. Plasmid pING4408 was then PCR amplified with oligonucleotide primers, RMA-G3 5'TCTAGGTCACCGTCTC-CTCACCATCTGGACAGGCTGGA3' (SEQ ID NO: 114), and gelo-10. The resulting PCR product was cut with BstEII and NcoI to generate an approximately 180 bp fragment containing the 3' end of $V_H$, RMA, and the 5' end of the Gelonin gene which was purified. The above three fragments were ligated to generate the final expression vector, pING4644.

E. Construction of SCA($V_H$-$V_L$)::RMA::Gelonin Vectors

Expression vectors containing SCA($V_H$-$V_L$)::RMA::Gelonin were constructed using DNA from pING4636, pING4410, and pING3825. Plasmid pING4636 was digested with SalI and HindIII and the resulting vector fragment was purified. Next, pING3825 was cut with NcoI and SalI and the 1344 bp fragment which resulted contained the 3' end of the gelonin gene and adjacent vector sequences encoding tetracycline resistance was purified. Finally, pING4410 was PCR amplified with primers RMA-G4, 5'TTCGAAGCTTGAGATGAAACCATCTGGA-CAGGCTGGA3' (SEQ ID NO: 115) and gelo-10. The PCR product was cut with HindIII and NcoI, resulting in a 180 bp fragment containing the 3' end of $V_L$, RMA, and the 5' end of Gelonin and was purified. The three above fragments were ligated together to generate the final expression vector, pING4645.

Gelonin::SCA fusions without a cleavable linker may be constructed by deletion of the SLT linker in pING4412 using the restriction enzymes EagI and FspI. Digestion at these sites and religation of the plasmid results in an in-frame deletion of the SLT sequence.

EXAMPLE 17
Multivalent Immunofusions

Multivalent forms of the above-described immunofusions may be constructed. For example a gene encoding an F(ab')$_2$ fragment may be fused to a gene encoding gelonin and to an Fd' or light chain gene. Alternatively, a gelonin sequence may be fused to both the Fd' and light chain genes.

A. Construction Of Vectors Containing Gel::RMA::Fd and Gel::RMA::K Fusions

In order to construct a plasmid comprising Gel::RMA::Fd and Gel::RMA::k fusions, plasmid pING3764 [described above in Example 15(b)] was digested with BsgI and SauI and a 5.7 kb vector fragment containing plasmid replication functions, Gel::RMA::k. anti the 3' end of Fd was isolated and purified. Plasmid pING3768 [described above in Example 15(E)] was digested with SauI and partially digested with PstI and a 1.5 kb fragment containing Gel-::RMA::Fd was purified. Finally, pING4000 [described above in Example 14] was digested with BsgI and PstI, generating a 350 bp fragment containing the 3'end of the kappa gene. That fragment was purified and the 5.7 kb, 1.5 kb, and 350 kb fragments described above were ligated together to form pING3770, containing the gelonin::R-MA::k and gelonin:RMA::Fd fusions.

B. Construction of Vectors Containing Gel::SLT::Fd and Gel::SLT::k Fusions

Plasmid pING3772 contains the above-entitled fusions and was constructed as follows. Plasmid pING3763 [described above in Example 15(D)] was digested with BsgI and SauI and a 5.7 kb fragment containing the replication functions, the 5' end of Gel::SLT::k and the 3' end of Fd was generated and purified. Next, plasmid pING3767 [described in Example 15(D) above] was digested with SauI and PstI, generating a 1.5 kb fragment containing the 5' end of the gel::SLT::Fd fusion. That fragment was purified and pING4000 [described in Example 14 above] was digested with BsgI and PstI. The resulting 350 bp fragment was purified and the above-described 5.7 kb, 1.5 kb, and 350 bp fragments were ligated to form pING3772.

C. Expression of multivalent fusions

Both pING3770 and pING3772 were transformed into *E. coli* (E104) cells by techniques known to those of ordinary skill in the art and induced with arabinose. Concentrated supernatants from the transformed cell cultures were analyzed by Western blot analysis with rabbit anti-gelonin antiserum. Transformants from both plasmids generated a reactive band on the gel at the size expected for a Fab molecule carrying two gelonins (approximately 105 kD). These results are consistent with the production of fusion proteins comprising monovalent Fab, with both Fd and kappa chains separately fused to gelonin.

EXAMPLE 18

Expression And Purification Of Gelonin Immunofusions

A. Expression Of Gelonin Immunofusions

Each of the gelonin gene fusions whose construction is described in Example 16 was co-expressed with its pair H65 Fab gene in arabinose-induced *E. coli* strain E104.

Expression products of the gene fusions were detected in the supernatant of induced cultures by ELISA. Typically, a plate was coated with antibody recognizing gelonin. Culture supernatant was applied and bound Fab was detected with antibody recognizing human kappa coupled to horseradish peroxidase. H65 Fab fragment chemically conjugated to gelonin was used a standard. Alternative ELISA protocols involving coating a plate with antibody recognizing either the kappa or Fd or involving a detection step with anti-human Fd rather than anti-human kappa yielded similar results. Only properly assembled fusion protein containing gelonin, kappa and Ed was detected by this assay. Unassociated chains were not detected.

The fusion protein produced from induced cultures containing expression vectors pING4406, 4407, 4408, and 4410 in *E. coli* E104 accumulated at about 20–50 ng/ml. The fusion proteins expressed upon induction of pING3754, 3334, 3758 and 3759 (but not pING3757) were expressed at much higher levels, at about 100 to 500 ng/ml. A fusion protein of about 70,000 Kd was detected in the concentrated *E. coli* culture supernatant by immunostaining of Western blots with either anti-human kappa or anti-gelonin antibodies.

The Gelonin::SLT::Fd' (kappa) fusion protein from pING3754 (ATCC 69102) was purified from induced 10 L fermentation broth. The 10 L fermentation broth was concentrated and buffer exchanged into 10 mM phosphate buffer at pH 7.0, using an S10Y10 cartridge (Amicon) and a DC10 concentrator. The supernatant was purified by passing the concentrated supernatant through a DE52 column (20×5 cm) equilibrated with 10 mM sodium phosphate buffer at pH 7.0. The flow-through was then further purified and concentrated by column chromatography on CM52 (5×10 cm) in 10 mM phosphate buffer. A 0–0.2M linear gradient of NaCl was used to the elute the fusion protein, and fractions containing the fusion protein were pooled and loaded onto a Protein G column (1 ml). The fusion protein was eluted from protein G with 0.2M sodium citrate, pH 5.5 and then 0.2M sodium acetate, pH 4.5, and finally, 0.2M glycine, pH 2.5. The Gelonin::RMA::Fd' (kappa) and Gelonin::RMA::kappa (Fd') fusions proteins were purified from fermentation broths by similar methods except that the CM52 column step was eliminated, and the DE52 column was equilibrated with 100 mM sodium phosphate buffer at pH 7.0. The fusion proteins were not purified to homogeneity.

Each of the three purified fusion proteins was then assayed for activity in the RLA assay and for cytotoxicity against the T-cell line HSB2. (T cells express the CD5 antigen which is recognized by H65 antibody.) The RLA assay was performed as described in Example 4 and results of the assay are presented below in Table 12.

TABLE 12

| Fusion Protein | IC50(pM) |
| --- | --- |
| rGelonin | 11 |
| Gelonin::SLT::Fd (kappa) | 19 |
| Gelonin::RMA::Fd (kappa) | 28 |
| Gelonin::RMA::kappa (Fd) | 10 |

Two fusion proteins were tested in whole cell cytotoxicity assays performed as described in Example 6 (Table 13). As shown in Table 13, the fusion proteins were active. Gelonin::SLT::Fd(kappa) killed two T cell lines, HSB2 and CEM, with respective IC$_{50}$s 2-fold (HSB2) or 10-fold (CEM) higher than that of the gelonin chemically linked to H65. See Table 13 below for results wherein IC$_{50}$ values were adjusted relative to the amount of fusion protein in each sample.

TABLE 13

| | IC$_{50}$ (pM) | |
| --- | --- | --- |
| Fusion Protein | HSB2 Cells | CEM Cells |
| he3Fab-Gel$_{A50(C44)}$ | 165 | 173 |
| Gelonin::SLT::Fd (kappa) | 180 | 1007 |
| Gelonin::RMA::Fd (kappa) | 150 | NT |

These fusion protein showed similar activity on peripheral blood mononuclear cells (data not shown).

B. Purification of Immnunofusions (i) Immunofusions Comprising cH65Fab'

Immunofusions comprising a cH65Fab' fragment were purified from cell-free supernatants by passing the supernatant through a CM Spheradex (Sepacor) column (5 cm×3 cm), equilibrated in 10 Mm Na phosphate at pH 7.0. Immunofusion proteins bind to the column and are eluted with 10 mM Na phosphate, 200 mM NaCl, pH 7.0. The eluate was diluted two-fold with 20 Mm HEPES, 3M ammonium sulfate, pH 7.6 and loaded onto a phenyl sepharose fast flow (Pharmacia) column (2.5×3.5 cm), equilibrated in 20 mM HEPES, 1.2M ammonium sulfate, pH 7.0. The column was next washed with 20 mM Hepes, 1.2M ammonium sulfate, pH 7.0 and eluted with 20 mM HEPES, 0.9M ammonium sulfate, pH 7.0. The phenyl sepharose eluate was concentrated to a volume of 2–4 ml in an Amicon stirred cell fitted with a YM10 membrane. The concentrated sample was loaded onto an S-200 (Pharmacia) column (3.2×38 cm), equilibrated in 10 mm Na phosphate, 150 mm NaCl, pH 7.0. The column was run in the same buffer and fractions were collected. Fractions containing the fusion protein of desired molecular weight were combined. For example, by selection of appropriate column fractions, both monovalent (gelonin-Fab') and bivalent (gelonin$_2$-F(ab')$_2$ forms encoded by pING3758 were purified.

(ii) Immunofusions Comprising he3Fab

Immunofusions comprising he3Fab were purified as in the preceding section with the exception that the phenyl sepharose column was eluted with 20 mM HEPES, 1.0M ammonium sulfate, pH 7.0.

(iii) Immunofusions Comprising SCA

Cell-free supernatant was passed through a CM sephadex column (5×3 cm), equilibrated with 10 mM Na phosphate, pH 7.0. Single-chain antibody binds to the column which is then washed with 10 mM Na phosphate, 45 mM NaCl, pH 7.0. The fusion protein was then eluted with 10 mM Na phosphate, 200 nM NaCl, pH 7.0. The eluate was diluted two-fold with 20 mM HEPES, 3M ammonium sulfate, pH 7.0 and loaded onto a butyl sepharose Fast Flow (Pharmacia) column (2.5×4.1 cm) equilibrated in 20 mM HEPES, 1.5M ammonium sulfate, pH 7.0. The column was then washed with 20 mM HEPES, 1.0M ammonium sulfate, pH 7.0 and eluted with 20 mM HEPES pH 7. 0. The butyl sepharose eluate was concentrated to a volume of 2–4 ml in an Amicon stirred cell fitted with a YM10 membrane. The (concentrated sample was loaded onto an S-200 (Pharmacia) column (3.2×38 cm) equilibrated in 10 mM Na phosphate, 150 mM NaCl, pH 7.0. The column was then run in the same buffer and the fractions were collected. Some of the fractions were analyzed by SDS-PAGE to determine which fractions to pool together for the final product.

EXAMPLE 19
Activity of Gelonin Immunofusions

A concern in constructing immunofusions comprising any RIP is that the targeting and enzymatic activities of the components of the fusion protein may be lost as a result of the fusion. For example, attachment of an RIP to the amino terminus of an antibody may affect the antigen-binding (complementarity-determining regions) of the antibody and may also result in steric hinderance at the active site. Similarly, the activity of an RIP may be hindered by attachment of an antibody or antibody portion. For example, RIPs chemically conjugated to antibodies via a disulfide bridge are typically inactive in the absence of reducing agents. In order to assess the foregoing in immunofusions of the present invention, such proteins were subjected to assays to determine their enzymatic, binding, and cytotoxic activities.

A. Reticulocyte Lysate Assay

The enzymatic activity of immunofusions comprising gelonin was assayed using the reticulocyte lysate assay (RLA) describe above. As noted in Example 4, the RLA assay measures the inhibition of protein synthesis in a cell-free system using endogenous globin mRNA from a rabbit red blood cell lysate. Decreased incorporation of tritiated leucine ($^3$H-Leu) was measured as a function of toxin concentration. Serial log dilutions of standard toxin (the 30 kD form of ricin A-chain, abbreviated as RTA 30), native gelonin, recombinant gelonin (rGelonin or rGel) and gelonin analogs were tested over a range of 1 μg/ml to 1 pg/ml. Samples were tested in triplicate, prepared on ice, incubated for 30 minutes at 37° C., and then counted on an Inotec Trace 96 cascade ionization counter. By comparison with an uninhibited sample, the picomolar concentration of toxin (pM) which corresponds to 50% inhibition of protein synthesis ($IC_{50}$) was calculated.

Representative data for various immunotoxins of the invention are shown below in Table 14.

TABLE 14

| Immunotoxin | Lot No. | $IC_{50}$(pM) |
|---|---|---|
| rGel::RMA::SCA($V_H - V_L$) | AB1136 | 12 |
| rGel::RMA::SCA($V_L - V_H$) | AB1137 | 18 |
| rGel::SLT::SCA($V_H - V_L$) | AB1133 | 26 |
| rGel::RMA::SCA($V_L - V_H$) | AB1124 | 33 |
| rGel::RMA::K + Fd'(cH65Fab') | AB1122 | 54 |
| rGel::RMA::K + Fd(he3Fab) | AB1160 | 40 |
| rGel::RMA::K + Fd(he3Fab) | AB1149 | 33 |
| rGel::RMA::Fd + K(he3Fab) | AB1163 | 14 |
| rGel::Fd' + K(cH65Fab') | AB1123 | 45 |

Contrary to the expectations discussed above, gelonin immunofusions of the invention exhibit enzymatic activity which is comparable to the activities of native and recombinant gelonin shown in Example 4. This was true for fusions made with either the reducible (SLT) or non-reducible (RMA) linkers.

B. Binding Activity of Immunofusions

Several immunofusions according to the present invention were assayed for their ability to compete with labelled antibody for binding to CD5-positive cells. The Kd of the immunofusions was estimated by three different means as shown in Table 15. The first Kd estimation ($Kd_1$ in Table 15) was obtained by competition with fluorescein-labelled H65 IgG for binding to MOLT-4X cells (ATCC CRL 1582) according to the procedure reported in Knebel, et al., *Cytometry Suppl.*, 1: 68 (1987), incorporated by reference herein.

The second Kd measurement ($Kd_2$ in Table15) was obtained by Scatchard analysis of competition of the immunofusion with $^{125}$I-cH65 IgG for binding on MOLT-4M cells as follows. A 20 μg aliquot of chimeric H65 IgG (cH65 IgG) was iodinated by exposure to 100 μl lactoperoxidase-glucose oxidase immobilized beads (Enzymobeads, Biopad), 100 μl of PBS, 1.0 mCi $I^{125}$ (Amersham, IMS30), 50 μl of 55 mM b-D-glucose for 45 minutes at 23° C. The reaction was quenched by the addition of 20 μl of 105 mM sodium metabisulfite and 120 mM potassium iodine followed by centrifugation for 1 minute to pellet the beads. $^{125}$I-cH65 IgG was purified by gel filtration using a 7 ml column of sephadex G25, eluted with PBS (137 mM NaCl, 1.47 mM KH$_2$PO$_4$, 8.1 mM Na$_2$HPO$_4$, 2.68 mM KCl at pH 7.2–7.4) plus 0.1% BSA. $^{125}$I-cH65 IgG recovery and specific activity were determined by TCA precipitation.

Competitive binding was performed as follows: 100 μl of Molt-4M cells were washed two times in ice-cold DHB binding buffer (Dubellco's modified Eagle's medium (Gibco, 320-1965PJ), 1.0% BSA and 10 mM Hepes at pH 7.2–7.4). Cells were resuspended in the same buffer, plated into 96 v-bottomed wells (Costar) at 3×10$^5$ cells per well and pelleted at 4° C. by centrifugation for 5 min at 1.000 rpm using a Beckman JS 4.2 rotor; 50 μl of 2×-concentrated 0.1 nM $^{125}$I-cH65 IgG in DHB was then added to each well and competed with 50 μl of 2×-concentrated cH65 IgG in DHB at final protein concentrations from 100 nM to 0.0017 nM. The concentrations of assayed proteins were determined by measuring absorbance ($A_{280}$ and using an extinction coefficient of 1.0 for fusion proteins;, 1.3 for Fab, and 1.22 for Fab conjugated to gelonin. Also, protein concentrations were determined by BCA assay (Pierce Chemical) with bovine serum albumin as the standard. Binding was allowed to proceed at 4° C. for 5 hrs and was terminated by washing cells three times with 200 μl of DHB binding buffer by centrifugation for 5 min. at 1,000 rpm. All buffers and operations were at 4° C. Radioactivity was determined by solubilizing cells in 100 μl of 1.0M NaOH and counting in a Cobra II auto gamma counter (Packard). Data from binding experiments were analyzed by the weighted nonlinear least squares curve fitting program, MacLigand, a Macintosh version of the computer program "Ligand" from Munson, *Analyt. Biochem.*, 107:220 (1980), incorporated by reference herein.

Finally, the Kd ($Kd_3$ in the Table) was estimated by examination of the $ED_{50}$ values obtained from separate competition binding assays, performed as described in the previous paragraph. All three measurements are shown in Table 15 below:

TABLE 15

| Molecule Type | $Kd_1$ | $Kd_2$ | $Kd_3$ |
|---|---|---|---|
| H65 IgG | 1.6 | ND | ND |
| cH65 IgG | ND | 3.0 | 2.5 |
| cH65Fab' | 4.0 | 14.0 | ND |
| cH65Fab'-rGel$_{A50(C44)}$ | 3.5 | 13.0 | ND |
| rGel::RMA::K + Fd'(cH65Fab') | 16.0 | ND | 100 |

TABLE 15-continued

| Molecule Type | $Kd_1$ | $Kd_2$ | $Kd_3$ |
|---|---|---|---|
| he3Fab | 1.20 | 2.60 | ND |
| he3Fab-rGel$_{A50(C44)}$ | 1.10 | 2.70 | ND |
| rGel::RMA::K + Fd'(he3Fab) | 2.60 | ND | 5.0 |
| rGel::SLT::K + Fd(he3Fab) | ND | ND | 30 |
| SCA($V_L - V_H$) | 2.20 | ND | 30 |
| rGel::RMA::SCA($V_H - V_L$) | 3.50 | ND | 20 |
| rGel::RMA::SCA($V_L - V_H$) | 4.70 | ND | 30 |
| SCA($V_L - V_H$) | ND | ND | 20 |
| rGel::RMA::SCA($V_L - V_H$) | 2.30 | ND | ND |

ND = not determined

The results presented in Table 15 suggest that Fab and SCA antibody forms may retain substantial binding activity even when fused to an RIP.

C. Comparative Cytotoxicity Assays

Fusion proteins and immunoconjugates according to the present invention were used in a comparative cytoxicity assay. Two assays were conducted, one targeting T cell line HSB2, and the other targeting lectin-activated peripheral blood mononuclear cells (PBMC) according to procedures in Example 6. The results of the assays are presented below in Tables 16a and 16b.

TABLE 16a

CYTOTOXIC POTENCIES:
CHEMICAL VS. GENE-FUSED CONJUGATES

| | | | HSB2 | | |
|---|---|---|---|---|---|
| Immunotoxin | Lot # | Fusion Plasmid | $IC_{50}$, pM Toxin | $IC_{50}$, pM Toxin | N |
| CD5 Plus | HR002002 | — | 148 | 24 | 8 |
| H65-M-rGel$_{A50(C44)}$ | 999 | — | 68* | NA | 1 |
| cH65-MM-rGel | 807 | — | 183* | NA | 1 |
| cH65Fab'-M-rGel$_{A50(C44)}$ | 941 | — | 99 | 6 | 2 |
| He2Fab-M-rGel$_{A50(C44)}$ | 970 | — | 468 | 195 | 4 |
| he3Fab-M-rGel$_{A50(C44)}$ | 1012/1047 | — | 190 | 70 | 12 |
| he3Fab-SMCC-rGel$_{A50(C44)}$ | 1086 | — | 5,904 | 2,442 | 2 |
| rGel::SLT::Fd' + K(1)⁺ | AB1095 | pING3754 | 320 | 25 | 2 |
| rGel::SLT::Fd' + K(3)⁺ | AB1095 | pING3754 | 374* | NA | 1 |
| rGel::SLT::K + Fd(he3) | AB1147 | pING3763 | 495* | NA | 1 |
| rGel::SLT::K + Fd(he3) | AB1160 | pING3763 | 746* | NA | 1 |
| rGel::SLT::SCA(Vh − Vl) | AB1133 | pING4639 | 422 | 31 | 5 |
| rGel::SLT::SCA(Vl − Vh) | AB1124 | pING4412 | 776 | 347 | 3 |
| rGel::RMA::K + Fd' | AB1122 | pING3758 | 1,506 | 1,033 | 2 |
| rGel::RMA::K + Fd' | AB1141 | pING3758 | 5,833* | NA | 1 |
| rGel::RMA::K + Fd(he3) | AB1149 | pING3764 | 9,154* | NA | 1 |
| rGel::RMA::K + Fd(he3) | AB1161 | pING3764 | 5,974* | NA | 1 |
| rGel::RMA::Fd' + K | RF524(1) | pING3759 | 1,955* | NA | 1 |
| rGel::RMA::Fd' + K | AB1121 | pING3759 | 32,051* | NA | 1 |
| rGel::RMA::Fd + K(he3) | AB1163 | pING3768 | 3,256* | NA | 1 |
| rGel::RMA::SCA(Vh − Vl) | AB1136 | pING4638 | 3,687* | 1,144 | 6 |
| rGel::RMA::SCA(Vh − Vl) | AB1152 | pING4638 | 41,218* | NA | 1 |
| rGel::RMA::SCA(Vl − Vh) | AB1137 | pING4637 | 11,979* | NA | 1 |
| rGel::RMA::SCA(Vl − Vh) | AB1164 | pING4637 | 1,146* | NA | 1 |
| rGel::Fd' + K | AB1123 | pING3334 | 6,346* | NA | 1 |
| K::RMA::rGel + Fd | AB1140 | pING4410 | 10,090* | NA | 1 |
| rGel | 1056 | — | 46,600 | 34,600 | 3 |
| B72.3Fab-M-rGel$_{A50(C44)}$ | 1057 | — | 129,032* | NA | 1 |

*Results represent single values and not a mean value.
⁺rGel::SLT::Fd' + k(1) and rGel::SLT::Fd' + k(3) are separate fractions from the final purification column.

TABLE 16b

CYTOTOXIC POTENCIES:
CHEMICAL VS. GENE-FUSED CONJUGATES

| Immunotoxin | Lot # | PBMC IC$_{50}$, pM Toxin | IC$_{50}$, pM Toxin | SD | N |
|---|---|---|---|---|---|
| CD5 Plus | HF002002 | 1,095 | 1,236 | 908 | 18 |
| H65-M-rGel$_{A50(C44)}$ | 999 | 133 | 133 | 129 | 2 |
| cH65-m2-rGel | 807 | 143 | 308 | 492 | 8 |
| cFab'-rGel$_{A50(C44)}$ | 941 | 434 | 405 | 280 | 4 |
| He2Fab-rGel$_{A50(C44)}$ | 970 | 397 | 397 | 146 | 2 |
| he3Fab-rGel$_{A50(C44)}$ | 1012/1047 | 206 | 307 | 274 | 18 |
| he3Fab-smcc-rGel$_{A50(C44)}$ | 1086 | 335 | 638 | 538 | 3 |
| rGel::SLT::Fd' + K(1)⁺ | AB1095 | 15,840 | 15,840 | 15,783 | 2 |
| rGel::SLT::Fd' + K(3)⁺ | AB1095 | 2,350 | 4,322 | 4,159 | 9 |
| rGel::SLT::K + Fd(he3) | AB1147 | 1,890 | 1,407 | 1,015 | 5 |
| rGel::SLT::K + Fd(he3) | AB1160 | 2,910 | 4,584 | 5,100 | 3 |
| rGel::SLT::SCA(Vh – Vl) | AB1133 | 1,125 | 1,870 | 1,637 | 6 |
| rGel::SLT::SCA(Vl – Vh) | AB1124 | 2,725 | 2,815 | 743 | 4 |
| rGel::RMA::K + Fd' | AB1122 | 211 | 307 | 250 | 14 |
| rGel::RMA::K + Fd' | AB1141 | 4,400 | 4,041 | 2,691 | 4 |
| rGel::RMA::K + Fd' | RF-532 | 15,000 | 9,114 | 8,325 | 3 |
| rGel::RMA::K + Fd(he3) | AB1149 | 7,124 | 10,764 | 14,081 | 5 |
| rGel::RMA::K + Fd(he3) | AB1161 | 1,854 | 2,990 | 3,324 | 3 |
| rGel::RMA::Fd' + K | RF524(1) | 1,760 | 1,893 | 1,049 | 5 |
| rGel::RMA::Fd' + K | AB1121 | 2,090 | 1,664 | 1,553 | 6 |
| rGel::RMA::Fd + K(he3) | AB1163 | 854 | 567 | 406 | 2 |
| rGel::RMA::SCA(Vh – Vl) | AB1136 | 393 | 567 | 510 | 7 |
| rGel::RMA::SCA(Vh – Vl) | AB1152 | 9,650 | 9,170 | 6,483 | 3 |
| rGel::RMA::SCA(Vl – Vh) | AB1137 | 4,040 | 4,554 | 4,310 | 7 |
| rGel::RMA::SCA(Vl – Vh) | AB1164 | 1,598 | 1,598 | 1,144 | 2 |
| rGel::Fd' + K | AB1123 | 2,606 | 2,777 | 2,167 | 4 |
| K::RMA::rGel + Fd | AB1140 | 1,545 | 1,545 | 417 | 2 |
| rGel | 1056 | 13,350 | 40,233 | 43,048 | 6 |
| 8B2.3Fab-m-rGel$_{A50(C44)}$ | 1057 | 12,400 | 13,174 | 14,339 | 11 |

*Results represent single values and not a mean value.
⁺rGel::SLT::Fd' + k(1) and rGel::SLT::Fd' + k(3) are separate fractions from the final purification column.

The results presented in Tables 16a and 16b demonstrate that gelonin immunofusion is may vary in their activity. In general, immunofusions of the invention which have IC$_{50}$ median or mean values of less than 2000 pM Toxin display strong activity; whereas those with IC$_{50}$ values equal to or less than 500 pM Toxin are considered highly active. In the PBMC assay, the immunofusions considered highly active are rGel::RMA::K+Fd' and rGel::RMA::SCA(V$_H$-V$_L$). In the HSB2 assay, the immunofusions considered highly active are rGel::SLT::Fd'+K, rGel::SLT::K+Fd(he3), and rGel::SLT::SCA(V$_H$-V$_L$). Interestingly, activity is observed regardless of whether a linker (RMA or SLT) is used, as the rGel::Fd'+K protein also displayed activity. In sum, the results in Tables 16a and 16b demonstrate that the optimum fusion protein for killing a particular cell line may vary depending upon the targeted cell.

EXAMPLE 20

Preparation Of BRIP

BRIP possesses characteristics which make it an attractive candidate for a component of immunotoxins. BRIP is a naturally unglycosylated protein that may have reduced uptake in the liver and enhanced circulatory residence time in vivo. Additionally, BRIP is less toxic and less immunogenic in animals than the A-chain of ricin. Cloning of the BRIP gene and expression of recombinant BRIP in an *E. coli* expression system obviates the need to purify native BRIP directly from barley, and enables the development of analogs of BRIP which may be conjugated with an available cysteine residue for conjugation to antibodies.

A. Purification Of BRIP And Generation Of Polyclonal Antibodies To BRIP

Native BRIP was purified from pearled barley flour. Four kilograms of flour was extracted with 16 liters of extraction buffer (10 mM NaPO4, 25 mM NaCl, pH 7.2) for 20 hours at 4° C. The sediment was removed by centrifugation, and 2 00 ml of packed S-Sepharose (Pharmacia, Piscataway, N.J.) was added to absorb BRIP. After mixing for 20 hours at 4° C., the resin was allowed to settle out, rinsed several times with extraction buffer and then packed into a 2.6×40 cm column. Once packed, the column was washed with extraction buffer (150 ml/h) until the absorbance of the effluent approached zero. BRIP was then eluted with a linear gradient of 0.025 to 0.3M NaCl in extraction buffer and 5 ml fractions were collected. BRIP-containing peaks (identified by Western analysis of column fractions) were pooled, concentrated to about 20 ml, and then chromatographed on a 2.6×100 cm Sephacryl S-200HR (Pharmacia) column equilibrated in 10 mM $NaPO_4$, 125 nM NaCl, pH 7.4 (10 ml/hr). BRIP-containing peaks were pooled again, concentrated, and stored at −70° C.

The resulting purified BRIP protein had a molecular weight of about 30,000 Daltons, based upon the mobility of Coomassie-stained protein brands following SDS-PAGE. The amino acid composition was consistent with that published by Asano et al., *Carlsberg Res. Comm.*, 49: 619–626 (1984).

Rabbits were immunized with purified BRIP to generate polyclonal antisera.

B. Cloning Of The BRIP Gene

A cDNA expression library prepared from germinating barley seeds in the phage λ expression vector λZAPII was purchased from Stratagene, La Jolla, Calif. Approximately 700,000 phage plaques were screened with anti-BRIP polyclonal antisera and 6 immunoreactive plaques were identified. One plaque was chosen, and the cDNA contained therein was excised from λZAPII with EcoRI and subcloned into pUC18 generating the vector pBS1. The cDNA insert was sequenced with Sequenase (United States Biochemical, Cleveland, Ohio). The DNA sequence of the native BRIP gene is set out in SEQ ID NO: 12. To confirm that cDNA encoded the native BRIP gene, the cDNA was expressed in the *E. coli* plasmid pKK233-2 (Pharmacia) BRIP protein was detected in IPTG-induced cells transformed with the plasmid by Western analysis with above-described rabbit anti-BRIP antisera.

C. Construction Of An *E. coli* Expression Vector Containing The BRIP Gene

Barley cDNA containing the BRIP gene was linked to a pelB leader sequence and placed under control of an araB promoter in a bacterial secretion vector.

An intermediate vector containing the BRIP gene linked to the pelb leader sequence was generated. Plasmid PBS1 was cut with NcoI, treated with Mung Bean Nuclease, cut with BamHI and the 760 bp fragment corresponding to amino acids 1-256 of BRIP was purified from an agarose gel. Concurrently, a unique XhoI site was introduced downstream of the 3'-end of the BRIP gene in pBS1 by PCR amplification with a pUC18 vector primer (identical to the Reverse® primer sold by NEB or BRL but synthesized on a Cyclone Model 8400 DNA synthesizer) and the specific primer BRIP 3'Xho. The sequence of each of the primers is set out below.

Reverse (SEQ ID NO: 45)
5' AACAGCTATGACCATG 3'
BRIP 3'Xho (SEQ ID NO: 46)
5' TGAACTCGAGGAAAACTACCTATTTCCCAC 3'

Primer BRIP 3'Xho includes a portion corresponding to the last 8 bp of the BRIP gene, the termination codon and several base pairs downstream of the BRIP gene, and an additional portion that introduces a XhoI site in the resulting PCR fragment. The PCR reaction product was digested with BamHI and XhoI, and an 87 bp fragment containing the 3'-end of the BRIP gene was purified on a 5% acrylamide gel. The 760 and 87 bp purified BRIP fragments were ligated in the vector pING1500 adjacent to the pelB leader sequence. pING1500 had previously been cut with SstI, treated with T4 polymerase, cut with XhoI, and purified. The DNA sequence at the junction of the pelB leader and the 5'-end of the BRIP gene was verified by DNA sequence analysis. This vector was denoted pING3321-1.

The final expression vector was assembled by placing the BRIP gene under the control of the inducible araB promoter. Plasmid pING3321-1 was cut with PstI and XhoI, and the BRIP gene linked to the pelB leader was purified from an agarose gel. The expression vector pING3217, containing the araB promoter, was cut with PstI and XhoI and ligated to the BRIP gene. The expression vector was denoted pING3322.

Arabinose induction of *E. coli* cells containing the plasmid pING3322 in a fermenter resulted in the production of about 100 mg per liter of recombinant BRIP. *E. coli*-produced BRIP displays properties identical to BRIP purified directly from barley seeds.

D. Construction Of BRIP Analogs With A Free Cysteine Residue

The BRIP protein contains no cysteine residues, and therefore contains no residues directly available which may form a disulfide linkage to antibodies or other proteins. Analogs of recombinant BRIP were generated which contain a free cysteine residue near the C-terminus of the protein. Three residues of the BRIP protein were targets for amino acid substitutions. Comparison of the amino acid sequence of BRIP to the known tertiary structure of the ricin A-chain (see FIG. 2) suggested that the three positions would be available near the surface of the molecule. The three BRIP analogs include cysteines substituted in place of serine$_{277}$, alanine$_{270}$, and leucine$_{256}$ of the native protein, and were designated BRIP $C_{277}$ (SEQ ID NO: 127), BRIP$_{C270}$ (SEQ ID NO: 128) and BRIP$_{C256}$ (SEQ ID NO: 129), respectively.

(1) A plasmid vector capable of expressing the BRIP$_{C277}$ analog was constructed by replacing the 3'-end of the BRIP gene with a DNA segment conferring the amino acid change. The EcoRI fragment containing the BRIP gene from pBS1 was subcloned into M13mp18, and single-stranded DNA (anti-sense strand) was amplified by PCR with primers OBM2 (corresponding nucleotides −11 to +8 of the BRIP gene) and OMB4 (corresponding to amino acids 264–280 of BRIP and the termination codon of BRIP, and incorporating the substitution of a cysteine codon for the native codon for serine$_{277}$ of native BRIP). The sequences of primers OBM2 and OMB4, wherein the underlined nucleotides encode the substituted cysteine, are set out below.

OBM2 (SEQ ID NO: 47)
5' GCATTACATCCATGGCGGC 3'
OMB4 (SEQ ID NO: 48)
5' GATATCTCGAGTTAACTATTTCCCACCACACG
CATGGAACAGCTCCAGCGCCTTGGCCACCGTC 3'

A fragment containing a BRIP gene in which the codon for the amino acid at position 277 was changed to a cysteine codon was amplified. The fragment was cloned into the SmaI site of pUC19 (BRL) and the plasmid generated was denoted pMB22. pMB22 was digested with EcoRI and an EcoRI-XhoI linker (Clonetech, Palo Alto, Calif.) was ligated into the vector. Subsequent digestion with XhoI and religation generated vector pINGMB2X. A BamHI to XhoI fragment encoding the 3'-end of BRIP with the altered amino acid was excised from pMB2X and the fragment was purified on a 5% acrylamide gel. This fragment along with an EcoRI to BamHI fragment containing the pelB leader sequence and sequences encoding the first 256 amino acids of BRIP were substituted in a three piece ligation into pING3322 cut with EcoRI and XhoI. The resulting vector containing the BRIP$_{C277}$ analog was designated pING3803 (ATCC Accession No. 68722).

(2) A BRIP analog with a free cysteine at position 256 was constructed using PCR to introduce the amino acid substitution. A portion of the expression plasmid pING3322 was amplified with primers BRIP-256 and HINDIII-2. The sequence of each primer is set out below.

BRIP-256 (SEQ ID NO: 49)
5' TGTCTGTTCGTGGAGGTGCCG 3'
HINDIII-2 (SEQ ID NO: 44)
5' CGTTAGCAATTTAACTGTGAT 3'

Nucleotides 4–21 of primer BRIP-256 encode amino acids 256–262 of BRIP while the underlined nucleotides specify the cysteine to be substituted for the leucine at the corresponding position of the native BRIP protein. Primer HINDIII-2 corresponds to a portion of the plasmid. The PCR product, which encodes the carboxyl terminal portion of the BRIP analog, was treated with T4 polymerase, cut with XhoI, and the resulting fragment was purified on a 5% acrylamide gel. Concurrently, plasmid pING3322 was cut with BamHI, treated with T4 polymerase, cut with EcoRI, and the fragment containing the pelB leader sequence and sequences encoding the first 256 amino acids of BRIP was purified. The two fragments were then assembled back into pING3322 to generate the gene encoding the analog BRIP$_{C256}$. This plasmid is denoted pING3801.

(3) A BRIP analog with a cysteine at position 270 was also generated using PCR. A portion of the expression plasmid pING3322 was amplified with primers BRIP-270 and the HINDIII-2 primer (SEQ. ID NO: 44). The sequence of primer BRIP-270 is set out below.

BRIP-270 (SEQ ID NO: 50)
5' CCAAGTGTCTGGAGCTGTTCCATGCGA 3'

Primer BRIP-270 corresponds to amino acids 268–276 of BRIP with the exception of residue 270. The codon of the primer corresponding to position 270 specifies; a cysteine instead of the alanine present in the corresponding position in native BRIP. The PCR product was; treated with T4 polymerase, cut with XhoI, and the 51 bp fragment, which encodes the carboxyl terminal portion of the analog, was purified on a 5% acrylamide gel. The fragment (corresponding to amino acids 268–276 of BRIP$_{C270}$) was cloned in a three piece ligation along with the internal 151 bp BRIP restriction fragment from SstII to MscI (corresponding to BRIP amino acids 217–267) from plasmid pING3322, and restriction fragment from SstII to XhoI from pING3322 containing the remainder of the BRIP gene. The plasmid generated contains the gene encoding the BRIP$_{C270}$ analog and is designated pING3802.

E. Purification Of Recombinant BRIP And The BRIP Analogs

Recombinant BRIP (rBRIP) and the BRIP analogs with free cysteine residues were purified essentially as described for native BRIP except they were prepared from concentrated fermentation broths. For rBRIP, concentrated broth from a 10 liter fermentation batch was exchanged into 10 mM Tris, 20 mM NaCl pH 7.5, loaded onto a Sephacryl S-200 column, and eluted with a 20 to 500 mM NaCl linear gradient. Pooled rBRIP was further purified on a Blue Toyopearl® column (TosoHaas) loaded in 20 mM NaCl and eluted in a 20 to 500 mM NaCl gradient in 10 mM Tris, pH 7.5. For BRIP analogs, concentrated fermentation broths were loaded onto a CM52 column (Whatman) in 10 mM phosphate buffer, pH 7.5, and eluted with a 0 to 0.3M NaCl linear gradient. Further purification was by chromatography on a Blue Toyopearl® column.

F. Reticulocyte Lysate Assay

The ability of the rBRIP and the BRIP analogs to inhibit protein synthesis in vitro was tested by reticulocyte lysate assay as described in Example 1. Serial log dilutions of standard toxin (RTA 30), native BRIP, rBRIP and BRIP analogs were tested over a range of 1 µg/ml to 1 pg/ml. By comparison with an uninhibited sample, the picomolar concentration of toxin (pM) which corresponds to 50% inhibition of protein synthesis (IC$_{50}$) was calculated. The results of the assays are presented below in Table 17.

TABLE 17

| Toxin | IC$_{50}$ (pM) |
|---|---|
| RTA 30 | 3.1 |
| Native BRIP | 15 |
| rBRIP | 18 |
| BRIP$_{C256}$ | 23 |
| BRIP$_{C270}$ | 20 |
| BRIP$_{C277}$ | 24 |

The RLA results indicate that the BRIP analogs exhibit ribosome-inactivating activity comparable to that of the recombinant and native BRIP toxin. All the analogs retained the natural ability of native BRIP to inhibit protein synthesis, suggesting that amino acid substitution at these positions does not affect protein folding and activity.

EXAMPLE 21
Construction Of BRIP Immunoconjugates

Immunoconjugates of native BRIP (SEQ ID NO: 3) with 4A2 (described in Morishima et al., J. Immunol., 129:1091 (1982) and H65 antibody (obtained from hybridoma ATCC HB9286) which recognize the T-cell determinants CD7 and CD5, respectively, were constructed. Immunoconjugates of ricin A-chains (RTAs) with 4A2 and H65 antibody were constructed as controls. The H65 antibody and ricin A-chains as well as the RTA immunoconjugates were prepared and purified according to methods described in U.S. patent application Serial No. 07/306,433 supra and in International Publication No. WO 89/06968.

To prepare immunoconjugates of native BRIP, both the antibody (4A2 or H65) and native BRIP were chemically modified with the hindered linker 5-methyl-2-iminothiolane (M2IT) at lysine residues to introduce a reactive sulfhydryl group as described in Goff et al., Bioconjugate Chem., 1:381–386 (1990). BRIP (3 mg/ml) was first incubated with 0.5 mM M2IT and 1 mM DTNB in 25 mM triethanolamine, 150 mM NaCl, pH 8.0, for 3 hours at 25° C. The derivitized BRIP-(M2IT)-S-S-TNB was then desalted on a column of Sephadex GF-05LS and the number of thiol groups introduced was quantitated by the addition of 0.1 mM DTT. On average, each BRIP molecule contained 0.7 SH/mol.

4A2 or H65 antibody (4 mg/ml) in triethanolamine buffer was similarly incubated with M2IT (0.3 mM) and DTNB (1 mM) for 3 hours at 25° C. Antibody-(M2IT)-S-S-TNB was then desalted and the TNB:antibody ratio was determined. To prepare the conjugate, the BRIP-(M2IT)-S-S-TNB was first reduced to BRIP-(M2IT)-SH by treatment with 0.5 mM DTT for 1 hour at 2520 C., desalted by gel filtration of Sephadex® GF-05LS to remove the reducing agent, and then mixed with antibody-(M2IT) -S-S-TNB.

Following a 3 hour incubation at 25° C., and an additional 13 hours at 4° C., the conjugate was purified by sequential chromatography on AcA44 (IBF) and Blue Toyopearl®. Samples of the final product were run on 5% non-reducing SDS PAGE, Coomassie stained, and scanned with a Shimadzu laser densitometer to quantitate the number of toxins per antibody.

The BRIP analogs containing a free cysteine were also conjugated to 4A2 and H65 antibodies. The analogs were treated with 50 mM DTT either for 2 hours at 25° C. or for 18 hours at 4° C. to expose the reactive sulfhydryl group of the cysteine and desalted. The presence of a free sulfhydryl was verified by reaction with DTNB [Ellman et al., Arch. Biochem. Biophys, 82:70–77 (1959)]. 4A2 or H65 antibody derivatized as described above with M2IT was incubated with the reduced BRIP analogs; at a ratio of 1:5 at room temperature for 3 hours and then overnight at 4° C. Immunoconjugates H65-BRIP$_{C256}$, 4A2-BRIP$_{C256}$, H65-BRIP$_{C277}$ were prepared in 25 mM triethanolamine, 150 mM NaCl pH 8, while immunoconjugates H65-BRIP$_{C270}$, 4A2-BRIP$_{C270}$ and 4A2-BRIP$_{C277}$ were prepared in 0.1M sodium phosphate, 150 mM NaCl pH 7.5. Following conjugation, 10 µM mercaptoethylamine was added for 15 minutes at 25° C. to quenched any unreacted m2IT linkers on the antibody. The quenched reaction solution was promptly loaded onto a gel filtration column (AcA44) to remove unconjugated ribosome-inactivating protein. Purification was completed using soft gel affinity chromatography on Blue Toyopearl® resin using a method similar to Knowles et al., *Analyt. Biochem.*, 160:440 (1987). Samples of the final product were run on 5% non-reduced SDS PAGE, Coomassie stained, and scanned with a Shimadzu laser densitometer to quantitate the number of toxins per antibody. The conjugation efficiency was substantially greater for BRIP$_{C277}$ (78%) than for either of the other two analogs, BRIP$_{C270}$ and BRIP$_{C256}$ (each of these was about 10%). Additionally, the BRIP$_{C277}$ product was a polyconjugate, i.e., several BRIP molecules conjugated to a single antibody, in contrast to the BRIP$_{C270}$ and BRIP$_{C256}$ products which were monoconjugates.

EXAMPLE 22
Properties Of BRIP Immunoconjugates
A. Whole Cell Kill Assay

Immunoconjugates of native BRIP and of the BRIP analogs were tested for the ability to inhibit protein synthesis in HSB2 cells by the whole cell kill assay described in Example 1. Standard immunoconjugates H65-RTA (H65 derivatized with SPDP linked to RTA) and 4MRTA (4A2 antibody derivatized with M2IT linked to RTA) and BRIP immunoconjugate samples were diluted with RPMI without leucine at half-log concentrations ranging from 2000 to 0.632 ng/ml. All dilutions were added in triplicate to microtiter plates containing 1×10$^5$ HSB2 cells. HSB2 plates were incubated for 20 hours at 37° C. and then pulsed with $^3$H-Leu for 4 hours before harvesting. Samples were counted on the Inotec Trace 96 cascade ionization counter. By comparison with an untreated sample, the picomolar toxin concentration (pM T) of immunoconjugate which resulted in a 50% inhibition of protein synthesis (IC$_{50}$) was calculated. The assay results are presented below in Table 18.

TABLE 18

| Conjugate | IC$_{50}$ (pM T) |
|---|---|
| 4A2-BRIP | 122.45 |
| 4A2-BRIP$_{C270}$ | 46.3 |
| 4A2-BRIP$_{C277}$ | 57.5 |
| 4A2-BRIP$_{C256}$ | 1116 |
| H65-BRIP | >5000 |
| H65-BRIP$_{C277}$ | 1176 |

The BRIP analog conjugates were less potent than the ricin conjugate control (data not shown). The immunotoxins containing antibody 4A2 and either the BRIP$_{C270}$ or the BRIP$_{C277}$ analog exhibited comparable to increased specific cytotoxicity toward target cells as compared to immunotoxin containing native BRIP. While 4A2-BRIP$_{C256}$ is less active than 4A2-BRIP, 4A2-BRIP$_{C270}$ and 4A2-BRIP$_{C277}$ are between 3 and 4 times more active. Similarly, the immunoconjugate of H65 to BRIP$_{C277}$ shows greater toxicity toward target cells than the immunoconjugate of H65 to native BRIP. Thus, linkage of antibody to BRIP derivatives which have an available cysteine residue in an appropriate location results in immunotoxins with enhanced specific toxicity toward target cells relative to conjugates with native BRIP.

B. Disulfide Bond Stability Assay

Immunoconjugates prepared with native BRIP and the BRIP analogs were examined by the disulfide bond stability assay described in Example 1. Briefly, conjugates were incubated with increasing concentrations of glutathione for 1 hour at 37° C. and, after terminating the reaction with iodoacetamide, the amount of RIP released was quantitated by size-exclusion HPLC on a TosoHaas TSK-G2000SW column.

By comparisons with the amount of RIP released by high concentrations of 2-mercaptoethanol (to determine 100% release), the concentration of glutathione required to release 50% of the RIP (the $RC_{50}$) was calculated. As shown below in Table 19, the conjugates prepared with $BRIP_{C270}$ or $BRIP_{C277}$ were significantly more stable than either the RTA conjugates or those prepared with native BRIP.

TABLE 19

| Conjugate | $RC_{50}$ (mM) |
|---|---|
| H65-RTA | 7.0 |
| H65-BRIP | 2.8 |
| H65-BRIPC277 | 196.0 |
| 4A2-RTA | 4.4 |
| 4A2-BRIP | 3.3 |
| 4A2-$BRIP_{C270}$ | 53.0 |
| 4A2-$BRIP_{C277}$ | 187.0 |

These unexpected results suggest that conjugates prepared with Type I RIP analogs according to the present invention may have enhanced stability and efficacy in vivo.

EXAMPLE 23

Preparation of Momordin and Analogs Thereof

Plants of the genus Momordica produce a number of related proteins known as momordins or momorcharins which are Type I RIPs. The gene encoding momordin II was cloned from *Momordica balsamina* seeds.

A. Preparation Of *M. balsamina* RNA

Total RNA was prepared from 4 g of *M. balsamina* seeds as described in Ausubel et al., supra. PolyA containing RNA was prepared from 1 mg of total RNA by chromatography on oligo-(dT)-cellulose. 40 mg of oligo-(dT)-cellulose Type 7 (Pharmacia) was added to 0.1N NaOH and poured into a disposable column (Biorad). The column was washed with water until the eluate was pH 5.5, and then was washed with 1× loading buffer (50 mM NaCitrate, 0.5M NaCl, 1 mM EDTA, 0.1% SDS, pH 7.0) until the eluate was pH 7.0. 1 mg of total RNA was suspended in 300 μl of water, heated to 65° C. for 5 minutes, and 300 μl of 2× loading buffer was added (100 mM Na Citrate, 1M NaCl, 2 mM EDTA, and 0.2% SDS). The RNA was loaded onto the column, and the flow through was reheated to 65° C., cooled to room temperature, and reloaded onto the column. Column-bound mRNA was washed 5 times with 0.5 ml of 1× loading buffer, and two times with 0.5 ml of 0.05M NaCitrate, 0.1M NaCl, 1 mM EDTA, 0.1% SDS. PolyA- containing RNA was eluted two times from the column with 0.5 ml of 25 mM NaCitrate, 1 mM EDTA, and 0.05% SDS.

B. Library Preparation

A cDNA library from the polyA-containing *M. balsamina* RNA was prepared in a bacterial expression plasmid with the SuperScript Plasmid System (BRL, Gaithersburg, Md.). The cDNA was synthesized from 2 μg of poly A-containing RNA, size fractionated, digested with NotI, and ligated into the expression vector pSPORT as recommended by the manufacturer of the vector, BRL.

C. Cloning Of The Momordin II Gene

A DNA fragment encoding the first 27 amino acids of momordin II was amplified from *M. balsamina* cDNA by PCR. First strand cDNA was prepared from 100 ng of polyA containing RNA with an RNA-PCR Kit (Perkin Elmer Cetus). Two partially degenerate primers were synthesized based on the amino acid sequence of the first 27 amino acids of momordin II described in Li et al., *Experientia*, 36:524–527 (1980). Because the amino acid sequence of amino acids 1–27 of momordin II is 52% homologous to amino acids 1–17 of momordin I [Ho et al., *BBA*, 1088:311–314 (1991)], some codon assignments in the degenerate primers were based on homology to the corresponding amino acid as well as codon preference in the momordin I gene. The sequences of primers momo-3 and momo-4 are set out below using IUPAC nucleotide symbols.

momo-3 (SEQ ID NO: 51)
5' GATGTTAAYTTYGAYTTGTCNACDGCTAC 3'
momo-4 (SEQ ID NO: 52)
5' ATTGGNAGDGTAGCCCTRAARTCYTCDAT 3'

The resulting 81 bp PCR product was purified on a 5% acrylamide gel and cloned into the SmaI site of pUC18. Three candidate clones were sequenced, and one clone, pMO110, was identified which encoded the N-terminal 27 amino acids of momordin II.

A hybridization probe was designed for screening of the momordin II cDNA library based on the sequence of the pMO110 momordin II DNA fragment. The sequence of the primer momo-5 is shown below.

momo-5 (SEQ ID NO: 53)
5' GCCACTGCAAAAACCTACACAAAATTTATTGA 3'

Primer momo-5 corresponds to amino acids 9–18 of mature momordin II. The underlined nucleotides of the primer were expected to match the DNA sequence of the momordin II gene exactly. Since this sequence is highly A/T-rich and may hybridize to the momordin II gene weakly, the additional adjacent nucleotides were included in the primer. Bases 3 and 30 (overlined) were in the "wobble" position (i.e., the third nucleotide in a codon) of amino acids 9 (alanine) and 18 (isoleucine), respectively, of momordin II and may not be identical to the nucleotide bases in the native gene.

A 90,000 member cDNA library in pSPORT was screened with $^{32}$P-kinased momo-5, and eight potential candidate clones were identified. One clone, pING3619, was sequenced and contains an open reading frame corresponding in part to the expected N-terminal 27 residues of Momordin II. The complete momordin gene contains 286 amino acids, the first 23 of which are a presumed leader signal (mature momordin II is 263 residues). The DNA sequence of the momordin II gene is set out in SEQ ID NO: 13.

D. Construction Of An Expression Vector Containing The Momordin II Gene

A bacterial expression vector for the momordin II gene was constructed. Two PCR primers were synthesized, one (momo-9) which primes from the +1 residue of the mature momordin II amino acid sequence, and one at the C-terminus (momo-10) of momordin II which introduces an XhoI restriction site:

momo-9 (SEQ ID NO: 54)
5' GATGTTAACTTCGATTTGTCGA 3'
momo-10 (SEQ ID NO: 55)
5' TCAACTCGAGGTACTCAATTCACAACAGATTCC 3' pING3619 was amplified with momo-9 and momo-10, and the product was treated with T4 polymerase, cut with XhoI, and purified on an agarose gel. This gene fragment was ligated along with the 131 bp pelB leader fragment from pIC100 which has been generated by SstI digestion, T4-polymerase treatment, and EcoRI digestion, into the araB expression vector cleaved with EcoRI and XhoI. The product of this three piece ligation was sequenced to verify that the pelB junction and momordin II coding sequence were correct. Arabinose induction of cells containing the momordin II expression plasmid pING3621 results in production of momordin II in *E. coli*.

E. Analogs Of Mormordin II

Mormordin II has no natural cysteines available for conjugation to antibody. Analogs of momordin which have a free cysteine for conjugation to an antibody may be constructed. Positions likely to be appropriate for substitution of a cysteine residue may be identified from FIG. 3 as positions near the ricin A-chain cysteine$_{259}$ and as positions including the last 26 amino acids of momordin II that are accessible to solvent. For example, the arginine at position 242 of momordin II aligns with the ricin A-chain cysteine at position 259 and is a preferred target for substitution. Additional preferred substitution positions for momordin II include the serine at position 241 and the alanine at position 243.

While the present invention has been described in terms of preferred embodiments, it is understood that variations and improvements will occur to those skilled in the art. Therefore, it is intended that the appended claims cover all such equivalent variations which come within the scope of the invention as claimed.

---

We claim:

1. A fusion protein comprising (a) a gelonin sequence that is SEQ ID NO. 2 or SEQ ID NO. 101 and (b) a targeting sequence that allows the internalization of said fusion protein, wherein said targeting sequence is an antibody, an antigen-binding portion of an antibody, a hormone, a lymphokine or a growth factor.

2. The fusion protein of claim 1, wherein said gelonin sequence is that of SEQ ID NO. 2.

3. The fission protein of claim 1, wherein said gelonin sequence is that of SEQ ID NO. 101.

4. The fusion protein of claim 1, further comprising a linker sequence between said gelonin sequence and said targeting sequence, wherein said gelonin possesses enzymatic activity, said antibody is capable of recognizing antigen and said hormone, lymphokine or growth factor is capable of binding to a cell that has a receptor for said hormone lymphokine or growth factor.

5. The fusion protein of claim 4, wherein said linker sequence is that of SEQ ID NO. 56 or SEQ ID NO. 57.

6. The fusion protein of any one of claims 1–5, wherein said targeting sequence is an antibody.

7. The fusion protein of any one of claims 1–5, wherein said targeting sequence is an antigen-binding portion of an antibody.

8. The fusion protein of claim 7, wherein said antigen-binding portion of said antibody is an Fab.

9. The fusion protein claim 7, wherein said antigen-binding portion of said antibody is an Fab.

10. The fusion protein claim 7, wherein said antigen-binding portion of said antibody is an F(ab')$_2$.

11. The fusion protein claim 7, wherein said antigen-binding portion of said antibody is an Fv.

12. The fusion protein claim 7, wherein said antigen-binding portion of said antibody has a single variable domain.

13. The fusion protein claim 7, wherein said antibody is a single-chain antibody.

14. The fusion protein claim 7, wherein said fusion protein is multivalent.

15. The fusion protein of any one of claims 1–5, wherein said targeting sequence is a hormone.

16. The fusion protein of any claims 1–5, wherein said targeting sequence is a lymphokine.

17. The fusion protein of any one of claims 1–5, wherein said targeting sequence is a growth factor.

18. A fusion protein comprising
   (a) a gelonin sequence that is a non-naturally occurring analog of gelonin SEQ ID NO. 2 or SEQ ID NO. 101, wherein a cysteine is substituted for another amino acid at an amino acid position not naturally available for intermolecular disulfide bonding in said gelonin SEQ ID NO. 2 or SEQ ID NO. 101, said cysteine being available for intermolecular disulfide bonding, said cysteine being substituted at an amino acid position in said gelonin from position 239 to the carboxy terminus of said gelonin SEQ ID NO. 2 or SEQ ID NO. 101, and wherein said analog retains the ability to inactivate ribosomes; and (b) a targeting sequence that allows the internalization of said fusion protein, wherein said targeting sequence is an antibody, an antigen-binding portion of an antibody, a hormone, a lymphokine or a growth factor.

19. The fusion protein of claim 18, wherein said cysteine is substituted at a position selected from the group consisting of positions 239, 244, 247 and 248 of the amino acid sequence of said analog.

20. The fusion protein of any one of claims 18 or 19, wherein additionally the native gelonin cysteine residues at positions 44 and 50 are replaced with alanine residues.

21. The fusion protein of claim 18, wherein said analog is an analog of gelonin SEQ ID NO. 2.

22. The fusion protein of claim 18, wherein said analog is an analog of gelonin SEQ ID NO. 101.

23. The fusion protein of claim 48, further comprising a linker sequence between said gelonin sequence and said targeting sequence, wherein said gelonin possesses enzymatic activity; said antibody is capable of recognizing, antigen and said hormone, lymphokine or growth factor is capable of binding to a cell that has a receptor for said hormone, lymphokine or growth factor.

24. The fusion protein of claim 23, wherein said linker sequence is that of SEQ ID NO. 56 or SEQ ID NO. 57.

25. The fusion protein of claim 18, wherein said targeting sequence is an antibody.

26. The fusion protein of claim 18, wherein said targeting sequence is an antigen-binding portion of an antibody.

27. The fusion protein of claim 26, wherein said antigen-binding portion of said antibody is an Fab.

28. The fusion protein of claim 26, wherein said antigen-binding portion of said antibody is an Fab'.

29. The fusion protein of claim 26, wherein said antigen-binding portion of said antibody is an $F(ab')_2$.

30. The fusion protein of claim 26, wherein said antigen-binding portion of said antibody is an Fv.

31. The fusion protein of claim 26, wherein said antigen-binding portion of said antibody has a single variable domain.

32. The fusion protein of claim 25, wherein said antibody is a single-chain antibody.

33. The fusion protein of claim 18, wherein said fusion protein is multivalent.

34. The fusion protein of claim 18, wherein said targeting sequence is a hormone.

35. The fusion protein of claim 18, wherein said targeting sequence is a lymphokine.

36. The fusion protein of claim 18, wherein said targeting sequence is a growth factor.

* * * * *

SEQUENCE LISTING ( 1 ) GENERAL INFORMATION:

( i i i ) NUMBER OF SEQUENCES: 169

( 2 ) INFORMATION FOR SEQ ID NO:1:

( i ) SEQUENCE CHARACTERISTICS:
      ( A ) LENGTH: 267 amino acids
      ( B ) TYPE: amino acid
      ( D ) TOPOLOGY: linear ( i i ) MOLECULE TYPE: protein ( x i ) SEQUENCE DESCRIPTION: SEQ ID NO:1:

```
Ile Phe Pro Lys Gln Tyr Pro Ile Ile Asn Phe Thr Thr Ala Gly Ala
 1               5                  10                  15

Thr Val Gln Ser Tyr Thr Asn Phe Ile Arg Ala Val Arg Gly Arg Leu
            20                  25                  30
```

| | | | | | | | | | | | | | | |
|---|---|---|---|---|---|---|---|---|---|---|---|---|---|---|
| Thr | Thr | Gly<br>35 | Ala | Asp | Val | Arg | His<br>40 | Glu | Ile | Pro | Val | Leu<br>45 | Pro | Asn | Arg |
| Val | Gly<br>50 | Leu | Pro | Ile | Asn<br>55 | Gln | Arg | Phe | Ile | Leu<br>60 | Val | Glu | Leu | Ser | Asn |
| His<br>65 | Ala | Glu | Leu | Ser | Val<br>70 | Thr | Leu | Ala | Leu | Asp<br>75 | Val | Thr | Asn | Ala | Tyr<br>80 |
| Val | Val | Gly | Tyr | Arg<br>85 | Ala | Gly | Asn | Ser | Ala<br>90 | Tyr | Phe | Phe | His | Pro<br>95 | Asp |
| Asn | Gln | Glu | Asp<br>100 | Ala | Glu | Ala | Ile | Thr<br>105 | His | Leu | Phe | Thr | Asp<br>110 | Val | Gln |
| Asn | Arg | Tyr<br>115 | Thr | Phe | Ala | Phe | Gly<br>120 | Gly | Asn | Tyr | Asp | Arg<br>125 | Leu | Glu | Gln |
| Leu | Ala<br>130 | Gly | Asn | Leu | Arg | Glu<br>135 | Asn | Ile | Glu | Leu | Gly<br>140 | Asn | Gly | Pro | Leu |
| Glu<br>145 | Glu | Ala | Ile | Ser | Ala<br>150 | Leu | Tyr | Tyr | Tyr | Ser<br>155 | Thr | Gly | Gly | Thr | Gln<br>160 |
| Leu | Pro | Thr | Leu | Ala<br>165 | Arg | Ser | Phe | Ile | Ile<br>170 | Cys | Ile | Gln | Met | Ile<br>175 | Ser |
| Glu | Ala | Ala | Arg<br>180 | Phe | Gln | Tyr | Ile | Glu<br>185 | Gly | Glu | Met | Arg | Thr<br>190 | Arg | Ile |
| Arg | Tyr | Asn<br>195 | Arg | Arg | Ser | Ala | Pro<br>200 | Asp | Pro | Ser | Val | Ile<br>205 | Thr | Leu | Glu |
| Asn | Ser<br>210 | Trp | Gly | Arg | Leu | Ser<br>215 | Thr | Ala | Ile | Gln | Glu<br>220 | Ser | Asn | Gln | Gly |
| Ala<br>225 | Phe | Ala | Ser | Pro | Ile<br>230 | Gln | Leu | Gln | Arg | Arg<br>235 | Asn | Gly | Ser | Lys | Phe<br>240 |
| Ser | Val | Tyr | Asp | Val<br>245 | Ser | Ile | Leu | Ile | Pro<br>250 | Ile | Ile | Ala | Leu | Met<br>255 | Val |
| Tyr | Arg | Cys | Ala<br>260 | Pro | Pro | Pro | Ser | Ser<br>265 | Gln | Phe | | | | | |

( 2 ) INFORMATION FOR SEQ ID NO:2:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Gly<br>1 | Leu | Asp | Thr | Val<br>5 | Ser | Phe | Ser | Thr | Lys<br>10 | Gly | Ala | Thr | Tyr | Ile<br>15 | Thr |
| Tyr | Val | Asn | Phe<br>20 | Leu | Asn | Glu | Leu | Arg<br>25 | Val | Lys | Leu | Lys | Pro<br>30 | Glu | Gly |
| Asn | Ser | His<br>35 | Gly | Ile | Pro | Leu | Leu<br>40 | Arg | Lys | Lys | Cys | Asp<br>45 | Asp | Pro | Gly |
| Lys | Cys<br>50 | Phe | Val | Leu | Val | Ala<br>55 | Leu | Ser | Asn | Asp | Asn<br>60 | Gly | Gln | Leu | Ala |
| Glu<br>65 | Ile | Ala | Ile | Asp | Val<br>70 | Thr | Ser | Val | Tyr | Val<br>75 | Val | Gly | Tyr | Gln | Val<br>80 |
| Arg | Asn | Arg | Ser | Tyr<br>85 | Phe | Phe | Lys | Asp | Ala<br>90 | Pro | Asp | Ala | Ala | Tyr<br>95 | Glu |
| Gly | Leu | Phe | Lys<br>100 | Asn | Thr | Ile | Lys | Thr<br>105 | Arg | Leu | His | Phe | Gly<br>110 | Gly | Ser |
| Tyr | Pro | Ser | Leu | Glu | Gly | Glu | Lys | Ala | Tyr | Arg | Glu | Thr | Thr | Asp | Leu |

```
                         115                         120                         125
      Gly  Ile  Glu  Pro  Leu  Arg  Ile  Gly  Ile  Lys  Lys  Leu  Asp  Glu  Asn  Ala
           130                         135                     140

Ile  Asp  Asn  Tyr  Lys  Pro  Thr  Glu  Ile  Ala  Ser  Ser  Leu  Leu  Val  Val
      145                          150                     155                      160

Ile  Gln  Met  Val  Ser  Glu  Ala  Ala  Arg  Phe  Thr  Phe  Ile  Glu  Asn  Gln
                          165                          170                      175

Ile  Arg  Asn  Asn  Phe  Gln  Gln  Arg  Ile  Arg  Pro  Ala  Asn  Asn  Thr  Ile
                     180                          185                     190

Ser  Leu  Glu  Asn  Lys  Trp  Gly  Lys  Leu  Ser  Phe  Gln  Ile  Arg  Thr  Ser
                195                          200                     205

Gly  Ala  Asn  Gly  Met  Phe  Ser  Glu  Ala  Val  Glu  Leu  Glu  Arg  Ala  Asn
           210                          215                     220

Gly  Lys  Lys  Tyr  Tyr  Val  Thr  Ala  Val  Asp  Gln  Val  Lys  Pro  Lys  Ile
      225                          230                     235                      240

Ala  Leu  Leu  Lys  Phe  Val  Asp  Lys  Asp  Pro  Lys
                          245                     250
```

( 2 ) INFORMATION FOR SEQ ID NO:3:

( i ) SEQUENCE CHARACTERISTICS:
       ( A ) LENGTH: 280 amino acids
       ( B ) TYPE: amino acid
       ( D ) TOPOLOGY: linear ( i i ) MOLECULE TYPE: protein ( x i ) SEQUENCE DESCRIPTION: SEQ ID NO:3:

```
      Ala  Ala  Lys  Met  Ala  Lys  Asn  Val  Asp  Lys  Pro  Leu  Phe  Thr  Ala  Thr
      1                    5                         10                       15

Phe  Asn  Val  Gln  Ala  Ser  Ser  Ala  Asp  Tyr  Ala  Thr  Phe  Ile  Ala  Gly
                     20                          25                      30

Ile  Arg  Asn  Lys  Leu  Arg  Asn  Pro  Ala  His  Phe  Ser  His  Asn  Arg  Pro
                35                          40                      45

Val  Leu  Pro  Pro  Val  Glu  Pro  Asn  Val  Pro  Pro  Ser  Arg  Trp  Phe  His
           50                          55                      60

Val  Val  Leu  Lys  Ala  Ser  Pro  Thr  Ser  Ala  Gly  Leu  Thr  Leu  Ala  Ile
      65                         70                      75                       80

Arg  Ala  Asp  Asn  Ile  Tyr  Leu  Glu  Gly  Phe  Lys  Ser  Ser  Asp  Gly  Thr
                          85                      90                       95

Trp  Trp  Glu  Leu  Thr  Pro  Gly  Leu  Ile  Pro  Gly  Ala  Thr  Tyr  Val  Gly
                     100                         105                     110

Phe  Gly  Gly  Thr  Tyr  Arg  Asp  Leu  Leu  Gly  Asp  Thr  Asp  Lys  Leu  Thr
                115                          120                     125

Asn  Val  Ala  Leu  Gly  Arg  Gln  Gln  Leu  Ala  Asp  Ala  Val  Thr  Ala  Leu
           130                          135                     140

His  Gly  Arg  Thr  Lys  Ala  Asp  Lys  Ala  Ser  Gly  Pro  Lys  Gln  Gln  Gln
      145                          150                     155                      160

Ala  Arg  Glu  Ala  Val  Thr  Thr  Leu  Val  Leu  Met  Val  Asn  Glu  Ala  Thr
                          165                     170                      175

Arg  Phe  Gln  Thr  Val  Ser  Gly  Phe  Val  Ala  Gly  Leu  Leu  His  Pro  Lys
                     180                          185                     190

Ala  Val  Glu  Lys  Lys  Ser  Gly  Lys  Ile  Gly  Asn  Glu  Met  Lys  Ala  Gln
                195                          200                     205

Val  Asn  Gly  Trp  Gln  Asp  Leu  Ser  Ala  Ala  Leu  Leu  Lys  Thr  Asp  Val
           210                          215                     220
```

```
Lys  Pro  Pro  Pro  Gly  Lys  Ser  Pro  Ala  Lys  Phe  Ala  Pro  Ile  Glu  Lys
225                 230                 235                 240

Met  Gly  Val  Arg  Thr  Ala  Glu  Gln  Ala  Ala  Asn  Thr  Leu  Gly  Ile  Leu
               245                      250                      255

Leu  Phe  Val  Glu  Val  Pro  Gly  Gly  Leu  Thr  Val  Ala  Lys  Ala  Leu  Glu
               260                 265                      270

Leu  Phe  His  Ala  Ser  Gly  Gly  Lys
          275                 280
```

( 2 ) INFORMATION FOR SEQ ID NO:4:

( i ) SEQUENCE CHARACTERISTICS:
        ( A ) LENGTH: 263 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asp  Val  Asn  Phe  Asp  Leu  Ser  Thr  Ala  Thr  Ala  Lys  Thr  Tyr  Thr  Lys
1               5                    10                      15

Phe  Ile  Glu  Asp  Phe  Arg  Ala  Thr  Leu  Pro  Phe  Ser  His  Lys  Val  Tyr
               20                     25                     30

Asp  Ile  Pro  Leu  Leu  Tyr  Ser  Thr  Ile  Ser  Asp  Ser  Arg  Arg  Phe  Ile
               35                     40                     45

Leu  Leu  Asp  Leu  Thr  Ser  Tyr  Ala  Tyr  Glu  Thr  Ile  Ser  Val  Ala  Ile
          50                     55                     60

Asp  Val  Thr  Asn  Val  Tyr  Val  Val  Ala  Tyr  Arg  Thr  Arg  Asp  Val  Ser
65                     70                     75                     80

Tyr  Phe  Phe  Lys  Glu  Ser  Pro  Pro  Glu  Ala  Tyr  Asn  Ile  Leu  Phe  Lys
               85                     90                     95

Gly  Thr  Arg  Lys  Ile  Thr  Leu  Pro  Tyr  Thr  Gly  Asn  Tyr  Glu  Asn  Leu
               100                    105                    110

Gln  Thr  Ala  Ala  His  Lys  Ile  Arg  Glu  Asn  Ile  Asp  Leu  Gly  Leu  Pro
               115                    120                    125

Ala  Leu  Ser  Ser  Ala  Ile  Thr  Thr  Leu  Phe  Tyr  Tyr  Asn  Ala  Gln  Ser
          130                    135                    140

Ala  Pro  Ser  Ala  Leu  Leu  Val  Leu  Ile  Gln  Thr  Thr  Ala  Glu  Ala  Ala
145                    150                    155                    160

Arg  Phe  Lys  Tyr  Ile  Glu  Arg  His  Val  Ala  Lys  Tyr  Val  Ala  Thr  Asn
               165                    170                    175

Phe  Lys  Pro  Asn  Leu  Ala  Ile  Ile  Ser  Leu  Glu  Asn  Gln  Trp  Ser  Ala
               180                    185                    190

Leu  Ser  Lys  Gln  Ile  Phe  Leu  Ala  Gln  Asn  Gln  Gly  Gly  Lys  Phe  Arg
          195                    200                    205

Asn  Pro  Val  Asp  Leu  Ile  Lys  Pro  Thr  Gly  Glu  Arg  Phe  Gln  Val  Thr
          210                    215                    220

Asn  Val  Asp  Ser  Asp  Val  Val  Lys  Gly  Asn  Ile  Lys  Leu  Leu  Leu  Asn
225                    230                    235                    240

Ser  Arg  Ala  Ser  Thr  Ala  Asp  Glu  Asn  Phe  Ile  Thr  Thr  Met  Thr  Leu
               245                    250                    255

Leu  Gly  Glu  Ser  Val  Val  Asn
               260
```

( 2 ) INFORMATION FOR SEQ ID NO:5:

( i ) SEQUENCE CHARACTERISTICS:
        ( A ) LENGTH: 248 amino acids (B) TYPE: amino acid
(D) TOPOLOGY: linear (ii) MOLECULE TYPE: protein (xi) SEQUENCE DESCRIPTION: SEQ ID NO:5:

```
Asp Val Arg Phe Ser Leu Ser Gly Ser Ser Thr Ser Tyr Ser Lys
1               5                  10                 15

Phe Ile Gly Asp Leu Arg Lys Ala Leu Pro Ser Asn Gly Thr Val Tyr
            20                  25                 30

Asn Leu Thr Ile Leu Leu Ser Ser Ala Ser Gly Ala Ser Arg Tyr Thr
        35                  40                  45

Leu Met Thr Leu Ser Asn Tyr Asp Gly Lys Ala Ile Thr Val Ala Val
    50                  55                  60

Asp Val Ser Gln Leu Tyr Ile Met Gly Tyr Leu Val Asn Ser Thr Ser
65                  70                  75                  80

Tyr Phe Phe Asn Glu Ser Asp Ala Lys Leu Ala Ser Gln Tyr Val Phe
                85                  90                  95

Lys Gly Ser Thr Ile Val Thr Leu Pro Tyr Ser Gly Asn Tyr Glu Lys
            100                 105                 110

Leu Gln Thr Ala Ala Gly Lys Ile Arg Glu Lys Ile Pro Leu Gly Phe
        115                 120                 125

Pro Ala Leu Asp Ser Ala Leu Thr Thr Ile Phe His Tyr Asp Ser Thr
    130                 135                 140

Ala Ala Ala Ala Ala Phe Leu Val Ile Leu Gln Thr Thr Ala Glu Ala
145                 150                 155                 160

Ser Arg Phe Lys Tyr Ile Glu Gly Gln Ile Ile Glu Arg Ile Ser Lys
                165                 170                 175

Asn Gln Val Pro Ser Leu Ala Thr Ile Ser Leu Glu Asn Ser Leu Trp
            180                 185                 190

Ser Ala Leu Ser Lys Gln Ile Gln Leu Ala Gln Thr Asn Asn Gly Thr
        195                 200                 205

Phe Lys Thr Pro Val Val Ile Thr Asp Asp Lys Gln Gln Arg Val Glu
    210                 215                 220

Ile Thr Asn Val Thr Ser Lys Val Val Thr Lys Asn Ile Gln Leu Leu
225                 230                 235                 240

Leu Asn Tyr Lys Gln Asn Val Ala
                245
```

(2) INFORMATION FOR SEQ ID NO:6:

(i) SEQUENCE CHARACTERISTICS:
(A) LENGTH: 247 amino acids
(B) TYPE: amino acid
(D) TOPOLOGY: linear (ii) MOLECULE TYPE: protein (xi) SEQUENCE DESCRIPTION: SEQ ID NO:6:

```
Asp Val Ser Phe Arg Leu Ser Gly Ala Thr Ser Ser Ser Tyr Gly Val
1               5                  10                 15

Phe Ile Ser Asn Leu Arg Lys Ala Leu Pro Asn Glu Arg Lys Leu Tyr
            20                  25                 30

Asp Ile Pro Leu Leu Arg Ser Ser Leu Pro Gly Ser Gln Arg Tyr Ala
        35                  40                  45

Leu Ile His Leu Thr Asn Tyr Ala Asp Glu Thr Ile Ser Val Ala Ile
    50                  55                  60

Asp Val Thr Asn Val Tyr Ile Met Gly Tyr Arg Ala Gly Asp Thr Ser
```

```
     65                          70                          75                          80
Tyr  Phe  Phe  Asn  Glu  Ala  Ser  Ala  Thr  Glu  Ala  Ala  Lys  Tyr  Val  Phe
                         85                      90                      95

Lys  Asp  Ala  Met  Arg  Lys  Val  Thr  Leu  Pro  Tyr  Ser  Gly  Asn  Tyr  Glu
               100                      105                     110

Arg  Leu  Gln  Thr  Ala  Ala  Gly  Lys  Ile  Arg  Glu  Asn  Ile  Pro  Leu  Gly
               115                      120                     125

Leu  Pro  Ala  Leu  Asp  Ser  Ala  Ile  Thr  Thr  Leu  Phe  Tyr  Tyr  Asn  Ala
          130                      135                     140

Asn  Ser  Ala  Ala  Ser  Ala  Leu  Met  Val  Leu  Ile  Gln  Ser  Thr  Ser  Glu
145                      150                     155                          160

Ala  Ala  Arg  Tyr  Lys  Phe  Ile  Glu  Gln  Gln  Ile  Gly  Lys  Arg  Val  Asp
               165                      170                     175

Lys  Thr  Phe  Leu  Pro  Ser  Leu  Ala  Ile  Ile  Ser  Leu  Glu  Asn  Ser  Trp
               180                      185                     190

Ser  Ala  Leu  Ser  Lys  Gln  Ile  Gln  Ile  Ala  Ser  Thr  Asn  Asn  Gly  Gln
               195                      200                     205

Phe  Glu  Ser  Pro  Val  Val  Leu  Ile  Asn  Ala  Gln  Asn  Gln  Val  Ala  Thr
     210                      215                     220

Ile  Thr  Asn  Val  Asp  Ala  Gly  Val  Val  Thr  Ser  Asn  Ile  Ala  Leu  Leu
225                      230                     235                          240

Leu  Asn  Arg  Asn  Asn  Met  Ala
                    245
```

( 2 ) INFORMATION FOR SEQ ID NO:7:

( i ) SEQUENCE CHARACTERISTICS:
      ( A ) LENGTH: 263 amino acids
      ( B ) TYPE: amino acid
      ( D ) TOPOLOGY: linear ( i i ) MOLECULE TYPE: protein ( x i ) SEQUENCE DESCRIPTION: SEQ ID NO:7:

```
Asp  Val  Ser  Phe  Arg  Leu  Ser  Gly  Ala  Asp  Pro  Arg  Ser  Tyr  Gly  Met
1                   5                        10                      15

Phe  Ile  Lys  Asp  Leu  Arg  Asn  Ala  Leu  Pro  Phe  Arg  Glu  Lys  Val  Tyr
               20                       25                      30

Asn  Ile  Pro  Leu  Leu  Leu  Pro  Ser  Val  Ser  Gly  Ala  Gly  Arg  Tyr  Leu
          35                       40                      45

Leu  Met  His  Leu  Phe  Asn  Tyr  Asp  Gly  Lys  Thr  Ile  Thr  Val  Ala  Val
     50                       55                      60

Asp  Val  Thr  Asn  Val  Tyr  Ile  Met  Gly  Tyr  Leu  Ala  Asp  Thr  Thr  Ser
65                       70                      75                           80

Tyr  Phe  Phe  Asn  Glu  Pro  Ala  Ala  Glu  Leu  Ala  Ser  Gln  Tyr  Val  Phe
                    85                       90                      95

Arg  Asp  Ala  Arg  Arg  Lys  Ile  Thr  Leu  Pro  Tyr  Ser  Gly  Asn  Tyr  Glu
               100                      105                     110

Arg  Leu  Gln  Ile  Ala  Ala  Gly  Lys  Pro  Arg  Glu  Lys  Ile  Pro  Ile  Gly
               115                      120                     125

Leu  Pro  Ala  Leu  Asp  Ser  Ala  Ile  Ser  Thr  Leu  Leu  His  Tyr  Asp  Ser
          130                      135                     140

Thr  Ala  Ala  Ala  Gly  Ala  Leu  Leu  Val  Leu  Ile  Gln  Thr  Thr  Ala  Glu
145                      150                     155                          160

Ala  Ala  Arg  Phe  Lys  Tyr  Ile  Glu  Gln  Gln  Ile  Gln  Glu  Arg  Ala  Tyr
               165                      170                     175
```

```
Arg  Asp  Glu  Val  Pro  Ser  Leu  Ala  Thr  Ile  Ser  Leu  Glu  Asn  Ser  Trp
              180                      185                      190

Ser  Gly  Leu  Ser  Lys  Gln  Ile  Gln  Leu  Ala  Gln  Gly  Asn  Asn  Gly  Ile
         195                      200                      205

Phe  Arg  Thr  Pro  Ile  Val  Leu  Val  Asp  Asn  Lys  Gly  Asn  Arg  Val  Gln
    210                      215                      220

Ile  Thr  Asn  Val  Thr  Ser  Lys  Val  Val  Thr  Ser  Asn  Ile  Gln  Leu  Leu
225                      230                      235                      240

Leu  Asn  Thr  Arg  Asn  Ile  Ala  Glu  Gly  Asp  Asn  Gly  Asp  Val  Ser  Thr
              245                      250                      255

Thr  His  Gly  Phe  Ser  Ser  Thr
              260
```

( 2 ) INFORMATION FOR SEQ ID NO:8:

( i ) SEQUENCE CHARACTERISTICS:
    ( A ) LENGTH: 250 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Ala  Pro  Thr  Leu  Glu  Thr  Ile  Ala  Ser  Leu  Asp  Leu  Asn  Asn  Pro  Thr
1                   5                        10                       15

Thr  Tyr  Leu  Ser  Phe  Ile  Thr  Asn  Ile  Arg  Thr  Lys  Val  Ala  Asp  Lys
              20                      25                       30

Thr  Glu  Gln  Cys  Thr  Ile  Gln  Lys  Ile  Ser  Lys  Thr  Phe  Thr  Gln  Arg
         35                      40                       45

Tyr  Ser  Tyr  Ile  Asp  Leu  Ile  Val  Ser  Ser  Thr  Gln  Lys  Ile  Thr  Leu
    50                       55                      60

Ala  Ile  Asp  Met  Ala  Asp  Leu  Tyr  Val  Leu  Gly  Tyr  Ser  Asp  Ile  Ala
65                   70                       75                           80

Asn  Asn  Lys  Gly  Arg  Ala  Phe  Phe  Phe  Lys  Asp  Val  Thr  Glu  Ala  Val
              85                      90                       95

Ala  Asn  Asn  Phe  Phe  Pro  Gly  Ala  Thr  Gly  Thr  Asn  Arg  Ile  Lys  Leu
              100                     105                      110

Thr  Phe  Thr  Gly  Ser  Tyr  Gly  Asp  Leu  Glu  Lys  Asn  Gly  Gly  Leu  Arg
         115                     120                      125

Lys  Asp  Asn  Pro  Leu  Gly  Ile  Phe  Arg  Leu  Glu  Asn  Ser  Ile  Val  Asn
    130                      135                     140

Ile  Tyr  Gly  Lys  Ala  Gly  Asp  Val  Lys  Lys  Gln  Ala  Lys  Phe  Phe  Leu
145                      150                     155                      160

Leu  Ala  Ile  Gln  Met  Val  Ser  Glu  Ala  Ala  Arg  Phe  Lys  Tyr  Ile  Ser
              165                     170                      175

Asp  Lys  Ile  Pro  Ser  Glu  Lys  Tyr  Glu  Glu  Val  Thr  Val  Asp  Glu  Tyr
              180                     185                      190

Met  Thr  Ala  Leu  Glu  Asn  Asn  Trp  Ala  Lys  Leu  Ser  Thr  Ala  Val  Tyr
         195                     200                      205

Asn  Ser  Lys  Pro  Ser  Thr  Thr  Thr  Ala  Thr  Lys  Cys  Gln  Leu  Ala  Thr
    210                      215                     220

Ser  Pro  Val  Thr  Ile  Ser  Pro  Trp  Ile  Phe  Lys  Thr  Val  Glu  Glu  Ile
225                      230                     235                       240

Lys  Leu  Val  Met  Gly  Leu  Leu  Lys  Ser  Ser
              245                     250
```

( 2 ) INFORMATION FOR SEQ ID NO:9:

( i ) SEQUENCE CHARACTERISTICS:
   ( A ) LENGTH: 261 amino acids
   ( B ) TYPE: amino acid
   ( D ) TOPOLOGY: linear ( i i ) MOLECULE TYPE: protein ( x i ) SEQUENCE DESCRIPTION: SEQ ID NO:9:

```
Ile Asn Thr Ile Thr Phe Asp Ala Gly Asn Ala Thr Ile Asn Lys Tyr
 1               5                  10                  15
Ala Thr Phe Met Glu Ser Leu Arg Asn Glu Ala Lys Asp Pro Ser Leu
                20                  25                  30
Lys Cys Tyr Gly Ile Pro Met Leu Pro Asn Thr Asn Ser Thr Ile Lys
            35                  40                  45
Tyr Leu Leu Val Lys Leu Gln Gly Ala Ser Leu Lys Thr Ile Thr Leu
    50                  55                  60
Met Leu Arg Arg Asn Asn Leu Tyr Val Met Gly Tyr Ser Asp Pro Tyr
65                  70                  75                  80
Asp Asn Lys Cys Arg Tyr His Ile Phe Asn Asp Ile Lys Gly Thr Glu
                85                  90                  95
Tyr Ser Asp Val Glu Asn Thr Leu Cys Pro Ser Ser Asn Pro Arg Val
           100                 105                 110
Ala Lys Pro Ile Asn Tyr Asn Gly Leu Tyr Pro Thr Leu Glu Lys Lys
       115                 120                 125
Ala Gly Val Thr Ser Arg Asn Glu Val Gln Leu Gly Ile Gln Ile Leu
   130                 135                 140
Ser Ser Asp Ile Gly Lys Ile Ser Gly Gln Gly Ser Phe Thr Glu Lys
145                 150                 155                 160
Ile Glu Ala Asp Phe Leu Leu Val Ala Ile Gln Met Val Ser Glu Ala
                165                 170                 175
Ala Arg Phe Lys Tyr Ile Glu Asn Gln Val Lys Thr Asn Phe Asn Arg
           180                 185                 190
Asp Phe Ser Pro Asn Asp Lys Val Leu Asp Leu Glu Glu Asn Trp Gly
       195                 200                 205
Lys Ile Ser Thr Ala Ile His Asn Ser Lys Asn Gly Ala Leu Pro Lys
   210                 215                 220
Pro Leu Glu Leu Lys Asn Ala Asp Gly Thr Lys Trp Ile Val Leu Arg
225                 230                 235                 240
Val Asp Glu Ile Lys Pro Asp Val Gly Leu Leu Asn Tyr Val Asn Gly
                245                 250                 255
Thr Cys Gln Ala Thr
            260
```

( 2 ) INFORMATION FOR SEQ ID NO:10:

( i ) SEQUENCE CHARACTERISTICS:
   ( A ) LENGTH: 259 amino acids
   ( B ) TYPE: amino acid
   ( D ) TOPOLOGY: linear ( i i ) MOLECULE TYPE: protein ( x i ) SEQUENCE DESCRIPTION: SEQ ID NO:10:

```
Val Thr Ser Ile Thr Leu Asp Leu Val Asn Pro Thr Ala Gly Gln Tyr
 1               5                  10                  15
Ser Ser Phe Val Asp Lys Ile Arg Asn Asn Val Lys Asp Pro Asn Leu
                20                  25                  30
Lys Tyr Gly Gly Thr Asp Ile Ala Val Ile Gly Pro Pro Ser Lys Glu
```

|  |  |  |  |  | 35 |  |  |  |  | 40 |  |  |  |  | 45 |  |  |  |
|---|---|---|---|---|---|---|---|---|---|---|---|---|---|---|---|---|---|---|
| Lys | Phe 50 | Leu | Arg | Ile | Asn | Phe 55 | Gln | Ser | Ser | Arg | Gly 60 | Thr | Val | Ser | Leu |
| Gly 65 | Leu | Lys | Arg | Asp | Asn 70 | Leu | Tyr | Val | Val | Ala 75 | Tyr | Leu | Ala | Met | Asp 80 |
| Asn | Thr | Asn | Val | Asn 85 | Arg | Ala | Tyr | Tyr | Phe 90 | Arg | Ser | Glu | Ile | Thr 95 | Ser |
| Ala | Glu | Ser | Thr 100 | Ala | Leu | Phe | Pro | Glu 105 | Ala | Thr | Thr | Ala | Asn 110 | Gln | Lys |
| Ala | Leu | Glu 115 | Tyr | Thr | Glu | Asp | Tyr 120 | Gln | Ser | Ile | Glu | Lys 125 | Asn | Ala | Gln |
| Ile | Thr 130 | Gln | Gly | Asp | Gln | Ser 135 | Arg | Lys | Glu | Leu | Gly 140 | Leu | Gly | Ile | Asp |
| Leu 145 | Leu | Ser | Thr | Ser | Met 150 | Glu | Ala | Val | Asn | Lys 155 | Lys | Ala | Arg | Val | Val 160 |
| Lys | Asp | Glu | Ala | Arg 165 | Phe | Leu | Leu | Ile | Ala 170 | Ile | Gln | Met | Thr | Ala 175 | Glu |
| Ala | Ala | Arg | Phe 180 | Arg | Tyr | Ile | Gln | Asn 185 | Leu | Val | Ile | Lys | Asn 190 | Phe | Pro |
| Asn | Lys | Phe 195 | Asn | Ser | Glu | Asn | Lys 200 | Val | Ile | Gln | Phe | Glu 205 | Val | Asn | Trp |
| Lys | Lys 210 | Ile | Ser | Thr | Ala | Ile 215 | Tyr | Gly | Asp | Ala | Lys 220 | Asn | Gly | Val | Phe |
| Asn 225 | Lys | Asp | Tyr | Asp | Phe 230 | Gly | Phe | Gly | Lys | Val 235 | Arg | Gln | Val | Lys | Asp 240 |
| Leu | Gln | Met | Gly | Leu 245 | Leu | Met | Tyr | Leu | Gly 250 | Lys | Pro | Lys | Ser | Ser 255 | Asn |
| Glu | Ala | Asn |  |  |  |  |  |  |  |  |  |  |  |  |  |

( 2 ) INFORMATION FOR SEQ ID NO:11:

( i ) SEQUENCE CHARACTERISTICS:
( A ) LENGTH: 813 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

```
GGGCTAGATA CCGTGTCATT CTCAACCAAA GGTGCCACTT ATATTACCTA CGTGAATTTC      60
TTGAATGAGC TACGAGTTAA ATTGAAACCC GAAGGTAACA GCCATGGAAT CCCATTGCTG     120
CGCAAAAAAT GTGATGATCC TGGAAAGTGT TTCGTTTTGG TAGCGCTTTC AAATGACAAT     180
GGACAGTTGG CGGAAATAGC TATAGATGTT ACAAGTGTTT ATGTGGTGGG CTATCAAGTA     240
AGAAACAGAT CTTACTTCTT TAAAGATGCT CCAGATGCTG CTTACGAAGG CCTCTTCAAA     300
AACACAATTA AAACAAGACT TCATTTTGGC GGCAGCTATC CCTCGCTGGA AGGTGAGAAG     360
GCATATAGAG AGACAACAGA CTTGGGCATT GAACCATTAA GGATTGGCAT CAAGAAACTT     420
GATGAAAATG CGATAGACAA TTATAAACCA ACGGAGATAG CTAGTTCTCT ATTGGTTGTT     480
ATTCAAATGG TGTCTGAAGC AGCTCGATTC ACCTTTATTG AGAACCAAAT TAGAAATAAC     540
TTTCAACAGA GAATTCGCCC GGCGAATAAT ACAATCAGCC TTGAGAATAA ATGGGGTAAA     600
CTCTCGTTCC AGATCCGGAC ATCAGGTGCA AATGGAATGT TTCGGAGGC AGTTGAATTG      660
GAACGTGCAA ATGGCAAAAA ATACTATGTC ACCGCAGTTG ATCAAGTAAA ACCCAAAATA     720
```

| GCACTCTTGA | AGTTCGTCGA | TAAAGATCCT | AAAACGAGCC | TTGCTGCTGA | ATTGATAATC | 780 |
| CAGAACTATG | AGTCATTAGT | GGGCTTTGAT | TAG | | | 813 |

( 2 ) INFORMATION FOR SEQ ID NO:12:

( i ) SEQUENCE CHARACTERISTICS:
    ( A ) LENGTH: 846 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

| ATGGCGGCAA | AGATGGCGAA | GAACGTGGAC | AAGCCGCTCT | TCACCGCGAC | GTTCAACGTC | 60 |
| CAGGCCAGCT | CCGCCGACTA | CGCCACCTTC | ATCGCCGGCA | TCCGCAACAA | GCTCCGCAAC | 120 |
| CCGGCGCACT | TCTCCCACAA | CCGCCCCGTG | CTGCCGCCGG | TCGAGCCCAA | CGTCCCGCCG | 180 |
| AGCAGGTGGT | TCCACGTCGT | GCTCAAGGCC | TCGCCGACCA | GCGCCGGGCT | CACGCTGGCC | 240 |
| ATCCGCGCGG | ACAACATCTA | CCTGGAGGGC | TTCAAGAGCA | GCGACGGCAC | CTGGTGGGAG | 300 |
| CTCACCCCGG | GCCTCATCCC | CGGCGCCACC | TACGTCGGGT | TCGGCGGCAC | CTACCGCGAC | 360 |
| CTCCTCGGCG | ACACCGACAA | GCTAACCAAC | GTCGCTCTCG | GCCGACAGCA | GCTGGCGGAC | 420 |
| GCGGTGACCG | CGCTCCACGG | GCGCACCAAG | GCCGACAAGG | CCTCCGGCCC | GAAGCAGCAG | 480 |
| CAGGCGAGGG | AGGCGGTGAC | GACGCTGGTC | CTCATGGTGA | CGAGGCCAC | GCGGTTCCAG | 540 |
| ACGGTGTCTG | GGTTCGTGGC | CGGGTTGCTG | CACCCCAAGG | CGGTGGAGAA | GAAGAGCGGG | 600 |
| AAGATCGGCA | ATGAGATGAA | GGCCCAGGTG | AACGGGTGGC | AGGACCTGTC | CGCGGCGCTG | 660 |
| CTGAAGACGG | ACGTGAAGCC | TCCGCCGGGA | AAGTCGCCAG | CGAAGTTCGC | GCCGATCGAG | 720 |
| AAGATGGGCG | TGAGGACGGC | TGAACAGGCC | GCCAACACGC | TGGGGATCCT | GCTGTTCGTG | 780 |
| GAGGTGCCGG | GTGGGTTGAC | GGTGGCCAAG | GCGCTGGAGC | TGTTCCATGC | GAGTGGTGGG | 840 |
| AAATAG | | | | | | 846 |

( 2 ) INFORMATION FOR SEQ ID NO:13:

( i ) SEQUENCE CHARACTERISTICS:
    ( A ) LENGTH: 913 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

| CGTCCGAAAA | TGGTGAAATG | CTTACTACTT | TCTTTTTTAA | TTATCGCCAT | CTTCATTGGT | 60 |
| GTTCCTACTG | CCAAAGGCGA | TGTTAACTTC | GATTTGTCGA | CTGCCACTGC | AAAAACCTAC | 120 |
| ACAAAATTTA | TCGAAGATTT | CAGGGCGACT | CTTCCATTTA | GCCATAAAGT | GTATGATATA | 180 |
| CCTCTACTGT | ATTCCACTAT | TTCCGACTCC | AGACGTTTCA | TACTCCTCGA | TCTTACAAGT | 240 |
| TATGCATATG | AAACCATCTC | GGTGGCCATA | GATGTGACGA | ACGTTTATGT | TGTGGCGTAT | 300 |
| CGCACCCGCG | ATGTATCCTA | CTTTTTTAAA | GAATCTCCTC | CTGAAGCTTA | TAACATCCTA | 360 |
| TTCAAAGGTA | CGCGGAAAAT | TACACTGCCA | TATACCGGTA | ATTATGAAAA | TCTTCAAACT | 420 |
| GCTGCACACA | AAATAAGAGA | GAATATTGAT | CTTGGACTCC | CTGCCTTGAG | TAGTGCCATT | 480 |
| ACCACATTGT | TTTATTACAA | TGCCCAATCT | GCTCCTTCTG | CATTGCTTGT | ACTAATCCAG | 540 |
| ACGACTGCAG | AAGCTGCAAG | ATTTAAGTAT | ATCGAGCGAC | ACGTTGCTAA | GTATGTTGCC | 600 |

```
ACTAACTTTA AGCCAAATCT AGCCATCATA AGCTTGGAAA ATCAATGGTC TGCTCTCTCC      660

AACAAATCTT TTTGGCGCAG AATCAAGGAG GAAAATTTAG AAATCCTGTC GACCTTATAA      720

AACCTACCGG GGAACGGTTT CAAGTAACCA ATGTTGATTC AGATGTTGTA AAAGGTAATA      780

TCAAACTCCT GCTGAACTCC AGAGCTAGCA CTGCTGATGA AAACTTTATC ACAACCATGA      840

CTCTACTTGG GGAATCTGTT GTGAATTGAA AGTTAATAA  TCCACCCATA TCGAAATAAG      900

GCATGTTCAT GAC                                                        913
```

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

```
TTYAARGAYG CNCCNGAYGC NGCNTAYGAR GG                                    32
```

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

```
ACYTGRTCNA CNGCNGTNAC RTARTAYTTY TT                                    32
```

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

```
GGNYTNGAYA CNGTNWSNTT YWSNACNAAR GG                                    32
```

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

```
AATGGTTCAA TGCCCAAGTC TGT                                              23
```

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

TGTCTCTCTA TATGCCTTCT CAC    23

( 2 ) INFORMATION FOR SEQ ID NO:19:

( i ) SEQUENCE CHARACTERISTICS:
                ( A ) LENGTH: 53 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:19:

TCAACCCGGG CTAGATACCG TGTCATTCTC AACCAAAGGT GCCACTTATA TTA    53

( 2 ) INFORMATION FOR SEQ ID NO:20:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:20:

CTTCATTTTG GCGGCACGTA TCC    23

( 2 ) INFORMATION FOR SEQ ID NO:21:

( i ) SEQUENCE CHARACTERISTICS:
                ( A ) LENGTH: 46 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:21:

CTCGAGGCTG CAAGCTTACG TGGGATTTTT TTTTTTTTT TTTTT    46

( 2 ) INFORMATION FOR SEQ ID NO:22:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:22:

CTCGCTGGAA GGTGAGAA    18

( 2 ) INFORMATION FOR SEQ ID NO:23:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:23:

```
CTCGAGGCTG CAAGCTTACG TGGGA                                                              25
```

( 2 ) INFORMATION FOR SEQ ID NO:24:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

```
TGATCTCGAG TACTATTTAG GATCTTTATC GACGA                                                   35
```

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

```
GTAAGCAGCA TCTGGAGCAT CT                                                                 22
```

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

```
CATTCAAGAA ATTCACGTAG G                                                                  21
```

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

```
GGCCTGGACA CCGTGAGCTT TAG                                                                23
```

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

```
TCGATTGCGA TCCTAAATAG TACTC                                                              25
```

( 2 ) INFORMATION FOR SEQ ID NO:29:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:29:

TTTAGGATCG CAATCGACGA ACTTCAAG 28

( 2 ) INFORMATION FOR SEQ ID NO:30:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:30:

GTTCGTCTGT AAAGATCCTA AATAGTACTC GA 32

( 2 ) INFORMATION FOR SEQ ID NO:31:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:31:

GGATCTTTAC AGACGAACTT CAAGAGT 27

( 2 ) INFORMATION FOR SEQ ID NO:32:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:32:

TCTTGTGCTT CGTCGATAAA GATCC 25

( 2 ) INFORMATION FOR SEQ ID NO:33:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:33:

ATCGACGAAG CACAAGAGTG CTATTTT 27

( 2 ) INFORMATION FOR SEQ ID NO:34:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear (i i) MOLECULE TYPE: DNA (x i) SEQUENCE DESCRIPTION: SEQ ID NO:34:

GTAAAACCAT GCATAGCACT CTTGAAGTTC GT    32

(2) INFORMATION FOR SEQ ID NO:35:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:35:

AGTGCTATGC ATGGTTTTAC TTGATCAACT GC    32

(2) INFORMATION FOR SEQ ID NO:36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:36:

AGCACATGTG GTGCCACTTA TATTACCTA    29

(2) INFORMATION FOR SEQ ID NO:37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:37:

TAAGTGGCAC CACATGTGCT AAAGCTCACG GTG    33

(2) INFORMATION FOR SEQ ID NO:38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:38:

TGACTGTGGA CAGTTGGCGG AAATA    25

(2) INFORMATION FOR SEQ ID NO:39:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:39:

GCCAACTGTC CACAGTCATT TGAAAGCGCT ACC 33

( 2 ) INFORMATION FOR SEQ ID NO:40:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

GATGATCCTG GAAAGGCTTT CGTTTGGTA GCGCTT 36

( 2 ) INFORMATION FOR SEQ ID NO:41:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

AAGCCTTTCC AGGATCATCA GCTTTTTGC GCAGCAATGG G 41

( 2 ) INFORMATION FOR SEQ ID NO:42:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

AAGCCTTTCC AGGATCATCA CAT 23

( 2 ) INFORMATION FOR SEQ ID NO:43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GCGACTCTCT ACTGTTTC 18

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CGTTAGCAAT TTAACTGTGA T 21

( 2 ) INFORMATION FOR SEQ ID NO:45:

( i ) SEQUENCE CHARACTERISTICS:
   ( A ) LENGTH: 16 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:45:

AACAGCTATG ACCATG                                                                                   16

( 2 ) INFORMATION FOR SEQ ID NO:46:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:46:

TGAACTCGAG GAAAACTACC TATTTCCCAC                                                                     30

( 2 ) INFORMATION FOR SEQ ID NO:47:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:47:

GCATTACATC CATGGCGGC                                                                                 19

( 2 ) INFORMATION FOR SEQ ID NO:48:

( i ) SEQUENCE CHARACTERISTICS:
      ( A ) LENGTH: 64 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:48:

GATATCTCGA GTTAACTATT TCCCACCACA CGCATGGAAC AGCTCCAGCG CCTTGGCCAC                                    60

CGTC                                                                                                64

( 2 ) INFORMATION FOR SEQ ID NO:49:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:49:

TGTCTGTTCG TGGAGGTGCC G                                                                              21

( 2 ) INFORMATION FOR SEQ ID NO:50:

( i ) SEQUENCE CHARACTERISTICS:
      ( A ) LENGTH: 27 base pairs
      ( B ) TYPE: nucleic acid ( C ) STRANDEDNESS: single
                ( D ) TOPOLOGY: linear ( i i ) MOLECULE TYPE: DNA ( x i ) SEQUENCE DESCRIPTION: SEQ ID NO:50:

CCAAGTGTCT GGAGCTGTTC CATGCGA                                                                27

( 2 ) INFORMATION FOR SEQ ID NO:51:

( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:51:

GATGTTAAYT TYGAYTTGTC NACDGCTAC                                                              29

( 2 ) INFORMATION FOR SEQ ID NO:52:

( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:52:

ATTGGNAGDG TAGCCCTRAA RTCYTCDAT                                                              29

( 2 ) INFORMATION FOR SEQ ID NO:53:

( i ) SEQUENCE CHARACTERISTICS:
                ( A ) LENGTH: 32 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:53:

GCCACTGCAA AAACCTACAC AAAATTTATT GA                                                          32

( 2 ) INFORMATION FOR SEQ ID NO:54:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:54:

GATGTTAACT TCGATTTGTC GA                                                                     22

( 2 ) INFORMATION FOR SEQ ID NO:55:

( i ) SEQUENCE CHARACTERISTICS:
                ( A ) LENGTH: 33 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:55:

TCAACTCGAG GTACTCAATT CACAACAGAT TCC 33

( 2 ) INFORMATION FOR SEQ ID NO:56:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

Cys His His His Ala Ser Arg Val Ala Arg Met Ala Ser Asp Glu Phe
1               5                   10                  15

Pro Ser Met Cys
            20

( 2 ) INFORMATION FOR SEQ ID NO:57:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:57:

Pro Ser Gly Gln Ala Gly Ala Ala Ala Ser Glu Ser Leu Phe Ile Ser
1               5                   10                  15

Asn His Ala Tyr
            20

( 2 ) INFORMATION FOR SEQ ID NO:58:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

CAGCCATGGA ATCCCATTGC TG 22

( 2 ) INFORMATION FOR SEQ ID NO:59:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

CACATGTAAA ACAAGACTTC ATTTTGGC 28

( 2 ) INFORMATION FOR SEQ ID NO:60:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

TGAAGTCTTG TTTTAGATGT GTTTTTGAAG AGGCCT 36

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

ATGCCATATG CAATTATAAA CCAACGGAGA 30

( 2 ) INFORMATION FOR SEQ ID NO:62:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

GGTTTATAAT TGCATATGGC ATTTTCATCA AGTTTCTTG 39

( 2 ) INFORMATION FOR SEQ ID NO:63:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

CTTTCAACAA TGCATTCGCC CGGCGAATAA TAC 33

( 2 ) INFORMATION FOR SEQ ID NO:64:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:64:

GCGAATGCAT TGTTGAAAGT TATTTCTAAT TTG 33

( 2 ) INFORMATION FOR SEQ ID NO:65:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:65:

GTTTTGTGAG GCAGTTGAAT TGGAAC 26

( 2 ) INFORMATION FOR SEQ ID NO:66:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:66:

```
TTCAACTGCC TCACAAAACA TTCCATTTGC ACCT                          34
```

( 2 ) INFORMATION FOR SEQ ID NO:67:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:67:

```
AAAAGCTGAT GATCCTGGAA AGTG                                     24
```

( 2 ) INFORMATION FOR SEQ ID NO:68:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:68:

```
TCCAGGATCA TCAGCTTTTT TGCGCAGCAA TGGGA                         35
```

( 2 ) INFORMATION FOR SEQ ID NO:69:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:69:

```
GACATCCAGA TGACTCAGTC TCCATCTTCC ATGTCTGCAT CTCTGGGAGA CAGAGTCACT    60
ATCACTTGCC GGGCGAGTCA GGACATTAAT AGCTATTTAA GCTGGTTCCA GCAGAAACCA   120
GGGAAATCTC CTAAGACCCT GATCTATCGT GCAAACAGAT TGGTAGATGG GGTCCCATCA   180
AGGTTCAGTG GCAGTGGATC TGGACAGAT TATACTCTCA CCATCAGCAG CCTGCAATAT    240
GAAGATTTTG GAATTTATTA TTGTCAACAG TATGATGAGT CTCCGTGGAC GTTCGGTGGA   300
GGCACCAAGC TTGAAATCAA A                                             321
```

( 2 ) INFORMATION FOR SEQ ID NO:70:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:70:

```
CAGATCCAGT  TGGTGCAGTC  TGGACCTGGC  CTGAAGAAGC  CTGGAGGGTC  CGTCAGAATC     60
TCCTGCGCAG  CTTCTGGGTA  TACCTTCACA  AACTATGGAA  TGAACTGGGT  GAAGCAGGCT    120
CCAGGAAAGG  GTTAAGGTG   GATGGGCTGG  ATAAACACCC  ACACTGGAGA  GCCAACATAT    180
GCTGATGACT  TCAAGGGACG  GTTTACCTTC  TCTTTGGACA  CGTCTAAGAG  CACTGCCTAT    240
TTACAGATCA  ACAGCCTCAG  AGCCGAGGAC  ACGGCTACAT  ATTTCTGTAC  AAGACGGGGT    300
TACGACTGGT  ACTTCGATGT  CTGGGGCCAA  GGGACCACGG  TCACCGTCTC  CTCC          354
```

( 2 ) INFORMATION FOR SEQ ID NO:71:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:71:

```
GAGATCCAGT  TGGTGCAGTC  TGGAGGAGGC  CTGGTGAAGC  CTGGAGGGTC  CGTCAGAATC     60
TCCTGCGCAG  CTTCTGGGTA  TACCTTCACA  AACTATGGAA  TGAACTGGGT  GCGCCAGGCT    120
CCAGGAAAGG  GTTTAGAGTG  GATGGGCTGG  ATAAACACCC  ACACTGGAGA  GCCAACATAT    180
GCTGATTCTT  TCAAGGGACG  GTTTACCTTC  TCTTTGGACG  ATTCTAAGAA  CACTGCCTAT    240
TTACAGATCA  ACAGCCTCAG  AGCCGAGGAC  ACGGCTGTGT  ATTTCTGTAC  AAGACGGGGT    300
TACGACTGGT  ACTTCGATGT  CTGGGGCCAA  GGGACCACGG  TCACCGTCTC  CTCC          354
```

( 2 ) INFORMATION FOR SEQ ID NO:72:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

```
GACATCCAGA  TGACTCAGTC  TCCATCTTCC  CTGTCTGCAT  CTGTAGGAGA  CAGAGTCACT     60
ATCACTTGCC  GGGCGAGTCA  GGACATTAAT  AGCTATTTAA  GCTGGTTCCA  GCAGAAACCA    120
GGGAAAGCTC  CTAAGACCCT  GATCTATCGT  GCAAACAGAT  TGGAATCTGG  GGTCCCATCA    180
AGGTTCAGTG  GCAGTGGATC  TGGGACAGAT  TATACTCTCA  CCATCAGCAG  CCTGCAATAT    240
GAAGATTTTG  GAATTTATTA  TTGTCAACAG  TATGATGAGT  CTCCGTGGAC  GTTCGGTGGA    300
GGCACCAAGC  TTGAAATCAA  A                                                 321
```

( 2 ) INFORMATION FOR SEQ ID NO:73:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:73:

```
TGTCATCATC  ATGCATCGCG  AGTTGCCAGA  ATGGCATCTG  ATGAGTTTCC  TTCTATGTGC     60
```

GCAAGTACTC                                                                                                          70

( 2 ) INFORMATION FOR SEQ ID NO:74:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

TCGAGAGTAC TTGCGCACAT AGAAGGAAAC TCATCAGATG CCATTCTGGC AACTCGCGAT        60

GCATGATGAT GACATGCA                                                     78

( 2 ) INFORMATION FOR SEQ ID NO:75:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

TGTTCGGCCG CATGTCATCA TCATGCATCG                                        30

( 2 ) INFORMATION FOR SEQ ID NO:76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

AGTCATGCCC CGCGC                                                        15

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

TCCCGGCTGT CCTACAGT                                                     18

( 2 ) INFORMATION FOR SEQ ID NO:78:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:78:

TCCAGCCTGT CCAGATGGTG TGTGAGTTTT GTCACAA                                 37

( 2 ) INFORMATION FOR SEQ ID NO:79:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:79:

```
CTAACTCGAG AGTACTGTAT GCATGGTTCG AGATGAACAA AGATTCTGAG GCTGCAGCTC      60

CAGCCTGTCC AGATGG                                                     76
```

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:80:

```
CTAACTCGAG AGTACTGTAT                                                 20
```

( 2 ) INFORMATION FOR SEQ ID NO:81:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:81:

```
TCCAGCCTGT CCAGATGGAC ACTCTCCCCT GTTGAA                               36
```

( 2 ) INFORMATION FOR SEQ ID NO:82:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:82:

```
GTACAGTGGA AGGTGGAT                                                   18
```

( 2 ) INFORMATION FOR SEQ ID NO:83:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:83:

```
CATGCGGCCG ATTTAGGATC TTTATCGACG A                                    31
```

( 2 ) INFORMATION FOR SEQ ID NO:84:

( i ) SEQUENCE CHARACTERISTICS:

( A ) LENGTH: 22 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:84:

AACATCCAGT TGGTGCAGTC TG					22

( 2 ) INFORMATION FOR SEQ ID NO:85:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:85:

GAGGAGACGG TGACCGTGGT					20

( 2 ) INFORMATION FOR SEQ ID NO:86:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:86:

GACATCAAGA TGACCCAGT					19

( 2 ) INFORMATION FOR SEQ ID NO:87:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:87:

GTTTGATTTC AAGCTTGGTG C					21

( 2 ) INFORMATION FOR SEQ ID NO:88:

( i ) SEQUENCE CHARACTERISTICS:
                    ( A ) LENGTH: 31 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:88:

ACTTCGGCCG CACCATCTGG ACAGGCTGGA G					31

( 2 ) INFORMATION FOR SEQ ID NO:89:

( i ) SEQUENCE CHARACTERISTICS:
                    ( A ) LENGTH: 723 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:89:

| GACATCCAGA | TGACTCAGTC | TCCATCTTCC | CTGTCTGCAT | CTGTAGGAGA | CAGAGTCACT | 60 |
| ATCACTTGCC | GGGCGAGTCA | GGACATTAAT | AGCTATTTAA | GCTGGTTCCA | GCAGAAACCA | 120 |
| GGGAAAGCTC | CTAAGACCCT | GATCTATCGT | GCAAACAGAT | TGGAATCTGG | GGTCCCATCA | 180 |
| AGGTTCAGTG | GCAGTGGATC | TGGGACAGAT | TATACTCTCA | CCATCAGCAG | CCTGCAATAT | 240 |
| GAAGATTTTG | GAATTTATTA | TTGTCAACAG | TATGATGAGT | CTCCGTGGAC | GTTCGGTGGA | 300 |
| GGCACCAAGC | TTGAGATGAA | AGGTGGCGGT | GGATCTGGTG | GAGGTGGGTC | CGGAGGTGGA | 360 |
| GGATCTGAGA | TCCAGTTGGT | GCAGTCTGGA | GGAGGCCTGG | TGAAGCCTGG | AGGGTCCGTC | 420 |
| AGAATCTCCT | GCGCAGCTTC | TGGGTATACC | TTCACAAACT | ATGGAATGAA | CTGGGTGCGC | 480 |
| CAGGCTCCAG | GAAAGGGTTT | AGAGTGGATG | GGCTGGATAA | ACACCCACAC | TGGAGAGCCA | 540 |
| ACATATGCTG | ATTCTTTCAA | GGGACGGTTT | ACCTTCTCTT | TGGACGATTC | TAAGAACACT | 600 |
| GCCTATTTAC | AGATCAACAG | CCTCAGAGCC | GAGGACACGG | CTGTGTATTT | CTGTACAAGA | 660 |
| CGGGGTTACG | ACTGGTACTT | CGATGTCTGG | GGCCAAGGGA | CCACGGTCAC | CGTCTCCTCA | 720 |
| TGA | | | | | | 723 |

( 2 ) INFORMATION FOR SEQ ID NO:90:

( i ) SEQUENCE CHARACTERISTICS:
        ( A ) LENGTH: 723 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:90:

| GAGATCCAGT | TGGTGCAGTC | TGGAGGAGGC | CTGGTGAAGC | CTGGAGGGTC | CGTCAGAATC | 60 |
| TCCTGCGCAG | CTTCTGGGTA | TACCTTCACA | AACTATGGAA | TGAACTGGGT | GCGCCAGGCT | 120 |
| CCAGGAAAGG | GTTTAGAGTG | GATGGGCTGG | ATAAACACCC | ACACTGGAGA | GCCAACATAT | 180 |
| GCTGATTCTT | TCAAGGGACG | GTTTACCTTC | TCTTTGGACG | ATTCTAAGAA | CACTGCCTAT | 240 |
| TTACAGATCA | ACAGCCTCAG | AGCCGAGGAC | ACGGCTGTGT | ATTTCTGTAC | AAGACGGGGT | 300 |
| TACGACTGGT | ACTTCGATGT | CTGGGGCCAA | GGGACCACGG | TCACCGTCTC | CTCAGGTGGC | 360 |
| GGTGGATCTG | GTGGAGGTGG | GTCCGGAGGT | GGAGGATCTG | ACATCCAGAT | GACTCAGTCT | 420 |
| CCATCTTCCC | TGTCTGCATC | TGTAGGAGAC | AGAGTCACTA | TCACTTGCCG | GGCGAGTCAG | 480 |
| GACATTAATA | GCTATTTAAG | CTGGTTCCAG | CAGAAACCAG | GGAAAGCTCC | TAAGACCCTG | 540 |
| ATCTATCGTG | CAAACAGATT | GGAATCTGGG | GTCCCATCAA | GGTTCAGTGG | CAGTGGATCT | 600 |
| GGGACAGATT | ATACTCTCAC | CATCAGCAGC | CTGCAATATG | AAGATTTTGG | AATTTATTAT | 660 |
| TGTCAACAGT | ATGATGAGTC | TCCGTGGACG | TTCGGTGGAG | GCACCAAGCT | TGAGATGAAA | 720 |
| TGA | | | | | | 723 |

( 2 ) INFORMATION FOR SEQ ID NO:91:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (x i) SEQUENCE DESCRIPTION: SEQ ID NO:91:

CGGACCCACC TCCACCAGAT CCACCGCCAC CTTTCATCTC AAGCTTGGTG C            51

(2) INFORMATION FOR SEQ ID NO:92:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:92:

GACATCCAGA TGACTCAGT            19

(2) INFORMATION FOR SEQ ID NO:93:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:93:

GGTGGAGGTG GGTCCGGAGG TGGAGGATCT GAGATCCAGT TGGTGCAGT            49

(2) INFORMATION FOR SEQ ID NO:94:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:94:

TGTACTCGAG CCCATCATGA GGAGACGGTG ACCGT            35

(2) INFORMATION FOR SEQ ID NO:95:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:95:

GGTGGAGGTG GGTCCGGAGG TGGAGGATCT GACATCCAGA TGACTCAGT            49

(2) INFORMATION FOR SEQ ID NO:96:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:96:

TGTACTCGAG CCCATCATTT CATCTCAAGC TTGGTGC            37

( 2 ) INFORMATION FOR SEQ ID NO:97:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:97:

GAGATCCAGT TGGTGCAGTC TG        22

( 2 ) INFORMATION FOR SEQ ID NO:98:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:98:

CGGACCCACC TCCACCAGAT CCACCGCCAC CTGAGGAGAC GGTGACCGT    49

( 2 ) INFORMATION FOR SEQ ID NO:99:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

| Gly | Leu | Asp | Thr | Val | Ser | Phe | Ser | Thr | Lys | Gly | Ala | Thr | Tyr | Ile | Thr |
|---|---|---|---|---|---|---|---|---|---|---|---|---|---|---|---|
| 1 | | | | 5 | | | | | 10 | | | | | 15 | |
| Tyr | Val | Asn | Phe | Leu | Asn | Glu | Leu | Arg | Val | Lys | Leu | Lys | Pro | Glu | Gly |
| | | | 20 | | | | 25 | | | | | 30 | | | |
| Asn | Ser | His | Gly | Ile | Pro | Leu | Leu | Arg | Lys | Lys | Cys | Asp | Asp | Pro | Gly |
| | | 35 | | | | 40 | | | | | 45 | | | | |
| Lys | Ala | Phe | Val | Leu | Val | Ala | Leu | Ser | Asn | Asp | Asn | Gly | Gln | Leu | Ala |
| | 50 | | | | | 55 | | | | | 60 | | | | |
| Glu | Ile | Ala | Ile | Asp | Val | Thr | Ser | Val | Tyr | Val | Val | Gly | Tyr | Gln | Val |
| 65 | | | | | 70 | | | | 75 | | | | | | 80 |
| Arg | Asn | Arg | Ser | Tyr | Phe | Phe | Lys | Asp | Ala | Pro | Asp | Ala | Ala | Tyr | Glu |
| | | | | 85 | | | | | 90 | | | | | 95 | |
| Gly | Leu | Phe | Lys | Asn | Thr | Ile | Lys | Thr | Arg | Leu | His | Phe | Gly | Gly | Ser |
| | | | 100 | | | | | 105 | | | | | 110 | | |
| Tyr | Pro | Ser | Leu | Glu | Gly | Glu | Lys | Ala | Tyr | Arg | Glu | Thr | Thr | Asp | Leu |
| | | 115 | | | | | 120 | | | | | 125 | | | |
| Gly | Ile | Glu | Pro | Leu | Arg | Ile | Gly | Ile | Lys | Lys | Leu | Asp | Glu | Asn | Ala |
| | | 130 | | | | 135 | | | | | 140 | | | | |
| Ile | Asp | Asn | Tyr | Lys | Pro | Thr | Glu | Ile | Ala | Ser | Ser | Leu | Leu | Val | Val |
| 145 | | | | | 150 | | | | 155 | | | | | | 160 |
| Ile | Gln | Met | Val | Ser | Glu | Ala | Ala | Arg | Phe | Thr | Phe | Ile | Glu | Asn | Gln |
| | | | | 165 | | | | | 170 | | | | | 175 | |
| Ile | Arg | Asn | Asn | Phe | Gln | Gln | Arg | Ile | Arg | Pro | Ala | Asn | Asn | Thr | Ile |
| | | | 180 | | | | | 185 | | | | | 190 | | |
| Ser | Leu | Glu | Asn | Lys | Trp | Gly | Lys | Leu | Ser | Phe | Gln | Ile | Arg | Thr | Ser |
| | | | 195 | | | | | 200 | | | | | 205 | | |

| | | | | | | | | | | | | | | |
|---|---|---|---|---|---|---|---|---|---|---|---|---|---|---|
| Gly | Ala | Asn | Gly | Met | Phe | Ser | Glu | Ala | Val | Glu | Leu | Glu | Arg | Ala | Asn |
| 210 | | | | | 215 | | | | | 220 | | | | | |
| Gly | Lys | Lys | Tyr | Tyr | Val | Thr | Ala | Val | Asp | Gln | Val | Lys | Pro | Lys | Ile |
| 225 | | | | | 230 | | | | | 235 | | | | | 240 |
| Ala | Leu | Leu | Lys | Phe | Val | Asp | Lys | Asp | Pro | Lys | | | | | |
| | | | | 245 | | | | | 250 | | | | | | |

( 2 ) INFORMATION FOR SEQ ID NO:100:

( i ) SEQUENCE CHARACTERISTICS:
  ( A ) LENGTH: 251 amino acids
  ( B ) TYPE: amino acid
  ( D ) TOPOLOGY: linear ( i i ) MOLECULE TYPE: protein ( x i ) SEQUENCE DESCRIPTION: SEQ ID NO:100:

| | | | | | | | | | | | | | | |
|---|---|---|---|---|---|---|---|---|---|---|---|---|---|---|
| Gly | Leu | Asp | Thr | Val | Ser | Phe | Ser | Thr | Lys | Gly | Ala | Thr | Tyr | Ile | Thr |
| 1 | | | | 5 | | | | | 10 | | | | | 15 | |
| Tyr | Val | Asn | Phe | Leu | Asn | Glu | Leu | Arg | Val | Lys | Leu | Lys | Pro | Glu | Gly |
| | | | 20 | | | | | 25 | | | | | 30 | | |
| Asn | Ser | His | Gly | Ile | Pro | Leu | Leu | Arg | Lys | Lys | Ala | Asp | Asp | Pro | Gly |
| | | 35 | | | | | 40 | | | | | 45 | | | |
| Lys | Cys | Phe | Val | Leu | Val | Ala | Leu | Ser | Asn | Asn | Gly | Gln | Leu | Ala | |
| | 50 | | | | | 55 | | | | 60 | | | | | |
| Glu | Ile | Ala | Ile | Asp | Val | Thr | Ser | Val | Tyr | Val | Val | Gly | Tyr | Gln | Val |
| 65 | | | | | 70 | | | | | 75 | | | | | 80 |
| Arg | Asn | Arg | Ser | Tyr | Phe | Phe | Lys | Asp | Ala | Pro | Asp | Ala | Ala | Tyr | Glu |
| | | | | 85 | | | | | 90 | | | | | 95 | |
| Gly | Leu | Phe | Lys | Asn | Thr | Ile | Lys | Thr | Arg | Leu | His | Phe | Gly | Gly | Ser |
| | | | 100 | | | | | 105 | | | | | 110 | | |
| Tyr | Pro | Ser | Leu | Glu | Gly | Glu | Lys | Ala | Tyr | Arg | Glu | Thr | Thr | Asp | Leu |
| | | 115 | | | | | 120 | | | | | 125 | | | |
| Gly | Ile | Glu | Pro | Leu | Arg | Ile | Gly | Ile | Lys | Lys | Leu | Asp | Glu | Asn | Ala |
| | 130 | | | | | 135 | | | | 140 | | | | | |
| Ile | Asp | Asn | Tyr | Lys | Pro | Thr | Glu | Ile | Ala | Ser | Ser | Leu | Leu | Val | Val |
| 145 | | | | | 150 | | | | | 155 | | | | | 160 |
| Ile | Gln | Met | Val | Ser | Glu | Ala | Ala | Arg | Phe | Thr | Phe | Ile | Glu | Asn | Gln |
| | | | | 165 | | | | | 170 | | | | | 175 | |
| Ile | Arg | Asn | Asn | Phe | Gln | Gln | Arg | Ile | Arg | Pro | Ala | Asn | Asn | Thr | Ile |
| | | | 180 | | | | | 185 | | | | | 190 | | |
| Ser | Leu | Glu | Asn | Lys | Trp | Gly | Lys | Leu | Ser | Phe | Gln | Ile | Arg | Thr | Ser |
| | | 195 | | | | | 200 | | | | | 205 | | | |
| Gly | Ala | Asn | Gly | Met | Phe | Ser | Glu | Ala | Val | Glu | Leu | Glu | Arg | Ala | Asn |
| 210 | | | | | 215 | | | | | 220 | | | | | |
| Gly | Lys | Lys | Tyr | Tyr | Val | Thr | Ala | Val | Asp | Gln | Val | Lys | Pro | Lys | Ile |
| 225 | | | | | 230 | | | | | 235 | | | | | 240 |
| Ala | Leu | Leu | Lys | Phe | Val | Asp | Lys | Asp | Pro | Lys | | | | | |
| | | | | 245 | | | | | 250 | | | | | | |

( 2 ) INFORMATION FOR SEQ ID NO:101:

( i ) SEQUENCE CHARACTERISTICS:
  ( A ) LENGTH: 251 amino acids
  ( B ) TYPE: amino acid
  ( D ) TOPOLOGY: linear ( i i ) MOLECULE TYPE: protein ( x i ) SEQUENCE DESCRIPTION: SEQ ID NO:101:

| | | | | | | | | | | | | | | | |
|---|---|---|---|---|---|---|---|---|---|---|---|---|---|---|---|
| Gly<br>1 | Leu | Asp | Thr | Val<br>5 | Ser | Phe | Ser | Thr | Lys<br>10 | Gly | Ala | Thr | Tyr | Ile<br>15 | Thr |
| Tyr | Val | Asn | Phe<br>20 | Leu | Asn | Glu | Leu | Arg<br>25 | Val | Lys | Leu | Lys | Pro<br>30 | Glu | Gly |
| Asn | Ser | His<br>35 | Gly | Ile | Pro | Leu | Leu<br>40 | Arg | Lys | Lys | Ala | Asp<br>45 | Asp | Pro | Gly |
| Lys | Ala<br>50 | Phe | Val | Leu | Val | Ala<br>55 | Leu | Ser | Asn | Asp | Asn<br>60 | Gly | Gln | Leu | Ala |
| Glu<br>65 | Ile | Ala | Ile | Asp | Val<br>70 | Thr | Ser | Val | Tyr | Val<br>75 | Val | Gly | Tyr | Gln | Val<br>80 |
| Arg | Asn | Arg | Ser | Tyr<br>85 | Phe | Phe | Lys | Asp | Ala<br>90 | Pro | Asp | Ala | Ala | Tyr<br>95 | Glu |
| Gly | Leu | Phe | Lys<br>100 | Asn | Thr | Ile | Lys | Thr<br>105 | Arg | Leu | His | Phe | Gly<br>110 | Gly | Ser |
| Tyr | Pro | Ser<br>115 | Leu | Glu | Gly | Glu | Lys<br>120 | Ala | Tyr | Arg | Glu | Thr<br>125 | Thr | Asp | Leu |
| Gly | Ile<br>130 | Glu | Pro | Leu | Arg | Ile<br>135 | Gly | Ile | Lys | Lys | Leu<br>140 | Asp | Glu | Asn | Ala |
| Ile | Asp<br>145 | Asn | Tyr | Lys | Pro<br>150 | Thr | Glu | Ile | Ala | Ser<br>155 | Ser | Leu | Leu | Val | Val<br>160 |
| Ile | Gln | Met | Val | Ser<br>165 | Glu | Ala | Ala | Arg | Phe<br>170 | Thr | Phe | Ile | Glu | Asn | Gln<br>175 |
| Ile | Arg | Asn | Asn<br>180 | Phe | Gln | Gln | Arg | Ile<br>185 | Arg | Pro | Ala | Asn | Asn<br>190 | Thr | Ile |
| Ser | Leu | Glu<br>195 | Asn | Lys | Trp | Gly | Lys<br>200 | Leu | Ser | Phe | Gln | Ile<br>205 | Arg | Thr | Ser |
| Gly | Ala<br>210 | Asn | Gly | Met | Phe | Ser<br>215 | Glu | Ala | Val | Glu | Leu<br>220 | Glu | Arg | Ala | Asn |
| Gly<br>225 | Lys | Lys | Tyr | Tyr | Val<br>230 | Thr | Ala | Val | Asp | Gln<br>235 | Val | Lys | Pro | Lys | Ile<br>240 |
| Ala | Leu | Leu | Lys | Phe<br>245 | Val | Asp | Lys | Asp | Pro<br>250 | Lys | | | | | |

( 2 ) INFORMATION FOR SEQ ID NO:102:

( i ) SEQUENCE CHARACTERISTICS:
( A ) LENGTH: 251 amino acids
( B ) TYPE: amino acid
( D ) TOPOLOGY: linear ( i i ) MOLECULE TYPE: protein ( x i ) SEQUENCE DESCRIPTION: SEQ ID NO:102:

| | | | | | | | | | | | | | | | |
|---|---|---|---|---|---|---|---|---|---|---|---|---|---|---|---|
| Gly<br>1 | Leu | Asp | Thr | Val<br>5 | Ser | Phe | Ser | Thr | Lys<br>10 | Gly | Ala | Thr | Tyr | Ile<br>15 | Thr |
| Tyr | Val | Asn | Phe<br>20 | Leu | Asn | Glu | Leu | Arg<br>25 | Val | Lys | Leu | Lys | Pro<br>30 | Glu | Gly |
| Asn | Ser | His<br>35 | Gly | Ile | Pro | Leu | Leu<br>40 | Arg | Lys | Lys | Cys | Asp<br>45 | Asp | Pro | Gly |
| Lys | Cys<br>50 | Phe | Val | Leu | Val | Ala<br>55 | Leu | Ser | Asn | Asp | Asn<br>60 | Gly | Gln | Leu | Ala |
| Glu<br>65 | Ile | Ala | Ile | Asp | Val<br>70 | Thr | Ser | Val | Tyr | Val<br>75 | Val | Gly | Tyr | Gln | Val<br>80 |
| Arg | Asn | Arg | Ser | Tyr<br>85 | Phe | Phe | Lys | Asp | Ala<br>90 | Pro | Asp | Ala | Ala | Tyr<br>95 | Glu |
| Gly | Leu | Phe | Lys | Asn | Thr | Ile | Lys | Thr | Arg | Leu | His | Phe | Gly | Gly | Ser |

|   |   |   | 100 |   |   |   | 105 |   |   |   | 110 |   |   |
|---|---|---|---|---|---|---|---|---|---|---|---|---|---|
| Tyr | Pro | Ser | Leu | Glu | Gly | Glu | Lys | Ala | Tyr | Arg | Glu | Thr | Thr | Asp | Leu |
|   |   | 115 |   |   |   |   | 120 |   |   |   |   | 125 |   |   |   |
| Gly | Ile | Glu | Pro | Leu | Arg | Ile | Gly | Ile | Lys | Lys | Leu | Asp | Glu | Asn | Ala |
|   |   | 130 |   |   |   |   | 135 |   |   |   |   | 140 |   |   |   |
| Ile | Asp | Asn | Tyr | Lys | Pro | Thr | Glu | Ile | Ala | Ser | Ser | Leu | Leu | Val | Val |
| 145 |   |   |   |   | 150 |   |   |   |   | 155 |   |   |   |   | 160 |
| Ile | Gln | Met | Val | Ser | Glu | Ala | Ala | Arg | Phe | Thr | Phe | Ile | Glu | Asn | Gln |
|   |   |   |   | 165 |   |   |   |   | 170 |   |   |   |   | 175 |   |
| Ile | Arg | Asn | Asn | Phe | Gln | Gln | Arg | Ile | Arg | Pro | Ala | Asn | Asn | Thr | Ile |
|   |   |   | 180 |   |   |   |   | 185 |   |   |   |   | 190 |   |   |
| Ser | Leu | Glu | Asn | Lys | Trp | Gly | Lys | Leu | Ser | Phe | Gln | Ile | Arg | Thr | Ser |
|   |   | 195 |   |   |   |   | 200 |   |   |   |   | 205 |   |   |   |
| Gly | Ala | Asn | Gly | Met | Phe | Ser | Glu | Ala | Val | Glu | Leu | Glu | Arg | Ala | Asn |
|   |   | 210 |   |   |   |   | 215 |   |   |   |   | 220 |   |   |   |
| Gly | Lys | Lys | Tyr | Tyr | Val | Thr | Ala | Val | Asp | Gln | Val | Lys | Pro | Lys | Ile |
| 225 |   |   |   |   | 230 |   |   |   |   | 235 |   |   |   |   | 240 |
| Ala | Leu | Leu | Lys | Phe | Val | Cys | Lys | Asp | Pro | Lys |   |   |   |   |   |
|   |   |   |   | 245 |   |   |   |   | 250 |   |   |   |   |   |   |

( 2 ) INFORMATION FOR SEQ ID NO:103:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

| Gly | Leu | Asp | Thr | Val | Ser | Phe | Ser | Thr | Lys | Gly | Ala | Thr | Tyr | Ile | Thr |
|---|---|---|---|---|---|---|---|---|---|---|---|---|---|---|---|
| 1 |   |   |   | 5 |   |   |   |   | 10 |   |   |   |   | 15 |   |
| Tyr | Val | Asn | Phe | Leu | Asn | Glu | Leu | Arg | Val | Lys | Leu | Lys | Pro | Glu | Gly |
|   |   |   | 20 |   |   |   |   | 25 |   |   |   |   | 30 |   |   |
| Asn | Ser | His | Gly | Ile | Pro | Leu | Leu | Arg | Lys | Lys | Cys | Asp | Asp | Pro | Gly |
|   |   | 35 |   |   |   |   | 40 |   |   |   |   | 45 |   |   |   |
| Lys | Cys | Phe | Val | Leu | Val | Ala | Leu | Ser | Asn | Asp | Asn | Gly | Gln | Leu | Ala |
|   | 50 |   |   |   |   | 55 |   |   |   |   | 60 |   |   |   |   |
| Glu | Ile | Ala | Ile | Asp | Val | Thr | Ser | Val | Tyr | Val | Val | Gly | Tyr | Gln | Val |
| 65 |   |   |   |   | 70 |   |   |   |   | 75 |   |   |   |   | 80 |
| Arg | Asn | Arg | Ser | Tyr | Phe | Phe | Lys | Asp | Ala | Pro | Asp | Ala | Ala | Tyr | Glu |
|   |   |   |   | 85 |   |   |   |   | 90 |   |   |   |   | 95 |   |
| Gly | Leu | Phe | Lys | Asn | Thr | Ile | Lys | Thr | Arg | Leu | His | Phe | Gly | Gly | Ser |
|   |   |   | 100 |   |   |   |   | 105 |   |   |   |   | 110 |   |   |
| Tyr | Pro | Ser | Leu | Glu | Gly | Glu | Lys | Ala | Tyr | Arg | Glu | Thr | Thr | Asp | Leu |
|   |   | 115 |   |   |   |   | 120 |   |   |   |   | 125 |   |   |   |
| Gly | Ile | Glu | Pro | Leu | Arg | Ile | Gly | Ile | Lys | Lys | Leu | Asp | Glu | Asn | Ala |
|   |   | 130 |   |   |   |   | 135 |   |   |   |   | 140 |   |   |   |
| Ile | Asp | Asn | Tyr | Lys | Pro | Thr | Glu | Ile | Ala | Ser | Ser | Leu | Leu | Val | Val |
| 145 |   |   |   |   | 150 |   |   |   |   | 155 |   |   |   |   | 160 |
| Ile | Gln | Met | Val | Ser | Glu | Ala | Ala | Arg | Phe | Thr | Phe | Ile | Glu | Asn | Gln |
|   |   |   |   | 165 |   |   |   |   | 170 |   |   |   |   | 175 |   |
| Ile | Arg | Asn | Asn | Phe | Gln | Gln | Arg | Ile | Arg | Pro | Ala | Asn | Asn | Thr | Ile |
|   |   |   | 180 |   |   |   |   | 185 |   |   |   |   | 190 |   |   |
| Ser | Leu | Glu | Asn | Lys | Trp | Gly | Lys | Leu | Ser | Phe | Gln | Ile | Arg | Thr | Ser |
|   |   | 195 |   |   |   |   | 200 |   |   |   |   | 205 |   |   |   |

|   |   |   |   |   |   |   |   |   |   |   |   |   |   |   |
|---|---|---|---|---|---|---|---|---|---|---|---|---|---|---|
| Gly | Ala | Asn | Gly | Met | Phe | Ser | Glu | Ala | Val | Glu | Leu | Glu | Arg | Ala | Asn |
|  | 210 |  |  |  |  | 215 |  |  |  |  | 220 |  |  |  |  |

Gly Lys Lys Tyr Tyr Val Thr Ala Val Asp Gln Val Lys Pro Lys Ile
225                     230              235                   240

Ala Leu Leu Lys Phe Val Asp Cys Asp Pro Lys
                245              250

(2) INFORMATION FOR SEQ ID NO:104:

(i) SEQUENCE CHARACTERISTICS:
  (A) LENGTH: 251 amino acids
  (B) TYPE: amino acid
  (D) TOPOLOGY: linear (ii) MOLECULE TYPE: protein (xi) SEQUENCE DESCRIPTION: SEQ ID NO:104:

Gly Leu Asp Thr Val Ser Phe Ser Thr Lys Gly Ala Thr Tyr Ile Thr
1               5                   10                  15

Tyr Val Asn Phe Leu Asn Glu Leu Arg Val Lys Leu Lys Pro Glu Gly
            20                  25                  30

Asn Ser His Gly Ile Pro Leu Leu Arg Lys Lys Cys Asp Pro Gly
        35                  40                  45

Lys Cys Phe Val Leu Val Ala Leu Ser Asn Asp Asn Gly Gln Leu Ala
    50                  55                  60

Glu Ile Ala Ile Asp Val Thr Ser Val Tyr Val Val Gly Tyr Gln Val
65                  70                  75                  80

Arg Asn Arg Ser Tyr Phe Phe Lys Asp Ala Pro Asp Ala Ala Tyr Glu
                85                  90                  95

Gly Leu Phe Lys Asn Thr Ile Lys Thr Arg Leu His Phe Gly Gly Ser
            100                 105                 110

Tyr Pro Ser Leu Glu Gly Glu Lys Ala Tyr Arg Glu Thr Thr Asp Leu
            115                 120                 125

Gly Ile Glu Pro Leu Arg Ile Gly Ile Lys Lys Leu Asp Glu Asn Ala
    130                 135                 140

Ile Asp Asn Tyr Lys Pro Thr Glu Ile Ala Ser Ser Leu Leu Val Val
145                 150                 155                 160

Ile Gln Met Val Ser Glu Ala Ala Arg Phe Thr Phe Ile Glu Asn Gln
                165                 170                 175

Ile Arg Asn Asn Phe Gln Gln Arg Ile Arg Pro Ala Asn Asn Thr Ile
            180                 185                 190

Ser Leu Glu Asn Lys Trp Gly Lys Leu Ser Phe Gln Ile Arg Thr Ser
    195                 200                 205

Gly Ala Asn Gly Met Phe Ser Glu Ala Val Glu Leu Glu Arg Ala Asn
    210                 215                 220

Gly Lys Lys Tyr Tyr Val Thr Ala Val Asp Gln Val Lys Pro Cys Ile
225                 230                 235                 240

Ala Leu Leu Lys Phe Val Asp Lys Asp Pro Lys
                245                 250

(2) INFORMATION FOR SEQ ID NO:105:

(i) SEQUENCE CHARACTERISTICS:
  (A) LENGTH: 251 amino acids
  (B) TYPE: amino acid
  (D) TOPOLOGY: linear (ii) MOLECULE TYPE: protein (xi) SEQUENCE DESCRIPTION: SEQ ID NO:105:

| | | | | | | | | | | | | | | |
|---|---|---|---|---|---|---|---|---|---|---|---|---|---|---|
| Gly<br>1 | Leu | Asp | Thr | Val<br>5 | Ser | Phe | Ser | Thr | Lys<br>10 | Gly | Ala | Thr | Tyr | Ile<br>15 | Thr |
| Tyr | Val | Asn | Phe<br>20 | Leu | Asn | Glu | Leu | Arg<br>25 | Val | Lys | Leu | Lys | Pro<br>30 | Glu | Gly |
| Asn | Ser | His<br>35 | Gly | Ile | Pro | Leu | Leu<br>40 | Arg | Lys | Lys | Cys | Asp<br>45 | Asp | Pro | Gly |
| Lys | Cys<br>50 | Phe | Val | Leu | Val | Ala<br>55 | Leu | Ser | Asn | Asp | Asn<br>60 | Gly | Gln | Leu | Ala |
| Glu<br>65 | Ile | Ala | Ile | Asp | Val<br>70 | Thr | Ser | Val | Tyr | Val<br>75 | Val | Gly | Tyr | Gln | Val<br>80 |
| Arg | Asn | Arg | Ser | Tyr<br>85 | Phe | Phe | Lys | Asp | Ala<br>90 | Pro | Asp | Ala | Ala | Tyr<br>95 | Glu |
| Gly | Leu | Phe | Lys | Asn<br>100 | Thr | Ile | Lys | Thr<br>105 | Arg | Leu | His | Phe | Gly<br>110 | Gly | Ser |
| Tyr | Pro | Ser<br>115 | Leu | Glu | Gly | Glu | Lys<br>120 | Ala | Tyr | Arg | Glu | Thr<br>125 | Thr | Asp | Leu |
| Gly | Ile<br>130 | Glu | Pro | Leu | Arg | Ile<br>135 | Gly | Ile | Lys | Lys | Leu<br>140 | Asp | Glu | Asn | Ala |
| Ile<br>145 | Asp | Asn | Tyr | Lys | Pro<br>150 | Thr | Glu | Ile | Ala | Ser<br>155 | Ser | Leu | Leu | Val | Val<br>160 |
| Ile | Gln | Met | Val | Ser<br>165 | Glu | Ala | Ala | Arg | Phe<br>170 | Thr | Phe | Ile | Glu | Asn<br>175 | Gln |
| Ile | Arg | Asn | Asn<br>180 | Phe | Gln | Gln | Arg | Ile<br>185 | Arg | Pro | Ala | Asn | Asn<br>190 | Thr | Ile |
| Ser | Leu | Glu<br>195 | Asn | Lys | Trp | Gly | Lys<br>200 | Leu | Ser | Phe | Gln | Ile<br>205 | Arg | Thr | Ser |
| Gly | Ala | Asn<br>210 | Gly | Met | Phe | Ser | Glu<br>215 | Ala | Val | Glu | Leu<br>220 | Glu | Arg | Ala | Asn |
| Gly | Lys<br>225 | Lys | Tyr | Tyr | Val<br>230 | Thr | Ala | Val | Asp<br>235 | Gln | Val | Lys | Pro | Lys | Ile<br>240 |
| Ala | Leu | Leu | Cys | Phe<br>245 | Val | Asp | Lys | Asp | Pro<br>250 | Lys | | | | | |

( 2 ) INFORMATION FOR SEQ ID NO:106:

( i ) SEQUENCE CHARACTERISTICS:
( A ) LENGTH: 251 amino acids
( B ) TYPE: amino acid
( D ) TOPOLOGY: linear ( i i ) MOLECULE TYPE: protein ( x i ) SEQUENCE DESCRIPTION: SEQ ID NO:106:

| | | | | | | | | | | | | | | |
|---|---|---|---|---|---|---|---|---|---|---|---|---|---|---|
| Gly<br>1 | Leu | Asp | Thr | Val<br>5 | Ser | Phe | Ser | Thr | Cys<br>10 | Gly | Ala | Thr | Tyr | Ile<br>15 | Thr |
| Tyr | Val | Asn | Phe<br>20 | Leu | Asn | Glu | Leu | Arg<br>25 | Val | Lys | Leu | Lys | Pro<br>30 | Glu | Gly |
| Asn | Ser | His<br>35 | Gly | Ile | Pro | Leu | Leu<br>40 | Arg | Lys | Lys | Cys | Asp<br>45 | Asp | Pro | Gly |
| Lys | Cys<br>50 | Phe | Val | Leu | Val | Ala<br>55 | Leu | Ser | Asn | Asp | Asn<br>60 | Gly | Gln | Leu | Ala |
| Glu<br>65 | Ile | Ala | Ile | Asp | Val<br>70 | Thr | Ser | Val | Tyr | Val<br>75 | Val | Gly | Tyr | Gln | Val<br>80 |
| Arg | Asn | Arg | Ser | Tyr<br>85 | Phe | Phe | Lys | Asp | Ala<br>90 | Pro | Asp | Ala | Ala | Tyr<br>95 | Glu |
| Gly | Leu | Phe | Lys | Asn | Thr | Ile | Lys | Thr | Arg | Leu | His | Phe | Gly | Gly | Ser |

|     |     |     |     | 100 |     |     |     |     | 105 |     |     |     |     | 110 |     |
| --- | --- | --- | --- | --- | --- | --- | --- | --- | --- | --- | --- | --- | --- | --- | --- |
| Tyr | Pro | Ser | Leu | Glu | Gly | Glu | Lys | Ala | Tyr | Arg | Glu | Thr | Thr | Asp | Leu |
|     |     | 115 |     |     |     |     | 120 |     |     |     |     | 125 |     |     |     |
| Gly | Ile | Glu | Pro | Leu | Arg | Ile | Gly | Ile | Lys | Lys | Leu | Asp | Glu | Asn | Ala |
|     | 130 |     |     |     |     | 135 |     |     |     |     | 140 |     |     |     |     |
| Ile | Asp | Asn | Tyr | Lys | Pro | Thr | Glu | Ile | Ala | Ser | Ser | Leu | Leu | Val | Val |
| 145 |     |     |     |     | 150 |     |     |     |     | 155 |     |     |     |     | 160 |
| Ile | Gln | Met | Val | Ser | Glu | Ala | Ala | Arg | Phe | Thr | Phe | Ile | Glu | Asn | Gln |
|     |     |     |     | 165 |     |     |     |     | 170 |     |     |     |     | 175 |     |
| Ile | Arg | Asn | Asn | Phe | Gln | Gln | Arg | Ile | Arg | Pro | Ala | Asn | Asn | Thr | Ile |
|     |     |     | 180 |     |     |     |     | 185 |     |     |     |     | 190 |     |     |
| Ser | Leu | Glu | Asn | Lys | Trp | Gly | Lys | Leu | Ser | Phe | Gln | Ile | Arg | Thr | Ser |
|     |     | 195 |     |     |     |     | 200 |     |     |     |     | 205 |     |     |     |
| Gly | Ala | Asn | Gly | Met | Phe | Ser | Glu | Ala | Val | Glu | Leu | Glu | Arg | Ala | Asn |
|     | 210 |     |     |     |     | 215 |     |     |     |     | 220 |     |     |     |     |
| Gly | Lys | Lys | Tyr | Tyr | Val | Thr | Ala | Val | Asp | Gln | Val | Lys | Pro | Lys | Ile |
| 225 |     |     |     |     | 230 |     |     |     |     | 235 |     |     |     |     | 240 |
| Ala | Leu | Leu | Lys | Phe | Val | Asp | Lys | Asp | Pro | Lys |     |     |     |     |     |
|     |     |     |     | 245 |     |     |     |     | 250 |     |     |     |     |     |     |

(2) INFORMATION FOR SEQ ID NO:107:

(i) SEQUENCE CHARACTERISTICS:
    (A) LENGTH: 251 amino acids
    (B) TYPE: amino acid
    (D) TOPOLOGY: linear (ii) MOLECULE TYPE: protein (xi) SEQUENCE DESCRIPTION: SEQ ID NO:107:

| Gly | Leu | Asp | Thr | Val | Ser | Phe | Ser | Thr | Lys | Gly | Ala | Thr | Tyr | Ile | Thr |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Tyr | Val | Asn | Phe | Leu | Asn | Glu | Leu | Arg | Val | Lys | Leu | Lys | Pro | Glu | Gly |
|     |     |     | 20  |     |     |     |     | 25  |     |     |     |     | 30  |     |     |
| Asn | Ser | His | Gly | Ile | Pro | Leu | Leu | Arg | Lys | Lys | Cys | Asp | Asp | Pro | Gly |
|     |     | 35  |     |     |     |     | 40  |     |     |     |     | 45  |     |     |     |
| Lys | Cys | Phe | Val | Leu | Val | Ala | Leu | Ser | Asn | Asp | Cys | Gly | Gln | Leu | Ala |
|     | 50  |     |     |     |     | 55  |     |     |     |     | 60  |     |     |     |     |
| Glu | Ile | Ala | Ile | Asp | Val | Thr | Ser | Val | Tyr | Val | Val | Gly | Tyr | Gln | Val |
| 65  |     |     |     |     | 70  |     |     |     |     | 75  |     |     |     |     | 80  |
| Arg | Asn | Arg | Ser | Tyr | Phe | Phe | Lys | Asp | Ala | Pro | Asp | Ala | Ala | Tyr | Glu |
|     |     |     |     | 85  |     |     |     |     | 90  |     |     |     |     | 95  |     |
| Gly | Leu | Phe | Lys | Asn | Thr | Ile | Lys | Thr | Arg | Leu | His | Phe | Gly | Gly | Ser |
|     |     |     | 100 |     |     |     |     | 105 |     |     |     |     | 110 |     |     |
| Tyr | Pro | Ser | Leu | Glu | Gly | Glu | Lys | Ala | Tyr | Arg | Glu | Thr | Thr | Asp | Leu |
|     |     | 115 |     |     |     |     | 120 |     |     |     |     | 125 |     |     |     |
| Gly | Ile | Glu | Pro | Leu | Arg | Ile | Gly | Ile | Lys | Lys | Leu | Asp | Glu | Asn | Ala |
|     | 130 |     |     |     |     | 135 |     |     |     |     | 140 |     |     |     |     |
| Ile | Asp | Asn | Tyr | Lys | Pro | Thr | Glu | Ile | Ala | Ser | Ser | Leu | Leu | Val | Val |
| 145 |     |     |     |     | 150 |     |     |     |     | 155 |     |     |     |     | 160 |
| Ile | Gln | Met | Val | Ser | Glu | Ala | Ala | Arg | Phe | Thr | Phe | Ile | Glu | Asn | Gln |
|     |     |     |     | 165 |     |     |     |     | 170 |     |     |     |     | 175 |     |
| Ile | Arg | Asn | Asn | Phe | Gln | Gln | Arg | Ile | Arg | Pro | Ala | Asn | Asn | Thr | Ile |
|     |     |     | 180 |     |     |     |     | 185 |     |     |     |     | 190 |     |     |
| Ser | Leu | Glu | Asn | Lys | Trp | Gly | Lys | Leu | Ser | Phe | Gln | Ile | Arg | Thr | Ser |
|     |     | 195 |     |     |     |     | 200 |     |     |     |     | 205 |     |     |     |

| Gly | Ala | Asn | Gly | Met | Phe | Ser | Glu | Ala | Val | Glu | Leu | Glu | Arg | Ala | Asn |
|---|---|---|---|---|---|---|---|---|---|---|---|---|---|---|---|
| | 210 | | | | | 215 | | | | | 220 | | | | |

| Gly | Lys | Lys | Tyr | Tyr | Val | Thr | Ala | Val | Asp | Gln | Val | Lys | Pro | Lys | Ile |
|---|---|---|---|---|---|---|---|---|---|---|---|---|---|---|---|
| 225 | | | | | 230 | | | | | 235 | | | | | 240 |

| Ala | Leu | Leu | Lys | Phe | Val | Asp | Lys | Asp | Pro | Lys |
|---|---|---|---|---|---|---|---|---|---|---|
| | | | | 245 | | | | | 250 | |

( 2 ) INFORMATION FOR SEQ ID NO:108:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:108:

| Gly | Leu | Asp | Thr | Val | Ser | Phe | Ser | Thr | Lys | Gly | Ala | Thr | Tyr | Ile | Thr |
|---|---|---|---|---|---|---|---|---|---|---|---|---|---|---|---|
| 1 | | | | 5 | | | | | 10 | | | | | 15 | |

| Tyr | Val | Asn | Phe | Leu | Asn | Glu | Leu | Arg | Val | Lys | Leu | Lys | Pro | Glu | Gly |
|---|---|---|---|---|---|---|---|---|---|---|---|---|---|---|---|
| | | | 20 | | | | | 25 | | | | | 30 | | |

| Asn | Ser | His | Gly | Ile | Pro | Leu | Leu | Arg | Lys | Lys | Cys | Asp | Asp | Pro | Gly |
|---|---|---|---|---|---|---|---|---|---|---|---|---|---|---|---|
| | | 35 | | | | | 40 | | | | | 45 | | | |

| Lys | Cys | Phe | Val | Leu | Val | Ala | Leu | Ser | Asn | Asp | Gly | Gln | Leu | Ala |
|---|---|---|---|---|---|---|---|---|---|---|---|---|---|---|
| | 50 | | | | | 55 | | | | | 60 | | | |

| Glu | Ile | Ala | Ile | Asp | Val | Thr | Ser | Val | Tyr | Val | Val | Gly | Tyr | Gln | Val |
|---|---|---|---|---|---|---|---|---|---|---|---|---|---|---|---|
| 65 | | | | | 70 | | | | | 75 | | | | | 80 |

| Arg | Asn | Arg | Ser | Tyr | Phe | Phe | Lys | Asp | Ala | Pro | Asp | Ala | Ala | Tyr | Glu |
|---|---|---|---|---|---|---|---|---|---|---|---|---|---|---|---|
| | | | | 85 | | | | | 90 | | | | | 95 | |

| Gly | Leu | Phe | Lys | Asn | Thr | Cys | Lys | Thr | Arg | Leu | His | Phe | Gly | Gly | Ser |
|---|---|---|---|---|---|---|---|---|---|---|---|---|---|---|---|
| | | | 100 | | | | | 105 | | | | | 110 | | |

| Tyr | Pro | Ser | Leu | Glu | Gly | Glu | Lys | Ala | Tyr | Arg | Glu | Thr | Thr | Asp | Leu |
|---|---|---|---|---|---|---|---|---|---|---|---|---|---|---|---|
| | | 115 | | | | | 120 | | | | | 125 | | | |

| Gly | Ile | Glu | Pro | Leu | Arg | Ile | Gly | Ile | Lys | Lys | Leu | Asp | Glu | Asn | Ala |
|---|---|---|---|---|---|---|---|---|---|---|---|---|---|---|---|
| | 130 | | | | | 135 | | | | | 140 | | | | |

| Ile | Asp | Asn | Tyr | Lys | Pro | Thr | Glu | Ile | Ala | Ser | Ser | Leu | Leu | Val | Val |
|---|---|---|---|---|---|---|---|---|---|---|---|---|---|---|---|
| 145 | | | | | 150 | | | | | 155 | | | | | 160 |

| Ile | Gln | Met | Val | Ser | Glu | Ala | Ala | Arg | Phe | Thr | Phe | Ile | Glu | Asn | Gln |
|---|---|---|---|---|---|---|---|---|---|---|---|---|---|---|---|
| | | | | 165 | | | | | 170 | | | | | 175 | |

| Ile | Arg | Asn | Asn | Phe | Gln | Gln | Arg | Ile | Arg | Pro | Ala | Asn | Asn | Thr | Ile |
|---|---|---|---|---|---|---|---|---|---|---|---|---|---|---|---|
| | | | 180 | | | | | 185 | | | | | 190 | | |

| Ser | Leu | Glu | Asn | Lys | Trp | Gly | Lys | Leu | Ser | Phe | Gln | Ile | Arg | Thr | Ser |
|---|---|---|---|---|---|---|---|---|---|---|---|---|---|---|---|
| | | 195 | | | | | 200 | | | | | 205 | | | |

| Gly | Ala | Asn | Gly | Met | Phe | Ser | Glu | Ala | Val | Glu | Leu | Glu | Arg | Ala | Asn |
|---|---|---|---|---|---|---|---|---|---|---|---|---|---|---|---|
| | 210 | | | | | 215 | | | | | 220 | | | | |

| Gly | Lys | Lys | Tyr | Tyr | Val | Thr | Ala | Val | Asp | Gln | Val | Lys | Pro | Lys | Ile |
|---|---|---|---|---|---|---|---|---|---|---|---|---|---|---|---|
| 225 | | | | | 230 | | | | | 235 | | | | | 240 |

| Ala | Leu | Leu | Lys | Phe | Val | Asp | Lys | Asp | Pro | Lys |
|---|---|---|---|---|---|---|---|---|---|---|
| | | | | 245 | | | | | 250 | |

( 2 ) INFORMATION FOR SEQ ID NO:109:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:109:

| Gly | Leu | Asp | Thr | Val | Ser | Phe | Ser | Thr | Lys | Gly | Ala | Thr | Tyr | Ile | Thr |
| 1 | | | | 5 | | | | | 10 | | | | | 15 | |

| Tyr | Val | Asn | Phe | Leu | Asn | Glu | Leu | Arg | Val | Lys | Leu | Lys | Pro | Glu | Gly |
| | | | 20 | | | | | 25 | | | | | 30 | | |

| Asn | Ser | His | Gly | Ile | Pro | Leu | Leu | Arg | Lys | Lys | Cys | Asp | Asp | Pro | Gly |
| | | | 35 | | | | 40 | | | | | 45 | | | |

| Lys | Cys | Phe | Val | Leu | Val | Ala | Leu | Ser | Asn | Asp | Asn | Gly | Gln | Leu | Ala |
| | 50 | | | | | 55 | | | | | 60 | | | | |

| Glu | Ile | Ala | Ile | Asp | Val | Thr | Ser | Val | Tyr | Val | Val | Gly | Tyr | Gln | Val |
| 65 | | | | | 70 | | | | 75 | | | | | | 80 |

| Arg | Asn | Arg | Ser | Tyr | Phe | Phe | Lys | Asp | Ala | Pro | Asp | Ala | Ala | Tyr | Glu |
| | | | | 85 | | | | | 90 | | | | | 95 | |

| Gly | Leu | Phe | Lys | Asn | Thr | Ile | Lys | Thr | Arg | Leu | His | Phe | Gly | Gly | Ser |
| | | | 100 | | | | | 105 | | | | | 110 | | |

| Tyr | Pro | Ser | Leu | Glu | Gly | Glu | Lys | Ala | Tyr | Arg | Glu | Thr | Thr | Asp | Leu |
| | | | 115 | | | | 120 | | | | | 125 | | | |

| Gly | Ile | Glu | Pro | Leu | Arg | Ile | Gly | Ile | Lys | Lys | Leu | Asp | Glu | Asn | Ala |
| | 130 | | | | | 135 | | | | | 140 | | | | |

| Ile | Asp | Asn | Tyr | Lys | Pro | Thr | Glu | Ile | Ala | Ser | Ser | Leu | Leu | Val | Val |
| 145 | | | | | 150 | | | | | 155 | | | | | 160 |

| Ile | Gln | Met | Val | Ser | Glu | Ala | Ala | Arg | Phe | Thr | Phe | Ile | Glu | Asn | Gln |
| | | | | 165 | | | | | 170 | | | | | 175 | |

| Ile | Arg | Asn | Asn | Phe | Gln | Gln | Cys | Ile | Arg | Pro | Ala | Asn | Asn | Thr | Ile |
| | | | 180 | | | | | 185 | | | | | 190 | | |

| Ser | Leu | Glu | Asn | Lys | Trp | Gly | Lys | Leu | Ser | Phe | Gln | Ile | Arg | Thr | Ser |
| | | 195 | | | | | 200 | | | | | 205 | | | |

| Gly | Ala | Asn | Gly | Met | Phe | Ser | Glu | Ala | Val | Glu | Leu | Glu | Arg | Ala | Asn |
| | 210 | | | | | 215 | | | | | 220 | | | | |

| Gly | Lys | Lys | Tyr | Tyr | Val | Thr | Ala | Val | Asp | Gln | Val | Lys | Pro | Lys | Ile |
| 225 | | | | | 230 | | | | | 235 | | | | | 240 |

| Ala | Leu | Leu | Lys | Phe | Val | Asp | Lys | Asp | Pro | Lys | | | | | |
| | | | | 245 | | | | | 250 | | | | | | |

( 2 ) INFORMATION FOR SEQ ID NO:110:

( i ) SEQUENCE CHARACTERISTICS:
  ( A ) LENGTH: 251 amino acids
  ( B ) TYPE: amino acid
  ( D ) TOPOLOGY: linear ( i i ) MOLECULE TYPE: protein ( x i ) SEQUENCE DESCRIPTION: SEQ ID NO:110:

| Gly | Leu | Asp | Thr | Val | Ser | Phe | Ser | Thr | Cys | Gly | Ala | Thr | Tyr | Ile | Thr |
| 1 | | | | 5 | | | | | 10 | | | | | 15 | |

| Tyr | Val | Asn | Phe | Leu | Asn | Glu | Leu | Arg | Val | Lys | Leu | Lys | Pro | Glu | Gly |
| | | | 20 | | | | | 25 | | | | | 30 | | |

| Asn | Ser | His | Gly | Ile | Pro | Leu | Leu | Arg | Lys | Lys | Ala | Asp | Asp | Pro | Gly |
| | | | 35 | | | | 40 | | | | | 45 | | | |

| Lys | Ala | Phe | Val | Leu | Val | Ala | Leu | Ser | Asn | Asp | Asn | Gly | Gln | Leu | Ala |
| | 50 | | | | | 55 | | | | | 60 | | | | |

| Glu | Ile | Ala | Ile | Asp | Val | Thr | Ser | Val | Tyr | Val | Val | Gly | Tyr | Gln | Val |
| 65 | | | | | 70 | | | | 75 | | | | | | 80 |

| Arg | Asn | Arg | Ser | Tyr | Phe | Phe | Lys | Asp | Ala | Pro | Asp | Ala | Ala | Tyr | Glu |
| | | | | 85 | | | | | 90 | | | | | 95 | |

| Gly | Leu | Phe | Lys | Asn | Thr | Ile | Lys | Thr | Arg | Leu | His | Phe | Gly | Gly | Ser |

```
                    100                         105                         110
Tyr  Pro  Ser  Leu  Glu  Gly  Glu  Lys  Ala  Tyr  Arg  Glu  Thr  Thr  Asp  Leu
               115                      120                     125
Gly  Ile  Glu  Pro  Leu  Arg  Ile  Gly  Ile  Lys  Lys  Leu  Asp  Glu  Asn  Ala
     130                      135                     140
Ile  Asp  Asn  Tyr  Lys  Pro  Thr  Glu  Ile  Ala  Ser  Ser  Leu  Leu  Val  Val
145                      150                     155                          160
Ile  Gln  Met  Val  Ser  Glu  Ala  Ala  Arg  Phe  Thr  Phe  Ile  Glu  Asn  Gln
                    165                     170                          175
Ile  Arg  Asn  Asn  Phe  Gln  Gln  Arg  Ile  Arg  Pro  Ala  Asn  Asn  Thr  Ile
               180                     185                     190
Ser  Leu  Glu  Asn  Lys  Trp  Gly  Lys  Leu  Ser  Phe  Gln  Ile  Arg  Thr  Ser
          195                     200                     205
Gly  Ala  Asn  Gly  Met  Phe  Ser  Glu  Ala  Val  Glu  Leu  Glu  Arg  Ala  Asn
     210                     215                     220
Gly  Lys  Lys  Tyr  Tyr  Val  Thr  Ala  Val  Asp  Gln  Val  Lys  Pro  Lys  Ile
225                     230                     235                          240
Ala  Leu  Leu  Lys  Phe  Val  Asp  Lys  Asp  Pro  Lys
               245                     250
```

( 2 ) INFORMATION FOR SEQ ID NO:111:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:111:

```
Gly  Leu  Asp  Thr  Val  Ser  Phe  Ser  Thr  Cys  Gly  Ala  Thr  Tyr  Ile  Thr
1                   5                        10                          15
Tyr  Val  Asn  Phe  Leu  Asn  Glu  Leu  Arg  Val  Lys  Leu  Lys  Pro  Glu  Gly
               20                      25                      30
Asn  Ser  His  Gly  Ile  Pro  Leu  Leu  Arg  Lys  Lys  Ala  Asp  Asp  Pro  Gly
          35                      40                      45
Lys  Ala  Phe  Val  Leu  Val  Ala  Leu  Ser  Asn  Asp  Asn  Gly  Gln  Leu  Ala
     50                      55                      60
Glu  Ile  Ala  Ile  Asp  Val  Thr  Ser  Val  Tyr  Val  Val  Gly  Tyr  Gln  Val
65                      70                      75                           80
Arg  Asn  Arg  Ser  Tyr  Phe  Phe  Lys  Asp  Ala  Pro  Asp  Ala  Ala  Tyr  Glu
               85                      90                      95
Gly  Leu  Phe  Lys  Asn  Thr  Ile  Lys  Thr  Arg  Leu  His  Phe  Gly  Gly  Ser
          100                     105                     110
Tyr  Pro  Ser  Leu  Glu  Gly  Glu  Lys  Ala  Tyr  Arg  Glu  Thr  Thr  Asp  Leu
               115                     120                     125
Gly  Ile  Glu  Pro  Leu  Arg  Ile  Gly  Ile  Lys  Lys  Leu  Asp  Glu  Asn  Ala
     130                     135                     140
Ile  Asp  Asn  Tyr  Lys  Pro  Thr  Glu  Ile  Ala  Ser  Ser  Leu  Leu  Val  Val
145                     150                     155                          160
Ile  Gln  Met  Val  Ser  Glu  Ala  Ala  Arg  Phe  Thr  Phe  Ile  Glu  Asn  Gln
                    165                     170                          175
Ile  Arg  Asn  Asn  Phe  Gln  Gln  Arg  Ile  Arg  Pro  Ala  Asn  Asn  Thr  Ile
               180                     185                     190
Ser  Leu  Glu  Asn  Lys  Trp  Gly  Lys  Leu  Ser  Phe  Gln  Ile  Arg  Thr  Ser
          195                     200                     205
```

| Gly | Ala | Asn | Gly | Met | Phe | Ser | Glu | Ala | Val | Glu | Leu | Glu | Arg | Ala | Asn |
|---|---|---|---|---|---|---|---|---|---|---|---|---|---|---|---|
| | 210 | | | | | 215 | | | | | 220 | | | | |

| Gly | Lys | Lys | Tyr | Tyr | Val | Thr | Ala | Val | Asp | Gln | Val | Lys | Pro | Lys | Ile |
|---|---|---|---|---|---|---|---|---|---|---|---|---|---|---|---|
| 225 | | | | | 230 | | | | 235 | | | | | | 240 |

| Ala | Leu | Leu | Lys | Phe | Val | Cys | Lys | Asp | Pro | Lys |
|---|---|---|---|---|---|---|---|---|---|---|
| | | | | 245 | | | | | 250 | |

( 2 ) INFORMATION FOR SEQ ID NO:112:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:112:

TGATGCGGCC GACATCTCAA GCTTGGTGC         29

( 2 ) INFORMATION FOR SEQ ID NO:113:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:113:

TGATGCGGCC GACATCTCAA GCTTGGTGC         29

( 2 ) INFORMATION FOR SEQ ID NO:114:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:114:

TCTAGGTCAC CGTCTCCTCA CCATCTGGAC AGGCTGGA         38

( 2 ) INFORMATION FOR SEQ ID NO:115:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:115:

TTCGAAGCTT GAGATGAAAC CATCTGGACA GGCTGGA         37

( 2 ) INFORMATION FOR SEQ ID NO:116:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:116:

AGTCGTCGAC ACGATGGACA TGAGGAC                                                27

( 2 ) INFORMATION FOR SEQ ID NO:117:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:117:

AGTCGTCGAC ACGATGGACA TGAGGACCCC TGCTCAGTTT CTTGGCATCC TCCTACTCTG    60

GTTTCCAGGT ATCAAATGTG ACATCCAGAT GACTCAGT                             98

( 2 ) INFORMATION FOR SEQ ID NO:118:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:118:

TCACTTGCCG GGCGAATCAG GACATTAATA GCTATTTAAG CTGGTTCCAG CAGAAACCAG    60

GGAAAGCTCC TAAGACCCT                                                  79

( 2 ) INFORMATION FOR SEQ ID NO:119:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:119:

TGACTCGCCC GGCAAGTGAT AGTGACTCTG TCTCCTACAG ATGCAGACAG GGAAGATGGA    60

GACTGAGTCA TCTGGATGTC                                                 80

( 2 ) INFORMATION FOR SEQ ID NO:120:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:120:

GATCCACTGC CACTGAACCT TGATGGGACC CCAGATTCCA ATCTGTTTGC ACGATAGATC    60

AGGGTCTTAG GAGCTTTCC                                                  79

( 2 ) INFORMATION FOR SEQ ID NO:121:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:121:

GGTTCAGTGG CAGTGGATCT GGGACAGATT ATACTCTCAC CATCAGCAGC CTGCAATATG    60

AAGATTTTGG AATTTATTAT TG    82

( 2 ) INFORMATION FOR SEQ ID NO:122:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:122:

GTTTGATTTC AAGCTTGGTG CCTCCACCGA ACGTCCACGG AGACTCATCA TACTGTTGAC    60

AATAATAAAT TCCAAAATCT TC    82

( 2 ) INFORMATION FOR SEQ ID NO:123:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:123:

| Asp | Ile | Lys | Met | Thr | Gln | Ser | Pro | Ser | Ser | Met | Tyr | Ala | Ser | Leu | Gly |
|---|---|---|---|---|---|---|---|---|---|---|---|---|---|---|---|
| 1 | | | | 5 | | | | | 10 | | | | | 15 | |

| Glu | Arg | Val | Thr | Ile | Thr | Cys | Lys | Ala | Ser | Gln | Asp | Ile | Asn | Ser | Tyr |
|---|---|---|---|---|---|---|---|---|---|---|---|---|---|---|---|
| | | | 20 | | | | | 25 | | | | | 30 | | |

| Leu | Ser | Trp | Phe | His | His | Lys | Pro | Gly | Lys | Ser | Pro | Lys | Thr | Leu | Ile |
|---|---|---|---|---|---|---|---|---|---|---|---|---|---|---|---|
| | | 35 | | | | | 40 | | | | | 45 | | | |

| Tyr | Arg | Ala | Asn | Arg | Leu | Val | Asp | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Gln | Asp | Tyr | Ser | Leu | Thr | Ile | Ser | Ser | Leu | Asp | Tyr |
|---|---|---|---|---|---|---|---|---|---|---|---|---|---|---|---|
| 65 | | | | | 70 | | | | | 75 | | | | | 80 |

| Glu | Asp | Met | Gly | Ile | Tyr | Tyr | Cys | Gln | Gln | Tyr | Asp | Glu | Ser | Pro | Trp |
|---|---|---|---|---|---|---|---|---|---|---|---|---|---|---|---|
| | | | | 85 | | | | | 90 | | | | | 95 | |

| Thr | Phe | Gly | Gly | Gly | Thr | Lys | Leu | Glu | Ile | Lys |
|---|---|---|---|---|---|---|---|---|---|---|
| | | | 100 | | | | | 105 | | |

( 2 ) INFORMATION FOR SEQ ID NO:124:

( i ) SEQUENCE CHARACTERISTICS:
        ( A ) LENGTH: 118 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:124:

| Gln | Ile | Gln | Leu | Val | Gln | Ser | Gly | Pro | Glu | Leu | Lys | Lys | Pro | Gly | Glu |
|---|---|---|---|---|---|---|---|---|---|---|---|---|---|---|---|
| 1 | | | | 5 | | | | | 10 | | | | | 15 | |

| Thr | Val | Lys | Ile | Ser | Cys | Lys | Ala | Ser | Gly | Tyr | Thr | Phe | Thr | Asn | Tyr |
|---|---|---|---|---|---|---|---|---|---|---|---|---|---|---|---|
| | | | 20 | | | | | 25 | | | | | 30 | | |

| Gly | Met | Asn | Trp | Val | Lys | Gln | Ala | Pro | Gly | Lys | Gly | Leu | Arg | Trp | Met |

5,744,580

151 152

-continued

|  |  |  | 35 |  |  |  | 40 |  |  |  | 45 |  |  |  |
|---|---|---|---|---|---|---|---|---|---|---|---|---|---|---|
| Gly | Trp 50 | Ile | Asn | Thr | His | Thr 55 | Gly | Glu | Pro | Thr | Tyr 60 | Ala | Asp | Phe |
| Lys 65 | Gly | Arg | Phe | Ala | Phe 70 | Ser | Leu | Glu | Thr | Ser 75 | Ala | Ser | Thr | Ala | Tyr 80 |
| Leu | Gln | Ile | Asn | Asn 85 | Leu | Lys | Asn | Glu | Asp 90 | Thr | Ala | Thr | Tyr | Phe 95 | Cys |
| Thr | Arg | Arg | Gly 100 | Tyr | Asp | Trp | Tyr | Phe 105 | Asp | Val | Trp | Gly | Ala 110 | Gly | Thr |
| Thr | Val | Thr 115 | Val | Ser | Ser |

( 2 ) INFORMATION FOR SEQ ID NO:125:

( i ) SEQUENCE CHARACTERISTICS:
( A ) LENGTH: 107 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:125:

| Asp 1 | Ile | Gln | Met | Thr 5 | Gln | Ser | Pro | Ser | Ser 10 | Leu | Ser | Ala | Ser | Val 15 | Gly |
| --- | --- | --- | --- | --- | --- | --- | --- | --- | --- | --- | --- | --- | --- | --- | --- |
| Asp | Arg | Val | Thr 20 | Ile | Thr | Cys | Arg | Ala 25 | Ser | Gln | Asp | Ile | Asn 30 | Ser | Tyr |
| Leu | Ser | Trp 35 | Phe | Gln | Gln | Lys | Pro 40 | Gly | Lys | Ala | Pro | Lys 45 | Thr | Leu | Ile |
| Tyr | Arg 50 | Ala | Asn | Arg | Leu | Glu 55 | Ser | Gly | Val | Pro | Ser 60 | Arg | Phe | Ser | Gly |
| Ser 65 | Gly | Ser | Gly | Thr | Asp 70 | Tyr | Thr | Leu | Thr | Ile 75 | Ser | Ser | Leu | Gln | Tyr 80 |
| Glu | Asp | Phe | Gly | Ile 85 | Tyr | Tyr | Cys | Gln | Gln 90 | Tyr | Asp | Glu | Ser | Pro 95 | Trp |
| Thr | Phe | Gly | Gly 100 | Gly | Thr | Lys | Leu | Glu 105 | Ile | Lys |

( 2 ) INFORMATION FOR SEQ ID NO:126:

( i ) SEQUENCE CHARACTERISTICS:
( A ) LENGTH: 118 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:126:

| Glu 1 | Ile | Gln | Leu | Val 5 | Gln | Ser | Gly | Gly | Gly 10 | Leu | Val | Lys | Pro | Gly 15 | Gly |
| --- | --- | --- | --- | --- | --- | --- | --- | --- | --- | --- | --- | --- | --- | --- | --- |
| Ser | Val | Arg | Ile 20 | Ser | Cys | Ala | Ala | Ser 25 | Gly | Tyr | Thr | Phe | Thr 30 | Asn | Tyr |
| Gly | Met | Asn 35 | Trp | Val | Arg | Gln | Ala 40 | Pro | Gly | Lys | Gly | Leu 45 | Glu | Trp | Met |
| Gly | Trp 50 | Ile | Asn | Thr | His | Thr 55 | Gly | Glu | Pro | Thr | Tyr 60 | Ala | Asp | Ser | Phe |
| Lys 65 | Gly | Arg | Phe | Thr | Phe 70 | Ser | Leu | Asp | Asp | Ser 75 | Lys | Asn | Thr | Ala | Tyr 80 |
| Leu | Gln | Ile | Asn | Ser | Leu | Arg | Ala | Glu | Asp | Thr | Ala | Val | Tyr | Phe | Cys |

```
                              85                    90                        95
        Thr  Arg  Arg  Gly  Tyr  Asp  Trp  Tyr  Phe  Asp  Val  Trp  Gly  Gln  Gly  Thr
                       100                      105                 110

Thr  Val  Thr  Val  Ser  Ser
                       115
```

( 2 ) INFORMATION FOR SEQ ID NO:127:

( i ) SEQUENCE CHARACTERISTICS:
    ( A ) LENGTH: 280 amino acids
    ( B ) TYPE: amino acid
    ( D ) TOPOLOGY: linear ( i i ) MOLECULE TYPE: protein ( x i ) SEQUENCE DESCRIPTION: SEQ ID NO:127:

```
Ala  Ala  Lys  Met  Ala  Lys  Asn  Val  Asp  Lys  Pro  Leu  Phe  Thr  Ala  Thr
1                  5                      10                      15

Phe  Asn  Val  Gln  Ala  Ser  Ser  Ala  Asp  Tyr  Ala  Thr  Phe  Ile  Ala  Gly
               20                      25                      30

Ile  Arg  Asn  Lys  Leu  Arg  Asn  Pro  Ala  His  Phe  Ser  His  Asn  Arg  Pro
          35                      40                      45

Val  Leu  Pro  Pro  Val  Glu  Pro  Asn  Val  Pro  Pro  Ser  Arg  Trp  Phe  His
     50                      55                      60

Val  Val  Leu  Lys  Ala  Ser  Pro  Thr  Ser  Ala  Gly  Leu  Thr  Leu  Ala  Ile
65                      70                      75                      80

Arg  Ala  Asp  Asn  Ile  Tyr  Leu  Glu  Gly  Phe  Lys  Ser  Ser  Asp  Gly  Thr
                    85                      90                      95

Trp  Trp  Glu  Leu  Thr  Pro  Gly  Leu  Ile  Pro  Gly  Ala  Thr  Tyr  Val  Gly
               100                     105                     110

Phe  Gly  Gly  Thr  Tyr  Arg  Asp  Leu  Leu  Gly  Asp  Thr  Asp  Lys  Leu  Thr
          115                     120                     125

Asn  Val  Ala  Leu  Gly  Arg  Gln  Gln  Leu  Ala  Asp  Ala  Val  Thr  Ala  Leu
     130                     135                     140

His  Gly  Arg  Thr  Lys  Ala  Asp  Lys  Ala  Ser  Gly  Pro  Lys  Gln  Gln  Gln
145                     150                     155                     160

Ala  Arg  Glu  Ala  Val  Thr  Thr  Leu  Val  Leu  Met  Val  Asn  Glu  Ala  Thr
                    165                     170                     175

Arg  Phe  Gln  Thr  Val  Ser  Gly  Phe  Val  Ala  Gly  Leu  Leu  His  Pro  Lys
               180                     185                     190

Ala  Val  Glu  Lys  Lys  Ser  Gly  Lys  Ile  Gly  Asn  Glu  Met  Lys  Ala  Gln
          195                     200                     205

Val  Asn  Gly  Trp  Gln  Asp  Leu  Ser  Ala  Ala  Leu  Leu  Lys  Thr  Asp  Val
     210                     215                     220

Lys  Pro  Pro  Pro  Gly  Lys  Ser  Pro  Ala  Lys  Phe  Ala  Pro  Ile  Glu  Lys
225                     230                     235                     240

Met  Gly  Val  Arg  Thr  Ala  Glu  Gln  Ala  Ala  Asn  Thr  Leu  Gly  Ile  Leu
                    245                     250                     255

Leu  Phe  Val  Glu  Val  Pro  Gly  Gly  Leu  Thr  Val  Ala  Lys  Ala  Leu  Glu
               260                     265                     270

Leu  Phe  His  Ala  Cys  Gly  Gly  Lys
          275                     280
```

( 2 ) INFORMATION FOR SEQ ID NO:128:

( i ) SEQUENCE CHARACTERISTICS:
    ( A ) LENGTH: 280 amino acids
    ( B ) TYPE: amino acid (D) TOPOLOGY: linear (ii) MOLECULE TYPE: protein (xi) SEQUENCE DESCRIPTION: SEQ ID NO:128:

```
Ala Ala Lys Met Ala Lys Asn Val Asp Lys Pro Leu Phe Thr Ala Thr
 1           5                  10                  15
Phe Asn Val Gln Ala Ser Ser Ala Asp Tyr Ala Thr Phe Ile Ala Gly
            20                  25                  30
Ile Arg Asn Lys Leu Arg Asn Pro Ala His Phe Ser His Asn Arg Pro
        35                  40                  45
Val Leu Pro Pro Val Glu Pro Asn Val Pro Pro Ser Arg Trp Phe His
    50                  55                  60
Val Val Leu Lys Ala Ser Pro Thr Ser Ala Gly Leu Thr Leu Ala Ile
 65                 70                  75                  80
Arg Ala Asp Asn Ile Tyr Leu Glu Gly Phe Lys Ser Ser Asp Gly Thr
                85                  90                  95
Trp Trp Glu Leu Thr Pro Gly Leu Ile Pro Gly Ala Thr Tyr Val Gly
            100                 105                 110
Phe Gly Gly Thr Tyr Arg Asp Leu Leu Gly Asp Thr Asp Lys Leu Thr
        115                 120                 125
Asn Val Ala Leu Gly Arg Gln Gln Leu Ala Asp Ala Val Thr Ala Leu
    130                 135                 140
His Gly Arg Thr Lys Ala Asp Lys Ala Ser Gly Pro Lys Gln Gln Gln
145                 150                 155                 160
Ala Arg Glu Ala Val Thr Thr Leu Val Leu Met Val Asn Glu Ala Thr
                165                 170                 175
Arg Phe Gln Thr Val Ser Gly Phe Val Ala Gly Leu Leu His Pro Lys
        180                 185                 190
Ala Val Glu Lys Lys Ser Gly Lys Ile Gly Asn Glu Met Lys Ala Gln
    195                 200                 205
Val Asn Gly Trp Gln Asp Leu Ser Ala Ala Leu Leu Lys Thr Asp Val
    210                 215                 220
Lys Pro Pro Pro Gly Lys Ser Pro Ala Lys Phe Ala Pro Ile Glu Lys
225                 230                 235                 240
Met Gly Val Arg Thr Ala Glu Gln Ala Ala Asn Thr Leu Gly Ile Leu
                245                 250                 255
Leu Phe Val Glu Val Pro Gly Gly Leu Thr Val Ala Lys Cys Leu Glu
        260                 265                 270
Leu Phe His Ala Ser Gly Gly Lys
    275                 280
```

(2) INFORMATION FOR SEQ ID NO:129:

(i) SEQUENCE CHARACTERISTICS:
  (A) LENGTH: 280 amino acids
  (B) TYPE: amino acid
  (D) TOPOLOGY: linear (ii) MOLECULE TYPE: protein (xi) SEQUENCE DESCRIPTION: SEQ ID NO:129:

```
Ala Ala Lys Met Ala Lys Asn Val Asp Lys Pro Leu Phe Thr Ala Thr
 1           5                  10                  15
Phe Asn Val Gln Ala Ser Ser Ala Asp Tyr Ala Thr Phe Ile Ala Gly
            20                  25                  30
Ile Arg Asn Lys Leu Arg Asn Pro Ala His Phe Ser His Asn Arg Pro
        35                  40                  45
```

| | | | | | | | | | | | | | | |
|---|---|---|---|---|---|---|---|---|---|---|---|---|---|---|
| Val | Leu | Pro | Pro | Val | Glu | Pro | Asn | Val | Pro | Pro | Ser | Arg | Trp | Phe | His |
| | 50 | | | | 55 | | | | | | 60 | | | | |
| Val | Val | Leu | Lys | Ala | Ser | Pro | Thr | Ser | Ala | Gly | Leu | Thr | Leu | Ala | Ile |
| 65 | | | | | 70 | | | | | 75 | | | | | 80 |
| Arg | Ala | Asp | Asn | Ile | Tyr | Leu | Glu | Gly | Phe | Lys | Ser | Ser | Asp | Gly | Thr |
| | | | | 85 | | | | | 90 | | | | | 95 | |
| Trp | Trp | Glu | Leu | Thr | Pro | Gly | Leu | Ile | Pro | Gly | Ala | Thr | Tyr | Val | Gly |
| | | | 100 | | | | | 105 | | | | | 110 | | |
| Phe | Gly | Gly | Thr | Tyr | Arg | Asp | Leu | Leu | Gly | Asp | Thr | Asp | Lys | Leu | Thr |
| | | | 115 | | | | 120 | | | | | 125 | | | |
| Asn | Val | Ala | Leu | Gly | Arg | Gln | Gln | Leu | Ala | Asp | Ala | Val | Thr | Ala | Leu |
| | | 130 | | | | 135 | | | | | 140 | | | | |
| His | Gly | Arg | Thr | Lys | Ala | Asp | Lys | Ala | Ser | Gly | Pro | Lys | Gln | Gln | Gln |
| 145 | | | | | 150 | | | | | 155 | | | | | 160 |
| Ala | Arg | Glu | Ala | Val | Thr | Thr | Leu | Val | Leu | Met | Val | Asn | Glu | Ala | Thr |
| | | | | 165 | | | | | 170 | | | | | 175 | |
| Arg | Phe | Gln | Thr | Val | Ser | Gly | Phe | Val | Ala | Gly | Leu | Leu | His | Pro | Lys |
| | | | 180 | | | | | 185 | | | | | 190 | | |
| Ala | Val | Glu | Lys | Lys | Ser | Gly | Lys | Ile | Gly | Asn | Glu | Met | Lys | Ala | Gln |
| | | 195 | | | | | 200 | | | | | 205 | | | |
| Val | Asn | Gly | Trp | Gln | Asp | Leu | Ser | Ala | Ala | Leu | Leu | Lys | Thr | Asp | Val |
| | 210 | | | | | 215 | | | | | 220 | | | | |
| Lys | Pro | Pro | Pro | Gly | Lys | Ser | Pro | Ala | Lys | Phe | Ala | Pro | Ile | Glu | Lys |
| 225 | | | | | 230 | | | | | 235 | | | | | 240 |
| Met | Gly | Val | Arg | Thr | Ala | Glu | Gln | Ala | Ala | Asn | Thr | Leu | Gly | Ile | Cys |
| | | | | 245 | | | | | 250 | | | | | 255 | |
| Leu | Phe | Val | Glu | Val | Pro | Gly | Gly | Leu | Thr | Val | Ala | Lys | Ala | Leu | Glu |
| | | | 260 | | | | | 265 | | | | | 270 | | |
| Leu | Phe | His | Ala | Ser | Gly | Gly | Lys |
| | | 275 | | | | | 280 |

( 2 ) INFORMATION FOR SEQ ID NO:130:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:130:

| | | | | | | |
|---|---|---|---|---|---|---|
| Ser | Cys | Asp | Lys | Thr | His | Thr |
| 1 | | | | 5 | | |

( 2 ) INFORMATION FOR SEQ ID NO:131:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:131:

```
TGTCGACATC ATGGCTTGGG TGTGGACCTT GCTATTCCTG ATGGCAGCTG CCCAAAGTGC    60
CCAAGCAGAG ATCCAGTTGG TGCAG                                          85
```

( 2 ) INFORMATION FOR SEQ ID NO:132:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:132:

| | | | | | | |
|---|---|---|---|---|---|---|
| AAGGTATACC | CAGAAGCTGC | GCAGGAGATT | CTGACGGACC | CTCCAGGCTT | CACCAGGCCT | 60 |
| CCTCCAGACT | GCACCAACTG | GATCTC | | | | 86 |

( 2 ) INFORMATION FOR SEQ ID NO:133:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:133:

| | | | | | | |
|---|---|---|---|---|---|---|
| GCAGCTTCTG | GGTATACCTT | CACAAACTAT | GGAATGAACT | GGGTGCGCCA | GGCTCCAGGA | 60 |
| AAGAATTTAG | AGTGGATGGG | CTGG | | | | 84 |

( 2 ) INFORMATION FOR SEQ ID NO:134:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:134:

| | | | | | | |
|---|---|---|---|---|---|---|
| AAAGAGAAGG | TAAACCGTCC | CTTGAAAGAA | TCAGCATATG | TTGGCTCTCC | AGTGTGGGTG | 60 |
| TTTATCCAGC | CCATCCACTC | TAAAC | | | | 85 |

( 2 ) INFORMATION FOR SEQ ID NO:135:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:135:

| | | | | | | |
|---|---|---|---|---|---|---|
| GACGGTTTAC | CTTCTCTTTG | GACGATTCTA | AGAACACTGC | CTATTTACAG | ATCAACAGCC | 60 |
| TCAGAGCCGA | GGACACGGCT | GTGTATT | | | | 87 |

( 2 ) INFORMATION FOR SEQ ID NO:136:

( i ) SEQUENCE CHARACTERISTICS:
    ( A ) LENGTH: 92 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:136:

| | | | | | | |
|---|---|---|---|---|---|---|
| GAGGAGACGG | TGACCGTGGT | CCCTTGGCCC | CAGACATCGA | AGTACCAGTC | GTAACCCCGT | 60 |

CTTGTACAGA AATACACAGC CGTGTCCTCG GC                                                92

( 2 ) INFORMATION FOR SEQ ID NO:137:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:137:

GCAGCTTCTG GGTATACCTT CACAAACTAT GGAATGAACT GGGTGAAGCA GGCTCCAGGA       60

AAGGGTTTAA GGTGGATGGG CTGG                                              84

( 2 ) INFORMATION FOR SEQ ID NO:138:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:138:

AAAGAGAAGG TAAACCGTCC CTTGAAGTCA TCAGCATATG TTGGCTCTCC AGTGTGGGTG       60

TTTATCCAGC CCATCCACCT TAAAC                                             85

( 2 ) INFORMATION FOR SEQ ID NO:139:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:139:

GACGGTTTAC CTTCTCTTTG GACACGTCTA AGTGCACTGC CTATTTACAG ATCAACAGCC       60

TCAGAGCCGA GGACACGGCT ACAT                                              84

( 2 ) INFORMATION FOR SEQ ID NO:140:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:140:

AGGAGACGGT GACCGTGGTC CCTTGGCCCC AGACATCGAA GTACCAGTCG TAACCCCGTC       60

TTGTACAGAA ATATGTAGCC GTGTCCTCGG C                                      91

( 2 ) INFORMATION FOR SEQ ID NO:141:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear (i i) MOLECULE TYPE: DNA (x i) SEQUENCE DESCRIPTION: SEQ ID NO:141:

```
TGACTCGCCC GGCAAGTGAT AGTGACTCTG TCTCCCAGAC ATGCAGACAT GGAAGATGAG    60
GACTGAGTCA TCTGGATGTC                                                80
```

(2) INFORMATION FOR SEQ ID NO:142:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:142:

```
TCACTTGCCG GGCGAGTCAG GACATTAATA GCTATTTAAG CTGGTTCCAG CAGAAACCAG    60
GGAAATCTCC TAAGACCCT                                                 79
```

(2) INFORMATION FOR SEQ ID NO:143:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:143:

```
GATCCACTGC CACTGAACCT TGATGGGACC CCATCTACCA ATCTGTTTGC ACGATAGATC    60
AGGGTCTTAG GAGATTTCC                                                 79
```

(2) INFORMATION FOR SEQ ID NO:144:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:144:

```
TGTCGACATC ATGGCTTGGG TGTGGACCTT GCTATTCCTG ATGGCAGCTG CCCAAAGTGC    60
CCAAGCACAG ATCCAGTTGG TGCAG                                          85
```

(2) INFORMATION FOR SEQ ID NO:145:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:145:

```
AAGGTATACC CAGAAGCTGC GCAGGAGATT CTGACGGACC CTCCAGGCTT CTTCAGGCCA    60
GGTCCAGACT GCACCAACTG GATCT                                          85
```

(2) INFORMATION FOR SEQ ID NO:146:

(i) SEQUENCE CHARACTERISTICS:

(A) LENGTH: 26 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:146:

ACTAGTGTCG ACATCATGGC TTGGGT 26

(2) INFORMATION FOR SEQ ID NO:147:

(i) SEQUENCE CHARACTERISTICS:
(A) LENGTH: 240 amino acids
(B) TYPE: amino acid
(D) TOPOLOGY: linear (ii) MOLECULE TYPE: protein (xi) SEQUENCE DESCRIPTION: SEQ ID NO:147:

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |
| Asp | Arg | Val | Thr | Ile | Thr | Cys | Arg | Ala | Ser | Gln | Asp | Ile | Asn | Ser | Tyr |
| | | | 20 | | | | | 25 | | | | | 30 | | |
| Leu | Ser | Trp | Phe | Gln | Gln | Lys | Pro | Gly | Lys | Ala | Pro | Lys | Thr | Leu | Ile |
| | | 35 | | | | | 40 | | | | | 45 | | | |
| Tyr | Arg | Ala | Asn | Arg | Leu | Glu | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Tyr | Thr | Leu | Thr | Ile | Ser | Ser | Leu | Gln | Tyr |
| 65 | | | | | 70 | | | | | 75 | | | | | 80 |
| Glu | Asp | Phe | Gly | Ile | Tyr | Tyr | Cys | Gln | Gln | Tyr | Asp | Glu | Ser | Pro | Trp |
| | | | | 85 | | | | | 90 | | | | | 95 | |
| Thr | Phe | Gly | Gly | Gly | Thr | Lys | Leu | Glu | Met | Lys | Gly | Gly | Gly | Gly | Ser |
| | | | 100 | | | | | 105 | | | | | 110 | | |
| Gly | Gly | Gly | Gly | Ser | Gly | Gly | Gly | Gly | Ser | Glu | Ile | Gln | Leu | Val | Gln |
| | | 115 | | | | | 120 | | | | | 125 | | | |
| Ser | Gly | Gly | Gly | Leu | Val | Lys | Pro | Gly | Gly | Ser | Val | Arg | Ile | Ser | Cys |
| | 130 | | | | | 135 | | | | | 140 | | | | |
| Ala | Ala | Ser | Gly | Tyr | Thr | Phe | Thr | Asn | Tyr | Gly | Met | Asn | Trp | Val | Arg |
| 145 | | | | | 150 | | | | | 155 | | | | | 160 |
| Gln | Ala | Pro | Gly | Lys | Gly | Leu | Glu | Trp | Met | Gly | Trp | Ile | Asn | Thr | His |
| | | | | 165 | | | | | 170 | | | | | 175 | |
| Thr | Gly | Glu | Pro | Thr | Tyr | Ala | Asp | Ser | Phe | Lys | Gly | Arg | Phe | Thr | Phe |
| | | | 180 | | | | | 185 | | | | | 190 | | |
| Ser | Leu | Asp | Asp | Ser | Lys | Asn | Thr | Ala | Tyr | Leu | Gln | Ile | Asn | Ser | Leu |
| | | 195 | | | | | 200 | | | | | 205 | | | |
| Arg | Ala | Glu | Asp | Thr | Ala | Val | Tyr | Phe | Cys | Thr | Arg | Arg | Gly | Tyr | Asp |
| | 210 | | | | | 215 | | | | | 220 | | | | |
| Trp | Tyr | Phe | Asp | Val | Trp | Gly | Gln | Gly | Thr | Thr | Val | Thr | Val | Ser | Ser |
| 225 | | | | | 230 | | | | | 235 | | | | | 240 |

(2) INFORMATION FOR SEQ ID NO:148:

(i) SEQUENCE CHARACTERISTICS:
(A) LENGTH: 240 amino acids
(B) TYPE: amino acid
(D) TOPOLOGY: linear (ii) MOLECULE TYPE: protein (xi) SEQUENCE DESCRIPTION: SEQ ID NO:148:

```
Glu Ile Gln Leu Val Gln Ser Gly Gly Leu Val Lys Pro Gly Gly
 1               5                  10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
210                 215                 220

Asp Glu Ser Pro Trp Thr Phe Gly Gly Gly Thr Lys Leu Glu Met Lys
225                 230                 235                 240
```

( 2 ) INFORMATION FOR SEQ ID NO:149:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( x i ) SEQUENCE DESCRIPTION: SEQ ID NO:149:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Xaa Ile Ser Xaa Tyr
            20                  25                  30

Leu Xaa Trp Tyr Gln Gln Lys Pro Gly Lys Ala Pro Lys Leu Leu Ile
        35                  40                  45

Tyr Ala Ala Ser Xaa Leu Xaa Ser Gly Val Pro Ser Arg Phe Ser Gly
    50                  55                  60

Ser Gly Ser Gly Thr Xaa Phe Thr Leu Thr Ile Ser Ser Leu Gln Pro
65                  70                  75                  80

Glu Asp Phe Ala Thr Tyr Tyr Cys Gln Gln Tyr Xaa Xaa Xaa Pro Xaa
                85                  90                  95

Thr Phe Gly Gln Gly Thr Lys Val Glu Ile Lys
            100                 105
```

( 2 ) INFORMATION FOR SEQ ID NO:150:

( i ) SEQUENCE CHARACTERISTICS:
    ( A ) LENGTH: 108 amino acids
    ( B ) TYPE: amino acid
    ( C ) STRANDEDNESS: double
    ( D ) TOPOLOGY: linear ( i i ) MOLECULE TYPE: protein ( x i ) SEQUENCE DESCRIPTION: SEQ ID NO:150:

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Gly Asp Phe Ala Val Tyr Tyr Cys Gln Gln Tyr Gly Ser Ser Pro
                85                  90                  95

Xaa Thr Phe Gly Gln Gly Thr Lys Val Glu Ile Lys
                100                 105
```

( 2 ) INFORMATION FOR SEQ ID NO:151:

( i ) SEQUENCE CHARACTERISTICS:
    ( A ) LENGTH: 108 amino acids
    ( B ) TYPE: amino acid
    ( C ) STRANDEDNESS: double
    ( D ) TOPOLOGY: linear ( x i ) SEQUENCE DESCRIPTION: SEQ ID NO:151:

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Asn
                20                  25                  30

Tyr Leu Asn Trp Tyr Leu Gln Lys Pro Gly Gln Ser Pro Gln Leu Leu
            35                  40                  45

Ile Tyr Leu Gly Ser Asn Arg Ala Ser Gly Val Pro Asp Arg Phe Ser
        50                  55                  60

Gly Ser Gly Ser Gly Thr Asp Phe Thr Leu Lys Ile Ser Arg Val Glu
65                  70                  75                  80

Ala Glu Asp Val Gly Val Tyr Tyr Cys Met Gln Ala Leu Gln Xaa Pro
                85                  90                  95

Xaa Thr Phe Gly Gln Gly Thr Lys Xaa Glu Ile Lys
                100                 105
```

( 2 ) INFORMATION FOR SEQ ID NO:152:

( i ) SEQUENCE CHARACTERISTICS:
    ( A ) LENGTH: 106 amino acids
    ( B ) TYPE: amino acid
    ( C ) STRANDEDNESS: double
    ( D ) TOPOLOGY: linear ( i i ) MOLECULE TYPE: protein ( x i ) SEQUENCE DESCRIPTION: SEQ ID NO:152:

```
Xaa Ser Val Leu Thr Gln Pro Pro Ser Ala Ser Gly Thr Pro Gly Gln
1               5                   10                  15

Arg Val Thr Ile Ser Cys Ser Gly Ser Ser Ser Ile Gly Xaa Asn Xaa
```

|  |  | 20 |  |  |  |  | 25 |  |  |  |  | 30 |  |  |  |
|--|--|--|--|--|--|--|--|--|--|--|--|--|--|--|--|

```
Val  Xaa  Trp  Tyr  Gln  Gln  Leu  Pro  Gly  Thr  Ala  Pro  Lys  Leu  Leu  Ile
          35                      40                      45

Tyr  Asn  Asn  Arg  Pro  Ser  Gly  Val  Pro  Asp  Arg  Phe  Ser  Gly  Ser  Lys
     50                      55                      60

Ser  Gly  Thr  Ser  Ala  Ser  Leu  Ala  Ile  Ser  Gly  Leu  Gln  Ser  Glu  Asp
65                           70                      75                      80

Glu  Ala  Asp  Tyr  Tyr  Cys  Ala  Thr  Trp  Asp  Asp  Ser  Leu  Asp  Pro  Val
               85                      90                      95

Phe  Gly  Gly  Gly  Thr  Lys  Thr  Val  Leu  Gly
               100                     105
```

(2) INFORMATION FOR SEQ ID NO:153:

(i) SEQUENCE CHARACTERISTICS:
        (A) LENGTH: 104 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:153:

```
Xaa  Ser  Ala  Leu  Thr  Gln  Pro  Ala  Ser  Val  Ser  Gly  Ser  Pro  Gly  Gln
1                   5                       10                      15

Ser  Ile  Thr  Ile  Ser  Cys  Thr  Gly  Thr  Ser  Ser  Val  Gly  Tyr  Asn  Xaa
               20                      25                      30

Val  Ser  Trp  Tyr  Gln  Gln  His  Pro  Gly  Lys  Ala  Pro  Lys  Leu  Ile  Tyr
          35                      40                      45

Asp  Val  Arg  Pro  Ser  Gly  Val  Arg  Phe  Ser  Gly  Ser  Lys  Ser  Gly  Asn
     50                      55                      60

Thr  Ala  Ser  Leu  Thr  Ile  Ser  Gly  Leu  Gln  Ala  Glu  Asp  Glu  Ala  Asp
65                           70                      75                      80

Tyr  Tyr  Cys  Ser  Ser  Tyr  Xaa  Gly  Xaa  Xaa  Xaa  Xaa  Val  Phe  Gly  Gly
               85                      90                      95

Gly  Thr  Lys  Leu  Thr  Val  Leu  Gly
               100
```

(2) INFORMATION FOR SEQ ID NO:154:

(i) SEQUENCE CHARACTERISTICS:
        (A) LENGTH: 100 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:154:

```
Ser  Tyr  Glu  Leu  Thr  Gln  Pro  Pro  Ser  Val  Ser  Val  Ser  Pro  Gly  Gln
1                   5                       10                      15

Thr  Ala  Ile  Thr  Cys  Ser  Gly  Asp  Xaa  Leu  Xaa  Xaa  Xaa  Tyr  Val  Xaa
               20                      25                      30

Trp  Tyr  Gln  Gln  Lys  Pro  Gly  Gln  Ala  Pro  Val  Leu  Val  Ile  Tyr  Asp
          35                      40                      45

Arg  Pro  Ser  Gly  Ile  Pro  Gln  Arg  Phe  Ser  Gly  Ser  Ser  Thr  Thr  Ala
     50                      55                      60

Thr  Leu  Thr  Ile  Ser  Gly  Val  Gln  Ala  Asp  Glu  Ala  Asp  Tyr  Tyr  Cys
65                           70                      75                      80

Gln  Xaa  Trp  Asp  Xaa  Xaa  Xaa  Val  Val  Phe  Gly  Gly  Gly  Thr  Lys  Leu
```

|   |   |   | 85 |   |   |   |   | 90 |   |   |   |   | 95 |   |
|---|---|---|---|---|---|---|---|---|---|---|---|---|---|---|

Thr Val Leu Gly
              100

( 2 ) INFORMATION FOR SEQ ID NO:155:

( i ) SEQUENCE CHARACTERISTICS:
        ( A ) LENGTH: 106 amino acids
        ( B ) TYPE: amino acid
        ( C ) STRANDEDNESS: double
        ( D ) TOPOLOGY: linear ( i i ) MOLECULE TYPE: protein ( x i ) SEQUENCE DESCRIPTION: SEQ ID NO:155:

Asn Phe Met Leu Thr Gln Pro His Ser Val Ser Glu Ser Pro Gly Lys
1               5                   10                  15

Thr Val Thr Ile Ser Cys Thr Xaa Ser Xaa Gly Ile Ala Ser Xaa Tyr
              20                  25                  30

Val Gln Trp Tyr Gln Gln Arg Pro Gly Ser Ala Pro Thr Thr Val Ile
          35                  40                  45

Tyr Glu Asp Asn Arg Pro Ser Gly Val Pro Asp Arg Phe Ser Gly Ser
      50                  55                  60

Ser Ser Asn Ser Ala Ser Leu Thr Ile Ser Gly Leu Lys Thr Glu Asp
65                  70                  75                  80

Glu Ala Asp Tyr Tyr Cys Gln Ser Tyr Asp Ser Xaa Xaa Trp Val Phe
                  85                  90                  95

Gly Gly Gly Thr Lys Leu Thr Val Leu Gly
              100                 105

( 2 ) INFORMATION FOR SEQ ID NO:156:

( i ) SEQUENCE CHARACTERISTICS:
        ( A ) LENGTH: 107 amino acids
        ( B ) TYPE: amino acid
        ( C ) STRANDEDNESS: double
        ( D ) TOPOLOGY: linear ( i i ) MOLECULE TYPE: protein ( x i ) SEQUENCE DESCRIPTION: SEQ ID NO:156:

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Lys Asn
              20                  25                  30

Tyr Leu Ala Trp Tyr Gln Gln Lys Pro Gly Gln Pro Pro Lys Leu Leu
          35                  40                  45

Ile Tyr Trp Ala Ser Arg Glu Ser Gly Val Pro Asp Arg Phe Ser Gly
      50                  55                  60

Ser Gly Ser Gly Thr Asp Phe Thr Leu Thr Ile Ser Ser Leu Gln Ala
65                  70                  75                  80

Gln Asp Val Ala Val Tyr Tyr Cys Gln Gln Tyr Tyr Ser Thr Pro Xaa
                  85                  90                  95

Thr Phe Gly Gln Gly Thr Lys Xaa Gly Ile Lys
              100                 105

( 2 ) INFORMATION FOR SEQ ID NO:157:

( i ) SEQUENCE CHARACTERISTICS:
        ( A ) LENGTH: 105 amino acids
        ( B ) TYPE: amino acid
        ( C ) STRANDEDNESS: double -continued ( D ) TOPOLOGY: linear ( i i ) MOLECULE TYPE: protein ( x i ) SEQUENCE DESCRIPTION: SEQ ID NO:157:

| Ser | Glu | Leu | Thr | Gln | Pro | Pro | Ser | Val | Ser | Val | Ala | Pro | Gly | Gln | Thr |
| 1 | | | | 5 | | | | | 10 | | | | | 15 | |
| Arg | Ile | Thr | Cys | Ser | Gly | Asp | Xaa | Leu | Gly | Xaa | Tyr | Asp | Ala | Xaa | Trp |
| | | | 20 | | | | | 25 | | | | | 30 | | |
| Tyr | Gln | Gln | Lys | Pro | Gly | Gln | Ala | Pro | Leu | Leu | Val | Ile | Tyr | Gly | Arg |
| | | 35 | | | | | 40 | | | | | 45 | | | |
| Asn | Arg | Pro | Ser | Gly | Ile | Pro | Asp | Arg | Phe | Ser | Gly | Ser | Ser | Ser | Gly |
| | | 50 | | | | 55 | | | | | 60 | | | | |
| His | Thr | Ala | Ser | Leu | Thr | Ile | Thr | Gly | Ala | Gln | Ala | Glu | Asp | Glu | Ala |
| 65 | | | | | 70 | | | | | 75 | | | | | 80 |
| Asp | Tyr | Tyr | Cys | Asn | Ser | Arg | Asp | Ser | Ser | Gly | Lys | Val | Leu | Phe | Gly |
| | | | | 85 | | | | | 90 | | | | | 95 | |
| Gly | Gly | Thr | Lys | Leu | Thr | Val | Leu | Gly | | | | | | | |
| | | | 100 | | | | | 105 | | | | | | | |

( 2 ) INFORMATION FOR SEQ ID NO:158:

( i ) SEQUENCE CHARACTERISTICS:
( A ) LENGTH: 96 amino acids
( B ) TYPE: amino acid
( C ) STRANDEDNESS: double
( D ) TOPOLOGY: linear ( i i ) MOLECULE TYPE: protein ( x i ) SEQUENCE DESCRIPTION: SEQ ID NO:158:

| Ser | Ala | Leu | Thr | Gln | Pro | Pro | Ser | Ala | Ser | Gly | Ser | Pro | Gly | Gln | Ser |
| 1 | | | | 5 | | | | | 10 | | | | | 15 | |
| Val | Thr | Ile | Ser | Cys | Thr | Gly | Thr | Ser | Ser | Val | Gly | Xaa | Xaa | Tyr | Val |
| | | | 20 | | | | | 25 | | | | | 30 | | |
| Ser | Trp | Tyr | Gln | Gln | His | Gly | Ala | Pro | Lys | Ile | Glu | Val | Arg | Pro | Ser |
| | | | 35 | | | | | 40 | | | | | 45 | | |
| Gly | Val | Pro | Asp | Arg | Phe | Ser | Gly | Ser | Lys | Ser | Asn | Thr | Ala | Ser | Leu |
| | | 50 | | | | | 55 | | | | | 60 | | | |
| Thr | Val | Ser | Gly | Leu | Ala | Glu | Asp | Glu | Ala | Asp | Tyr | Tyr | Cys | Ser | Ser |
| 65 | | | | | 70 | | | | | 75 | | | | | 80 |
| Tyr | Xaa | Xaa | Xaa | Xaa | Xaa | Phe | Val | Phe | Gly | Gly | Thr | Lys | Thr | Val | Leu |
| | | | | 85 | | | | | 90 | | | | | 95 | |

( 2 ) INFORMATION FOR SEQ ID NO:159:

( i ) SEQUENCE CHARACTERISTICS:
( A ) LENGTH: 119 amino acids
( B ) TYPE: amino acid
( C ) STRANDEDNESS: double
( D ) TOPOLOGY: linear ( i i ) MOLECULE TYPE: protein ( x i ) SEQUENCE DESCRIPTION: SEQ ID NO:159:

| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Xaa | Xaa |
| | | | 20 | | | | | 25 | | | | | 30 | | |
| Xaa | Met | Xaa | Trp | Val | Arg | Gln | Ala | Pro | Gly | Lys | Gly | Leu | Glu | Trp | Val |
| | | | 35 | | | | | 40 | | | | | 45 | | |

177

-continued

```
Xaa  Xaa  Ile  Xaa  Xaa  Xaa  Xaa  Xaa  Gly  Xaa  Xaa  Tyr  Ala  Asp  Ser  Val
     50                       55                      60

Lys  Gly  Arg  Phe  Thr  Ile  Ser  Arg  Asp  Asp  Ser  Lys  Asn  Thr  Leu  Tyr
65                       70                      75                           80

Leu  Gln  Met  Asn  Ser  Leu  Arg  Ala  Glu  Asp  Thr  Ala  Val  Tyr  Tyr  Cys
                    85                       90                      95

Ala  Arg  Xaa  Xaa  Xaa  Xaa  Xaa  Xaa  Xaa  Xaa  Xaa  Trp  Gly  Gln  Gly
               100                      105                     110

Thr  Leu  Val  Thr  Val  Ser  Ser
          115
```

( 2 ) INFORMATION FOR SEQ ID NO:160:

( i ) SEQUENCE CHARACTERISTICS:
  ( A ) LENGTH: 119 amino acids
  ( B ) TYPE: amino acid
  ( C ) STRANDEDNESS: double
  ( D ) TOPOLOGY: linear ( x i ) SEQUENCE DESCRIPTION: SEQ ID NO:160:

```
Gln  Val  Gln  Leu  Val  Gln  Ser  Gly  Ala  Glu  Val  Lys  Lys  Pro  Gly  Xaa
1                   5                        10                          15

Ser  Val  Xaa  Val  Ser  Cys  Lys  Xaa  Ser  Gly  Tyr  Tyr  Phe  Xaa  Xaa  Tyr
          20                       25                      30

Xaa  Ile  Xaa  Trp  Val  Arg  Gln  Ala  Pro  Gly  Xaa  Gly  Leu  Glu  Trp  Val
          35                       40                      45

Gly  Xaa  Ile  Xaa  Pro  Xaa  Xaa  Gly  Xaa  Thr  Xaa  Tyr  Ala  Pro  Xaa  Phe
     50                       55                      60

Gln  Gly  Arg  Val  Thr  Xaa  Thr  Arg  Asp  Xaa  Ser  Xaa  Asn  Thr  Ala  Tyr
65                       70                      75                           80

Met  Glu  Leu  Xaa  Ser  Leu  Arg  Ser  Glu  Asp  Thr  Ala  Val  Tyr  Tyr  Cys
                    85                       90                      95

Ala  Arg  Xaa  Xaa  Xaa  Xaa  Xaa  Xaa  Xaa  Xaa  Xaa  Trp  Gly  Gln  Gly
               100                      105                     110

Thr  Leu  Val  Thr  Val  Ser  Ser
          115
```

( 2 ) INFORMATION FOR SEQ ID NO:161:

( i ) SEQUENCE CHARACTERISTICS:
  ( A ) LENGTH: 117 amino acids
  ( B ) TYPE: amino acid
  ( C ) STRANDEDNESS: double
  ( D ) TOPOLOGY: linear ( i i ) MOLECULE TYPE: protein ( x i ) SEQUENCE DESCRIPTION: SEQ ID NO:161:

```
Xaa  Val  Thr  Leu  Xaa  Glu  Ser  Gly  Pro  Xaa  Leu  Val  Leu  Pro  Thr  Gln
1                   5                        10                          15

Thr  Leu  Thr  Leu  Thr  Cys  Thr  Val  Ser  Gly  Xaa  Ser  Leu  Ser  Xaa  Xaa
          20                       25                      30

Xaa  Val  Xaa  Trp  Ile  Arg  Gln  Pro  Pro  Gly  Lys  Xaa  Leu  Glu  Trp  Leu
          35                       40                      45

Ala  Xaa  Ile  Xaa  Xaa  Asp  Asp  Asp  Xaa  Tyr  Xaa  Thr  Ser  Leu  Arg  Ser
     50                       55                      60

Arg  Leu  Thr  Ile  Ser  Lys  Asp  Thr  Ser  Lys  Asn  Gln  Val  Val  Leu  Xaa
65                       70                      75                           80

Xaa  Xaa  Xaa  Xaa  Asp  Pro  Xaa  Asp  Thr  Ala  Thr  Tyr  Tyr  Cys  Ala  Arg
               85                       90                           95
```

5,744,580

179                                                                                                      180

-continued

```
Xaa Xaa Xaa Xaa Xaa Xaa Xaa Xaa Asp Val Trp Gly Gln Gly Thr Thr
            100                     105                         110

Val Thr Val Ser Ser
            115
```

( 2 ) INFORMATION FOR SEQ ID NO:162:

( i ) SEQUENCE CHARACTERISTICS:
    ( A ) LENGTH: 107 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:162:

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Met
        35                  40                  45

Tyr Lys Ala Ser Ser Leu Glu Ser Gly Val Pro Ser Arg Phe Ile Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Asp Ser Lys
                85                  90                  95

Met Phe Gly Gln Gly Thr Lys Val Glu Val Lys
            100                 105
```

( 2 ) INFORMATION FOR SEQ ID NO:163:

( i ) SEQUENCE CHARACTERISTICS:
    ( A ) LENGTH: 106 amino acids
    ( B ) TYPE: amino acid
    ( C ) STRANDEDNESS: double
    ( D ) TOPOLOGY: linear ( i i ) MOLECULE TYPE: protein ( x i ) SEQUENCE DESCRIPTION: SEQ ID NO:163:

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Ile Ser Tyr Met
            20                  25                  30

His Trp Phe Gln Gln Lys Pro Gly Thr Ser Pro Lys Leu Trp Ile Tyr
        35                  40                  45

Thr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Ser Gly Thr Lys Leu Glu Leu Lys
            100                 105
```

( 2 ) INFORMATION FOR SEQ ID NO:164:

( i ) SEQUENCE CHARACTERISTICS:
    ( A ) LENGTH: 106 amino acids ( B ) TYPE: amino acid
( C ) STRANDEDNESS: double
( D ) TOPOLOGY: linear ( i i ) MOLECULE TYPE: protein ( x i ) SEQUENCE DESCRIPTION: SEQ ID NO:164:

```
Asp Ile Gln Leu Thr Gln Ser Pro Ser Ser Met Ser Ala Ser Pro Gly
1               5                  10                 15

Asp Arg Val Thr Ile Thr Cys Arg Ala Ser Ser Ser Ile Ser Tyr Met
                20              25                  30

His Trp Phe Gln Gln Lys Pro Gly Lys Ser Pro Lys Leu Trp Ile Tyr
        35                  40                  45

Thr Thr Ser Asn Leu Ala Ser Gly Val Pro Ser Arg Phe Ser Gly Ser
        50              55                  60

Gly Ser Gly Thr Ser Tyr Thr Leu Thr Ile Ser Ser Met Gln Ala Glu
65              70                  75                      80

Asp Phe Ala Thr Tyr Tyr Cys His Gln Arg Ser Thr Tyr Pro Leu Thr
                85              90                  95

Phe Gly Gln Gly Thr Lys Leu Glu Leu Lys
                100                 105
```

( 2 ) INFORMATION FOR SEQ ID NO:165:

( i ) SEQUENCE CHARACTERISTICS:
( A ) LENGTH: 106 amino acids
( B ) TYPE: amino acid
( C ) STRANDEDNESS: double
( D ) TOPOLOGY: linear ( i i ) MOLECULE TYPE: protein ( x i ) SEQUENCE DESCRIPTION: SEQ ID NO:165:

```
Asp Ile Gln Met Thr Gln Ser Pro Ser Thr Leu Ser Ala Ser Val Gly
1               5                  10                 15

Asp Arg Val Thr Ile Thr Cys Ser Ala Ser Ser Ser Ile Ser Tyr Met
                20              25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
        50              55                  60

Gly Ser Gly Thr Glu Phe Thr Leu Thr Ile Ser Ser Leu Gln Pro Asp
65              70                  75                      80

Asp Phe Ala Thr Tyr Tyr Cys His Gln Arg Ser Thr Tyr Pro Leu Thr
                85              90                  95

Phe Gly Gln Gly Thr Lys Val Glu Val Lys
                100                 105
```

( 2 ) INFORMATION FOR SEQ ID NO:166:

( i ) SEQUENCE CHARACTERISTICS:
( A ) LENGTH: 117 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:166:

```
Gln Val Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Arg Ser
```

-continued

```
                        20                        25                        30
    Ala  Ile  Ile  Trp  Val  Arg  Gln  Ala  Pro  Gly  Gln  Gly  Leu  Glu  Trp  Met
              35                        40                        45
    Gly  Gly  Ile  Val  Pro  Met  Phe  Gly  Pro  Pro  Asn  Tyr  Ala  Gln  Lys  Phe
         50                        55                        60
    Gln  Gly  Arg  Val  Thr  Ile  Thr  Ala  Asp  Glu  Ser  Thr  Asn  Thr  Ala  Tyr
    65                        70                        75                        80
    Met  Glu  Leu  Ser  Ser  Leu  Arg  Ser  Glu  Asp  Thr  Ala  Phe  Tyr  Phe  Cys
                        85                        90                        95
    Ala  Gly  Gly  Tyr  Gly  Ile  Tyr  Ser  Pro  Glu  Glu  Tyr  Asn  Gly  Gly  Leu
                   100                       105                       110
    Val  Thr  Val  Ser  Ser
                   115
```

( 2 ) INFORMATION FOR SEQ ID NO:167:

( i ) SEQUENCE CHARACTERISTICS:
       ( A ) LENGTH: 116 amino acids
       ( B ) TYPE: amino acid
       ( C ) STRANDEDNESS: double
       ( D ) TOPOLOGY: linear ( i i ) MOLECULE TYPE: protein ( x i ) SEQUENCE DESCRIPTION: SEQ ID NO:167:

```
    Gln  Val  Gln  Leu  Gln  Gln  Ser  Gly  Ala  Glu  Leu  Ala  Lys  Pro  Gly  Ala
    1                  5                        10                        15
    Ser  Val  Lys  Met  Ser  Cys  Lys  Ala  Ser  Gly  Tyr  Thr  Phe  Thr  Ser  Tyr
                   20                        25                        30
    Arg  Met  His  Trp  Val  Lys  Gln  Arg  Pro  Gly  Gln  Gly  Leu  Glu  Trp  Ile
              35                        40                        45
    Gly  Tyr  Ile  Asn  Pro  Ser  Thr  Gly  Tyr  Thr  Glu  Tyr  Asn  Gln  Lys  Phe
         50                        55                        60
    Lys  Asp  Lys  Ala  Thr  Leu  Thr  Ala  Asp  Lys  Ser  Ser  Ser  Thr  Ala  Tyr
    65                        70                        75                        80
    Met  Gln  Leu  Ser  Ser  Leu  Thr  Phe  Glu  Asp  Ser  Ala  Val  Tyr  Tyr  Cys
                        85                        90                        95
    Ala  Arg  Gly  Gly  Gly  Val  Phe  Asp  Tyr  Trp  Gly  Gln  Gly  Thr  Thr  Leu
                   100                       105                       110
    Thr  Val  Ser  Ser
                   115
```

( 2 ) INFORMATION FOR SEQ ID NO:168:

( i ) SEQUENCE CHARACTERISTICS:
       ( A ) LENGTH: 116 amino acids
       ( B ) TYPE: amino acid
       ( C ) STRANDEDNESS: double
       ( D ) TOPOLOGY: linear ( i i ) MOLECULE TYPE: protein ( x i ) SEQUENCE DESCRIPTION: SEQ ID NO:168:

```
    Gln  Val  Gln  Leu  Gln  Gln  Ser  Gly  Ala  Glu  Val  Ala  Lys  Pro  Gly  Ala
    1                  5                        10                        15
    Ser  Val  Lys  Met  Ser  Cys  Lys  Ala  Ser  Gly  Tyr  Thr  Phe  Thr  Ser  Tyr
                   20                        25                        30
    Arg  Met  His  Trp  Val  Lys  Gln  Ala  Pro  Gly  Gln  Gly  Leu  Glu  Trp  Ile
              35                        40                        45
    Gly  Tyr  Ile  Asn  Pro  Ser  Thr  Gly  Tyr  Thr  Glu  Tyr  Asn  Gln  Lys  Phe
         50                        55                        60
```

```
                       5 0                        5 5                            6 0

Lys  Gly  Lys  Ala  Thr  Leu  Thr  Ala  Asp  Lys  Ser  Ser  Ser  Thr  Ala  Tyr
        6 5                      7 0                      7 5                           8 0

Met  Glu  Leu  Ser  Ser  Leu  Arg  Ser  Glu  Asp  Thr  Ala  Val  Tyr  Tyr  Cys
                            8 5                      9 0                      9 5

Ala  Arg  Gly  Gly  Gly  Val  Phe  Asp  Tyr  Trp  Gly  Gln  Gly  Thr  Thr  Leu
                       1 0 0                     1 0 5                     1 1 0

Thr  Val  Ser  Ser
                       1 1 5
```

( 2 ) INFORMATION FOR SEQ ID NO:169:

( i ) SEQUENCE CHARACTERISTICS:
      ( A ) LENGTH: 116 amino acids
      ( B ) TYPE: amino acid
      ( C ) STRANDEDNESS: double
      ( D ) TOPOLOGY: linear ( x i ) SEQUENCE DESCRIPTION: SEQ ID NO:169:

```
        Gln  Val  Gln  Leu  Val  Gln  Ser  Gly  Ala  Glu  Val  Lys  Lys  Pro  Gly  Ser
        1                   5                        1 0                      1 5

Ser  Val  Lys  Val  Ser  Cys  Lys  Ala  Ser  Gly  Tyr  Thr  Phe  Thr  Ser  Tyr
                       2 0                      2 5                      3 0

Arg  Met  His  Trp  Val  Arg  Gln  Ala  Pro  Gly  Gln  Gly  Leu  Glu  Trp  Ile
                  3 5                      4 0                      4 5

Gly  Tyr  Ile  Asn  Pro  Ser  Thr  Gly  Tyr  Thr  Glu  Tyr  Asn  Gln  Lys  Phe
             5 0                      5 5                      6 0

Lys  Asp  Lys  Ala  Thr  Ile  Thr  Ala  Asp  Glu  Ser  Thr  Asn  Thr  Ala  Tyr
        6 5                      7 0                      7 5                           8 0

Met  Glu  Leu  Ser  Ser  Leu  Arg  Ser  Glu  Asp  Thr  Ala  Val  Tyr  Tyr  Cys
                            8 5                      9 0                      9 5

Ala  Arg  Gly  Gly  Gly  Val  Phe  Asp  Tyr  Trp  Gly  Gln  Gly  Thr  Leu  Val
                       1 0 0                     1 0 5                     1 1 0

Thr  Val  Ser  Ser
                       1 1 5
```